US009416126B2

(12) United States Patent
Miller et al.

(10) Patent No.: US 9,416,126 B2
(45) Date of Patent: Aug. 16, 2016

(54) COMPOUNDS INHIBITING LEUCINE-RICH REPEAT KINASE ENZYME ACTIVITY

(71) Applicant: Merck Sharp & Dohme Corp., Rahway, NJ (US)

(72) Inventors: Michael Miller, Scotch Plains, NJ (US); Kallol Basu, Hillsborough, NJ (US); Duane DeMong, Somerset, NJ (US); Jack Scott, Scotch Plains, NJ (US); Wei Li, Audubon, PA (US); Joel Harris, Blaine, MN (US); Andrew Stamford, Chatham, NJ (US); Marc Poirier, Stewartsville, NJ (US); Paul Tempest, Shanghai (CN)

(73) Assignee: Merck Sharp & Dohme Corp., Rahway, NJ (US)

( * ) Notice: Subject to any disclaimer, the term of this patent is extended or adjusted under 35 U.S.C. 154(b) by 0 days.

(21) Appl. No.: 14/772,290

(22) PCT Filed: Feb. 27, 2014

(86) PCT No.: PCT/US2014/018876
§ 371 (c)(1),
(2) Date: Sep. 2, 2015

(87) PCT Pub. No.: WO2014/137719
PCT Pub. Date: Sep. 12, 2014

(65) Prior Publication Data
US 2016/0009696 A1    Jan. 14, 2016

(30) Foreign Application Priority Data
Mar. 4, 2013 (WO) ................ PCT/CN2013/072128

(51) Int. Cl.
| | |
|---|---|
| *A61K 31/505* | (2006.01) |
| *C07D 403/14* | (2006.01) |
| *C07D 401/14* | (2006.01) |
| *C07D 405/14* | (2006.01) |
| *C07D 413/14* | (2006.01) |
| *C07D 409/14* | (2006.01) |
| *C07D 417/14* | (2006.01) |
| *A61K 31/506* | (2006.01) |
| *C07D 471/10* | (2006.01) |
| *C07D 491/107* | (2006.01) |
| *C07D 498/08* | (2006.01) |
| *C07D 403/04* | (2006.01) |

(52) U.S. Cl.
CPC ............ *C07D 403/14* (2013.01); *A61K 31/506* (2013.01); *C07D 401/14* (2013.01); *C07D 405/14* (2013.01); *C07D 409/14* (2013.01); *C07D 413/14* (2013.01); *C07D 417/14* (2013.01); *C07D 471/10* (2013.01); *C07D 491/107* (2013.01); *C07D 498/08* (2013.01); *A61K 31/505* (2013.01); *C07D 403/04* (2013.01)

(58) Field of Classification Search
CPC ............................. C07D 403/04; A61K 31/505
See application file for complete search history.

(56) References Cited

U.S. PATENT DOCUMENTS

| | | | |
|---|---|---|---|
| 7,776,890 B2 | 8/2010 | Oinuma et al. | |
| 8,629,132 B2 * | 1/2014 | Lee ....................... | A61K 31/505 514/210.2 |
| 2004/0127536 A1 | 7/2004 | Bhagwat et al. | |
| 2006/0079564 A1 | 4/2006 | Jansen et al. | |
| 2009/0203690 A1 | 8/2009 | Akritopoulou-Zanze et al. | |
| 2009/0221602 A1 | 9/2009 | Charrier et al. | |
| 2011/0281841 A1 * | 11/2011 | Lee ....................... | A61K 31/505 514/210.21 |
| 2011/0301141 A1 * | 12/2011 | Baker-Glenn ....... | C07D 403/14 514/210.16 |
| 2012/0157427 A1 * | 6/2012 | Baker-Glenn ....... | C07D 401/14 514/210.2 |
| 2012/0329780 A1 | 12/2012 | Thormann et al. | |
| 2013/0158006 A1 * | 6/2013 | Baker-Glenn ....... | A61K 31/506 514/211.05 |
| 2013/0158032 A1 * | 6/2013 | Baker-Glenn ....... | C07D 401/04 514/235.8 |
| 2013/0158057 A1 * | 6/2013 | Baker-Glenn ....... | C07D 403/12 514/275 |
| 2014/0031360 A1 * | 1/2014 | Wang ................... | C07D 401/14 514/252.11 |
| 2015/0284337 A1 * | 10/2015 | Aubele ................ | C07D 237/28 514/230.8 |
| 2015/0336942 A1 * | 11/2015 | Mikkelsen ........... | C07D 401/14 514/236.2 |
| 2016/0009682 A1 * | 1/2016 | Miller .................. | C07D 401/14 514/210.18 |
| 2016/0009689 A1 * | 1/2016 | Miller .................. | C07D 403/04 514/210.21 |
| 2016/0009696 A1 * | 1/2016 | Miller .................. | C07D 417/14 514/210.21 |

FOREIGN PATENT DOCUMENTS

| | | |
|---|---|---|
| EP | 1380576 B1 | 1/2004 |
| EP | 1510516 | 3/2005 |
| WO | 0153268 A2 | 7/2001 |
| WO | 0210137 | 2/2002 |

(Continued)

OTHER PUBLICATIONS

Deng et al., Nature Chemical Biology, 2011, vol. 7 Issue 4, p. 203-205.*

(Continued)

*Primary Examiner* — Alexander R Pagano
(74) *Attorney, Agent, or Firm* — Keith D. MacMillan; John C. Todaro

(57) ABSTRACT

The present invention is directed to indazole compounds which are potent inhibitors of LRRK2 kinase and useful in the treatment or prevention of diseases in which the LRRK2 kinase is involved, such as Parkinson's Disease. The invention is also directed to pharmaceutical compositions comprising these compounds and the use of these compounds and compositions in the prevention or treatment of such diseases in which LRRK-2 kinase is involved.

18 Claims, No Drawings

(56) References Cited

FOREIGN PATENT DOCUMENTS

| | | |
|---|---|---|
| WO | 02083648 | 10/2002 |
| WO | 03035005 | 5/2003 |
| WO | 2006081230 | 8/2006 |
| WO | 2008068171 | 6/2008 |
| WO | 2008137105 | 11/2008 |
| WO | 2008154241 | 12/2008 |
| WO | 2009054984 | 4/2009 |
| WO | 2010017046 A1 | 2/2010 |
| WO | 2010083145 A1 | 7/2010 |
| WO | 2011141756 | 11/2011 |
| WO | 2012038743 | 3/2012 |
| WO | 2012058193 | 5/2012 |
| WO | 2012078777 | 6/2012 |
| WO | 2014137719 A1 | 9/2014 |
| WO | 2014137723 A1 | 9/2014 |
| WO | 2014137725 A1 | 9/2014 |
| WO | 2014137728 | 9/2014 |
| WO | 2015026683 A1 | 2/2015 |
| WO | 2015073344 A1 | 5/2015 |
| WO | 2016036586 A1 | 3/2016 |

OTHER PUBLICATIONS

Bonifati et al., European Journal of Human Genetics, (2006), 14, 1061-1062.*

* cited by examiner

COMPOUNDS INHIBITING LEUCINE-RICH REPEAT KINASE ENZYME ACTIVITY

CROSS-REFERENCE TO RELATED APPLICATIONS

This Application is a U.S. National Stage Application under 35 U.S.C. §371 of PCT Application No. PCT/US2014/018876 filed Feb. 27, 2014 which claims priority under 35 U.S.C. §119(e) of PCT Application No. PCT/CN2013/072128 filed Mar. 4, 2013.

BACKGROUND OF THE INVENTION

Parkinson's disease (PD) is a common neurodegenerative disease caused by progressive loss of mid-brain dopaminergic neurons leading to abnormal motor symptoms such as bradykinesia, rigidity and resting tremor. Many PD patients also experience a variety of non-motor symptoms including cognitive dysfunction, autonomic dysfunction, emotional changes and sleep disruption. The combined motor and non-motor symptoms of Parkinson's disease severely impact patient quality of life.

While the majority of PD cases are idiopathic, there are several genetic determinants such as mutations in SNCA, Parkin, PINK1, DJ-1 and LRRK2. Linkage analysis studies have demonstrated that multiple missense mutations in the Leucine-Rich Repeat Kinase 2 (LRRK2) gene lead to an autosomal late onset form of PD. LRRK2 is a 286 kDa cytoplasmic protein containing kinase and GTPase domains as well as multiple protein-protein interaction domains. See for example, Aasly et al., Annals of Neurology, Vol. 57(5), May 2005, pp. 762-765; Adams et al., Brain, Vol. 128, 2005, pp. 2777-85; Gilks et al., Lancet, Vol. 365, Jan. 29, 2005, pp. 415-416, Nichols et al., Lancet, Vol. 365, Jan. 29, 2005, pp. 410-412, and U. Kumari and E. Tan, FEBS journal 276 (2009) pp. 6455-6463.

In vitro biochemical studies have demonstrated that LRRK2 proteins harboring the PD associated proteins generally confer increased kinase activity and decreased GTP hydrolysis compared to the wild type protein (Guo et al., Experimental Cell Research, Vol, 313, 2007, pp. 3658-3670) thereby suggesting that small molecule LRRK2 kinase inhibitors may be able to block aberrant LRRK2-dependent signaling in PD. In support of this notion, it has been reported that inhibitors of LRRK2 are protective in models of PD (Lee et al., Nature Medicine, Vol 16, 2010, pp. 998-1000).

LRRK2 protein has also been demonstrated to be associated with Lewy bodies, a pathological hallmark of PD as well as other neurodegenerative diseases such as Lewy body dementia (Zhu et al., Molecular Neurodegeneration, Vol 30, 2006, pp. 1-17) thereby suggesting that LRRK2 may be associated with the pathogenesis of these diseases.

A growing body of evidence also suggests a role for LRRK2 in immune cell function in the brain with LRRK2 inhibition demonstrated to attenuate microglial inflammatory responses (Moehle et al., The Journal of Neuroscience Vol 32, 2012, pp. 1602-1611). Neuroinflammation is a hallmark of a number of neurodegenerative diseases such as PD and Alzheimer's disease, thereby suggesting that LRRK2 inhibitors may have utility in the treatment of neuroinflammation in these disorders.

Genome-wide association studies also highlight LRRK2 in the modification of susceptibility to the chronic autoimmune Crohn's disease and leprosy (Zhang et al., The New England Journal of Medicine, Vol 361, 2009, pp. 2609-2618; Umeno et al., Inflammatory Bowel Disease Vol 17, 2011, pp. 2407-2415). LRRK2 is also associated with certain types of cancer, e.g. melanoma as well as renal and thyroid carcinomas (Saunders-Pullman et al., Movement Disorders, Vol 25, 2010, pp. 2536-2541; Looyenga, et al., Proceedings of the National Academy of Sciences, USA, Vol 108, 2011, pp. 1439-1444).

Accordingly, compounds and compositions effective at modulating LRRK2 activity may provide a treatment for neurodegenerative diseases such as Parkinson's disease, Lewy body dementia, neuroinflammation, and for disease such as Crohn's disease, leprosy and cancer.

SUMMARY OF THE INVENTION

The present invention is directed to indazole compounds which are potent inhibitors of LRRK2 kinase and may be useful in the treatment or prevention of diseases in which the LRRK2 kinase is involved, such as Parkinson's Disease. The invention is also directed to pharmaceutical compositions comprising these compounds and the use of these compounds and compositions in the prevention or treatment of such diseases in which LRRK-2 kinase is involved.

DETAILED DESCRIPTION OF THE INVENTION

The present invention is directed to compounds of Formula I:

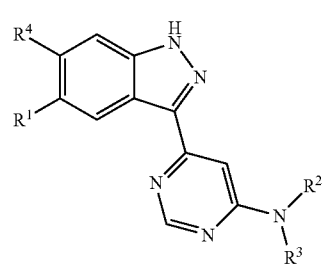

or a pharmaceutically acceptable salt thereof, wherein:
$R^1$ is selected from the group consisting of:
a) hydrogen,
b) halo,
c) cyano,
d) hydroxyl,
e) $C_{2-6}$ alkenyl, which is optionally substituted with one to three substitutents independently selected from the group consisting of halo, cyano and $R^5$;
f) $OC_{2-6}$ alkenyl, which is optionally substituted with one to three substitutents independently selected from the group consisting of halo, cyano and $R^5$;
g) $R^5$,
h) $OR^5$,
i) $R^7$,
j) $S(O)_m R^5$,
k) $S(O)_m R^7$,
l) $(C=O)R^7$,
m) $(C=O)R^5$,
n) $(C=O)OR^5$, and
o) $NR^c R^d$;
$R^2$ is selected from the group consisting of hydrogen and $C_{1-6}$ alkyl, which is optionally substituted with one to three substitutents independently selected from the group consisting of:
a) halo,
b) cyano, c) R$^5$,
d) R$^7$,
e) OR$^5$, and
f) NR$^c$R$^d$;

R$^3$ is selected from the group consisting of:
a) hydrogen,
b) C$_{1-6}$ alkyl, which is optionally substituted with one to three substituents independently selected from the group consisting of halo, cyano, OR$^5$ and NR$^c$R$^d$,
c) C$_{3-8}$ cycloalkyl, which is optionally substituted with one to three substituents independently selected from the group consisting of halo, cyano, OR$^5$ and NR$^c$R$^d$,
d) heterocyclyl, which is optionally substituted with one to three substituents independently selected from the group consisting of halo, cyano, oxo, R$^5$, OR$^5$ and NR$^c$R$^d$,
e) heteroaryl, which is optionally substituted with one to three substituents independently selected from the group consisting of halo, cyano, oxo, R$^5$, OR$^5$ and NR$^c$R$^d$;
C$_{4-8}$ cycloalkenyl, which is optionally substituted with one to three substituents independently selected from the group consisting of halo, cyano, OR$^5$ and NR$^c$R$^d$,
g) (C=O)R$^7$,
h) (C=O)R$^5$,
i) S(O)$_m$R$^5$, and
j) S(O)$_m$R$^7$;

or R$^2$ and R$^3$ can be taken together with the atoms to which they are attached to form a 3 to 8 membered heterocyclic ring, wherein said ring may contain from one to three heteroatoms selected from N, O and S, wherein the sulfur is optionally oxidized to the sulfone or sulfoxide, and which ring is optionally substituted with one to four substituents each independently selected from the group consisting of:
a) halo,
b) oxo,
c) cyano,
d) OR$^5$,
e) NR$^c$R$^d$,
f) SO$_3$H,
g) S(O)$_m$R$^5$,
h) S(O)$_m$R$^7$,
i) R$^5$,
j) R$^6$,
k) R$^7$,
l) (C=O)R$^5$,
m) (C=O)OR$^5$,
n) (C=O)R$^7$, and
o) (C=O)NR$^c$R$^d$;

R$^4$ is selected from the group consisting of: hydrogen, halo, cyano, OR$^5$, aryl, heteroaryl, C$_{3-8}$ cycloalkyl, C$_{4-8}$ cycloalkenyl, C$_{4-8}$ heterocyclyl and C$_{1-6}$ alkyl, which is optionally substituted with one to three substituents independently selected from the group consisting of halo, cyano, OC$_{1-3}$ alkyl, NR$^c$R$^d$ and hydroxyl;

or R$^1$ and R$^4$ can be taken together with the atoms to which they are attached to form a 5 to 10 membered heterocyclic ring, wherein said ring may contain from one to three heteroatoms selected from N, O and S, wherein the sulfur is optionally oxidized to the sulfone or sulfoxide, and which ring is optionally substituted with one to four substituents each independently selected from the group consisting of:
a) halo,
b) oxo,
c) cyano,
d) R$^5$, and
e) R$^7$;

R$^5$ is selected from the group consisting of hydrogen or C$_{1-6}$ alkyl, which is optionally substituted with one to three substituents independently selected from the group consisting of:
a) halo,
b) hydroxyl,
c) OC$_{1-6}$ alkyl,
d) NR$^c$R$^d$,
e) (C=O)NR$^c$R$^d$,
f) S(O)$_m$R$^8$,
g) S(O)$_m$R$^7$,
h) R$^7$, and
i) OR$^7$;

R$^6$ is C$_{1-6}$ alkyl, which is optionally substituted with one to three substituents independently selected from the group consisting of halo and hydroxyl;

or R$^5$ and R$^6$ can be taken together with the atoms to which they are attached to form a 4 to 8 membered heterocyclic, 3 to 8 membered carbocyclic, aryl or heteroaryl ring, wherein said heterocyclic and heteroaryl rings may contain from one to three heteroatoms selected from N, O and S, wherein said heterocyclic, carbocyclic, aryl and heteroaryl rings are optionally substituted with one to three substituents independently selected from the group consisting of:
a) halo,
b) oxo,
c) cyano,
d) hydroxyl,
e) C$_{1-3}$ alkyl, which is optionally substituted with one to three halo,
f) C$_{3-8}$ cycloalkyl,
g) OC$_{1-3}$ alkyl, which is optionally substituted with one to three halo, and
h) OC$_{3-8}$ cycloalkyl;

R$^7$ is selected from the group consisting of C$_{4-8}$ heterocyclyl, C$_{3-8}$ cycloalkyl, C$_{4-8}$ cycloalkenyl, aryl or heteroaryl, wherein said heterocyclyl, cycloalkyl, cycloalkenyl, aryl and heteroaryl groups are optionally substituted with one to three substituents independently selected from the group consisting of:
a) halo,
b) cyano,
c) hydroxyl,
d) oxo,
e) C$_{1-3}$ alkyl, which is optionally substituted with one to four substituents independently selected from the group consisting of hydroxyl, halo, cyano, heterocyclyl, OC$_{1-3}$ alkyl and NR$^c$R$^d$,
f) OC$_{1-3}$ alkyl, which is optionally substituted with one to four substituents independently selected from the group consisting of hydroxyl, halo, cyano, heterocyclyl, OC$_{1-3}$ alkyl and NR$^c$R$^d$, aryl and heteroaryl,
g) C$_{3-8}$ cycloalkyl, which is optionally substituted with one to four substituents independently selected from the group consisting of hydroxyl, halo, cyano, heterocyclyl, OC$_{1-3}$ alkyl and NR$^c$R$^d$,
h) aryl, which is optionally substituted with one to four substituents independently selected from the group consisting of hydroxyl, halo, cyano, heterocyclyl, OC$_{1-3}$ alkyl, S(O)$_m$NR$^c$R$^d$, C(O)NR$^c$R$^d$ and NR$^c$R$^d$,
i) heteroaryl, which is optionally substituted with one to four substituents independently selected from the group consisting of hydroxyl, halo, cyano, heterocyclyl, OC$_{1-3}$ alkyl, S(O)$_m$NR$^c$R$^d$, C(O)NR$^c$R$^d$ and NR$^c$R$^d$,
j) heterocyclyl, which is optionally substituted with one to four substituents independently selected from the group consisting of hydroxyl, halo, cyano, OC$_{1-3}$ alkyl and NR$^c$R$^d$, k) $C_{4-8}$ cycloalkenyl, which is optionally substituted with one to four substituents independently selected from the group consisting of hydroxyl, halo, cyano, heterocyclyl, $OC_{1-3}$ alkyl and $NR^cR^d$;

$R^8$ is hydrogen or $C_{1-6}$ alkyl, which is optionally substituted with one to three substituents independently selected from the group consisting of:
  a) halo,
  b) cyano,
  c) hydroxyl,
  d) $OC_{1-3}$ alkyl, which is optionally substituted with one to four substituents independently selected from the group consisting of hydroxyl, halo and $NR^cR^d$, and
  e) $C_{3-8}$ cycloalkyl;

$R^c$ is selected from the group consisting of:
  a) hydrogen,
  b) $C_{1-3}$ alkyl, which is optionally substituted with one to three substituents independently selected from the group consisting of halo, hydroxyl, cyano, heteroaryl, aryl, $NH(C_{1-3}$ alkyl), $N(C_{1-3}$ alkyl$)_2$, $OC_{1-6}$ alkyl, and $C_{3-8}$ cycloalkyl;

$R^d$ is selected from the group consisting of:
  a) hydrogen,
  b) $C_{3-8}$ cycloalkyl,
  c) $C_{3-6}$ heterocyclyl,
  d) $C_{1-3}$ alkyl,
  e) (C=O)$C_{1-3}$ alkyl,
  f) aryl, and
  g) heteroaryl;

wherein said cycloalkyl, heterocyclyl, alkyl, aryl and heteroaryl groups are each optionally substituted with one to three substituents independently selected from the group consisting of halo, hydroxyl, cyano, $R^8$, $SO_2R^8$, $OC_{1-6}$ alkyl and $C_{3-8}$ cycloalkyl;

or $R^c$ and $R^d$ can be taken together with the atoms to which they are attached to form a 3 to 8 membered heterocyclic ring, wherein said ring may contain from one to three heteroatoms selected from N, O and S, wherein the sulfur is optionally oxidized to the sulfone or sulfoxide, and which ring is optionally substituted with one to four substituents each independently selected from the group consisting of halo, cyano, hydroxyl, $C_{1-3}$ alkyl and $OC_{1-3}$ alkyl; m is an integer from zero to two.

In a class of the invention, $R^1$ is selected from the group consisting of: $R^5$, $OR^5$ and $R^7$. In a subclass of the invention, $R^1$ is selected from the group consisting of: $OR^5$ and $R^7$. In another subclass of the invention, $R^1$ is $R^5$. In another subclass of the invention, $R^1$ is $OR^5$. In another subclass of the invention, $R^1$ is and $R^7$. In another subclass of the invention, $R^1$ is selected from the group consisting of: $OC_{1-3}$ alkyl, aryl and heteroaryl, wherein said aryl and heteroaryl groups are optionally substituted with one to three substituents independently selected from the group consisting of halo, hydroxyl, $C_{1-3}$ alkyl and $OC_{1-3}$ alkyl.

In a class of the invention, $R^2$ and $R^3$ can be taken together with the atoms to which they are attached to form a 3 to 8 membered heterocyclic ring, wherein said ring may contain from one to three heteroatoms selected from N, O and S, wherein the sulfur is optionally oxidized to the sulfone or sulfoxide, and which ring is optionally substituted with one to four substituents each independently selected from the group consisting of:
  a) halo,
  b) oxo,
  c) cyano,
  d) $OR^5$,
  e) $NR^cR^d$,
  f) $SO_3H$,
  g) $S(O)_mR^5$,
  h) $S(O)_mR^7$,
  i) $R^5$,
  j) $R^6$,
  k) $R^7$,
  l) (C=O)$R^5$,
  m) (C=O)$OR^5$,
  n) (C=O)$R^7$, and
  o) (C=O)$NR^cR^d$.

In a subclass of the invention, $R^2$ and $R^3$ can be taken together with the atoms to which they are attached to form a 6 membered heterocyclic ring, wherein said ring may contain from one to three heteroatoms selected from N, O and S, wherein the sulfur is optionally oxidized to the sulfone or sulfoxide, and which ring is optionally substituted with one to four substituents each independently selected from the group consisting of:
  a) halo,
  b) oxo,
  c) $OR^5$,
  d) $NR^cR^d$,
  e) $S(O)_mR^5$,
  f) $S(O)_mR^7$,
  g) $R^5$,
  h) $R^6$,
  i) $R^7$,
  j) (C=O)$R^5$,
  k) (C=O)$OR^5$, and
  l) (C=O)$R^7$.

In a class of the invention, $R^4$ is selected from the group consisting of: hydrogen and halo. In a subclass of the invention, $R^4$ is hydrogen. In a subclass of the invention, $R^4$ is halo.

In a class of the invention, $R^5$ is selected from the group consisting of hydrogen or $C_{1-6}$ alkyl. In a subclass of the invention, $R^5$ is hydrogen. In another subclass of the invention, $R^5$ is $C_{1-6}$ alkyl.

In a class of the invention, $R^6$ is $C_{1-6}$ alkyl.

In a class of the invention, $R^8$ is selected from the group consisting of hydrogen or $C_{1-6}$ alkyl. In a subclass of the invention, $R^8$ is hydrogen. In another subclass of the invention, $R^8$ is $C_{1-6}$ alkyl.

In a class of the invention, $R^c$ is selected from the group consisting of hydrogen or $C_{1-3}$ alkyl. In a subclass of the invention, $R^c$ is hydrogen. In another subclass of the invention, $R^c$ is $C_{1-3}$ alkyl.

In a class of the invention, $R^d$ is hydrogen.

Reference to the preferred classes and subclasses set forth above is meant to include all combinations of particular and preferred groups unless stated otherwise.

Specific embodiments of the present invention include, but are not limited to the compounds identified herein as Examples A1-A15, D1-D72, E1-E13, F1-F13, G1-G13, H1-H17, I1-I2, J1-J26, K1-K21, L1-L26, M1-M29, N1-N25, O1-O23m P1-P18, Q1-Q20, S1-S6, T1-T2, U1-U29, and V, or pharmaceutically acceptable salts thereof.

The invention also encompasses a pharmaceutical composition which comprises an inert carrier and the compound of Formula I, or a pharmaceutically acceptable salt thereof.

The invention may also encompass a method of treating Parkinson's Disease in a mammalian patient in need of such treatment, which comprises administering to the patient a therapeutically effective amount of the compound of Formula I, or a pharmaceutically acceptable salt thereof.

The invention may also encompass the use of a compound of Formula I, or a pharmaceutically acceptable salt thereof, and a pharmaceutically acceptable carrier, for the manufacture of a medicament for the treatment of Parkinson's Disease.

The invention is also directed to medicaments or pharmaceutical compositions which may be useful for treating diseases or disorders in which LRRK2 is involved, such as Parkinson's Disease, which comprise a compound of Formula I, or a pharmaceutically acceptable salt thereof, and a pharmaceutically acceptable carrier.

The invention is also directed to the use of a compound of Formula I which may be useful for treating diseases or disorders in which LRRK2 is involved, such as Parkinson's Disease.

The invention is further directed to a method for the manufacture of a medicament or a composition which may be useful for treating diseases or disorders in which LRRK2 is involved, such as Parkinson's Disease, comprising combining a compound of Formula I with one or more pharmaceutically acceptable carriers.

The compounds of the present invention may contain one or more asymmetric centers and can thus occur as racemates and racemic mixtures, single enantiomers, diastereomeric mixtures and individual diastereomers. Additional asymmetric centers may be present depending upon the nature of the various substituents on the molecule. Each such asymmetric center will independently produce two optical isomers and it is intended that all of the possible optical isomers and diastereomers in mixtures and as pure or partially purified compounds are included within the ambit of this invention. Unless a specific stereochemistry is indicated, the present invention is meant to comprehend all such isomeric forms of these compounds.

The independent syntheses of these diastereomers or their chromatographic separations may be achieved as known in the art by appropriate modification of the methodology disclosed herein. Their absolute stereochemistry may be determined by the x-ray crystallography of crystalline products or crystalline intermediates which are derivatized, if necessary, with a reagent containing an asymmetric center of known absolute configuration.

If desired, racemic mixtures of the compounds may be separated so that the individual enantiomers are isolated. The separation can be carried out by methods well known in the art, such as the coupling of a racemic mixture of compounds to an enantiomerically pure compound to form a diastereomeric mixture, followed by separation of the individual diastereomers by standard methods, such as fractional crystallization or chromatography. The coupling reaction is often the formation of salts using an enantiomerically pure acid or base. The diasteromeric derivatives may then be converted to the pure enantiomers by cleavage of the added chiral residue. The racemic mixture of the compounds can also be separated directly by chromatographic methods utilizing chiral stationary phases, which methods are well known in the art.

Alternatively, any enantiomer of a compound may be obtained by stereoselective synthesis using optically pure starting materials or reagents of known configuration by methods well known in the art.

In the compounds of Formula I, the atoms may exhibit their natural isotopic abundances, or one or more of the atoms may be artificially enriched in a particular isotope having the same atomic number, but an atomic mass or mass number different from the atomic mass or mass number predominantly found in nature. The present invention is meant to include all suitable isotopic variations of the compounds of generic Formula I. For example, different isotopic forms of hydrogen (H) include protium (1H) and deuterium (2H). Protium is the predominant hydrogen isotope found in nature. Enriching for deuterium may afford certain therapeutic advantages, such as increasing in vivo half-life or reducing dosage requirements, or may provide a compound useful as a standard for characterization of biological samples. Isotopically-enriched compounds within generic Formula I can be prepared without undue experimentation by conventional techniques well known to those skilled in the art or by processes analogous to those described in the Schemes and Examples herein using appropriate isotopically-enriched reagents and/or intermediates.

Tautomers of compounds defined in Formula I are also included within the scope of the present invention. For example, compounds including carbonyl —CH2C(O)— groups (keto forms) may undergo tautomerism to form hydroxyl —CH=C(OH)— groups (enol forms). Both keto and enol forms are included within the scope of the present invention.

When any variable (e.g. $R^5$, etc.) occurs more than one time in any constituent, its definition on each occurrence is independent at every other occurrence. Also, combinations of substituents and variables are permissible only if such combinations result in stable compounds. Lines drawn into the ring systems from substituents represent that the indicated bond may be attached to any of the substitutable ring atoms. If the ring system is bicyclic, it is intended that the bond be attached to any of the suitable atoms on either ring of the bicyclic moiety.

It is understood that one or more silicon (Si) atoms can be incorporated into the compounds of the instant invention in place of one or more carbon atoms by one of ordinary skill in the art to provide compounds that are chemically stable and that can be readily synthesized by techniques known in the art from readily available starting materials. Carbon and silicon differ in their covalent radius leading to differences in bond distance and the steric arrangement when comparing analogous C-element and Si-element bonds. These differences lead to subtle changes in the size and shape of silicon-containing compounds when compared to carbon. One of ordinary skill in the art would understand that size and shape differences can lead to subtle or dramatic changes in potency, solubility, lack of off-target activity, packaging properties, and so on. (Diass, J. O. et al. Organometallics (2006) 5:1188-1198; Showell, G. A. et al. Bioorganic & Medicinal Chemistry Letters (2006) 16:2555-2558).

It is understood that substituents and substitution patterns on the compounds of the instant invention can be selected by one of ordinary skill in the art to provide compounds that are chemically stable and that can be readily synthesized by techniques known in the art, as well as those methods set forth below, from readily available starting materials. If a substituent is itself substituted with more than one group, it is understood that these multiple groups may be on the same carbon or on different carbons, so long as a stable structure results. The phrase "optionally substituted with one or more substituents" should be understood as meaning that the group in question is either unsubstituted or may be substituted with one or more substituents.

As used herein, "alkyl" is intended to mean linear or branched structures having no carbon-to-carbon double or triple bonds. Thus, $C_{1-4}$ alkyl is defined to identify the group as having 1, 2, 3 or 4 carbons in a linear or branched arrangement, such that $C_{1-4}$ alkyl specifically includes, but is not limited to, methyl, ethyl, n-propyl, iso-propyl, n-butyl, iso-butyl and tert-butyl.

As appreciated by those of skill in the art, "halo" or "halogen" as used herein is intended to include chloro (Cl), fluoro (F), bromo (Br) and iodo (I).

The term "cycloalkyl" or shall mean cyclic rings of alkanes of three to eight total carbon atoms, unless otherwise indicated, or any number within this range (i.e., cyclopropyl, cyclobutyl, cyclopentyl, cyclohexyl, cycloheptyl, methyl-cyclopropyl, 2,2-dimethyl-cyclobutyl, 2-ethyl-cyclopentyl or cyclooctyl) and also includes bicyclic or fused spirocyclic compounds.

The term "cycloalkenyl" shall mean cyclic rings of four to eight total carbon atoms, unless otherwise indicated, or any number within this range where one or two degrees of unsaturation are present. Non-limiting examples of said cycloalkenyl groups are: cyclohexenyl, cyclopentenyl, cyclooctadienyl.

The term "carbocycle" shall mean cyclic rings of three to eight total carbon atoms, unless otherwise indicated, or any number within this range, where zero, one or two degrees of unsaturation are present and where said "carbocycle" can be bicyclic or fused spirocyclic in nature. Non-limiting examples of said carbocyclyl groups are: cyclohexenyl, cyclopentenyl, cyclooctadienyl, cyclohexyl or cyclopropyl.

If no number of carbon atoms is specified, the term "alkenyl" refers to a non-aromatic hydrocarbon radical, straight or branched, containing from 2 to 10 carbon atoms and at least 1 carbon to carbon double bond. Preferably 1 carbon to carbon double bond is present, and up to 4 non-aromatic carbon-carbon double bonds may be present. Thus, "C2-C6 alkenyl" means an alkenyl radical having from 2 to 6 carbon atoms. Alkenyl groups include ethenyl, propenyl, butenyl and cyclohexenyl. As described above with respect to alkyl, the straight, branched or cyclic portion of the alkenyl group may contain double bonds and may be substituted if a substituted alkenyl group is indicated.

"Aryl" means an aromatic monocyclic or multicyclic ring system comprising about 6 to about 14 carbon atoms, preferably about 6 to about 10 carbon atoms. The aryl group can be optionally substituted with one or more "ring system substituents" which may be the same or different, and are as defined herein. Non-limiting examples of suitable aryl groups include phenyl and naphthyl.

The term "heteroaryl", as used herein, represents a stable monocyclic, bicyclic or tricyclic ring of up to 10 atoms in each ring, wherein at least one ring is aromatic and contains from 1 to 4 heteroatoms selected from the group consisting of O, N and S. Heteroaryl groups within the scope of this definition include but are not limited to: benzoimidazolyl, benzofuranyl, benzofurazanyl, benzopyrazolyl, benzotriazolyl, benzothiophenyl, benzoxazolyl, carbazolyl, carbolinyl, cinnolinyl, furanyl, indolinyl, indolyl, indolazinyl, indazolyl, isobenzofuranyl, isoindolyl, isoquinolyl, isothiazolyl, isoxazolyl, naphthpyridinyl, oxadiazolyl, oxazolyl, oxazoline, isoxazoline, pyranyl, pyrazinyl, pyrazolyl, pyridazinyl, pyridopyridinyl, pyridyl, pyrimidinyl, pyrrolyl, quinazolinyl, quinolyl, quinoxalinyl, tetrazolyl, tetrazolopyridyl, thiadiazolyl, thiazolyl, thienyl, triazolyl, dihydrobenzoimidazolyl, dihydrobenzofuranyl, dihydrobenzothiophenyl, dihydrobenzoxazolyl, dihydroindolyl, dihydroquinolinyl, methylenedioxybenzene, benzothiazolyl, benzothienyl, quinolinyl, isoquinolinyl, oxazolyl, and tetra-hydroquinoline. In cases where the heteroaryl substituent is bicyclic and one ring is non-aromatic or contains no heteroatoms, it is understood that attachment is via the aromatic ring or via the heteroatom containing ring, respectively. If the heteroaryl contains nitrogen atoms, it is understood that the corresponding N-oxides thereof are also encompassed by this definition.

The term "heterocycle" or "heterocyclyl" as used herein is intended to mean a 5- to 10-membered nonaromatic ring, unless otherwise specified, containing from 1 to 4 heteroatoms selected from the group consisting of O, N, S, SO, or $SO_2$ and includes bicyclic groups. The heterocyclyl group also includes rings that possess one or two degrees of unsaturation. "Heterocyclyl" therefore includes, but is not limited to the following: piperazinyl, piperidinyl, pyrrolidinyl, morpholinyl, thiomorpholinyl, tetrahydropyranyl, dihydropiperidinyl, tetrahydrothiophenyl and the like. If the heterocycle contains a nitrogen, it is understood that the corresponding N-oxides thereof are also emcompassed by this definition.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, "pharmaceutically acceptable salts" refer to derivatives wherein the parent compound is modified by making acid or base salts thereof. Salts in the solid form may exist in more than one crystal structure, and may also be in the form of hydrates. Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and the like. Salts derived from inorganic bases include aluminum, ammonium, calcium, copper, ferric, ferrous, lithium, magnesium, manganic salts, manganous, potassium, sodium, zinc, and the like.

When the compound of the present invention is basic, salts may be prepared from pharmaceutically acceptable non-toxic acids, including inorganic and organic acids. Such acids include acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid, and the like. In one aspect of the invention the salts are citric, hydrobromic, hydrochloric, maleic, phosphoric, sulfuric, fumaric, and tartaric acids. It will be understood that, as used herein, references to the compounds of Formula I are meant to also include the pharmaceutically acceptable salts.

Exemplifying the invention is the use of the compounds disclosed in the Examples and herein. Specific compounds within the present invention include a compound which may be selected from the group consisting of the compounds disclosed in the following Examples and pharmaceutically acceptable salts thereof and individual diastereomers thereof.

The subject compounds are useful in a method of inhibition of LRRK2 receptors in a patient such as a mammal in need of such antagonism comprising the administration of an effective amount of the compound. The present invention is directed to the use of the compounds disclosed herein as inhibitors of LRRK2 receptors. In addition to primates, especially humans, a variety of other mammals can be treated according to the method of the present invention.

Another embodiment of the present invention is directed to a method for the treatment, control, amelioration, or reduction of risk of a disease or disorder in which the LRRK2 kinase is involved in a patient that comprises administering to the patient a therapeutically effective amount of a compound that is an inhibitor of LRRK2 kinase.

The present invention is further directed to a method for the manufacture of a medicament for inhibition of LRRK2 receptors activity in humans and animals comprising combining a compound of the present invention with a pharmaceutical carrier or diluent.

The subject treated in the present methods is generally a mammal, for example a human being, male or female, in whom inhibition of LRRK2 kinase activity is desired. The term "therapeutically effective amount" means the amount of the subject compound that will elicit the biological or medical response of a tissue, system, animal or human that is being sought by the researcher, veterinarian, medical doctor or other clinician.

The terms "treating" or "treatment" of a disease as used herein includes: inhibiting the disease, i.e., arresting or reducing the development of the disease or its clinical symptoms; or relieving the disease, i.e., causing regression of the disease or its clinical symptoms. The term "preventing" or "prevention" of a disease as used herein includes: causing the clinical symptoms of the disease not to develop in a mammal that may be exposed to or predisposed to the disease but does not yet experience or display symptoms of the disease, and the like.

The term "composition" as used herein is intended to encompass a product comprising the specified ingredients in the specified amounts, as well as any product which results, directly or indirectly, from combination of the specified ingredients in the specified amounts. Such term in relation to pharmaceutical composition, is intended to encompass a product comprising the active ingredient(s), and the inert ingredient(s) that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the present invention encompass any composition made by admixing a compound of the present invention and a pharmaceutically acceptable carrier, By "pharmaceutically acceptable" it is meant the carrier, diluent or excipient must be compatible with the other ingredients of the formulation and not deleterious to the recipient thereof.

The present invention includes within its scope prodrugs of the compounds of this invention. In general, such prodrugs will be functional derivatives of the compounds of this invention which are readily convertible in vivo into the required compound. Thus, in the methods of treatment of the present invention, the terms "administration of" or "administering a" compound shall encompass the treatment of the various conditions described with the compound specifically disclosed or with a compound which may not be specifically disclosed, but which converts to the specified compound in vivo after administration to the patient. Conventional procedures for the selection and preparation of suitable prodrug derivatives are described, for example, in "Design of Prodrugs," ed. H. Bundgaard, Elsevier, 1985. Metabolites of these compounds include active species produced upon introduction of compounds of this invention into the biological milieu.

The ability of the compounds of the present invention to act as LRRK2 kinase inhibitors may make them useful pharmacological agents for disorders that involve LRRK2 kinase in humans and animals, but particularly in humans.

In another embodiment the invention provides a method of inhibiting LRRK2 Kinase activity (this is to say, inhibiting the kinase activity associated with Leucine-Rich Repeat Kinase 2 [LRRK2], a multidomain protein containing kinase and GTPase enzymatic activities) in a patient in need of therapy for a condition amenable to treatment by such kinase activity inhibition, for example, treatment or prevention of neurologic damage associated with Parkinson's disease, for example, improvement in dopaminergic tone and in providing symptomatic benefit, for example, in treating, alleviating, ameliorating, or managing motor and non-motor symptoms of Parkinson's disease, and other conditions that may be treated or prevented by inhibition of LRRK2 kinase. Of particular importance is the acute or prophylactic treatment of Parkinson's Disease.

The subject compounds may be further useful in a method for the prevention, treatment, control, amelioration, or reduction of risk of the diseases, disorders and conditions noted herein.

The subject compounds may be further useful in a method for the prevention, treatment, control, amelioration, or reduction of risk of the aforementioned diseases, disorders and conditions in combination with other agents, The compounds of the present invention may be used in combination with one or more other drugs in the treatment, prevention, control, amelioration, or reduction of risk of diseases or conditions for which compounds of Formula I or the other drugs may have utility, where the combination of the drugs together are safer or more effective than either drug alone. Such other drug(s) may be administered, by a route and in an amount commonly used therefore, contemporaneously or sequentially with a compound of Formula I. When a compound of Formula I is used contemporaneously with one or more other drugs, a pharmaceutical composition in unit dosage form containing such other drugs and the compound of Formula I is preferred. However, the combination therapy may also include therapies in which the compound of Formula I and one or more other drugs are administered on different overlapping schedules. It is also contemplated that when used in combination with one or more other active ingredients, the compounds of the present invention and the other active ingredients may be used in lower doses than when each is used singly. Accordingly, the pharmaceutical compositions of the present invention include those that contain one or more other active ingredients, in addition to a compound of Formula I.

For example, the present compounds may be used in conjunction with one or more additional therapeutic agents, for example: L-DOPA; dopaminergic agonists such as quinpirole, ropinirole, pramipexole, pergolide and bromocriptine; MAO-B inhibitors such as rasagiline, deprenyl and selegiline; DOPA decarboxylase inhibitors such as carbidopa and benserazide; and COMT inhibitors such as tolcapone and entacapone; or potential therapies such as an adenosine A2a antagonists, metabotropic glutamate receptor 4 modulators, or growth factors such as brain derived neurotrophic factor (BDNF), and a pharmaceutically acceptable carrier.

The above combinations include combinations of a compound of the present invention not only with one other active compound, but also with two or more other active compounds. Likewise, compounds of the present invention may be used in combination with other drugs that are used in the prevention, treatment, control, amelioration, or reduction of risk of the diseases or conditions for which compounds of the present invention are useful. Such other drugs may be administered, by a route and in an amount commonly used therefore, contemporaneously or sequentially with a compound of the present invention. When a compound of the present invention is used contemporaneously with one or more other drugs, a pharmaceutical composition containing such other drugs in addition to the compound of the present invention is preferred. Accordingly, the pharmaceutical compositions of the present invention include those that also contain one or more other active ingredients, in addition to a compound of the present invention.

The weight ratio of the compound of the present invention to the other active ingredient(s) may be varied and will depend upon the effective dose of each ingredient. Generally, an effective dose of each will be used. Thus, for example, when a compound of the present invention is combined with another agent, the weight ratio of the compound of the present invention to the other agent will generally range from about 1000:1 to about 1:1000, or from about 200:1 to about 1:200. Combinations of a compound of the present invention and other active ingredients will generally also be within the aforementioned range, but in each case, an effective dose of each active ingredient should be used.

In such combinations the compound of the present invention and other active agents may be administered separately or in conjunction. In addition, the administration of one element may be prior to, concurrent to, or subsequent to the administration of other agent(s), and via the same or different routes of administration.

The compounds of the present invention may be administered by oral, parenteral (e.g., intramuscular, intraperitoneal, intravenous, ICV, intracisternal injection or infusion, subcutaneous injection, or implant), by inhalation spray, nasal, vaginal, rectal, sublingual, buccal or topical routes of administration and may be formulated, alone or together, in suitable dosage unit formulations containing conventional non-toxic pharmaceutically acceptable carriers, adjuvants and vehicles appropriate for each route of administration. In addition to the treatment of warm-blooded animals the compounds of the invention are effective for use in humans.

The pharmaceutical compositions for the administration of the compounds of this invention may conveniently be presented in dosage unit form and may be prepared by any of the methods well known in the art of pharmacy. All methods include the step of bringing the active ingredient into association with the carrier which constitutes one or more accessory ingredients. In general, the pharmaceutical compositions are prepared by uniformly and intimately bringing the active ingredient into association with a liquid carrier or a finely divided solid carrier or both, and then, if necessary, shaping the product into the desired formulation. In the pharmaceutical composition the active compound is included in an amount sufficient to produce the desired effect upon the process or condition of diseases. As used herein, the term "composition" is intended to encompass a product comprising the specified ingredients in the specified amounts, as well as any product which results, directly or indirectly, from combination of the specified ingredients in the specified amounts.

The pharmaceutical compositions containing the active ingredient may be in a form suitable for oral use, for example, as tablets, troches, lozenges, aqueous or oily suspensions, dispersible powders or granules, emulsions, solutions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia; and lubricating agents, for example magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated by the techniques described in the U.S. Pat. Nos. 4,256,108; 4,166,452; and 4,265,874 to form osmotic therapeutic tablets for control release. Oral tablets may also be formulated for immediate release, such as fast melt tablets or wafers, rapid dissolve tablets or fast dissolve films.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin, or olive oil.

Aqueous suspensions contain the active materials in admixture with excipients suitable for the manufacture of aqueous suspensions. Such excipients are suspending agents, for example sodium carboxymethylcellulose, methylcellulose, hydroxy-propylmethylcellulose, sodium alginate, polyvinyl-pyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl, p-hydroxybenzoate, one or more coloring agents, one or more flavoring agents, and one or more sweetening agents, such as sucrose or saccharin.

Oily suspensions may be formulated by suspending the active ingredient in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

The pharmaceutical compositions of the invention may also be in the form of oil-in-water emulsions. The oily phase may be a vegetable oil, for example olive oil or arachis oil, or a mineral oil, for example liquid paraffin or mixtures of these. Suitable emulsifying agents may be naturally-occurring gums, for example gum acacia or gum tragacanth, naturally-occurring phosphatides, for example soy bean, lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening and flavoring agents.

Syrups and elixirs may be formulated with sweetening agents, for example glycerol, propylene glycol, sorbitol or sucrose. Such formulations may also contain a demulcent, a preservative and flavoring and coloring agents.

The pharmaceutical compositions may be in the form of a sterile injectable aqueous or oleagenous suspension. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butane diol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

The compounds of the present invention may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials are cocoa butter and polyethylene glycols.

For topical use, creams, ointments, jellies, solutions or suspensions and the like, containing the compounds of the present invention are employed. Similarly, transdermal patches may also be used for topical administration.

The pharmaceutical composition and method of the present invention may further comprise other therapeutically active compounds as noted herein which are usually applied in the treatment of the above mentioned pathological conditions.

In the treatment, prevention, control, amelioration, or reduction of risk of conditions which require inhibition of LRRK2 kinase activity an appropriate dosage level will generally be about 0.01 to 500 mg per kg patient body weight per day which can be administered in single or multiple doses. A suitable dosage level may be about 0.01 to 250 mg/kg per day, about 0.05 to 100 mg/kg per day, or about 0.1 to 50 mg/kg per day. Within this range the dosage may be 0.05 to 0.5, 0.5 to 5 or 5 to 50 mg/kg per day. For oral administration, the compositions are may be provided in the form of tablets containing 1.0 to 1000 milligrams of the active ingredient, particularly 1.0, 5.0, 10.0, 15.0, 20.0, 25.0, 50.0, 75.0, 100.0, 150.0, 200.0, 250.0, 300.0, 400.0, 500.0, 600.0, 750.0, 800.0, 900.0, and 1000.0 milligrams of the active ingredient for the symptomatic adjustment of the dosage to the patient to be treated. The compounds may be administered on a regimen of 1 to 4 times per day, or may be administered once or twice per day.

When treating, preventing, controlling, ameliorating, or reducing the risk of Parkinson's Disease, or other diseases for which compounds of the present invention are indicated, generally satisfactory results are obtained when the compounds of the present invention are administered at a daily dosage of from about 0.1 milligram to about 100 milligram per kilogram of animal body weight, given as a single daily dose or in divided doses two to six times a day, or in sustained release form. For most large mammals, the total daily dosage is from about 1.0 milligrams to about 1000 milligrams, or from about 1 milligrams to about 50 milligrams. In the case of a 70 kg adult human, the total daily dose will generally be from about 7 milligrams to about 350 milligrams. This dosage regimen may be adjusted to provide the optimal therapeutic response.

It will be understood, however, that the specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

Methods for preparing the compounds of this invention are illustrated in the following Schemes and Examples. Starting materials are made according to procedures known in the art or as illustrated herein.

The compounds of the present invention can be prepared readily according to the following Schemes and specific examples, or modifications thereof, using readily available starting materials, reagents and conventional synthesis procedures. In these reactions, it is also possible to make use of variants which are themselves known to those of ordinary skill in this art but are not mentioned in greater detail. The general procedures for making the compounds claimed in this invention can be readily understood and appreciated by one skilled in the art from viewing the following Schemes.

While the invention has been described and illustrated with reference to certain particular embodiments thereof, those skilled in the art will appreciate that various adaptations, changes, modifications, substitutions, deletions, or additions of procedures and protocols may be made without departing from the spirit and scope of the invention. For example, effective dosages other than the particular dosages as set forth herein above may be applicable as a consequence of variations in the responsiveness of the mammal being treated for any of the indications with the compounds of the invention indicated above. Likewise, the specific pharmacological responses observed may vary according to and depending upon the particular active compounds selected or whether there are present pharmaceutical carriers, as well as the type of formulation and mode of administration employed, and such expected variations or differences in the results are contemplated in accordance with the objects and practices of the present invention. It is intended, therefore, that the invention be defined by the scope of the claims which follow and that such claims be interpreted as broadly as is reasonable.

General Schemes:

A general procedure for the preparation of substituted indazoles such as Formula I wherein R' is aryl, heteroaryl, cycloalkyl and heterocyclyl is shown in Scheme 1. Treatment of a suitable bromo-indazole i under palladium catalyzed cross coupling conditions with a boronic acid will afford ii. Treatment with iodine/$K_2CO_3$ and the like in a solvent such as MeCN and the like will provide compound iii. The indazole can be protected with trityl chloride and the like to provide the protected indazole iv. The iodo group in iv can be converted to the pinacol boronic ester upon treatment with pinacol diborane under palladium catalyzed conditions and the like followed by treatment under palladium mediated cross coupling conditions with 4,6-dichloropyrimidine to afford v. Treatment of v with the appropriate amine in a solvent such as DMSO and the like with a base such as triethylamine and the like will provide vi. Cleavage of the trityl group with a mixture of TFA/EtSiH and the like will provide examples such as Formula I. Alternatively, the trityl group can be removed with aqueous HCl and the like in a solvent such as methanol and the like or aqueous TFA and the like with a solvent such as dichloromethane and the like.

Scheme 1

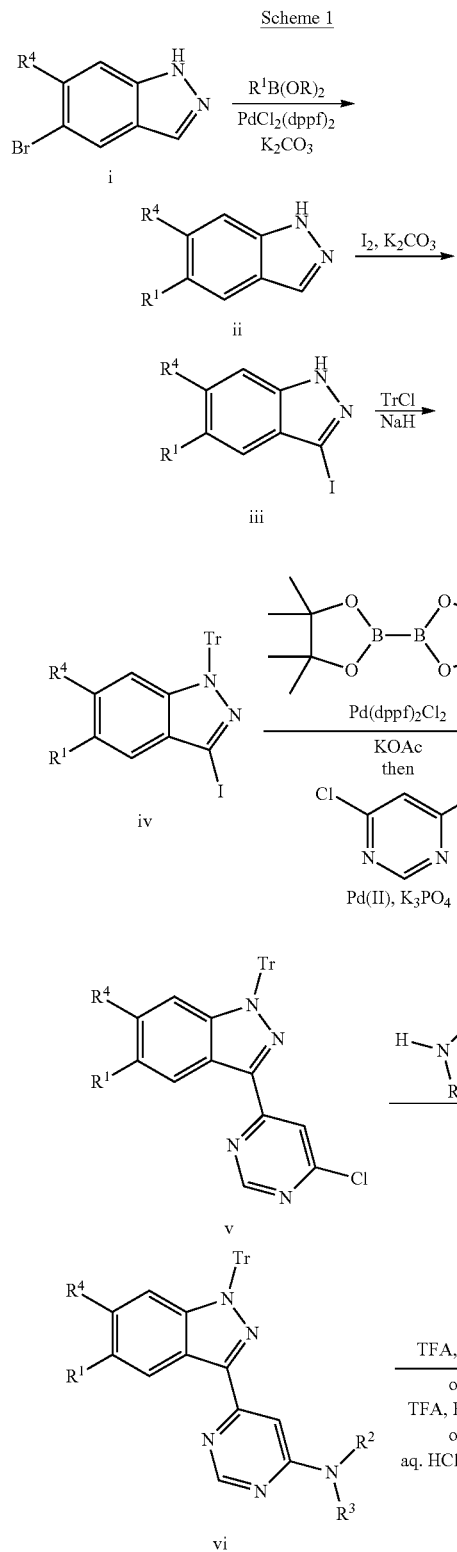

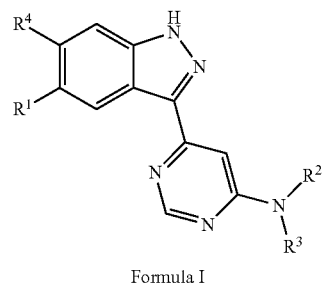

Formula I

An alternate general procedure for the preparation of indazoles such as Formula I is shown in Scheme 2. Treatment of a suitable bromo indazole i with SEMCl and dicyclohexylmethyl amine and the like will provide viii. Treatment with an appropriate boronic acid under palladium catalyzed conditions and the like will provide ix. Deprotonation of the indazole with n-BuLi and transmetallation with ZnCl$_2$ followed by palladium catalyzed cross coupling using 4,6-dichloropyrimidine will afford x. Treatment with the appropriate amines in solvents such as DMSO and the like will provide xi. Cleavage of the SEM group with either HCl in MeOH and 1,4-dioxane and the like or a two-step procedure of aq. TFA and CH$_2$Cl$_2$ and the like followed by aq. NH$_4$OH or TBAF in THF and the like will provide examples such as Formula I.

Scheme 2

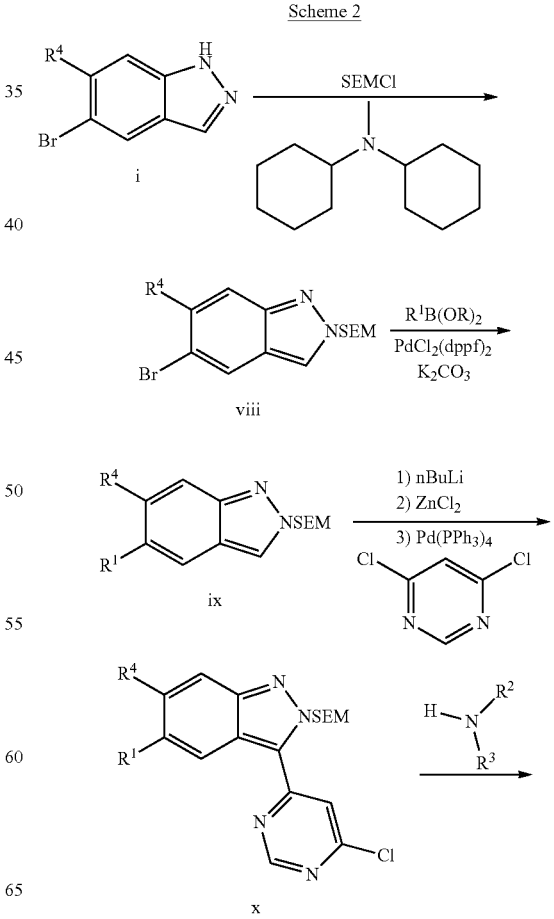

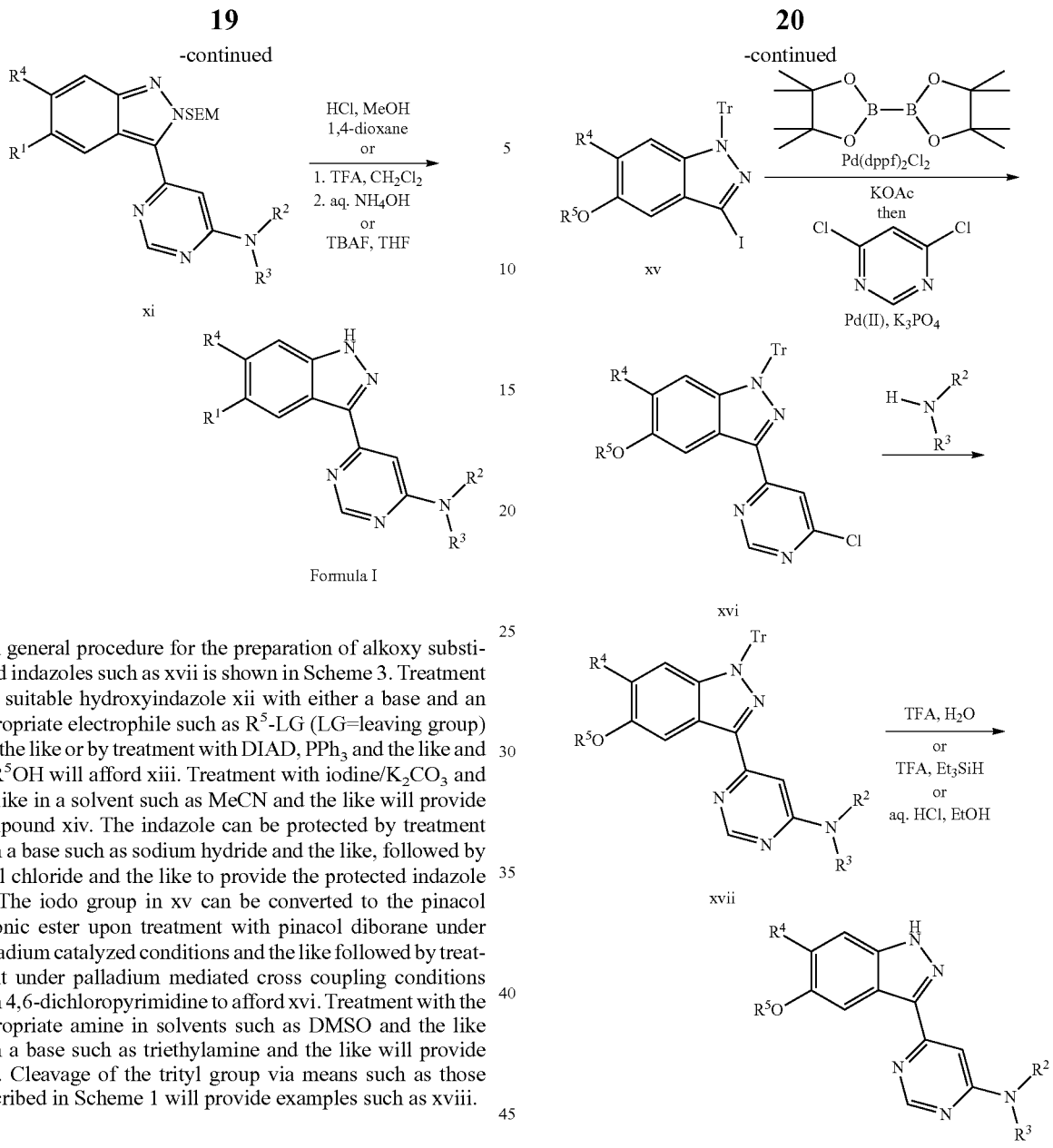

A general procedure for the preparation of alkoxy substituted indazoles such as xvii is shown in Scheme 3. Treatment of a suitable hydroxyindazole xii with either a base and an appropriate electrophile such as $R^5$-LG (LG=leaving group) and the like or by treatment with DIAD, $PPh_3$ and the like and an $R^5OH$ will afford xiii. Treatment with iodine/$K_2CO_3$ and the like in a solvent such as MeCN and the like will provide compound xiv. The indazole can be protected by treatment with a base such as sodium hydride and the like, followed by trityl chloride and the like to provide the protected indazole xv. The iodo group in xv can be converted to the pinacol boronic ester upon treatment with pinacol diborane under palladium catalyzed conditions and the like followed by treatment under palladium mediated cross coupling conditions with 4,6-dichloropyrimidine to afford xvi. Treatment with the appropriate amine in solvents such as DMSO and the like with a base such as triethylamine and the like will provide xvii. Cleavage of the trityl group via means such as those described in Scheme 1 will provide examples such as xviii.

Scheme 3

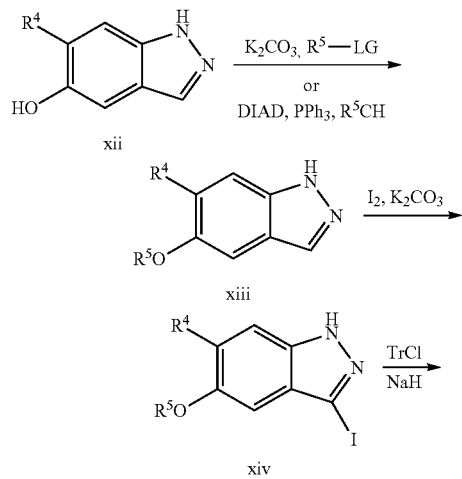

Alternatively, a general procedure for the preparation substituted indazoles such as xviii is shown in Scheme 4. Treatment of a suitable hydroxyindazole xii with TBSCl and the like will provide xix. Treatment with SEMCl and dicyclohexylmethyl amine and the like will provide xx. Deprotonation of the indazole with n-BuLi and transmetallation with $ZnCl_2$ followed by palladium catalyzed cross coupling using 4,6-dichloropyrimidine and the like will afford xxi. Cleavage of the TBS group using TBAF and the like will provide hydroxyindazole xxii. Treatment of xxii with either a base and an appropriate electrophile such as $R^5$-LG (LG=leaving group) and the like or by treatment with DIAD, $PPh_3$ and the like and an $R^5OH$ will afford xxiii. Treatment with the appropriate amine in solvents such as DMSO and the like with a base such as triethylamine and the like will provide xxiv. Cleavage of the SEM group with HCl and the like will provide examples such as xviii.

Scheme 4

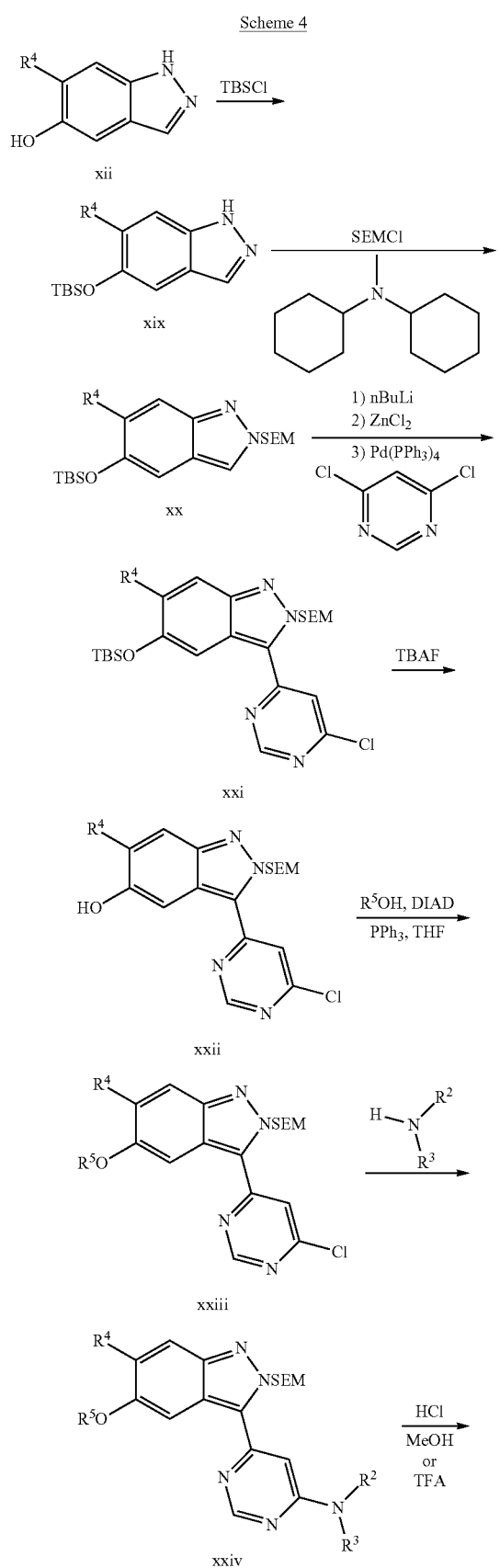

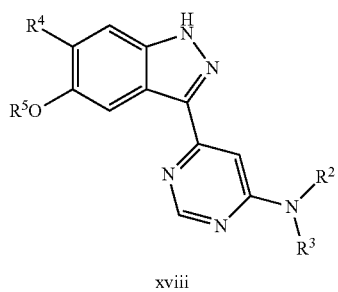

Alternatively, a general procedure for the preparation of substituted indazoles such as Formula I is shown in Scheme 5. Treatment of xxii with the appropriate amine in solvents such as DMSO and the like in the presence of a base such as triethylamine and the like will provide xxv. Conversion of the hydroxyl to the triflate using Tf$_2$O and the like will afford xxvi. Treatment of xxvi with the appropriate boronic acid or ester under palladium catalyzed conditions will afford xi. Cleavage of the SEM group with HCl or TFA and the like will provide examples such as vii.

Scheme 5

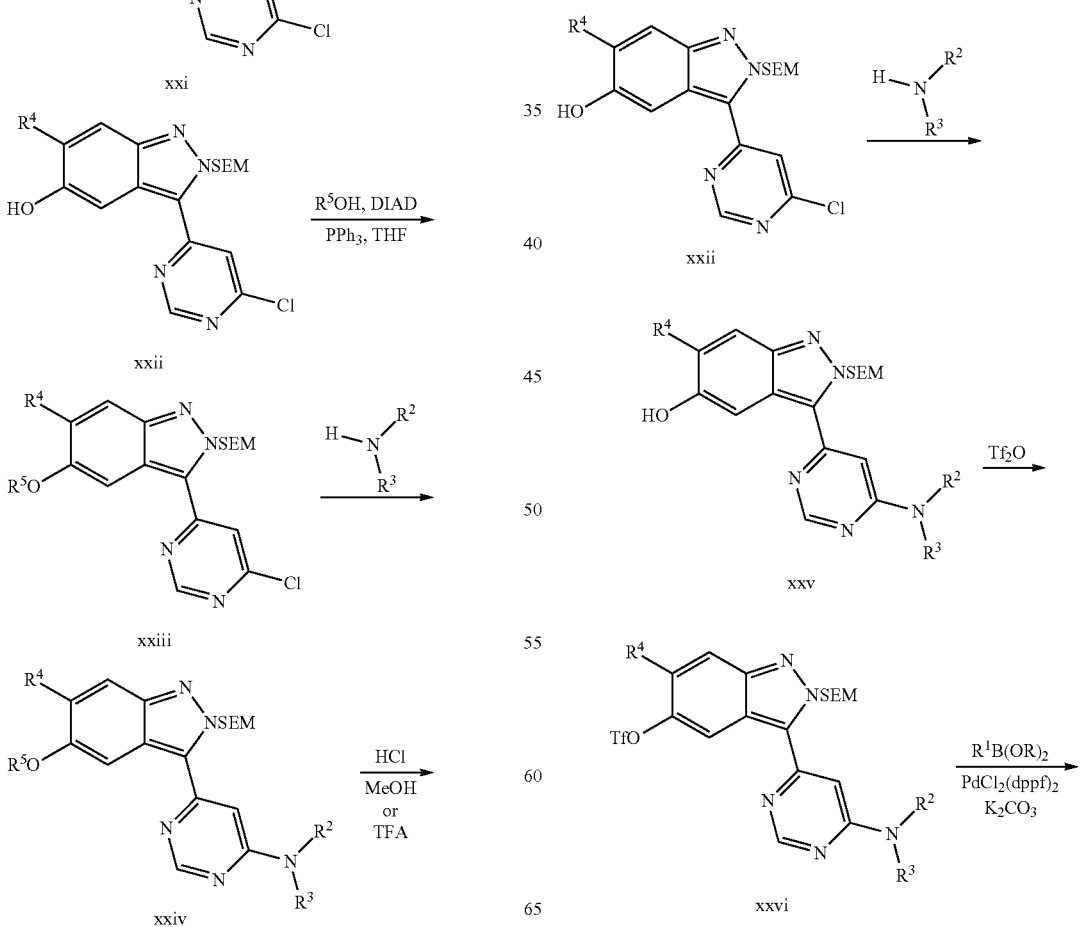

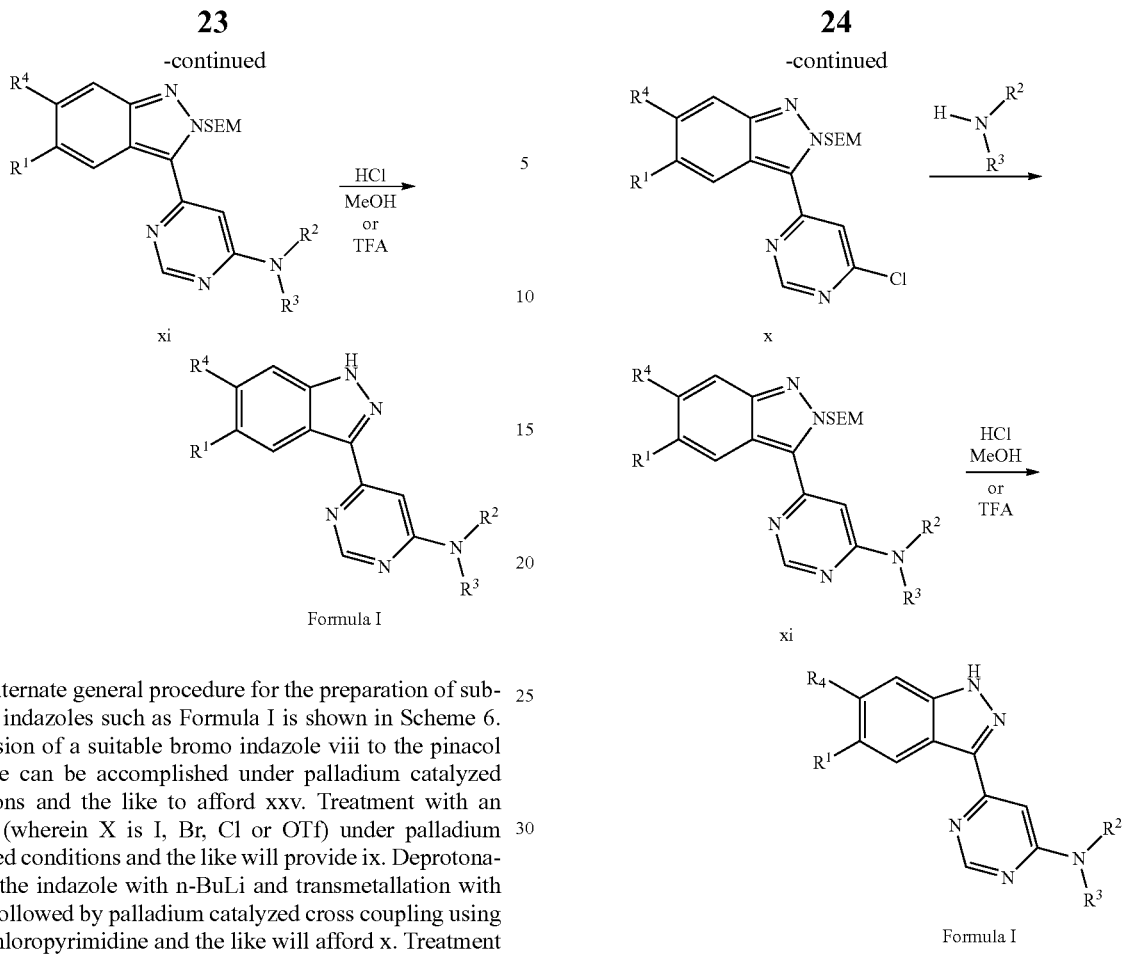

An alternate general procedure for the preparation of substituted indazoles such as Formula I is shown in Scheme 6. Conversion of a suitable bromo indazole viii to the pinacol boronate can be accomplished under palladium catalyzed conditions and the like to afford xxv. Treatment with an $R^1$—X (wherein X is I, Br, Cl or OTf) under palladium catalyzed conditions and the like will provide ix. Deprotonation of the indazole with n-BuLi and transmetallation with $ZnCl_2$ followed by palladium catalyzed cross coupling using 4,6-dichloropyrimidine and the like will afford x. Treatment with the appropriate amine in solvents such as DMSO and the like with a base such as triethylamine and the like will provide xi. Cleavage of the SEM group via a method outlined in Scheme 2 will provide examples such as Formula I.

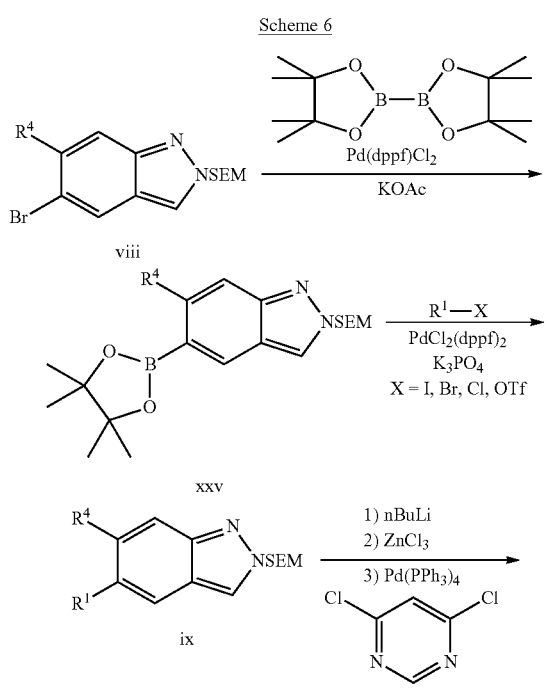

Alternatively, a general procedure for the preparation substituted indazoles such as xviii is shown in Scheme 7. Treatment of a suitable indazole xiii with SEMCl and dicyclohexylmethyl amine and the like will provide xxvi. Deprotonation of the indazole with n-BuLi and transmetallation with $ZnCl_2$ followed by palladium catalyzed cross coupling using 4,6-dichloropyrimidine will afford xxiii. Treatment with the appropriate amine in solvents such as DMSO and the like with a base such as triethylamine and the like will provide xxiv. Cleavage of the SEM group via a method described in Scheme 2 will provide examples such as xviii.

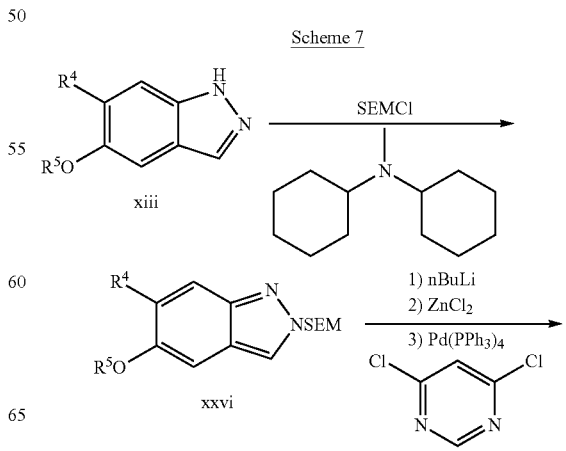

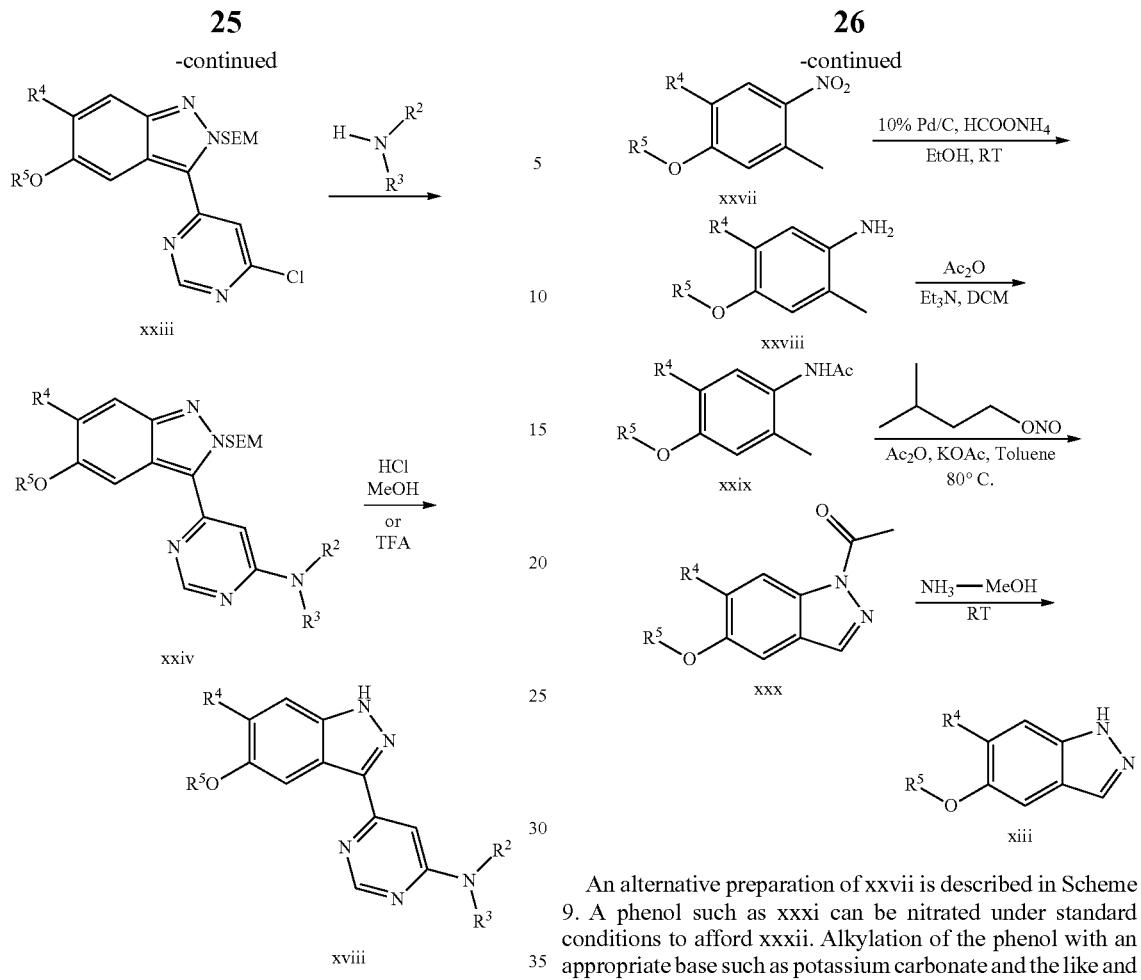

An approach to compounds such as xiii is outlined in Scheme 8. Treatment of an appropriate alcohol R⁵—OH and a base such as NaH and the like, followed by addition of xxv will provide the ether xxvi. The bromide xxvi can be converted into the methylated intermediate xxvii via palladium-mediated cross coupling with Me₃B₃O₃ and the like. The nitro derivative xxvii can be treated with Pd/C in the presence of HCOONH₄ to produce the amine xxviii. The amine xxviii can be acylated to provide xxix. The acylated amine xxix can be treated with iso-amyl nitrate in the presence of Ac₂O/KOAc and the like to provide the N-acyl indazole xxx. Compounds such as xxx can be treated with ammonia and the like to produce indazoles xiii.

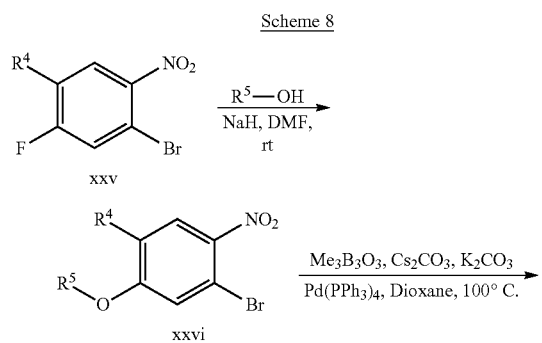

An alternative preparation of xxvii is described in Scheme 9. A phenol such as xxxi can be nitrated under standard conditions to afford xxxii. Alkylation of the phenol with an appropriate base such as potassium carbonate and the like and an R⁵—X (wherein X=I, Br, OTs, OMs) will afford the desired xxvii.

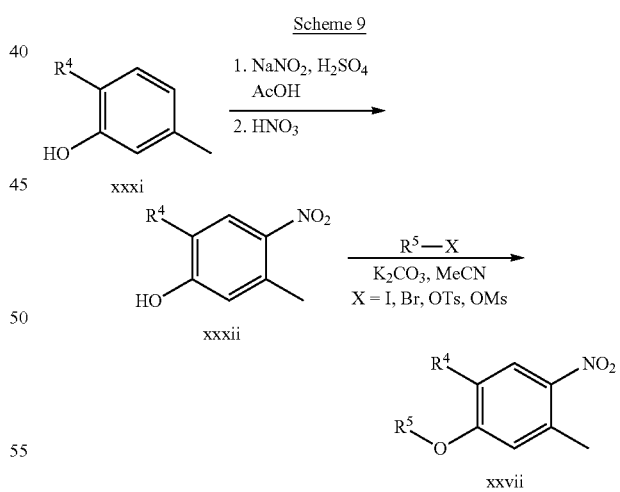

An alternate general procedure for the preparation of substituted indazoles such as Formula I is shown in Scheme 10. Bromoindazole of type xxxiii can be protected with SEM in presence of a base such as NaH and the like and SEMCl in a solvent such as DMF and the like. Palladium-mediated boronate ester formation followed by Pd-mediated coupling with substituted chloropyrimidines of type xxxvi will provide compound xxxvii. Removal of the SEM group in xxxvii with HCl in MeOH and the like will provide examples such as Formula I.

Scheme 10

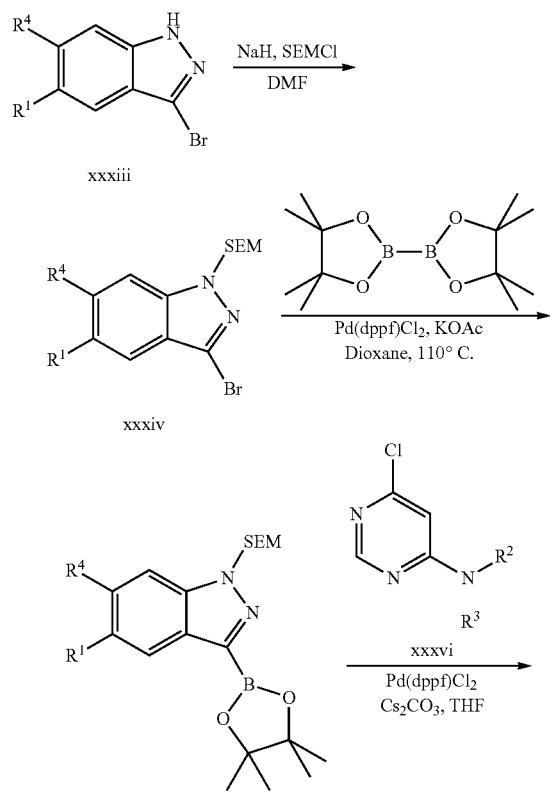

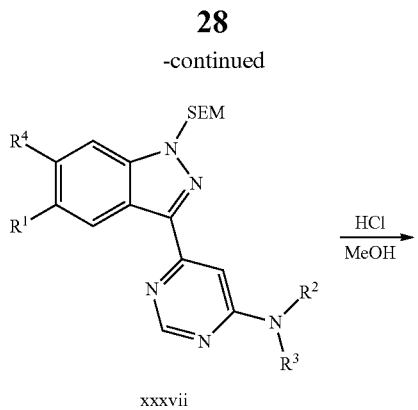

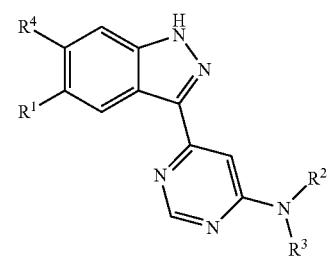

EXPERIMENTALS

Abbreviations used in the experimentals may include the following:

| | | | |
|---|---|---|---|
| ACN | Acetonitrile | AcOH | Acetic acid |
| Aq | Aqueous | Bn | Benzyl |
| BOC | tert-Butoxycarbonyl | BOC$_2$O | BOC Anhydride |
| Bu | Butyl | C. (or ° C.) | degrees Celsius |
| Cbz | benzyloxycarbonyl | DBU | 1,8-Diazabicyclo[5.4.0]undec-7-ene |
| DCM | Dichloromethane | DIPEA | Diisopropylethylamine |
| DEAD | diethylazodicarboxylate | DIAD | diisopropylazodicarboxylate |
| DMA | N,N-Dimethylacetamide | DMAP | 4-Dimethylaminopyridine |
| DME | 1,2-dimethoxyethane | DMF | Dimethylformamide |
| DMSO | Dimethyl sulfoxide | dppf | 1,1'-(bis-diphenylphosphino) ferrocene |
| EDCI | 1-(3-Dimethylaminopropyl)-3-ethylcarbodiimide hydrochloride | EDC | 1-(3-Dimethylaminopropyl)-3-ethylcarbodiimide hydrochloride |
| EI | Electron ionization | Eq | Equivalents |
| Et | Ethyl | EtOAc | Ethyl acetate |
| EtOH | Ethanol | g | grams |
| h, hr | hours | $^1$H | proton |
| HATU | N,N,N',N'-Tetramethyl-O-(7-Azabenzotriazol-1-yl)uronium hexafluorophosphate | Hex | hexanes |
| HOBT | 1-Hydroxybenzotriazole | HOBT•H$_2$O | 1-Hydroxybenzotriazole hydrate |
| HOTS | para-toluene sulfonic acid (see also TsOH) | HOTS•H$_2$O | para-toluene sulfonic acid hydrate (see also TsOH•H$_2$O) |
| HMPA | hexamethylphosphoramide | HPLC | High pressure liquid chromatography |
| IPA | isopropanol, 2-propanol | LDA | lithium diisopropylamide |
| M | Molar | mmol | milimolar |
| mCPBA | meta-Chloroperoxy benzoic acid | Me | Methyl |
| MeCN | Acetonitrile | MeOH | Methanol |
| min | Minutes | mg | Milligrams |
| MHZ | Megahertz | mL (or ml) | Milliliter |
| Mol sieves | molecular sieves | N | normal |

| | | | |
|---|---|---|---|
| NMR | Nuclear Magnetic Resonance | MS | Mass Spectroscopy |
| NBS | N-Bromosuccinimide | NMM | N-Methylmorpholine |
| NMP | 1-methyl-2-pyrrolidone | ON | Overnight |
| PTLC | Preparative thin layer chromatography | PyBrOP | Bromo-tris-pyrrolidino-phosphonium hexafluorophosphate |
| | | pin | pinacol |
| PyBOP | (Benzotriazol-1-yloxy)tripyrrolidinophosphonium hexa-fluorophosphate | Pyr | Pyridine |
| Quant | quantitative | RT or rt | Room temperature |
| sat (or sat. or sat'd.) | Saturated | SFC | supercritical fluid chromatography |
| | | SiliaMetS ® DMT | Silica bound equivalent of 2,4,6-trimercaptotriazine (metal scavenger) |
| sgc | Silica gel 60 chromatography | SiO$_2$ | Silica gel |
| tBOC | tert-Butoxycarbonyl | t-Bu | tert-butyl |
| TEA | Triethylamine | Tf | Trifluoromethane sulfonyl |
| TFA | Trifluoroacetic acid | THF | Tetrahydrofuran |
| TLC | Thin layer chromatography | Ts | Toluene sulfonyl |
| SEM | 2-(Trimethylsilyl)ethoxy-methyl | Tr | Triphenylmethyl |
| TsOH | para-toluene sulfonic acid | TsOH•H$_2$O | para-toluene sulfonic acid hydrate |
| TBAF | Tetrabutylammonium fluoride | TBS | Tert-butyldimethyl silyl |

General Experimental Information:

Unless otherwise noted, all reactions are magnetically stirred.

Unless otherwise noted, when ethyl acetate, hexanes, dichloromethane, 2-propanol, and methanol are used in the experiments described below, they are Fisher Optima grade solvents.

Unless otherwise noted, when diethyl ether is used in the experiments described below, it is Fisher ACS certified material and is stabilized with BHT.

Unless otherwise noted, "concentrated to dryness" means evaporating the solvent from a solution or mixture using a rotary evaporator.

Unless otherwise noted, flash chromatography is carried out on an Isco, Analogix, or Biotage automated chromatography system using a commercially available cartridge as the column. Columns may be purchased from Isco, Analogix, Biotage, Varian, or Supelco and are usually filled with silica gel as the stationary phase.

Unless otherwise noted, all LRRK2 IC$_{50}$ data presented in tables refers to the LRRK2 K$_m$ ATP LanthaScreen™ Assay that is described in the Biological Assay section.

Scheme A

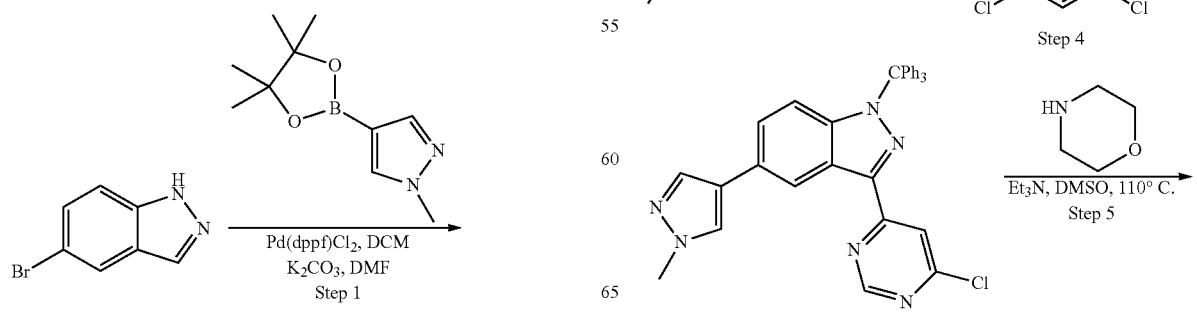

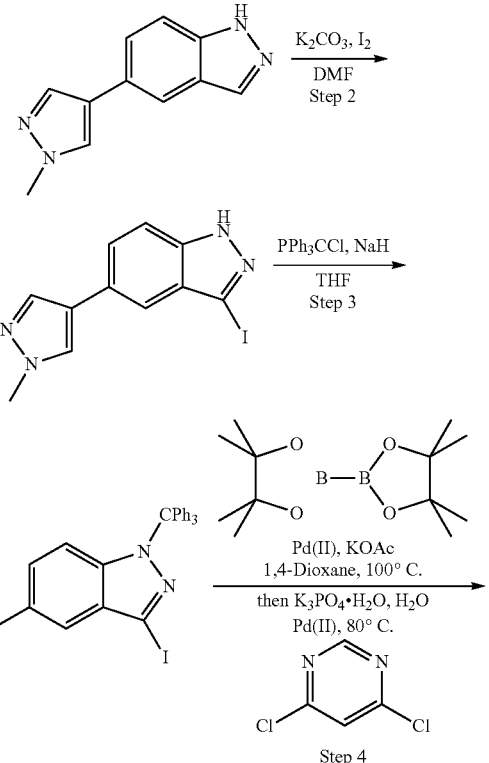

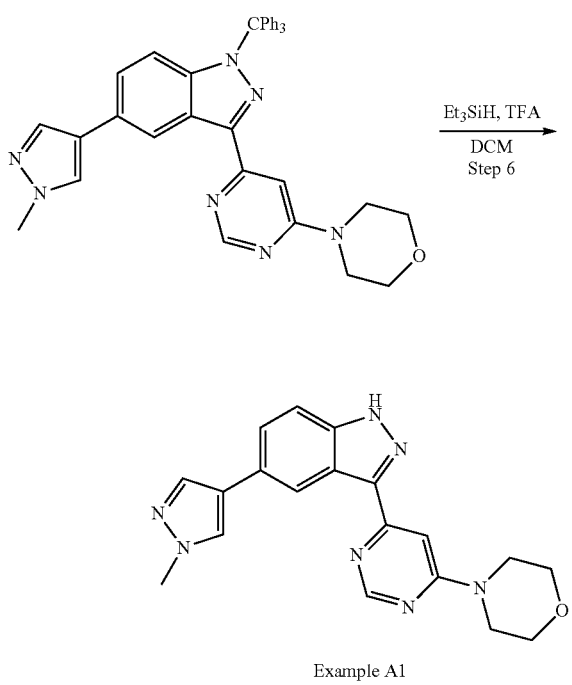

Example A1

Step 1: Into a 3000-mL 3-necked round-bottom flask purged and maintained with an inert atmosphere of nitrogen was placed a solution of 5-bromo-1H-indazole (130 g, 659.79 mmol) in DMF (1300 mL) at room temperature. To this were added 1-methyl-4-(tetramethyl-1,3,2-dioxaborolan-2-yl)-1H-pyrazole (240 g, 1.15 mol), potassium carbonate (247.1 g, 1.79 mol) and Pd(dppf)Cl$_2$-DCM (26 g, 31.82 mmol) at room temperature. The resulting solution was stirred overnight at 80° C. The reaction mixture was cooled to 20° C., then quenched by the addition of 1500 mL of water. The resulting mixture was extracted with ethyl acetate (4×1000 mL). The organic layers were combined, washed with brine (2×1000 mL), dried over anhydrous sodium sulfate, filtered, and concentrated under vacuum to leave a residue which was re-crystallized from petroleum ether:EtOAc (10:1).

Step 2: Into a 2000-mL 3-necked round-bottom flask was placed a solution of 5-(1-methyl-1H-pyrazol-4-yl)-1H-indazole (66 g, 332.96 mmol) in CH$_3$CN (700 mL) and potassium carbonate (68.9 g, 498.52 mmol) at room temperature. This was followed by the addition of I$_2$ (101.6 g, 400.00 mmol) in portions at room temperature. The resulting solution was stirred at room temperature overnight and then quenched by the addition of 1000 mL of water. The resulting solution was extracted with ethyl acetate (4×500 mL). The organic layers were combined, washed with brine (1000 mL), dried over anhydrous sodium sulfate, filtered, and concentrated under vacuum to leave a residue which was re-crystallized from diethyl ether to afford the iodoindazole.

Step 3: Into a 2000-mL 3-necked round-bottom flask purged and maintained with an inert atmosphere of nitrogen was placed a solution of 3-iodo-5-(1-methyl-1H-pyrazol-4-yl)-1H-indazole (71.5 g, 213.98 mmol) in THF (1000 mL) at room temperature. The solution was cooled to 0° C. This was followed by the addition of NaH (12.7 g of 60% in oil, 317.50 mmol) in portions at 0° C. The resulting solution was stirred at 0° C. for 15 min followed by the addition of (chlorodiphenylmethyl)benzene (76 g, 272.62 mmol) at 0° C. The resulting mixture was stirred at room temperature overnight. The reaction was then quenched by the addition of water (1000 mL). The resulting solution was extracted with ethyl acetate (3×1000 mL). The organic layers were combined, washed with brine (2×1000 mL), dried over anhydrous sodium sulfate, filtered, and concentrated under vacuum to leave a residue which was purified by column chromatography on silica gel (elution with 2:1 Petroleum ether:EtOAc) to yield the product. LCMS 567 [M+H]$^+$.

Step 4: A stirred solution of the iodide (450 mg, 0.794 mmol), bis(pinacolato)diboron (403 mg, 1.589 mmol) and KOAc (234 mg, 2.383 mmol) in dioxane (5 mL) was purged with Ar for 15 min. Then Pd(dppf)Cl$_2$-DCM adduct (29.1 mg, 0.040 mmol) was added and the mixture was heated at 100° C. for 20 h. The reaction was cooled to room temperature, diluted with 5:1 hexane:EtOAc (500 mL) and filtered through a pad of silica. The solid was thoroughly washed with 5:1 hexane:EtOAc (1500 mL) and the filtrate was concentrated under vacuum to leave a residue which was used in the next step without further purification.

The boronate ester from above was dissolved in 1,4-dioxane (5 ml) followed by the addition of 4,6-dichloropyrimidine (237 mg, 1.588 mmol), K$_3$PO$_4$ (506 mg, 2.382 mmol) and water (0.5 ml). After being purged with Ar for 15 min dichloro[1,1'-bis(di-tert-butylphosphino)ferrocene]palladium (II) (25.9 mg, 0.040 mmol) was added and the mixture was heated at 75° C. overnight. Upon cooling to room temperature, silica gel was added and a slurry was prepared which was then purified by column chromatography (gradient elution with 5:1 to 1:1 hex:EtOAc) to yield the chloropyrimidine. LCMS 553.2 [M$^+$].

Step 5: A mixture of the chloropyrimidine (70 mg, 0.127 mmol), morpholine (33.1 mg, 0.38 mmol) and Et$_3$N (0.09 mL, 0.63 mmol) in DMSO (1 mL) was heated in a sealed tube at 100° C. overnight. Upon cooling to room temperature the mixture was diluted with water and the resulting layer was extracted with EtOAc (×3). The combined organic layers were washed with water and brine, dried over MgSO$_4$, filtered and concentrated under vacuum to leave a residue which was purified by column chromatography (SiO$_2$; elution with 20:1 DCM:MeOH) to yield the morpholine adduct. LCMS 604.4 [M+H]$^+$.

Step 6: To a stirred mixture of morpholine adduct (45.0 mg, 0.075 mmol) and Et$_3$SiH (0.238 ml, 1.491 mmol) in DCM (1.5 ml) was added TFA (0.391 ml, 5.07 mmol) and the mixture was stirred at room temperature for 2 h. The reaction was carefully quenched with a saturated aqueous solution of NaHCO$_3$ and the resulting layer was extracted with DCM (×3). The combined organic layers were dried over MgSO$_4$, filtered and concentrated under vacuum to leave a residue which was purified by Preparative TLC (elution with 15:1 DCM:MeOH) to yield Example A1. LCMS 362.2 [M+H]$^+$.

TABLE A

Examples A2-A15 were prepared following procedures similar to those described in Scheme A using the appropriate amine in Step 5.

| Example | Structure | LRRK2 IC$_{50}$ (nM) | LCMS data m/z | RT (min) | Method |
|---|---|---|---|---|---|
| A1 | 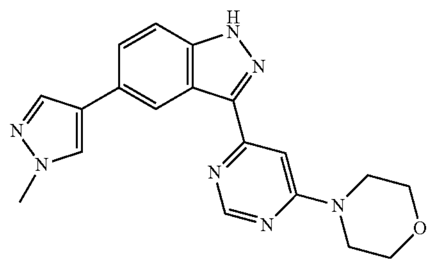 [SMILES: Cn1cc(-c2ccc3[nH]nc(-c4cc(N5CCOCC5)ncn4)c3c2)cn1] | 2.31 | 362.2 | 1.65 | B |
| A2 | 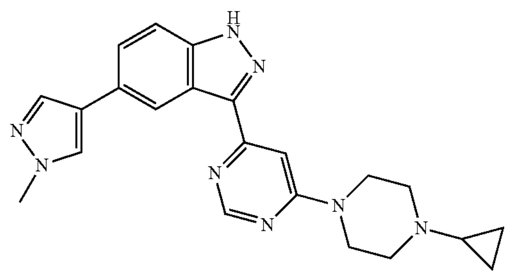 [SMILES: Cn1cc(-c2ccc3[nH]nc(-c4cc(N5CCN(C6CC6)CC5)ncn4)c3c2)cn1] | 2.62 | 401.0 | 1.61 | B |
| A3 | 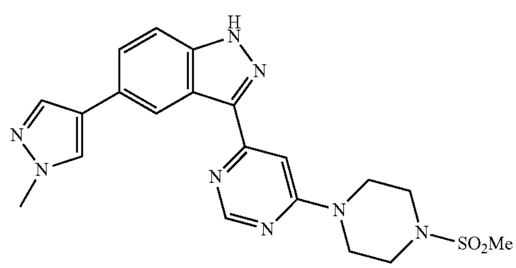 [SMILES: Cn1cc(-c2ccc3[nH]nc(-c4cc(N5CCN(S(C)(=O)=O)CC5)ncn4)c3c2)cn1] | 3.28 | 439.2 | 1.69 | B |
| A4 | 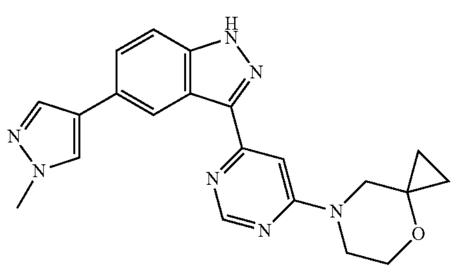 [SMILES: Cn1cc(-c2ccc3[nH]nc(-c4cc(N5CCOC6(CC6)C5)ncn4)c3c2)cn1] | 2.01 | 388.0 | 1.93 | B |
| A5 | 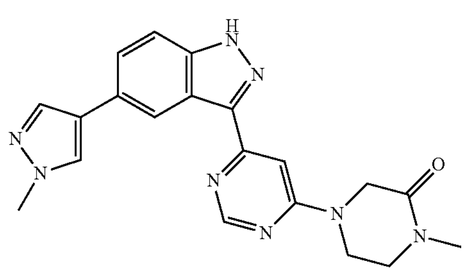 [SMILES: CN1CCN(c2cc(-c3n[nH]c4ccc(-c5cnn(C)c5)cc34)ncn2)CC1=O] | 4.91 | 389.2 | 1.65 | B |

TABLE A-continued

Examples A2-A15 were prepared following procedures similar to those described in Scheme A using the appropriate amine in Step 5.

| Example | Structure | LRRK2 IC$_{50}$ (nM) | LCMS data m/z | RT (min) | Method |
|---------|-----------|----------------------|---------------|----------|--------|
| A6 | | 2.85 | 375.2 | 1.51 | C2 |
| A7 | | 14.96 | 350.1 | 1.48 | C2 |
| A8 | | 0.76 | 389.2 | 1.59 | C2 |
| A9 | | 1.87 | 434.2 | 1.63 | C2 |
| A10 | | 5.18 | 388.1 | 0.92 | C2 |

TABLE A-continued
Examples A2-A15 were prepared following procedures similar to those described in Scheme A using the appropriate amine in Step 5.
| Example | Structure | LRRK2 IC$_{50}$ (nM) | LCMS data m/z | RT (min) | Method |
|---|---|---|---|---|---|
| A11 | 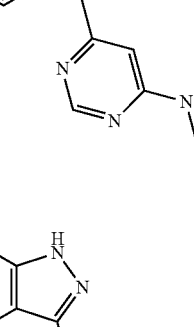 | 1.40 | 390.1 | 1.72 | C1 |
| A12 | 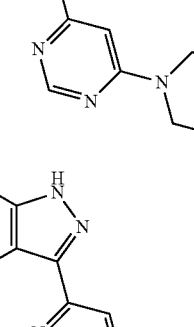 | 2.04 | 390.2 | 1.64 | C2 |
| A13 | 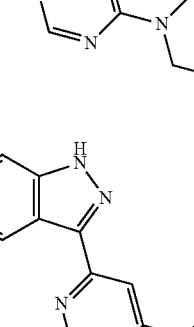 | 3.15 | 403.3 | 1.46 | C2 |
| A14 | 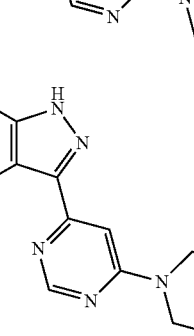 | 2.84 | 375.2 | 1.39 | C2 |
| A15 | 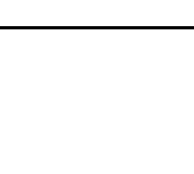 | 0.73 | 403.1 | 1.66 | C1 |

Scheme B

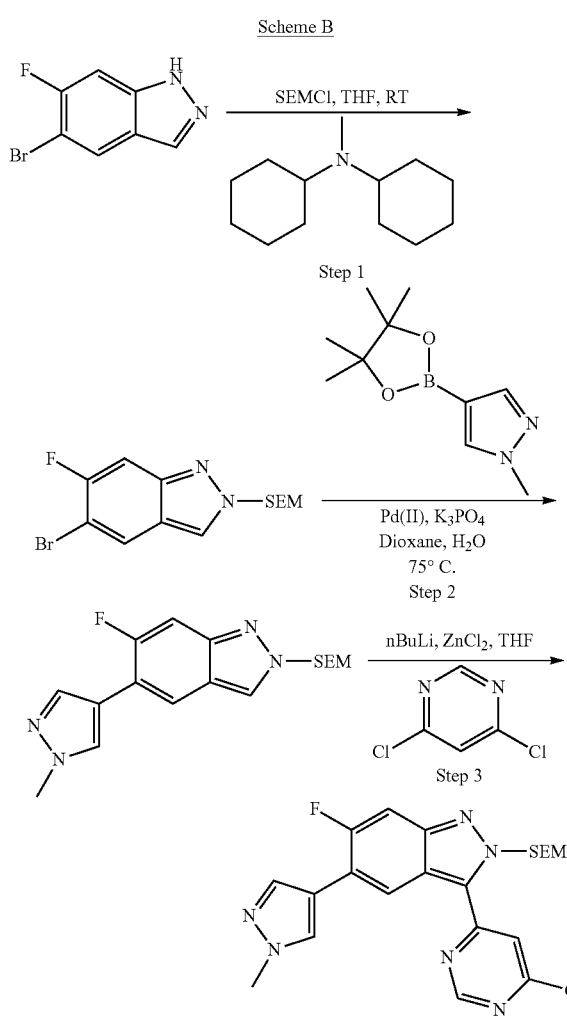

Step 1: To a stirred solution of 5-bromo-6-fluoroindazole (2.0 g, 9.30 mmol) in THF (20 mL) were added N,N-dicyclohexylmethylamine (2.59 ml, 12.09 mmol) and SEMCl (1.97 ml, 11.16 mmol) and the mixture was stirred at room temperature overnight. The reaction was quenched with water and the mixture was extracted with EtOAc (×3). The combined organic layers were then washed with 1 N HCl (×2), 1 N NaOH (×2), brine, dried over MgSO$_4$, filtered and concentrated under vacuum to leave a residue which was purified by column chromatography (elution with 10:1 hexane:EtOAc) to yield the SEM protected indazole. LCMS 345.2 [M+].

Step 2: To a stirred solution of SEM-protected indazole (1.82 g, 5.27 mmol) in 1,4-dioxane (25 ml) were added 1-methyl-4-(4,4-5,5-tetramethyl-1,3,2-dioxaborolan-2-yl)-1H-pyrazole (1.65 g, 7.91 mmol), K$_3$PO$_4$ (3.36 g, 15.81 mmol) and water (2.5 ml). The mixture was then purged with Ar for 15 min. After that time, dichloro[1,1'-bis(di-tert-butylphosphino)ferrocene]palladium (II) (0.17 g, 0.26 mmol) was added and the mixture was heated at 75° C. overnight. The reaction was cooled to room temperature and diluted with water and the mixture was extracted with DCM (×3). The combined organic layers were dried over MgSO$_4$, filtered and concentrated under vacuum to leave a residue which was purified by column chromatography (SiO$_2$; gradient elution with 2:1 to 1:1 hexane:EtOAc) to yield the pyrazoloindazole adduct. LCMS 347.2 [M+H]+.

Step 3: To a cold (−78° C.), stirred solution of pyrazoloindazole (1.74 g, 5.02 mmol) in THF (12 ml) was added n-BuLi (4.08 ml of 1.6 M solution in hexane, 6.53 mmol). After the addition was complete the mixture was stirred at −78° C. for 15 min and then warmed to −20° C. for 5 min. The mixture was recooled to −78° C. after which time a freshly prepared solution of ZnCl$_2$ (15.07 ml of 0.5 M solution in THF, 7.53 mmol) was added. The mixture was then warmed to −20° C. and stirred for 10 min at −20° C. when a mixture of 2,4-dichloropyrimidine (0.89 g, 6.03 mmol)) and Pd(PPh$_3$)$_4$ (0.29 g, 0.25 mmol) was added. The cold bath was removed and the mixture was stirred at room temperature for 24 h. After that time, the reaction mixture was quenched with a saturated aqueous solution of NH$_4$Cl. The mixture was then extracted with CH$_2$Cl$_2$ (×3). The combined organic layers were dried over MgSO$_4$, filtered and concentrated under vacuum to leave a residue which was purified by column chromatography (SiO$_2$; gradient elution with 2:1 to 1:1 hexane:EtOAc) to yield the chloropyrimidine. LCMS 459.2 [M+H]+.

Scheme C

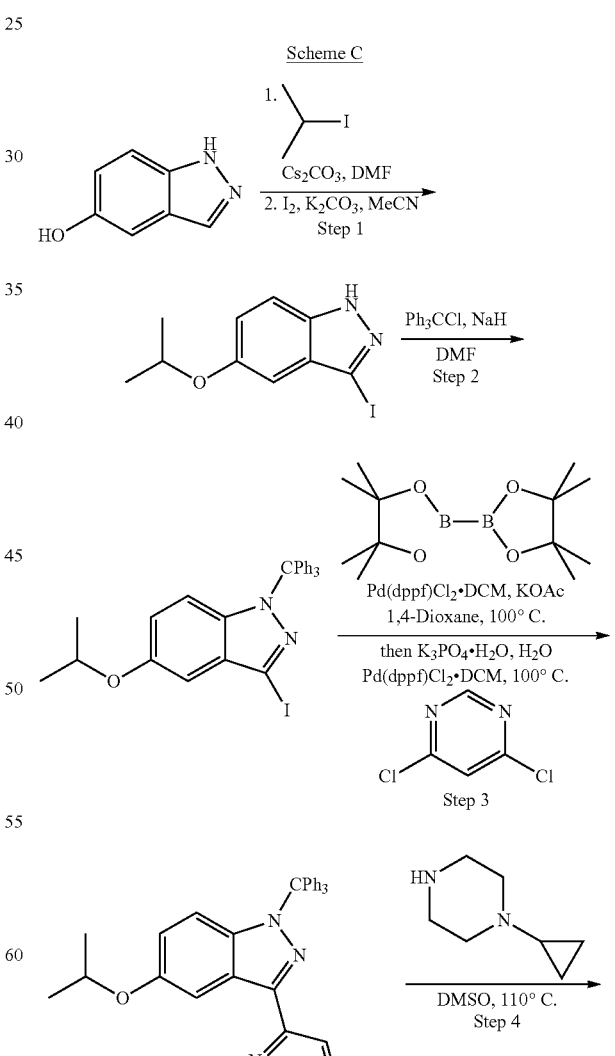

-continued

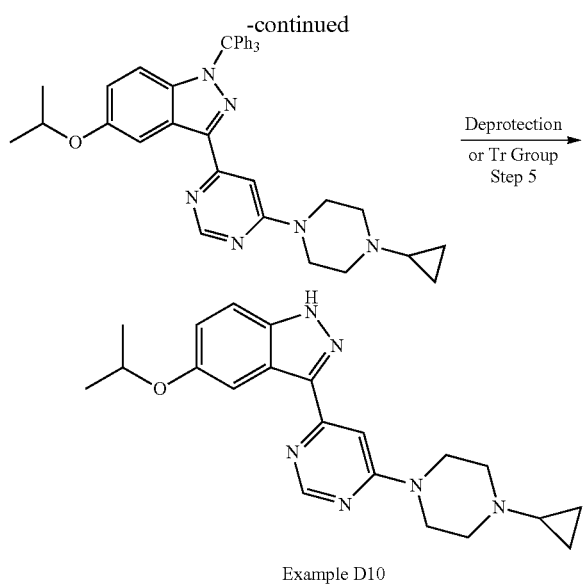

Example D10

Step 1: To a stirred suspension of Cs$_2$CO$_3$ (18.2 g, 55.9 mmol) in DMF (45 ml) was added 5-hydroxyindazole (5 g, 37.3 mmol) followed by 2-iodopropane (10.1 g, 59.4 mmol). The mixture was stirred at room temperature for 6 h before being quenched with water. The layer was extracted with EtOAc (×3). The combined organic layers were washed with water (×2), brine, dried over MgSO$_4$, filtered and concentrated under vacuum to leave a residue which was used directly in the next step without further purification. LCMS 303.0 [M+H]$^+$.

The product from above was dissolved in MeCN (100 ml) followed by the addition of K$_2$CO$_3$ (10.30 g, 74.6 mmol) and I$_2$ (14.19 g, 55.9 mmol). The resulting mixture was stirred overnight. The reaction was diluted with brine and the layer was extracted with DCM (×3). The combined organic layers were dried over MgSO$_4$, filtered and concentrated to leave a residue which was purified by column chromatography (SiO$_2$; elution with 5:1 hexane:EtOAc) to afford the desired 3-iodo-5-isopropoxy indazole as a light yellow solid.

Step 2: To a cold (0° C.), stirred solution of 3-iodo-5-isopropoxy indazole (4.6 g, 15.23 mmol) in THF (30 ml) was added NaH (0.731 g of 60% in oil, 18.27 mmol). After additional stirring for 15 min at 0° C. TrCl (5.09 g, 18.27 mmol) was added rapidly. The cold bath was removed and the mixture was stirred at room temperature overnight. The reaction was quenched with water and extracted with DCM (×3). The combined organic layers were dried over MgSO$_4$, filtered and concentrated to leave a residue which was purified by column chromatography (SiO$_2$; gradient elution with 100:0 to 20:1 hexane:EtOAc) to afford the trityl-protected indazole.

Step 3: A stirred solution of the 3-iodo indazole (10.0 g, 18.37 mmol), bis(pinacolato)diboron (7.00 g, 27.6 mmol) and KOAc (5.41 g, 55.1 mmol) in dioxane (100 mL) was purged Ar for 15 min. After that time, Pd(dppf)Cl$_2$-DCM adduct (1.34 g, 1.84 mmol) was added and the mixture was heated at 100° C. for 20 h. The mixture was cooled to room temperature followed by the addition of 4,6-dichloropyrimidine (4.10 g, 27.6 mmol), K$_3$PO$_4$ (11.70 g, 55.1 mmol) and water (10 mL). The mixture was degassed with Ar for 20 min followed by heating at 100° C. for 15 h. The reaction was cooled to room temperature and then concentrated under vacuum to leave a residue which was redissolved in 5:1 hexane:EtOAc (500 mL) and filtered through a pad of silica. The filtrate was concentrated and the residue was purified by column chromatography (SiO$_2$; elution with 10:1 hexane:EtOAc) to yield the chloropyrimidine.

Step 4: A mixture of the chloropyrimidine (200 mg, 0.38 mmol), the piperazine (238 mg, 1.88 mmol) and N,N-diisopropylethylamine (0.26 mL, 1.51 mmol) in DMSO (1.5 mL) was heated in a sealed tube at 110° C. for 2 h. The reaction was cooled to room temperature and diluted with water. The layer was then extracted with EtOAc (×2). The combined organic layers were washed with water and brine, dried over MgSO$_4$, filtered and concentrated to leave a residue which was used purified by column chromatography (SiO$_2$; elution with 2:1 hexane:EtOAc) to yield the desired adduct. LCMS 621 [M+H]$^+$.

Step 5: General Methods for Removal of Trityl Group.

Method A: To a stirred solution of the trityl protected indazole (0.12 mmol) in CH$_2$Cl$_2$ (5 mL) was added TFA (1 mL) followed by Et$_3$SiH (0.5 mL). After being stirred at room temperature for 3 h the reaction was concentrated under reduced pressure to yield a residue which was purified by reverse phase chromatography (Analogix 55 g C18 column, gradient elution 0% to 100% MeCN in water w/ 0.1% TFA) to yield the indazole.

Method B: To a stirred solution of amine-adduct (0.24 mmol) in DCM (6 mL) and water (0.6 mL) was added TFA (2.02 mL) and the mixture was stirred at room temperature overnight before being quenched with a saturated aqueous solution of NaHCO$_3$. The layer was then extracted with DCM (×3). The combined organic layers were dried over MgSO$_4$, filtered and concentrated to leave a residue which was purified by reverse phase chromatography (Analogix 55 g C18 column, gradient elution 0% to 100% MeCN in water w/ 0.1% TFA) to yield the desired indazole.

Scheme D:

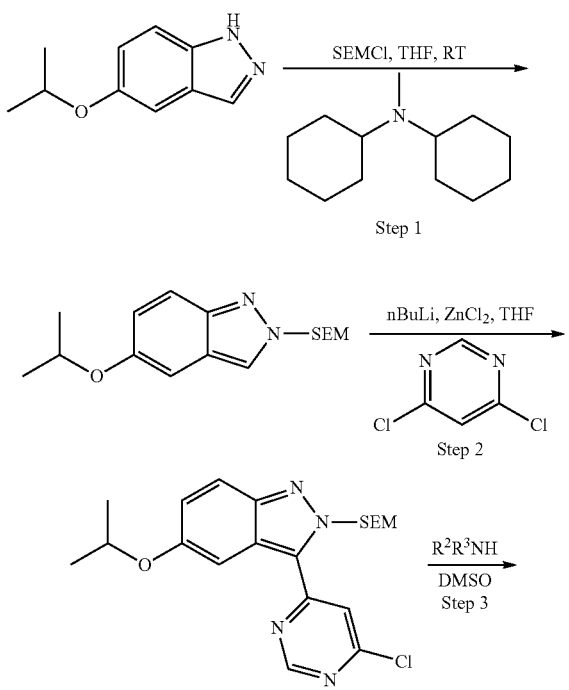

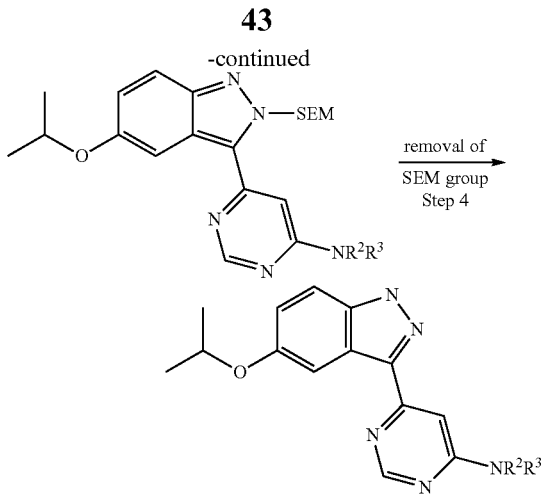

Step 1: To a stirred solution of the indazole (1.5 g, 7.97 mmol) in THF (20 ml) was added N,N-dicyclohexylmethylamine (2.22 ml, 10.36 mmol) followed by SEMCl (1.69 ml, 9.56 mmol) dropwise. After the addition was complete, the mixture was stirred at room temperature overnight before being quenched with water. The mixture was extracted with EtOAc (×3). The combined organic layers were then washed with 1 N HCl (×2), 1 N NaOH (×2), brine, dried over MgSO₄, filtered and concentrated to leave a residue which was purified by column chromatography (SiO₂; elution with 10:1 hexane:EtOAc) to yield the SEM-protected indazole.

Step 2: To a cold (−78° C.), stirred solution of SEM-protected indazole (8.79 g, 28.7 mmol) in THF (100 ml) was added n-BuLi (12.6 ml of 2.5 M solution in hexane, 31.5 mmol). After the addition was complete the mixture was stirred at −78° C. for 20 min and then warmed to −20° C. for 5 min. The mixture was cooled to −78° C. when a freshly prepared solution of ZnCl₂ (30.1 ml of 1.0 M in THF, 30.1 mmol) was added. The mixture was then warmed to −20° C. and stirred for 10 min at −20° C. after which time a mixture of 4,6-dichloropyrimidine (4.70 g, 31.5 mmol) and Pd(PPh₃)₄ (1.66 g, 1.4 mmol) was added. The cold bath was removed and the mixture was stirred at room temperature overnight before being quenched by a saturated aqueous solution of NH₄Cl. The layer was then extracted with CH₂Cl₂ (×3). The combined organic layers were dried, filtered and concentrated to leave a residue which was purified by column chromatography (SiO₂; elution with 10:1 hexane:EtOAc) to yield the chloropyrimidine. LCMS 431.2 [M+H]⁺.

Step 3: Displacement of chloropyrimidine with amines were carried out following the method described in Scheme C step 4.

Step 4: General Methods for Deprotection of SEM Group
Method A: To a stirred solution of amine-adduct (4.77 mmol) in DCM (15 mL) was added TFA (3.68 mL) and the mixture was stirred at room temperature for 3 h. The reaction was carefully quenched with a saturated aqueous solution of NaHCO₃ and the resultant mixture was extracted with DCM (×3). The combined organic layers were dried over MgSO₄, filtered and concentrated to leave a residue which was dissolved in 1:1:1 DCM:water:20% NH₄OH in water (5 mL each). The resulting mixture was stirred at room temperature overnight followed by the addition of water. The resulting mixture was extracted with DCM (×3). The combined organic layers were dried over MgSO₄, filtered and concentrated under reduced pressure to leave a residue which was purified by reverse phase chromatography (Analogix 55 g C18 column, gradient elution 0% to 100% MeCN in water w/ 0.1% TFA) to yield the product.

Method B: To a stirred solution of amine-adduct (0.48 mmol) in MeOH (3 ml) was added a solution of HCl in 1,4-dioxane (19.02 mmol). The mixture was heated at 75° C. for 2 h. The mixture was cooled to room temperature and diluted with EtOAc, washed with a saturated aqueous solution of NaHCO₃. The organic phase was dried over MgSO₄, filtered and concentrated under reduced pressure to yield a residue which was directly purified by reverse phase HPLC (Sunfire Prep. C18 OBO 5 µm 50×100 mm column, gradient elution 25-75% CH₃CN 0.1 TFA in water 0.1 TFA, injection volume 4.5 mL).

Scheme D2:

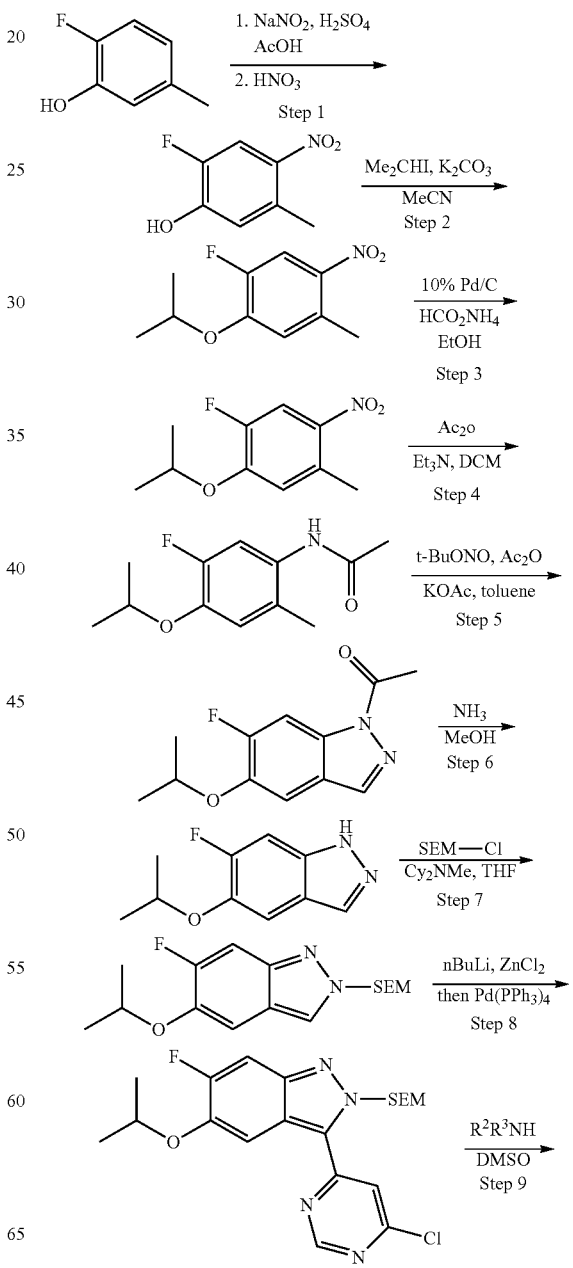

-continued

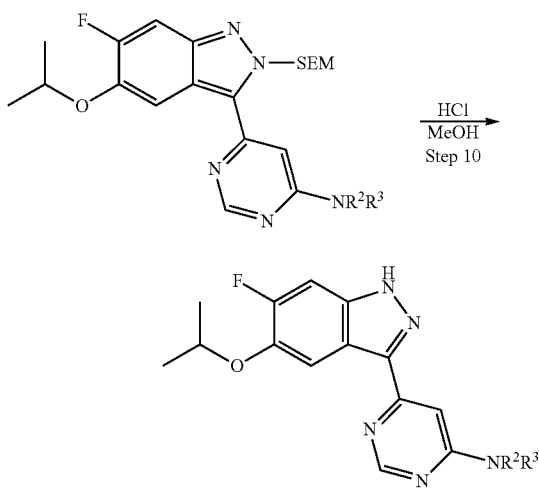

Step 1: To a cold (0° C.), stirred solution of 2-fluoro-5-methylphenol (30.0 g, 238 mmol) in a mixture of AcOH (66 mL) and concentrated $H_2SO_4$ (9.0 mL) was added dropwise a solution of $NaNO_2$ (15.6 g, 226 mmol) in water (45 mL). The reaction was stirred for 30 min (temperature <15° C.), and then poured into ice/water (500 mL). The precipitate was collected by filtration followed by washing with water (3×100 mL). The resulting solid was added portionwise to a mixture of $HNO_3$ (50 mL) and water (150 mL) with the temperature varying within the range of 45 to 50° C. The resulting suspension was stirred at 45° C. until the evolution of brown gas ceased (ca. 2.0 h). After being cooled to room temperature the mixture was diluted with cold water (400 mL) and filtered. The solid was washed with water (2×100 mL) and then dissolved in ethyl acetate (300 mL). The organic layer was washed with brine (2×100 mL), dried over $Na_2SO_4$, filtered and concentrated under reduced pressure to provide the desired nitro compound as a brown solid.

Step 2: To a solution of above nitro compound (28.0 g, 163.7 mmol) in $CH_3CN$ (500 mL) was added $K_2CO_3$ (45.0 g, 330 mmol) and 2-iodopropane (56.0 g, 330 mmol). The mixture was stirred at 80° C. overnight. The reaction mixture was concentrated under reduced pressure to leave a residue which was dissolved in a mixture of ethyl acetate (300 mL) and water (150 mL). The organic layer was separated and washed with brine (3×100 mL), dried ($Na_2SO_4$), filtered and concentrated to afford the desired isopropyl ether as a brown solid MS (ESI) m/z=214.1 $[M+1]^+$.

Step 3: To a stirred solution of nitro compound (24.0 g, 112.7 mmol) in EtOH (600 mL) was added $HCOONH_4$ (85.0 g, 1352 mmol) followed by 10% Pd/C (12.0 g, 12.0 mmol). The flask was evacuated and back-filled with $N_2$ and then stirred at rt for 3 h. The reaction mixture was filtered and the filtrate was concentrated in vacuo to provide the desired amine as a brown oil MS (ESI) m/z=184.1 $[M+1]^+$.

Step 4: To a cold (0° C.), stirred solution of above amine (20.0 g, 109.3 mmol) in DCM (400 mL) was added $Et_3N$ (22.0 g, 219 mmol) followed by $Ac_2O$ (16.7 g, 164 mmol). The mixture was stirred at room temperature overnight before being washed with brine (3×100 mL), dried over $Na_2SO_4$, filtered and concentrated under reduced pressure to leave a residue which was purified by column chromatography on silica (elution with 2:1 to 1:1 petroleum ether:EtOAc) to afford the desired acetamide as a yellow solid. MS (ESI) m/z=226.1 $[M+1]^+$.

Step 5: To a stirred solution of acetamide (20.0 g, 88.9 mmol) in toluene (300 mL) were added KOAc (13.0 g, 133 mmol) and $Ac_2O$ (42.0 g, 409 mmol). The mixture was heated to 80° C. when tert-butyl nitrite (36.6 g, 355.6 mmol) was added dropwise. After the addition was complete the reaction was stirred at 80° C. overnight. After being cooled to room temperature, the reaction was filtered through a pad of celite and the filtrate was concentrated to leave a residue which was purified by column chromatography on silica (elution with 20:1 petroleum ether:EtOAc) to provide the desired product as a yellow solid. MS (ESI) m/z=237.0 [M+1]+.

Step 6: The compound from Step 5 (20.0 g, 84.7 mmol) was taken up into $NH_3$ (90 mL of 7.0 M solution in MeOH). After being stirred at room temperature for 2 h the reaction was concentrated to leave a residue which was purified by column chromatography on silica (elution 5:1 to 1: petroleum ether:EtOAc) to yield the desired indazole as a yellow solid. MS (ESI) m/z=195.1 $[M+1]^+$.

Step 7, 8, 9 and 10 are carried out following the procedure outlined in Scheme D.

TABLE D

| Example | Structure | LRRK2 IC$_{50}$ (nM) | LCMS data m/z | RT (min) | Method |
|---|---|---|---|---|---|
| D1 | 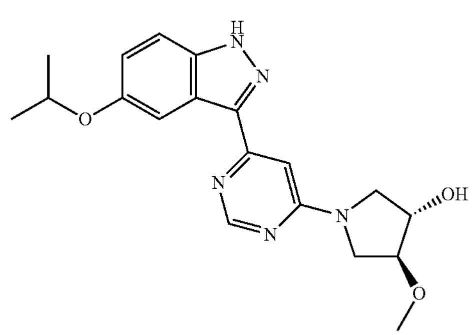 [SMILES: CO[C@H]1CN(c2cc(-c3n[nH]c4ccc(OC(C)C)cc34)ncn2)C[C@@H]1O] | 9.9 | 370.2 | 1.18 | C4 |

TABLE D-continued

| Example | Structure | LRRK2 IC$_{50}$ (nM) | m/z | RT (min) | Method |
|---|---|---|---|---|---|
| D2 | 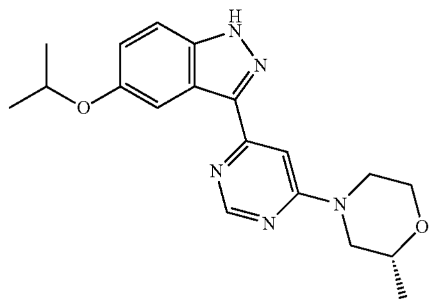 [SMILES: CC(C)Oc1ccc2[nH]nc(-c3cc(N4CCO[C@H](C)C4)ncn3)c2c1] | 5.09 | 354.1 | 1.02 | C3 |
| D3 | 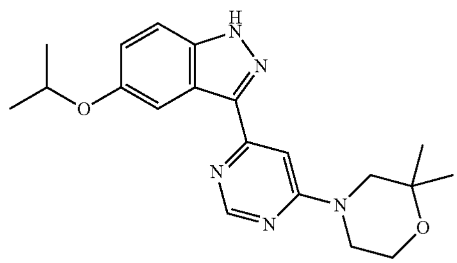 [SMILES: CC(C)Oc1ccc2[nH]nc(-c3cc(N4CCOC(C)(C)C4)ncn3)c2c1] | 6.37 | 368.3 | 1.94 | C2 |
| D4 | 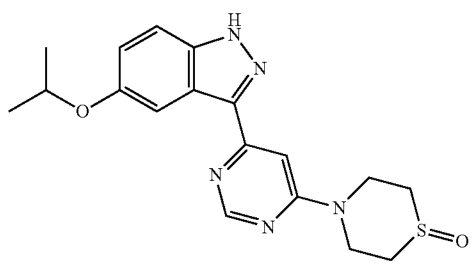 [SMILES: CC(C)Oc1ccc2[nH]nc(-c3cc(N4CCS(=O)CC4)ncn3)c2c1] | 11.5 | 372.2 | 0.97 | C3 |
| D5 | 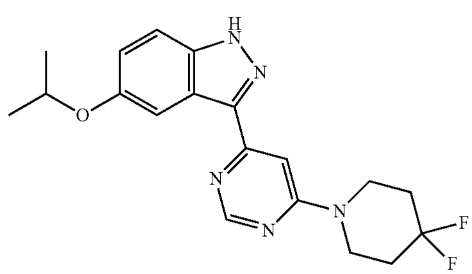 [SMILES: CC(C)Oc1ccc2[nH]nc(-c3cc(N4CCC(F)(F)CC4)ncn3)c2c1] | 14.8 | 374.1 | 1.42 | C6 |
| D6 | 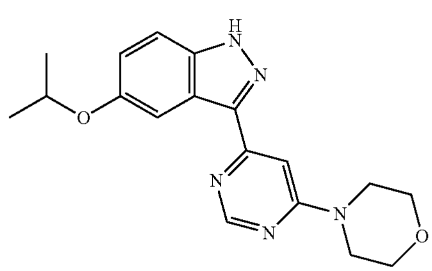 [SMILES: CC(C)Oc1ccc2[nH]nc(-c3cc(N4CCOCC4)ncn3)c2c1] | 5.95 | 340.0 | 1.8 | B |

TABLE D-continued

| Example | Structure | LRRK2 IC$_{50}$ (nM) | m/z | RT (min) | Method |
|---------|-----------|------|-----|------|--------|
| D7 | 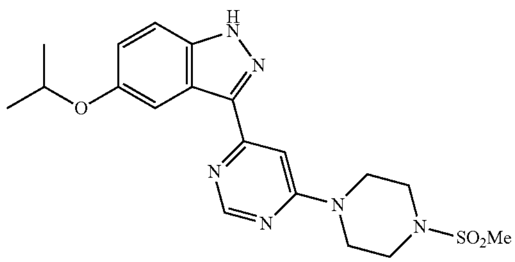 [SMILES: CC(C)Oc1ccc2[nH]nc(-c3cc(N4CCN(S(C)(=O)=O)CC4)ncn3)c2c1] | 7.99 | 417.0 | 1.8 | B |
| D8 | 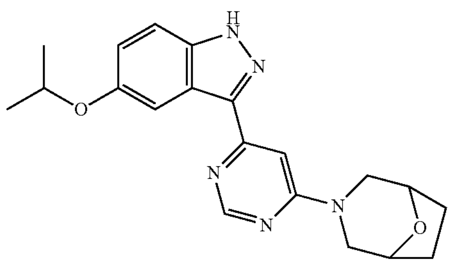 [SMILES: CC(C)Oc1ccc2[nH]nc(-c3cc(N4CC5CCC(C4)O5)ncn3)c2c1] | 29.2 | 366.2 | 2.01 | B |
| D9 | 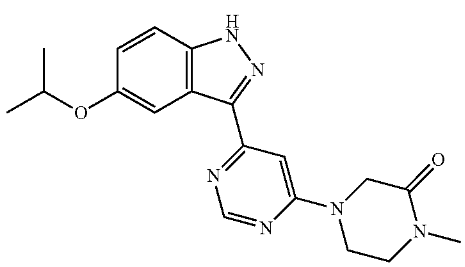 [SMILES: CC(C)Oc1ccc2[nH]nc(-c3cc(N4CCN(C)C(=O)C4)ncn3)c2c1] | 11.2 | 367.2 | 1.89 | B |
| D10 | 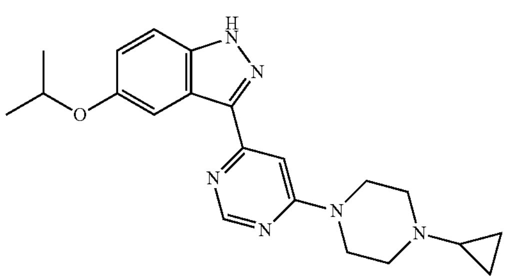 [SMILES: CC(C)Oc1ccc2[nH]nc(-c3cc(N4CCN(C5CC5)CC4)ncn3)c2c1] | 8.28 | 379.2 | 1.80 | B |
| D11 | 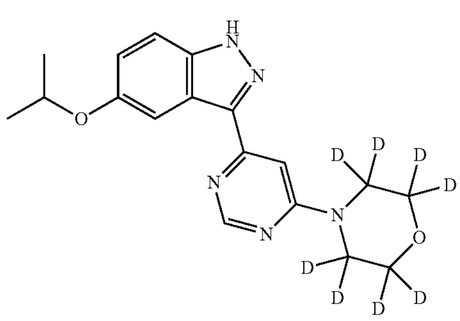 [SMILES: [2H]C1([2H])OC([2H])([2H])C([2H])([2H])N(c2cc(-c3n[nH]c4ccc(OC(C)C)cc34)ncn2)C1([2H])[2H]] | 7.12 | 348.3 | 2.0 | B |

TABLE D-continued

| Example | Structure | LRRK2 IC$_{50}$ (nM) | LCMS data m/z | RT (min) | Method |
|---|---|---|---|---|---|
| D12 | 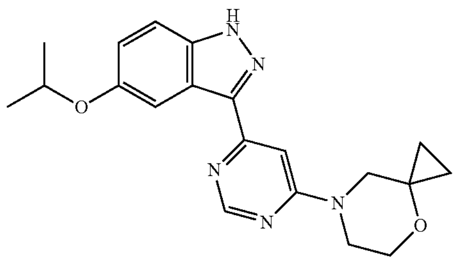 [SMILES: CC(C)Oc1ccc2[nH]nc(-c3cc(N4CCOC5(CC5)C4)ncn3)c2c1] | 4.04 | 366.0 | 2.1 | B |
| D13 | 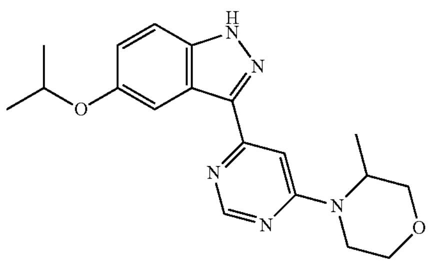 [SMILES: CC(C)Oc1ccc2[nH]nc(-c3cc(N4CCOCC4C)ncn3)c2c1] | 19.82 | 354.2 | 1.50 | C6 |
| D14 | 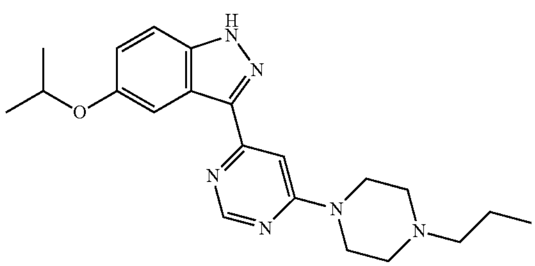 [SMILES: CCCN1CCN(c2cc(-c3n[nH]c4ccc(OC(C)C)cc34)ncn2)CC1] | 8.14 | 381.2 | 1.22 | C6 |
| D15 | 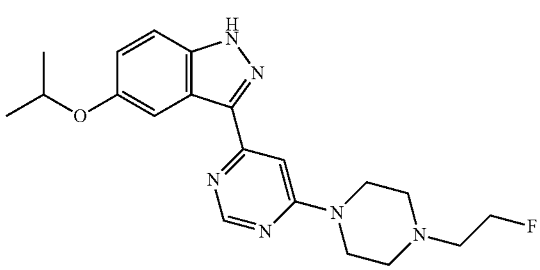 [SMILES: CC(C)Oc1ccc2[nH]nc(-c3cc(N4CCN(CCF)CC4)ncn3)c2c1] | 5.50 | 385.2 | 1.85 | C2 |
| D16 | 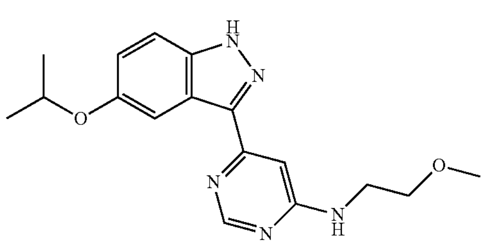 [SMILES: COCCNc1cc(-c2n[nH]c3ccc(OC(C)C)cc23)ncn1] | 26.3 | 328.3 | 1.73 | C2 |

TABLE D-continued

| Example | Structure | LRRK2 IC₅₀ (nM) | m/z | RT (min) | Method |
|---------|-----------|-----------------|-----|----------|--------|
| D17 | 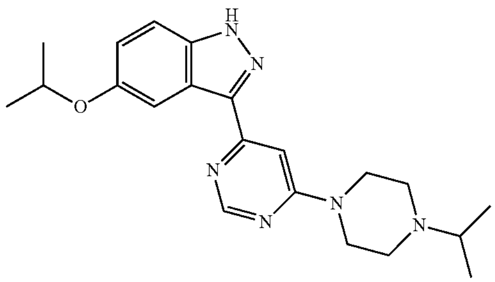 [SMILES: CC(C)Oc1ccc2[nH]nc(-c3cc(N4CCN(C(C)C)CC4)ncn3)c2c1] | 7.68 | 381.2 | 1.95 | C2 |
| D18 | 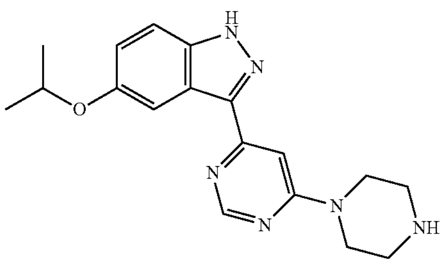 [SMILES: CC(C)Oc1ccc2[nH]nc(-c3cc(N4CCNCC4)ncn3)c2c1] | 12.38 | 339.2 | 1.16 | C6 |
| D19 | 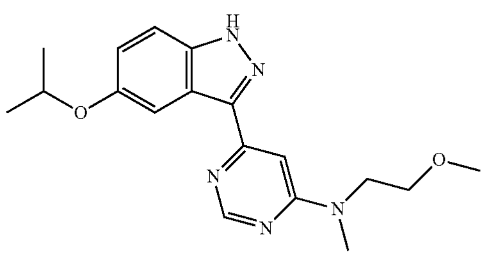 [SMILES: COCCN(C)c1cc(-c2n[nH]c3ccc(OC(C)C)cc23)ncn1] | 66.54 | 342.3 | 1.84 | C2 |
| D20 | 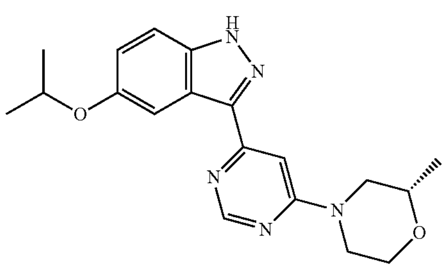 [SMILES: CC(C)Oc1ccc2[nH]nc(-c3cc(N4CCO[C@@H](C)C4)ncn3)c2c1] | 21.44 | 354.2 | 1.88 | C2 |
| D21 | 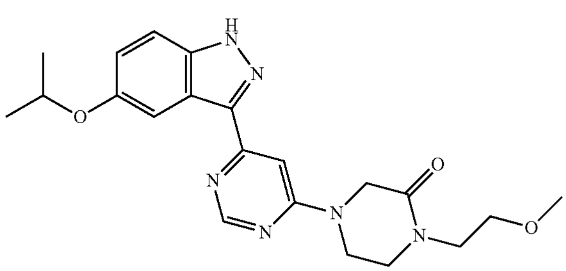 [SMILES: COCCN1CCN(c2cc(-c3n[nH]c4ccc(OC(C)C)cc34)ncn2)CC1=O] | 5.59 | 411.2 | 1.02 | C3 |

TABLE D-continued
| Example | Structure | LRRK2 IC$_{50}$ (nM) | m/z | RT (min) | Method |
|---|---|---|---|---|---|
| D22 | 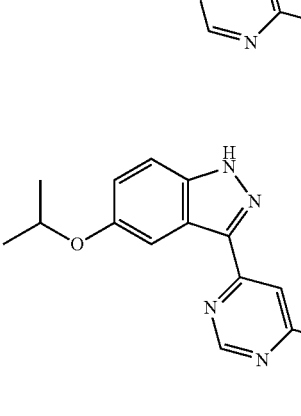 | 4.15 | 407.2 | 1.05 | C3 |
| D23 | 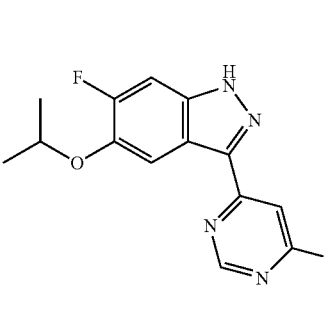 | 5.51 | 443.1 | 1.11 | C3 |
| D24 | 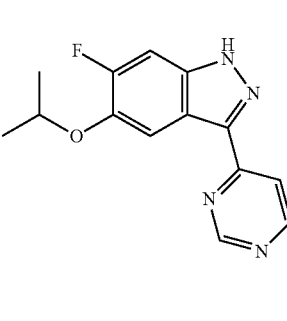 | 3.09 | 435.1 | 1.33 | C6 |
| D25 | 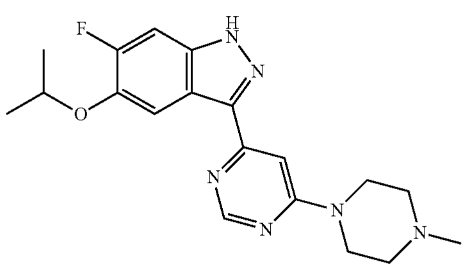 [SMILES: CC(C)Oc1cc2c(-c3cc(N4CCN(C)CC4)ncn3)n[nH]c2cc1F] | 4.35 | 371.1 | 1.47 | C4 |
| D26 | 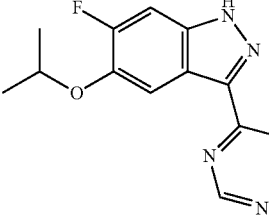 | 2.39 | 358.2 | 1.64 | C4 |

TABLE D-continued

| Example | Structure | LRRK2 IC$_{50}$ (nM) | m/z | RT (min) | Method |
|---|---|---|---|---|---|
| D27 | 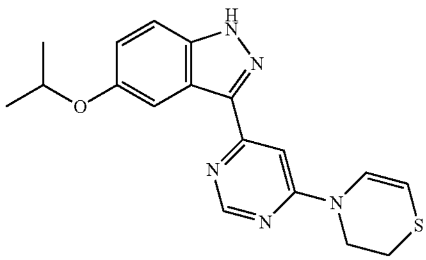 [SMILES: CC(C)Oc1ccc2[nH]nc(-c3cc(N4C=CSCC4)ncn3)c2c1] | 6.08 | 354.2 | 1.27 | C3 |
| D28 | 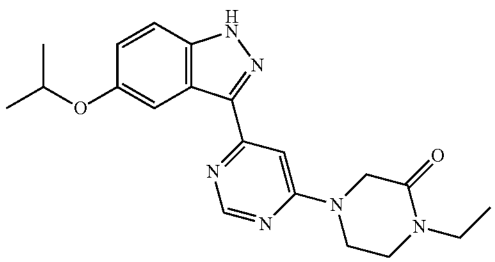 [SMILES: CCN1CCN(c2cc(-c3n[nH]c4ccc(OC(C)C)cc34)ncn2)CC1=O] | 5.60 | 381.2 | 1.05 | C3 |
| D29 | 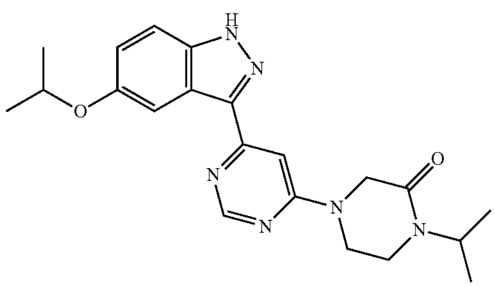 [SMILES: CC(C)Oc1ccc2[nH]nc(-c3cc(N4CCN(C(C)C)C(=O)C4)ncn3)c2c1] | 5.28 | 395.2 | 1.10 | C3 |
| D30 | 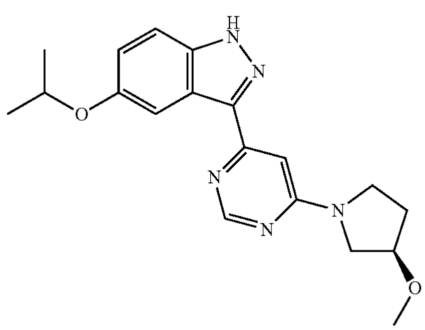 [SMILES: CO[C@@H]1CCN(c2cc(-c3n[nH]c4ccc(OC(C)C)cc34)ncn2)C1] | 7.47 | 354.2 | 1.03 | A |
| D31 | 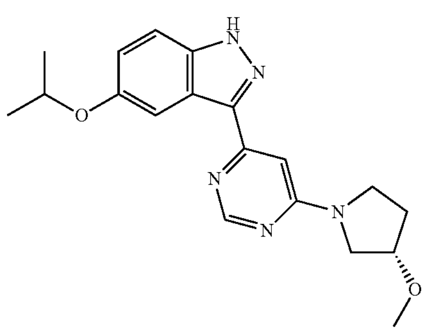 [SMILES: CO[C@H]1CCN(c2cc(-c3n[nH]c4ccc(OC(C)C)cc34)ncn2)C1] | 8.79 | 354.2 | 1.03 | A |

TABLE D-continued

| Example | Structure | LRRK2 IC$_{50}$ (nM) | m/z | RT (min) | Method |
|---|---|---|---|---|---|
| D32 | 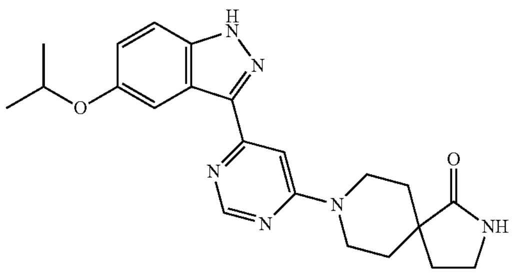 [SMILES: CC(C)Oc1ccc2[nH]nc(-c3cc(N4CCC5(CCNC5=O)CC4)ncn3)c2c1] | 2.31 | 407.2 | 1.01 | A |
| D33 | 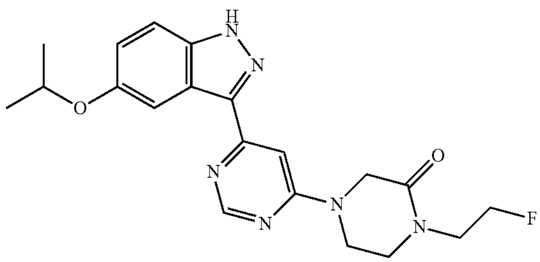 [SMILES: CC(C)Oc1ccc2[nH]nc(-c3cc(N4CCN(CCF)C(=O)C4)ncn3)c2c1] | 3.30 | 399.1 | 1.0 | C3 |
| D34 | 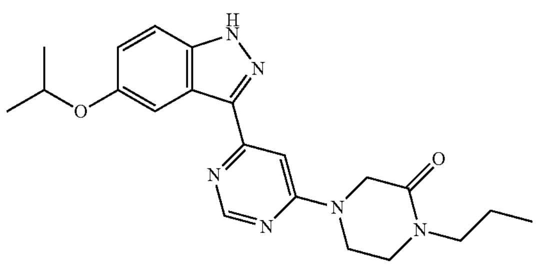 [SMILES: CCCN1CCN(c2cc(-c3n[nH]c4ccc(OC(C)C)cc34)ncn2)CC1=O] | 4.39 | 395.2 | 1.05 | C3 |
| D35 | 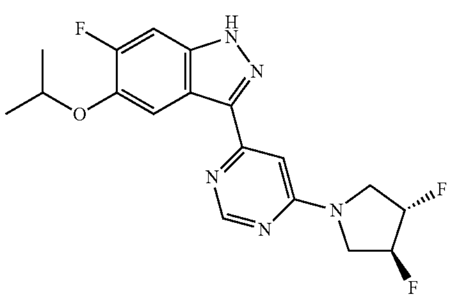 [SMILES: CC(C)Oc1cc2c(-c3cc(N4C[C@H](F)[C@@H](F)C4)ncn3)n[nH]c2cc1F] | 4.78 | 378.1 | 1.89 | C2 |
| D36 | 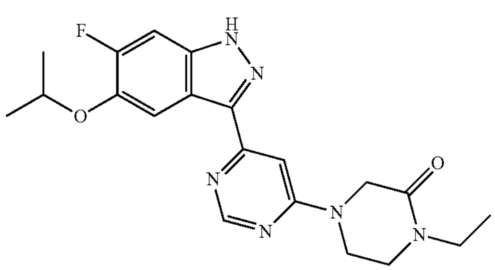 [SMILES: CCN1CCN(c2cc(-c3n[nH]c4cc(F)c(OC(C)C)cc34)ncn2)CC1=O] | 4.16 | 399.2 | 1.06 | C3 |

TABLE D-continued

| Example | Structure | LRRK2 IC$_{50}$ (nM) | LCMS data m/z | RT (min) | Method |
|---|---|---|---|---|---|
| D37 | 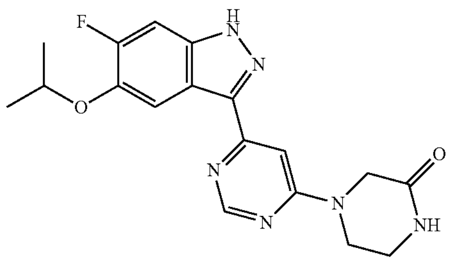 [SMILES: CC(C)Oc1cc2c(-c3cc(N4CCNC(=O)C4)ncn3)n[nH]c2cc1F] | 2.89 | 371.2 | 1.23 | C6 |
| D38 | 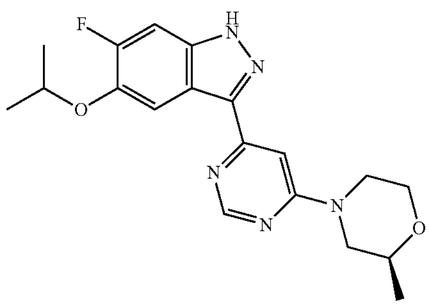 [SMILES: CC(C)Oc1cc2c(-c3cc(N4CCO[C@@H](C)C4)ncn3)n[nH]c2cc1F] | 5.01 | 372.2 | 1.36 | C6 |
| D39 | 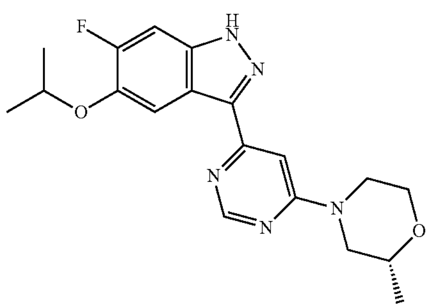 [SMILES: CC(C)Oc1cc2c(-c3cc(N4CCO[C@H](C)C4)ncn3)n[nH]c2cc1F] | 2.87 | 372.2 | 1.35 | C6 |
| D40 | 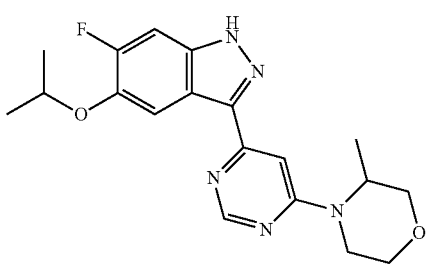 [SMILES: CC(C)Oc1cc2c(-c3cc(N4CCOCC4C)ncn3)n[nH]c2cc1F] | 5.54 | 372.2 | 1.09 | C3 |
| D41 | 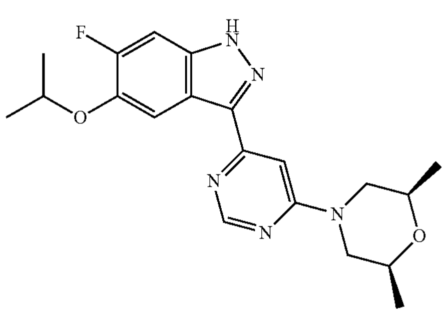 [SMILES: CC(C)Oc1cc2c(-c3cc(N4C[C@@H](C)O[C@@H](C)C4)ncn3)n[nH]c2cc1F] | 2.89 | 386.2 | 1.39 | C6 |

TABLE D-continued
| Example | Structure | LRRK2 IC50 (nM) | LCMS data m/z | RT (min) | Method |
|---|---|---|---|---|---|
| D42 | 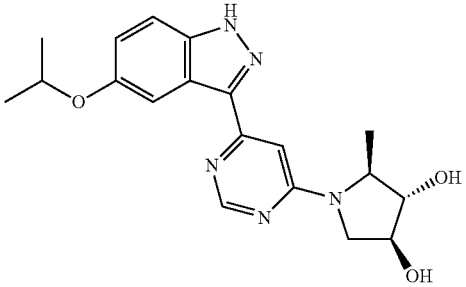 [SMILES: CC(C)Oc1ccc2[nH]nc(-c3cc(N4C[C@H](O)[C@@H](O)[C@@H]4C)ncn3)c2c1] | 18.13 | 370.1 | 0.91 | C3 |
| D43 | 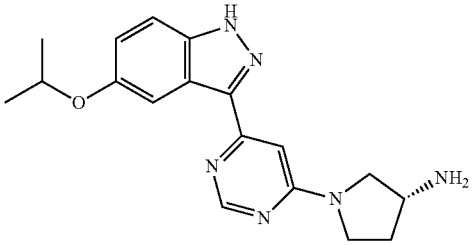 [SMILES: CC(C)Oc1ccc2[nH]nc(-c3cc(N4CC[C@@H](N)C4)ncn3)c2c1] | 8.78 | 339.2 | 0.82 | C3 |
| D44 | 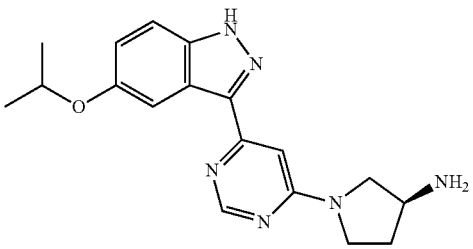 [SMILES: CC(C)Oc1ccc2[nH]nc(-c3cc(N4CC[C@H](N)C4)ncn3)c2c1] | 6.68 | 339.2 | 0.82 | C3 |
| D45 | 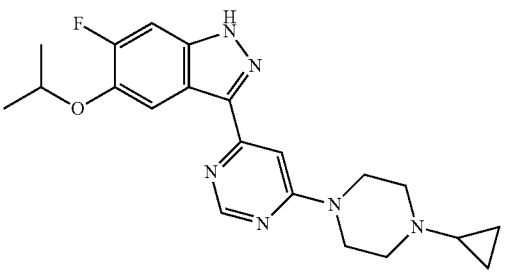 [SMILES: CC(C)Oc1cc2c(-c3cc(N4CCN(C5CC5)CC4)ncn3)n[nH]c2cc1F] | 3.99 | 397.2 | 1.24 | C6 |
| D46 | 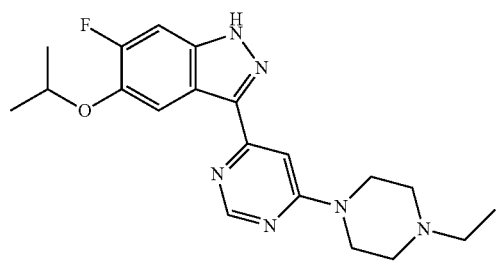 [SMILES: CCN1CCN(c2cc(-c3n[nH]c4cc(F)c(OC(C)C)cc34)ncn2)CC1] | 2.97 | 385.2 | 1.45 | C4 |

TABLE D-continued

| Example | Structure | LRRK2 IC$_{50}$ (nM) | m/z | RT (min) | Method |
|---|---|---|---|---|---|
| D47 | 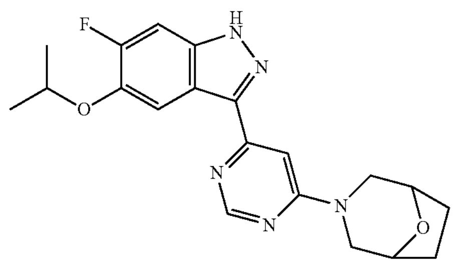 [SMILES: CC(C)Oc1cc2c(-c3cc(N4CC5CCC(C4)O5)ncn3)n[nH]c2cc1F] | 14.58 | 384.2 | 1.68 | C4 |
| D48 | 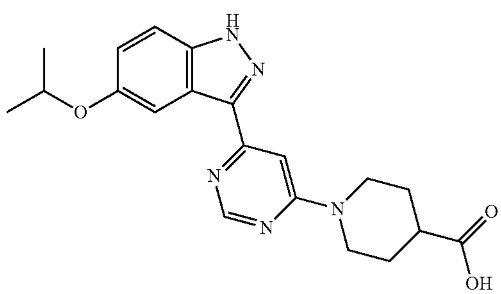 [SMILES: CC(C)Oc1ccc2[nH]nc(-c3cc(N4CCC(C(=O)O)CC4)ncn3)c2c1] | 4.45 | 396.1 | 1.06 | A |
| D49 | 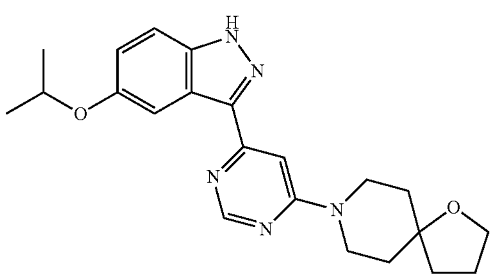 [SMILES: CC(C)Oc1ccc2[nH]nc(-c3cc(N4CCC5(CCCO5)CC4)ncn3)c2c1] | 4.13 | 394.2 | 1.07 | A |
| D50 | 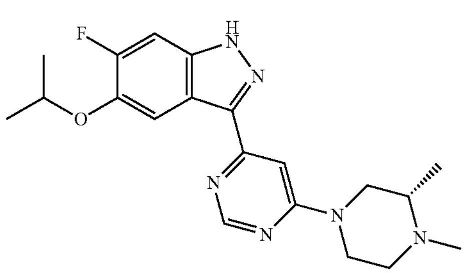 [SMILES: CC(C)Oc1cc2c(-c3cc(N4CCN(C)[C@@H](C)C4)ncn3)n[nH]c2cc1F] | 1.2 | 385.2 | 1.88 | C2 |
| D51 | 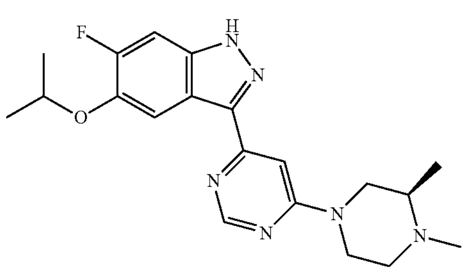 [SMILES: CC(C)Oc1cc2c(-c3cc(N4CCN(C)[C@H](C)C4)ncn3)n[nH]c2cc1F] | 1.3 | 385.2 | 1.88 | C2 |

TABLE D-continued

| Example | Structure | LRRK2 IC₅₀ (nM) | LCMS data m/z | RT (min) | Method |
|---|---|---|---|---|---|
| D52 | 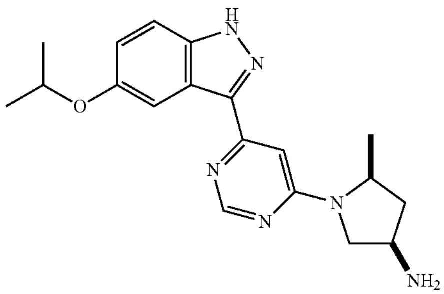 [SMILES: CC(C)Oc1ccc2[nH]nc(-c3cc(N4C[C@H](N)C[C@@H]4C)ncn3)c2c1] | 11.1 | 353.2 | 1.67 | C2 |
| D53 | 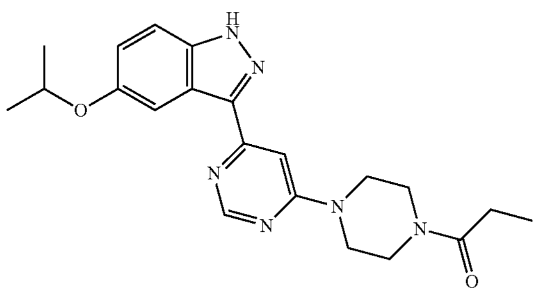 [SMILES: CCC(=O)N1CCN(c2cc(-c3n[nH]c4ccc(OC(C)C)cc34)ncn2)CC1] | 4.26 | 395.2 | 1.29 | C6 |
| D54 | 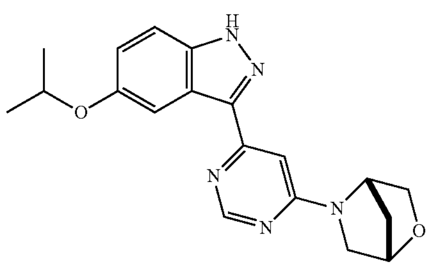 | 5.94 | 352.3 | 1.74 | C2 |
| D55 | 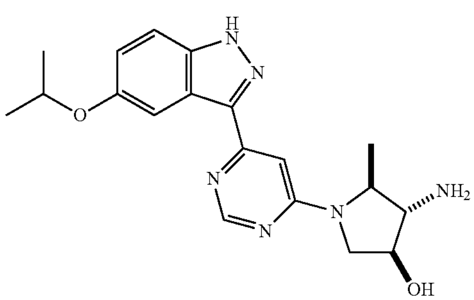 [SMILES: CC(C)Oc1ccc2[nH]nc(-c3cc(N4C[C@H](O)[C@@H](N)[C@@H]4C)ncn3)c2c1] | 14.4 | 369.2 | 1.57 | C2 |
| D56 | 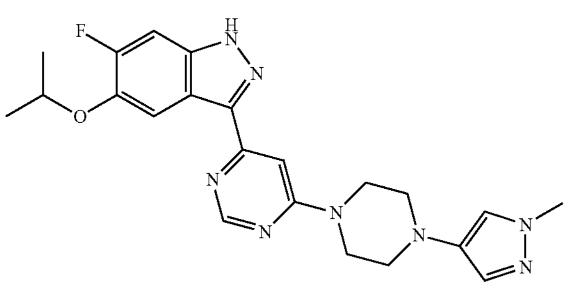 [SMILES: CC(C)Oc1cc2c(-c3cc(N4CCN(c5cnn(C)c5)CC4)ncn3)n[nH]c2cc1F] | 2.19 | 437.3 | 1.81 | C2 |

TABLE D-continued

| Example | Structure | LRRK2 IC$_{50}$ (nM) | m/z | RT (min) | Method |
|---|---|---|---|---|---|
| D57 | 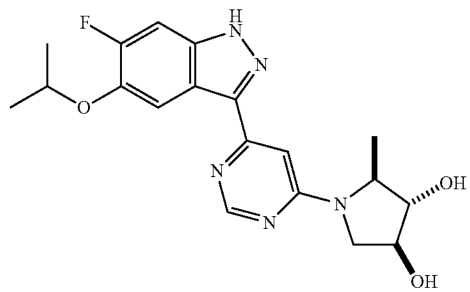 [SMILES: CC(C)Oc1cc2c(-c3cc(N4C[C@H](O)[C@@H](O)[C@@H]4C)ncn3)n[nH]c2cc1F] | 15.5 | 388.3 | 1.61 | C2 |
| D58 | 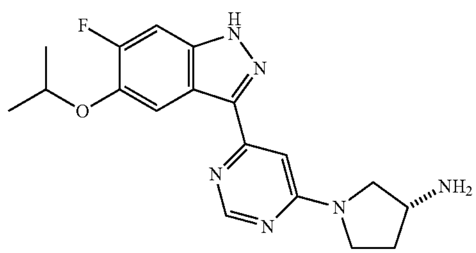 [SMILES: CC(C)Oc1cc2c(-c3cc(N4CC[C@@H](N)C4)ncn3)n[nH]c2cc1F] | 7.3 | 357.2 | 1.61 | C2 |
| D59 | 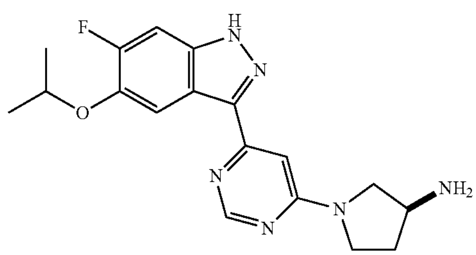 [SMILES: CC(C)Oc1cc2c(-c3cc(N4CC[C@H](N)C4)ncn3)n[nH]c2cc1F] | 10.4 | 357.2 | 1.60 | C2 |
| D60 | 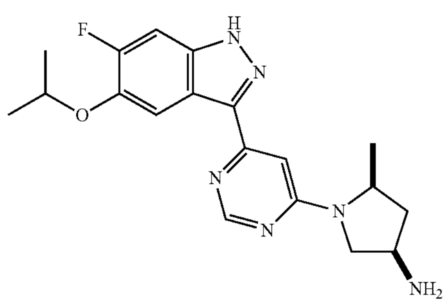 [SMILES: CC(C)Oc1cc2c(-c3cc(N4C[C@H](N)C[C@@H]4C)ncn3)n[nH]c2cc1F] | 7.6 | 371.2 | 1.67 | C2 |
| D61 | 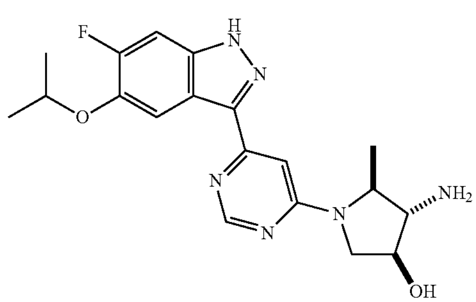 [SMILES: CC(C)Oc1cc2c(-c3cc(N4C[C@H](O)[C@@H](N)[C@@H]4C)ncn3)n[nH]c2cc1F] | 11.7 | 387.2 | 1.58 | C2 |

TABLE D-continued

| Example | Structure | LRRK2 IC$_{50}$ (nM) | m/z | RT (min) | Method |
|---|---|---|---|---|---|
| D62 | 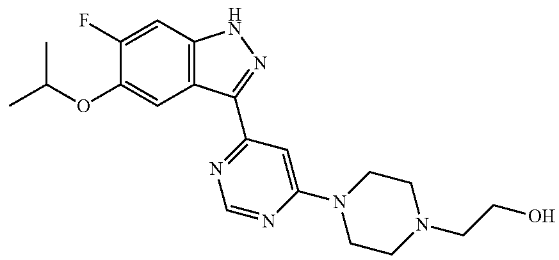 [SMILES: CC(C)Oc1cc2c(-c3cc(N4CCN(CCO)CC4)ncn3)n[nH]c2cc1F] | 1.65 | 401.3 | 1.68 | C2 |
| D63 | 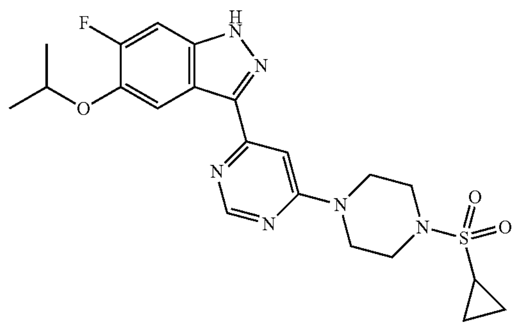 [SMILES: CC(C)Oc1cc2c(-c3cc(N4CCN(S(=O)(=O)C5CC5)CC4)ncn3)n[nH]c2cc1F] | 4.17 | 461.2 | 1.89 | C2 |
| D64 | 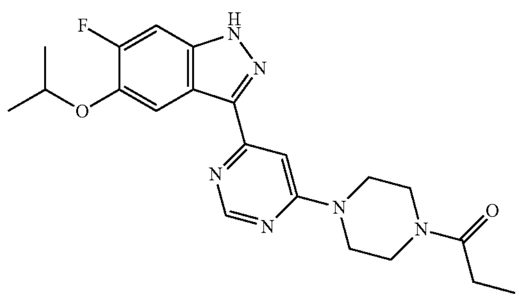 [SMILES: CCC(=O)N1CCN(c2cc(-c3n[nH]c4cc(F)c(OC(C)C)cc34)ncn2)CC1] | 4.32 | 413.2 | 1.80 | C2 |
| D65 | 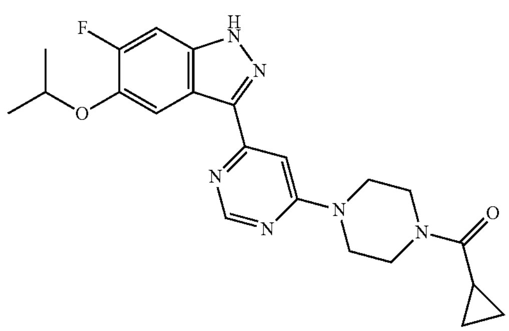 [SMILES: CC(C)Oc1cc2c(-c3cc(N4CCN(C(=O)C5CC5)CC4)ncn3)n[nH]c2cc1F] | 2.98 | 425.2 | 1.83 | C2 |
| D66 | 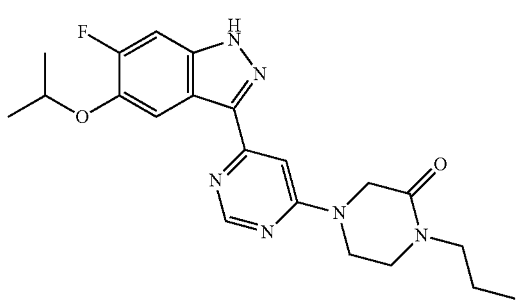 [SMILES: CCCN1CCN(c2cc(-c3n[nH]c4cc(F)c(OC(C)C)cc34)ncn2)CC1=O] | 2.77 | 413.2 | 1.82 | C2 |

TABLE D-continued

| Example | Structure | LRRK2 IC$_{50}$ (nM) | LCMS data m/z | RT (min) | Method |
|---|---|---|---|---|---|
| D67 | 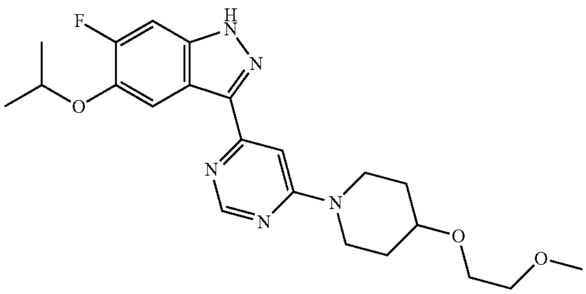 [SMILES: COCCOC1CCN(c2cc(-c3n[nH]c4cc(F)c(OC(C)C)cc34)ncn2)CC1] | 2.1 | 430.3 | 1.91 | C2 |
| D68 | 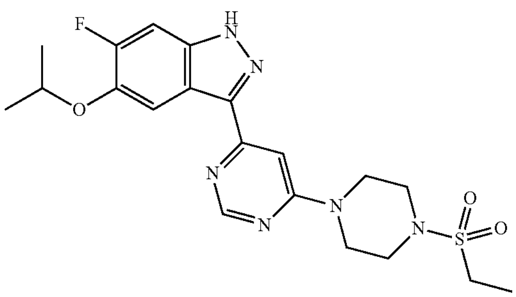 [SMILES: CCS(=O)(=O)N1CCN(c2cc(-c3n[nH]c4cc(F)c(OC(C)C)cc34)ncn2)CC1] | 2.24 | 449.2 | 1.86 | C2 |
| D69 | 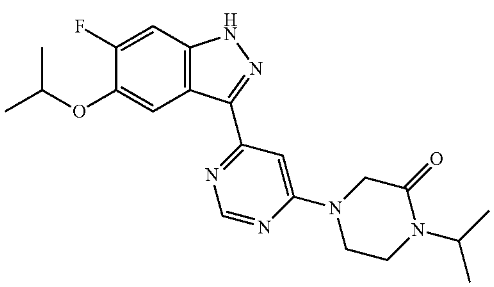 [SMILES: CC(C)Oc1cc2c(-c3cc(N4CCN(C(C)C)C(=O)C4)ncn3)n[nH]c2cc1F] | 3.09 | 413.3 | 1.84 | C2 |
| D70 | 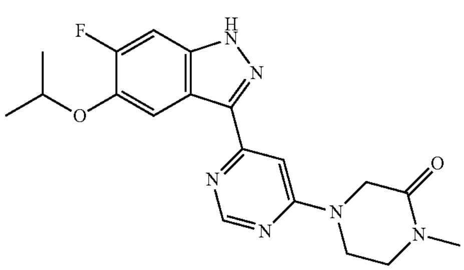 [SMILES: CC(C)Oc1cc2c(-c3cc(N4CCN(C)C(=O)C4)ncn3)n[nH]c2cc1F] | 2.19 | 385.2 | 1.72 | C2 |
| D71 | 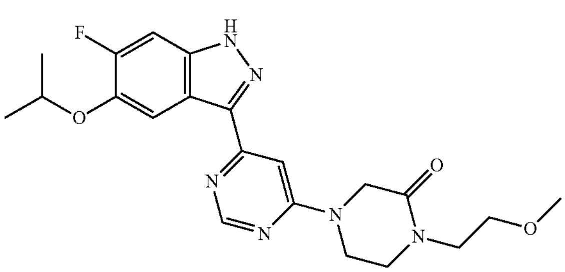 [SMILES: COCCN1CCN(c2cc(-c3n[nH]c4cc(F)c(OC(C)C)cc34)ncn2)CC1=O] | 1.63 | 429.2 | 1.75 | C2 |

TABLE D-continued
| Example | Structure | LRRK2 IC$_{50}$ (nM) | LCMS data m/z | RT (min) | Method |
|---|---|---|---|---|---|
| D72 | 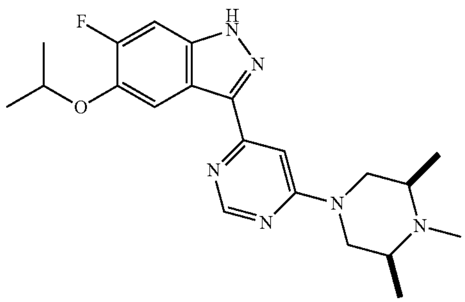 [SMILES: CC(C)Oc1cc2c(-c3cc(N4C[C@@H](C)N(C)[C@@H](C)C4)ncn3)n[nH]c2cc1F] | 1.33 | 399.1 | 1.20 | C6 |
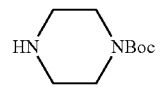
(D18)
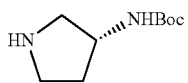
(D43, D58)
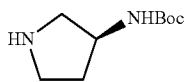
(D44, D59)
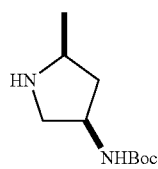
(D52, D60)
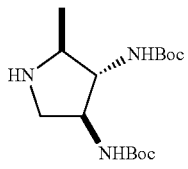
(D55, D61)
Examples D18, D43, D44, D52, D55, D58, D59, D60 and D61 the amines were protected with a Boc group which was removed during the final SEM deprotection.
Scheme E:
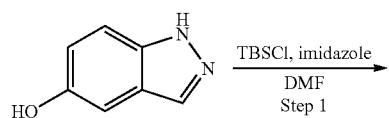
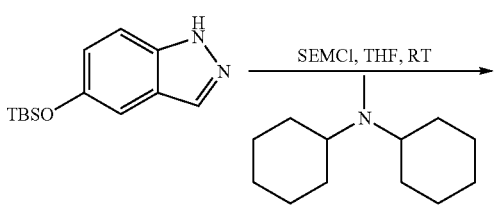
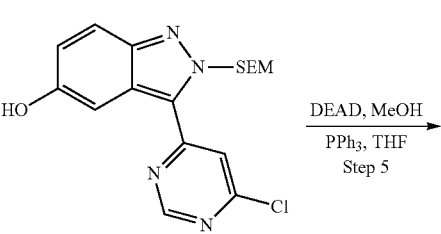

-continued

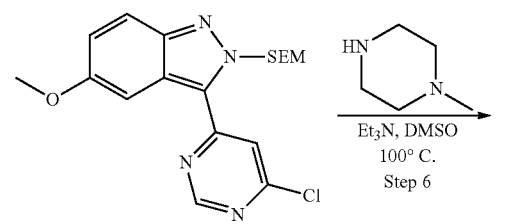

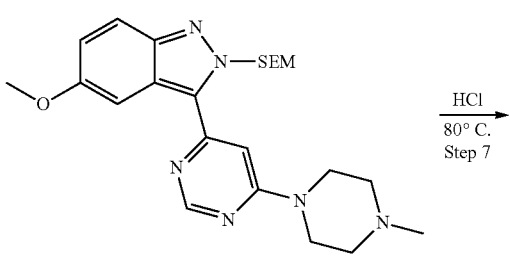

Example
E1

Step 1: To an ice-cooled mixture of 5-hydroxyindazole (516 g, 400 mmol) and imidazole (40.8 g, 600 mmol) in DMF (1 L) was added TBSCl (72 g, 480 mmol) over a period of 30 min. The ice-bath was removed and the reaction was stirred overnight. Water (1 L) was added to the reaction slowly and the resulting mixture was extracted with EtOAc (2×500 mL). The combined organic layers were washed with water (2×500 mL) and brine (500 mL), dried over $Na_2SO_4$, filtered, and evaporated under reduced pressure to afford a residue which was purified by flash chromatography on silica gel (gradient elution with 6:1 to 2:1 petroleum ether:EtOAc) to afford the silyl ether: MS (ESI): m/z=249.1 [M+1]$^+$.

Step 2: To a solution of above compound (92 g, 371 mmol) and N,N-dicyclohexyl methylamine (86.8 g, 445 mmol) in THF (600 mL) was slowly added SEMCl (681 g, 408 mmol). The resulting mixture was stirred at room temperature overnight and then filtered. The filtrate was concentrated in vacuo to give a residue which was purified by flash chromatography on silica gel (gradient elution with 60:1 to 10:1 petroleum ether:EtOAc) to afford the SEM protected indazole: MS (ESI) m/z=379 [M+1]$^+$.

Step 3: To a cold (−78° C.), stirred solution of SEM-protected indazole (60 g, 159 mmol) in THF (480 mL) was added n-BuLi (218 mL of 1.6M in hexane, 349 mmol) dropwise under $N_2$. The mixture was stirred for 2 h at −78° C. and then $ZnCl_2$ (280 mL of 1M solution in diethyl ether, 279 mmol) was added dropwise. After being stirred at −78° C. for additional 1 h, the cooling bath was removed and the mixture was allowed to warm to room temperature. A degassed solution of 4,6-dichloropyrimidine (21 g, 173 mmol) and $(Ph_3P)_4$Pd (9.1 g, 7.9 mmol) in THF (120 mL) was then added under $N_2$. The reaction was stirred at room temperature overnight and then concentrated in vacuo to leave a residue which was purified by flash chromatography on silica gel (gradient elution with 100:1 to 60:1 petroleum ether:EtOAc) to yield the chloropyrimidine. MS (ESI) m/z=491.1 [M]$^+$.

Step 4: The chloropyrimidine prepared above (28 g, 57 mmol) and TBAF (22.4 g, 86 mmol) were mixed in THF (300 mL) and stirred at room temperature for 2 h. The THF was evaporated under reduced pressure and the residue was purified by flash chromatography on silica gel (gradient elution with 3:1 to 1:1 petroleum ether:EtOAc) to yield the hydroxyindazole. MS (ESI) m/z=377.1 [M+1]$^+$.

Step 5: To a stirred mixture of $PPh_3$ (1.67 g, 6.4 mmol), MeOH (204 mg, 6.4 mmol) and the hydroxyindazole prepared above (2.0 g, 5.3 mmol) in THF (20 mL) was added DEAD (1.11 g, 6.4 mmol) dropwise under $N_2$. The resulting mixture was stirred at room temperature overnight. The solvent was removed under reduced pressure and the residue was purified with flash chromatography on silica gel (gradient elution with 50:1 to 5:1 petroleum ether:EtOAc) to afford the desired 5-methoxyindazole as a yellow oil. MS (ESI) m/z=391.1 [M+1]$^+$.

Step 6: The chloropyrimidine from step 5 (50 mg, 0.13 mmol), 1-methylpiperazine (38 mg, 0.39 mmol) and $Et_3N$ (78 mg, 0.78 mmol) were taken up into DMSO (2 mL). The reaction was stirred at 100° C. overnight. Water (50 ml) was added, and the resulting mixture was extracted with EA (3×20 mL). The combined organic layers were dried over $Na_2SO_4$, filtered and evaporated under vacuum to yield the crude product which was directly taken to the next step without further purification. MS (ESI) m/z=455.2 [M+1]$^+$.

Step 7: A solution of amine-adduct from step 6 (57 mg, 0.13 mmol) in MeOH (5 mL) was added a solution HCl in dioxane (0.5 mL of 3.5M solution in dioxane). The reaction was stirred at 60° C. for 0.5 h, and then concentrated under reduced pressure. Water (3 mL) was added followed by the addition of an aqueous solution of $NaHCO_3$. The resulting layer was extracted with EtOAc (3×15 mL). The combined organic layers were dried over $Na_2SO_4$, filtered and concentrated under vacuum to yield a residue which was purified by reverse phase chromatography (Analogix 55 g C18 column, gradient elution 0% to 100% MeCN in water w/0.1% TFA) to provide Example E1. MS (ESI) m/z=325.2 [M+1]$^+$ (ret. time=1.60 min, condition C2)

TABLE E

Examples E2-E13 were synthesized following the procedure described in Scheme E.

| Example | Structure | LRRK2 IC$_{50}$ (nM) | m/z | RT (min) | Method |
|---|---|---|---|---|---|
| E2 | | 68.6 | 332.1 | 1.68 | C1 |
| E3 | | 29.3 | 340.2 | 1.80 | C1 |
| E4 | | 35.4 | 389.1 | 1.63 | C1 |
| E5 | | 74.5 | 353.2 | 1.54 | C2 |
| E6 | | 148.2 | 338.2 | 1.71 | C1 |

TABLE E-continued
Examples E2-E13 were synthesized following the procedure described in Scheme E.
| Example | Structure | LRRK2 IC$_{50}$ (nM) | m/z | RT (min) | Method |
|---|---|---|---|---|---|
| E7 | 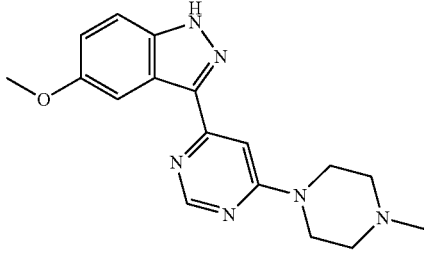 | 28.2 | 325.2 | 1.60 | C2 |
| E8 | 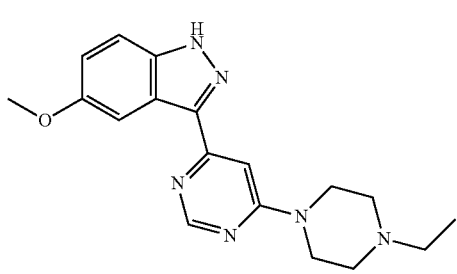 [SMILES: CCN1CCN(c2cc(-c3n[nH]c4ccc(OC)cc34)ncn2)CC1] | 24.3 | 339.2 | 1.68 | C2 |
| E9 | 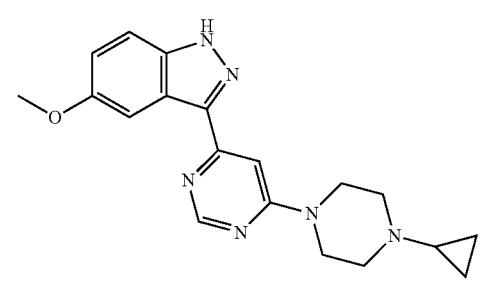 [SMILES: COc1ccc2[nH]nc(-c3cc(N4CCN(C5CC5)CC4)ncn3)c2c1] | 25.9 | 351.2 | 1.76 | C2 |
| E10 | 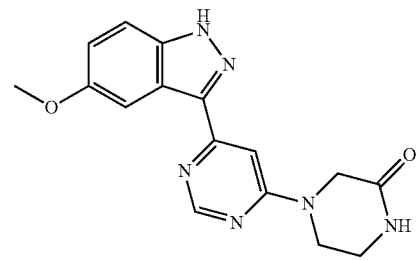 [SMILES: COc1ccc2[nH]nc(-c3cc(N4CCNC(=O)C4)ncn3)c2c1] | 100.9 | 325.2 | 1.50 | C2 |
| E11 | 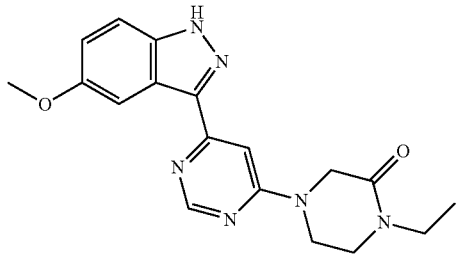 [SMILES: CCN1CCN(c2cc(-c3n[nH]c4ccc(OC)cc34)ncn2)CC1=O] | 78.3 | 353.1 | 1.61 | C1 |

TABLE E-continued

Examples E2-E13 were synthesized following the procedure described in Scheme E.

| Example | Structure | LRRK2 IC$_{50}$ (nM) | LCMS data m/z | RT (min) | Method |
|---|---|---|---|---|---|
| E12 | 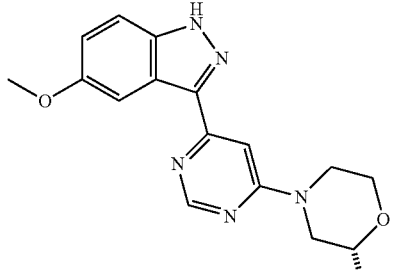 | 28.5 | 326.1 | 1.74 | C1 |
| E13 | 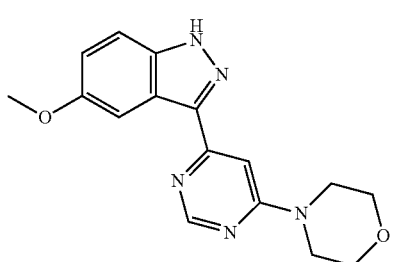 | 76.9 | 326.0 | 1.73 | C1 |

Scheme F:

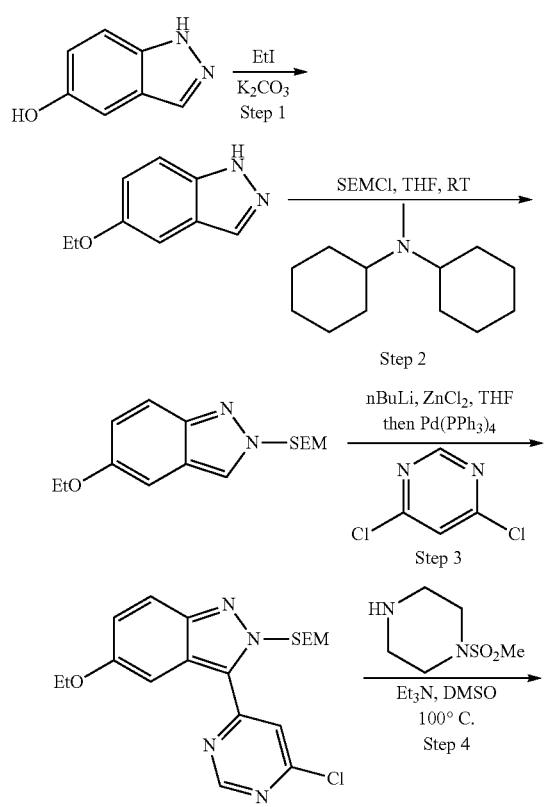

Step 1: A mixture of 5-hydroxyindazole (10 g, 75 mmol), ethyl iodide (12.8 g, 82 mmol) and K$_2$CO$_3$ (20.6 g, 149 mmol) in DMF (100 mL) was heated at 60° C. for 16 h. The reaction was cooled to room temperature and diluted with water (200 mL) and then extracted with EtOAc (3×200 mL). The combined organic layers were washed with water (3×300 mL) and brine (300 mL), dried over Na$_2$SO$_4$, filtered and concentrated under vacuum to leave a residue which was purified by column chromatography on silica gel (elution with 50:1 petroleum ether:EtOAc) to yield the ethoxyindazole. MS (ESI) m/z=163.0 [M+1]$^+$.

Step 2: To a solution of above ethoxyindazole (8.0 g, 49 mmol) and N,N-dicyclohexylmethylamine (12.5 g, 64 mmol) in THF (100 mL) was slowly added SEMCl (9.9 g, 59 mmol). The resulting mixture was stirred at room temperature overnight and then filtered. The filtrate was concentrated under reduced pressure to yield a residue which was purified by column chromatography on silica gel (gradient elution with 60:1-40:1 petroleum ether:EtOAc) to afford the desired SEM-protected indazole. MS (ESI) m/z=293.0 [M+1]$^+$.

Step 3: n-BuLi (1.6 M in hexane, 4.7 mL, 7.5 mmol) was added dropwise into a solution of SEM-protected indazole (2 g, 6.8 mmol) in THF (50 mL) under $N_2$ at −78° C. The mixture was stirred for 2 h at −78° C. followed by the dropwise addition of $ZnCl_2$ (7.2 mL of 1M solution in $Et_2O$, 7.2 mmol). After being stirred at −78° C. for 1 h the cooling bath was removed and the mixture was allowed to warm to room temperature. A degassed solution of 4,6-dichloropyrimidine (1.12 g, 7.5 mmol) and $(Ph_3P)_4Pd$ (395 mg, 0.34 mmol) in THF (5 mL) was then added under $N_2$. The reaction was stirred at room temperature overnight and then concentrated under reduced pressure to leave a residue which was dissolved in EtOAc (200 mL) and filtered. The filtrate was concentrated under reduced pressure to leave a residue which was purified by column chromatography on silica gel (gradient elution with 30:1 to 20:1 petroleum ether:EtOAc) to yield the chloropyrimidine. MS (ESI) m/z=405.1 [M]$^+$.

Step 4: A mixture of the chloropyrimidine (50 mg, 0.12 mmol), 1-(methylsulfonyl)piperazine (122 mg, 0.742 mmol), and $Et_3N$ (150 mg, 1.48 mmol) in DMSO (2 mL) was heated at 110° C. in a sealed tube for 16 h. After that time, the reaction was cooled to room temperature and diluted with water (10 mL). The resulting layer was then extracted with EtOAc (3×30 mL). The combined organic layers were washed with water (2×45 mL) and brine (45 mL), dried over $MgSO_4$, filtered and concentrated under vacuum to leave a residue which was purified by column chromatography on silica gel (eluted with 20:1 petroleum ether:EtOAc) to yield the piperazine adduct. MS (ESI) m/z=533.2 [M+1]$^+$.

Step 5: To a stirred solution of the above piperazine adduct (55 mg, 0.1 mmol) in methanol (4 mL) was added HCl (1 mL of 3M solution in MeOH, 3.0 mmol). The mixture was heated at 70° C. for 2 h. After cooling to room temperature, the pH of the resulting mixture was adjusted to 7-8 using $NaHCO_3$. The mixture was filtered and the filtrate was concentrated under reduced pressure to leave a residue which was purified by column chromatography on silica gel (elution with 10:1 EtOAc:MeOH) to yield Example F1. MS (ESI) m/z=403.1 [M+1]$^+$.

TABLE F

Examples F2-F10 were prepared from the chloropyrimidine product from Step 3 Scheme F using the requisite amine following procedures similar to those desribed in steps 4 and 5 of Scheme F.

| Example | Structure | LRRK2 IC$_{50}$ (nM) | LCMS data m/z | RT (min) | Method |
|---|---|---|---|---|---|
| F1 | 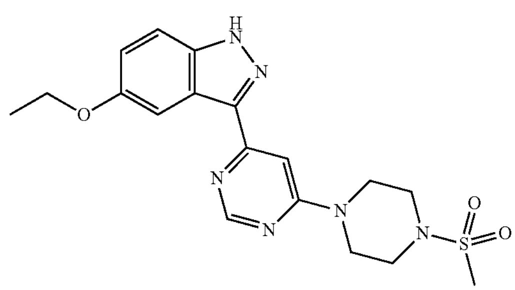 [SMILES: CCOc1ccc2[nH]nc(-c3cc(N4CCN(S(C)(=O)=O)CC4)ncn3)c2c1] | 15.38 | 403.1 | 1.74 | C2 |
| F2 | 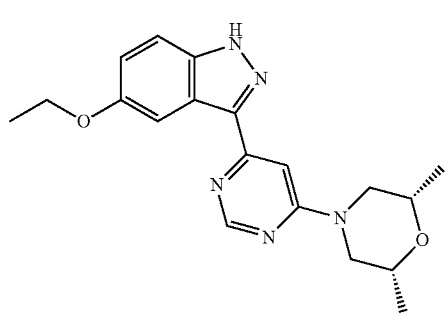 [SMILES: CCOc1ccc2[nH]nc(-c3cc(N4C[C@@H](C)O[C@@H](C)C4)ncn3)c2c1] | 12.75 | 354.2 | 1.94 | C2 |

TABLE F-continued

Examples F2-F10 were prepared from the chloropyrimidine product from Step 3 Scheme F using the requisite amine following procedures similar to those desribed in steps 4 and 5 of Scheme F.

| Example | Structure | LRRK2 IC$_{50}$ (nM) | m/z | RT (min) | Method |
|---|---|---|---|---|---|
| F3 | 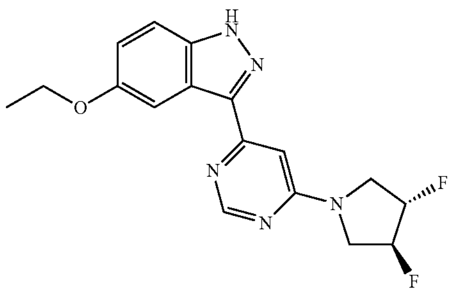 [SMILES: CCOc1ccc2[nH]nc(-c3cc(N4C[C@H](F)[C@@H](F)C4)ncn3)c2c1] | 26.56 | 346.1 | 1.80 | C2 |
| F4 | 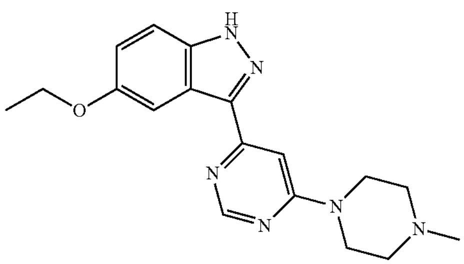 [SMILES: CCOc1ccc2[nH]nc(-c3cc(N4CCN(C)CC4)ncn3)c2c1] | 26.91 | 339.2 | 1.72 | C2 |
| F5 | 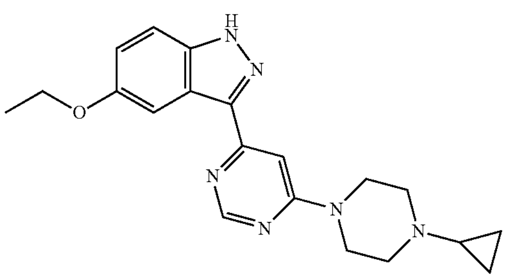 [SMILES: CCOc1ccc2[nH]nc(-c3cc(N4CCN(C5CC5)CC4)ncn3)c2c1] | 16.68 | 365.2 | 2.13 | C2 |
| F6 | 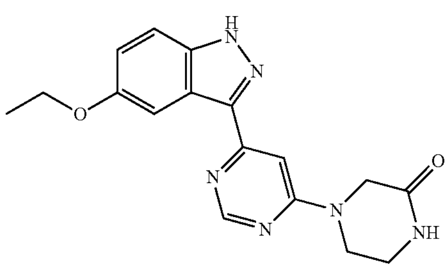 [SMILES: CCOc1ccc2[nH]nc(-c3cc(N4CCNC(=O)C4)ncn3)c2c1] | 63.85 | 339.2 | 1.58 | C2 |
| F7 | 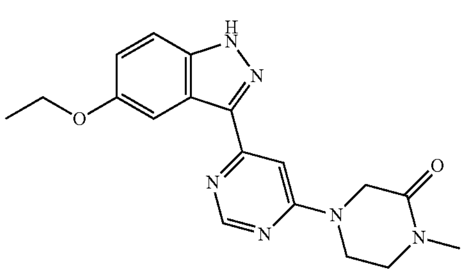 [SMILES: CCOc1ccc2[nH]nc(-c3cc(N4CCN(C)C(=O)C4)ncn3)c2c1] | 37.13 | 353.2 | 1.62 | C2 |

TABLE F-continued

Examples F2-F10 were prepared from the chloropyrimidine product from Step 3 Scheme F using the requisite amine following procedures similar to those desribed in steps 4 and 5 of Scheme F.

| Example | Structure | LRRK2 IC$_{50}$ (nM) | LCMS data m/z | RT (min) | Method |
|---|---|---|---|---|---|
| F8 | 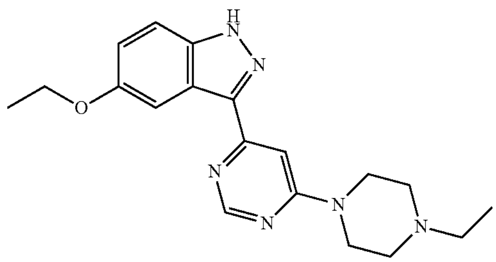 [SMILES: CCOc1ccc2[nH]nc(-c3cc(N4CCN(CC)CC4)ncn3)c2c1] | 12.57 | 353.2 | 1.79 | C2 |
| F9 | 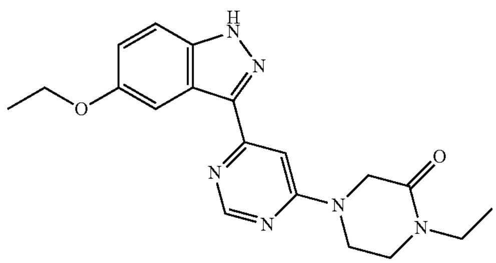 [SMILES: CCOc1ccc2[nH]nc(-c3cc(N4CCN(CC)C(=O)C4)ncn3)c2c1] | 16.7 | 367.3 | 1.68 | C2 |
| F10 | 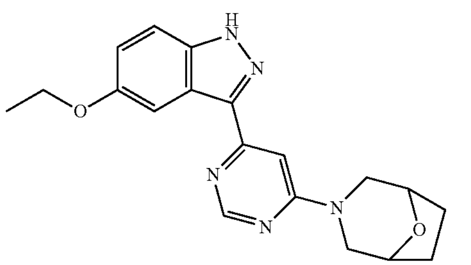 [SMILES: CCOc1ccc2[nH]nc(-c3cc(N4CC5CCC(C4)O5)ncn3)c2c1] | 32.69 | 352.3 | 1.83 | C2 |
| F11 | 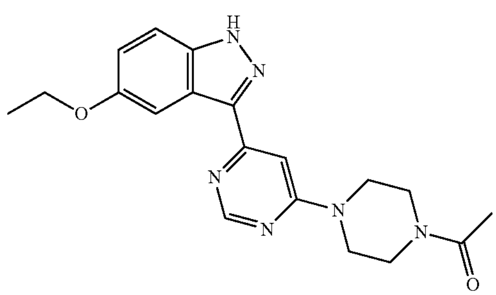 [SMILES: CCOc1ccc2[nH]nc(-c3cc(N4CCN(C(C)=O)CC4)ncn3)c2c1] | 18 | 367.3 | 1.64 | C2 |
| F12 | 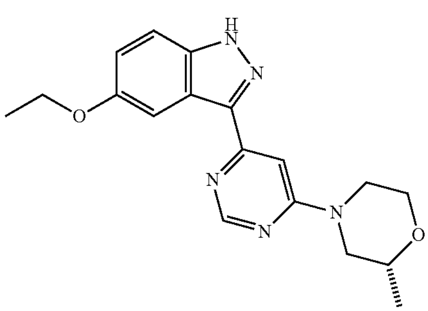 [SMILES: CCOc1ccc2[nH]nc(-c3cc(N4CCO[C@H](C)C4)ncn3)c2c1] | 10.5 | 340.3 | 1.83 | C2 |

TABLE F-continued

Examples F2-F10 were prepared from the chloropyrimidine product from Step 3 Scheme F using the requisite amine following procedures similar to those desribed in steps 4 and 5 of Scheme F.

| Example | Structure | LRRK2 IC$_{50}$ (nM) | LCMS data m/z | RT (min) | Method |
|---|---|---|---|---|---|
| F13 | 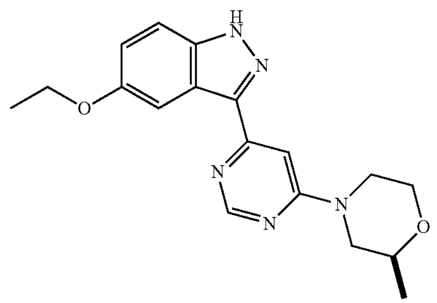 [SMILES: CCOc1ccc2[nH]nc(-c3cc(N4CCO[C@@H](C)C4)ncn3)c2c1] | 41.2 | 340.3 | 1.81 | C2 |

Scheme G:

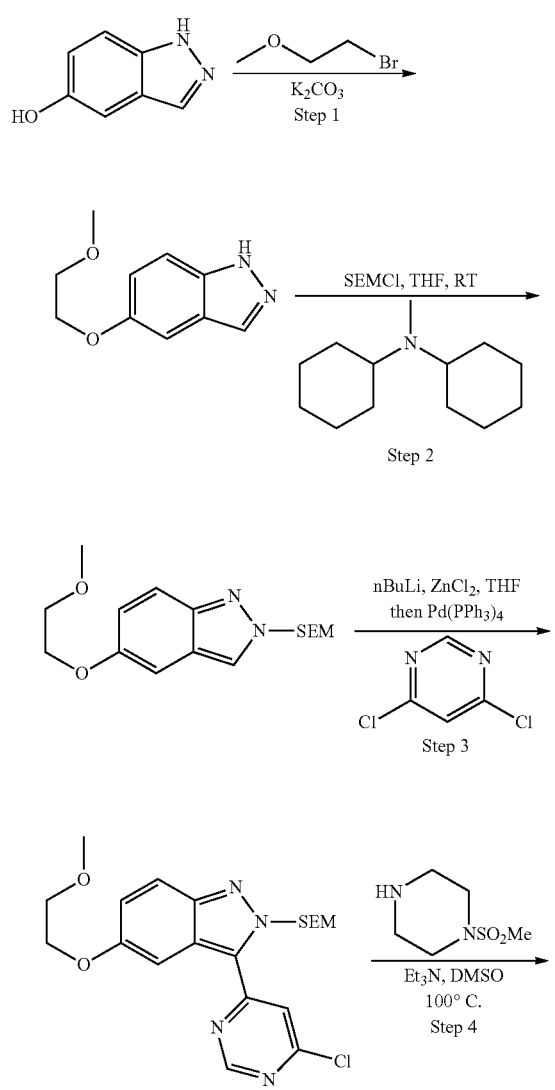

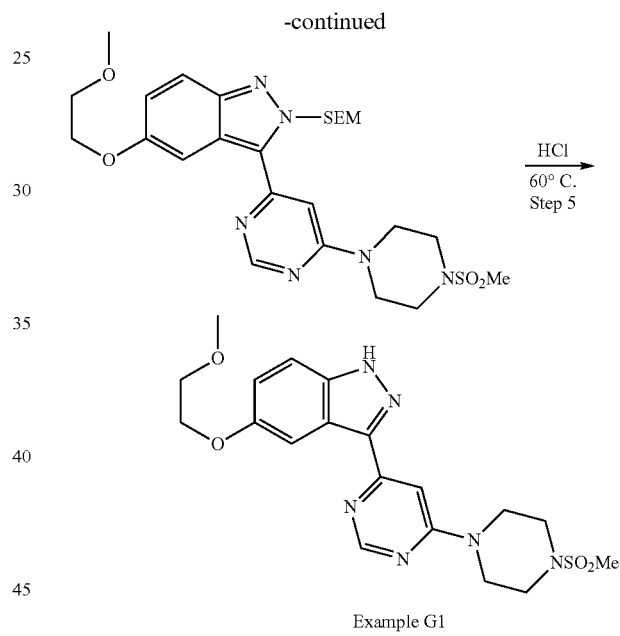

Example G1

Step 1: A mixture of 5-hydroxyindazole (10 g, 75 mmol), 1-bromo-2-methoxyethane (11.4 g, 82 mmol) and K$_2$CO$_3$ (20.6 g, 149 mmol) in DMF (100 mL) was heated at 60° C. for 16 h. The reaction was cooled to room temperature and diluted with water (200 mL) and then extracted with EtOAc (3×200 mL). The combined organic layers were washed with water (3×300 mL) and brine (300 mL), dried over Na$_2$SO$_4$, filtered and concentrated under vacuum to leave a residue which was purified by column chromatography on silica gel (elution with 50:1 petroleum ether:EtOAc) to yield the ether. MS (ESI) m/z=193.0 [M+1]$^+$.

Step 2: To a solution of the indazole (10 g, 52 mmol) and N,N-dicyclohexylmethylamine (13.2 g, 68 mmol) in THF (150 mL) was slowly added SEMCl (10.4 g, 62 mmol). The resulting mixture was stirred at room temperature overnight and then filtered. The filtrate was concentrated in vacuo to leave a residue which was purified by column chromatography on silica gel (gradient elution with 60:1 to 40:1 petroleum ether:EtOAc) to afford the desired SEM-protected indazole. MS (ESI) m/z=323.1 [M+1]$^+$.

Step 3: n-BuLi (1.6 M in hexane, 7.2 mL, 11.5 mmol) was added dropwise into a solution of SEM-protected indazole (2 g, 6.2 mmol) in THF (50 mL) under $N_2$ at −78° C. The mixture was stirred for 2 h at −78° C. and then $ZnCl_2$ (11 mL of 1M solution in $Et_2O$, 10.9 mmol) was added dropwise. The reaction was stirred at −78° C. for 1 h at which time, the cooling bath was removed. The mixture was allowed to warm to room temperature. A degassed solution of 4,6-dichloropyrimidine (1.7 g, 11.5 mmol) and $(Ph_3P)_4Pd$ (601 mg, 0.52 mmol) in THF (5 mL) was then added under $N_2$. The reaction was stirred at room temperature overnight and then concentrated in vacuo. The residue was washed thoroughly with EtOAc (200 mL) and filtered. The filtrate was concentrated under reduced pressure to leave a residue which was purified by column chromatography on silica gel (gradient elution with 30:1 to 20:1 petroleum ether:EtOAc) to afford the desired chloropyrimidine. MS (ESI) m/z=435.1 $[M]^+$.

Step 4: The mixture of chloropyrimidine (50 mg, 0.11 mmol), 1-(methylsulfonyl)piperazine (113 mg, 0.689 mmol), and $Et_3N$ (139 mg, 1.38 mmol) in DMSO (2 mL) was heated at 110° C. in a sealed tube for 16 hours. The reaction was cooled to room temperature and diluted with water (10 mL). The mixture was then extracted with EtOAc (3×30 mL), The combined organic layers were washed with water (2×45 mL) and brine (45 mL), dried over $MgSO_4$, filtered and concentrated under vacuum to leave a residue which was purified by column chromatography on silica gel (elution with 20:1 petroleum ether:EtOAc) to afford the piperizine-adduct. MS (ESI) m/z=563.2 $[M+1]^+$.

Step 5: To a stirred solution of the above indazole (45 mg, 0.08 mmol) in methanol (4 mL) was added a solution of hydrochloric acid in methanol (1 mL, 3 M, 3.0 mmol). The mixture was heated at 70° C. for 2 h. After cooling to room temperature, the pH of the resulting mixture was adjusted to 7-8 using $NaHCO_3$. The mixture was filtered and the filtrate was evaporated and purified with a silica gel chromatography column (eluted with EtOAc/MeOH=10/1) to yield Example G1.

TABLE G

Examples G2-G13 were prepared from the chloropyrimidine from Step 3 Scheme G using the requisite amine following procedures similar to those described in steps 4 and 5.

| Example | Structure | LRRK2 IC$_{50}$ (nM) | LCMS data m/z | RT (min) | Method |
|---|---|---|---|---|---|
| G1 | 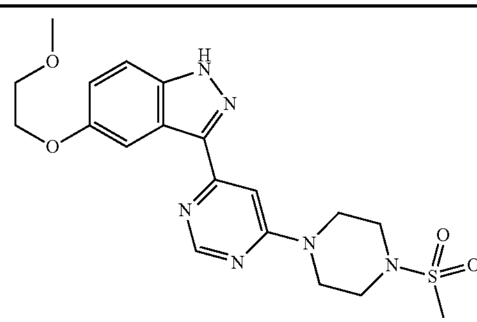 | 64.73 | 432.5 | 1.62 | C2 |
| G2 | 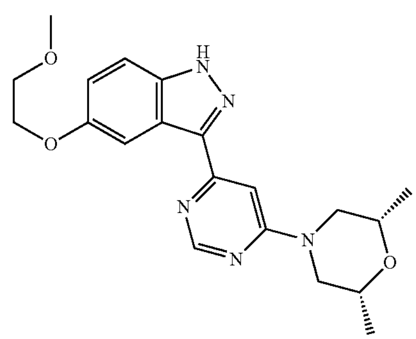 [SMILES: COCCOc1ccc2[nH]nc(-c3cc(N4C[C@@H](C)O[C@@H](C)C4)ncn3)c2c1] | 76.57 | 384.2 | 1.80 | C2 |
| G3 | 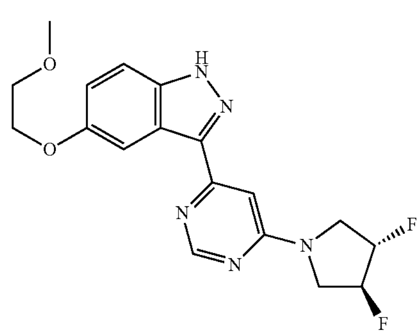 [SMILES: COCCOc1ccc2[nH]nc(-c3cc(N4C[C@H](F)[C@@H](F)C4)ncn3)c2c1] | 138.5 | 376.2 | 1.67 | C2 |

TABLE G-continued

Examples G2-G13 were prepared from the chloropyrimidine from Step 3 Scheme G using the requisite amine following procedures similar to those described in steps 4 and 5.

| Example | Structure | LRRK2 IC$_{50}$ (nM) | LCMS data m/z | RT (min) | Method |
|---|---|---|---|---|---|
| G4 | | 67.21 | 369.2 | 1.59 | C2 |
| G5 | | 97.04 | 395.3 | 1.80 | C2 |
| G6 | | 135.6 | 369.2 | 1.46 | C2 |
| G7 | | 69.01 | 383.3 | 1.50 | C2 |
| G8 | | 96.99 | 383.3 | 1.66 | C2 |

TABLE G-continued

Examples G2-G13 were prepared from the chloropyrimidine from Step 3 Scheme G using the requisite amine following procedures similar to those described in steps 4 and 5.

| Example | Structure | LRRK2 IC$_{50}$ (nM) | LCMS data m/z | RT (min) | Method |
|---|---|---|---|---|---|
| G9 | | 107.3 | 397.3 | 1.56 | C2 |
| G10 | | 42.84 | 370.2 | 1.69 | C2 |
| G11 | | 100.7 | 370.2 | 1.67 | C2 |
| G12 | | 154 | 382.3 | 1.69 | C2 |

TABLE G-continued

Examples G2-G13 were prepared from the chloropyrimidine from Step 3 Scheme G using the requisite amine following procedures similar to those described in steps 4 and 5.

| Example | Structure | LRRK2 IC$_{50}$ (nM) | m/z | RT (min) | Method |
|---|---|---|---|---|---|
| G13 | 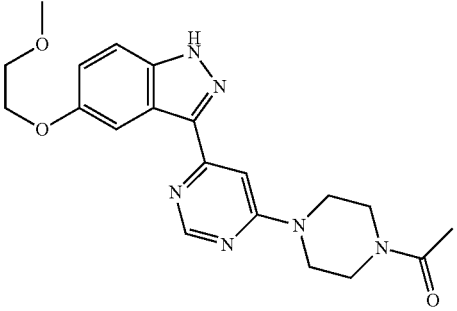 [SMILES: COCCOc1ccc2[nH]nc(-c3cc(N4CCN(C(C)=O)CC4)ncn3)c2c1] | 127.5 | 397.3 | 1.53 | C2 |

Scheme H:

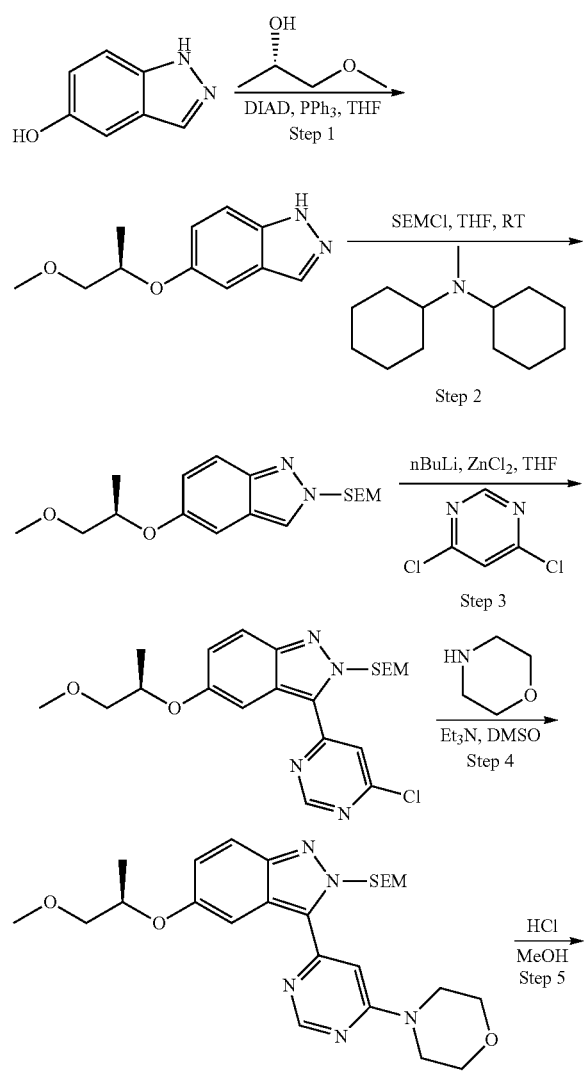

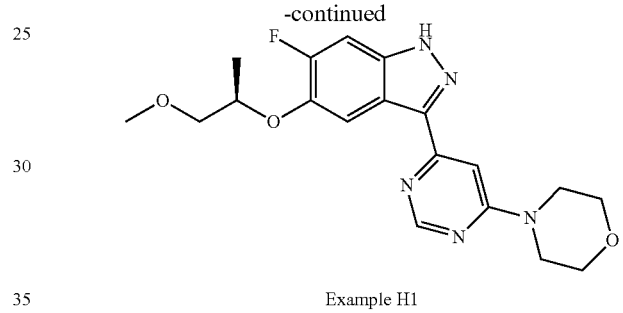

Example H1

Step 1: To a stirred mixture of 5-hydroxyindazole (4.0 g, 29.8 mmol), (S)-(+)-1-methoxy-2-propanol (3.2 g, 35.8 mmol) and PPh$_3$ (11.73 g, 44.7 mmol) in THF (50 ml) at room temperature was added DIAD (8.78 ml, 44.7 mmol) under N$_2$. The resulting mixture was stirred at room temperature overnight. The mixture was diluted with EtOAc, washed with water, dried over MgSO$_4$ and concentrated under vacuum to leave a residue which was purified by flash column chromatography (SiO$_2$; gradient elution with 4:1 to 1:1 hexane:EtOAc) to afford the desired ether. LCMS 207.17 [M+1].

Step 2: To a stirred solution of above ether (4.68 g, 22.69 mmol) in THF (50 ml) was added N,N-dicyclohexylmethylamine (6.32 ml, 29.5 mmol) followed by SEMCl (4.80 ml, 27.2 mmol) at room temperature. The mixture was stirred at room temperature under N$_2$ overnight. The mixture was filtered and the solid was washed with EtOAc. The filtrate was concentrated under vacuum to leave a residue which was purified by flash column chromatography (SiO$_2$; gradient elution 100:0 to 7:1 hexane:EtOAc) to afford the desired SEM-protected indazole. LCMS 337.2 [M+1].

Step 3: To a cold (−78° C.), stirred solution of SEM-protected indazole (0.79 g, 2.35 mmol) in THF (8 ml) was added n-BuLi (1.03 ml of 2.5 M solution in hexane, 2.58 mmol). After the addition was complete, the mixture was stirred at −78° C. for 20 min and then the temperature was raised to −20° C. for 5 min. The mixture was cooled to −78° C. when a freshly prepared solution of ZnCl$_2$ (5.16 ml of 0.5 M solution in THF, 2.58 mmol) was added. The mixture was then raised to −20° C. and stirred for 10 min at −20° C. when a mixture of 4,6-dichloropyrimidine (0.39 g, 2.58 mmol) and Pd(PPh$_3$)$_4$ (0.27 g, 0.24 mmol) was added. The cold bath was removed and the mixture was stirred at room temperature overnight. The mixture was diluted with EtOAc, washed with a saturated aqueous solution of NaHCO$_3$ and water, dried over MgSO$_4$, filtered and concentrated under vacuum to leave a residue which was purified by flash column chromatography (SiO$_2$; gradient elution with 100:1 to 5:1 hexane:EtOAc in hexane) to afford the desired chloropyrimidine. LCMS 449.1 [M+1].

Step 4: A mixture of chloropyrimidine (150 mg, 0.334 mmol), morpholine (0.088 ml, 1.002 mmol) and Et$_3$N (0.279 ml, 2.004 mmol) in DMSO (3 ml) was heated at 100° C. in a sealed tube overnight. The mixture was cooled to room temperature, diluted with EtOAc, washed with water and brine, dried over MgSO$_4$, filtered, and concentrated under vacuum to yield the morpholine adduct which was used in the next step without further purification. LCMS 500.21 [M+1].

Step 5: The morpholine adduct from Step 4 was dissolved in MeOH (3 ml) followed by the addition of HCl (3.20 ml of 4.0M solution in 1,4-dioxane, 12.81 mmol). The mixture was heated at 65° C. for 1 h. The mixture was diluted with EtOAc, washed with a saturated aqueous solution of NaHCO$_3$. The organic layer was dried over MgSO$_4$, filtered and concentrated under vacuum to leave a residue which was purified by flash chromatography (SiO$_2$; gradient elution with 2:1 to 0:100 hexane:EtOAc) to afford Example H1.

TABLE H

Examples H2-H17 were prepared from the chloropyrimidine from Step 3 Scheme H using the requisite amine following procedures similar to those described in steps 4 and 5.

| Example | Structure | LRRK2 IC$_{50}$ (nM) | m/z | RT (min) | Method |
|---|---|---|---|---|---|
| H1 | 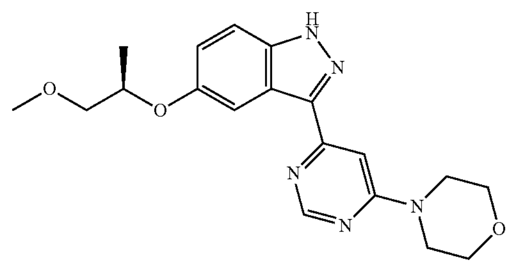 [SMILES: COC[C@@H](C)Oc1ccc2[nH]nc(-c3cc(N4CCOCC4)ncn3)c2c1] | 56.2 | 370.2 | 0.97 | A |
| H2 | 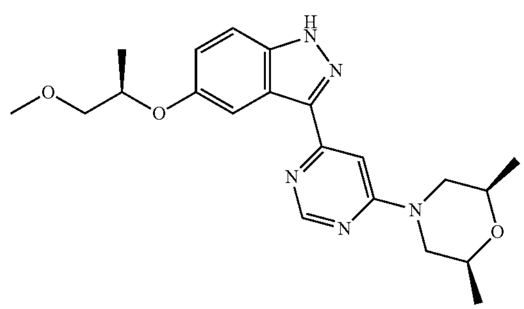 | 39.12 | 398.2 | 1.02 | A |
| H3 | 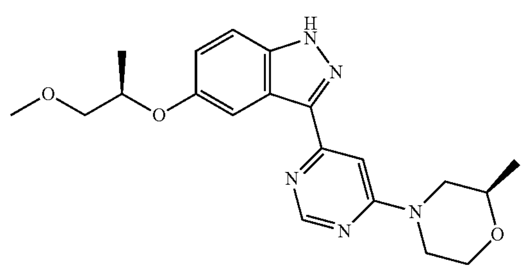 | 35.5 | 384.2 | 1.0 | A |
| H4 | 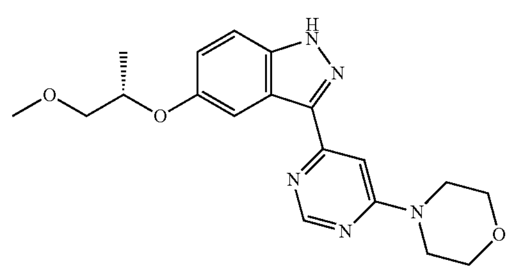 [SMILES: COC[C@H](C)Oc1ccc2[nH]nc(-c3cc(N4CCOCC4)ncn3)c2c1] | 2.6 | 370.1 | 0.97 | A |

TABLE H-continued

Examples H2-H17 were prepared from the chloropyrimidine from Step 3 Scheme H using the requisite amine following procedures similar to those described in steps 4 and 5.

| Example | Structure | LRRK2 IC$_{50}$ (nM) | m/z | RT (min) | Method |
|---------|-----------|----------------------|-----|----------|--------|
| H5 | 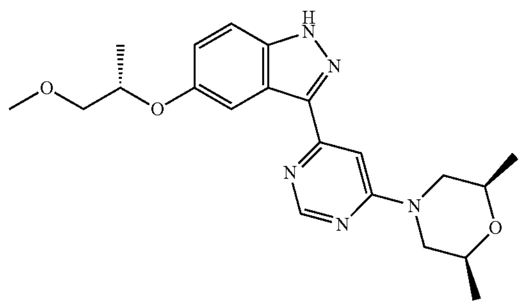 | 1.70 | 398.1 | 1.03 | A |
| H6 | 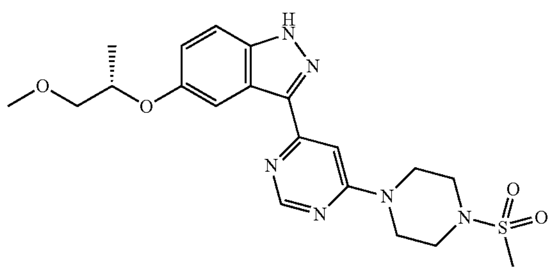 [SMILES: COC[C@H](C)Oc1ccc2[nH]nc(-c3cc(N4CCN(S(C)(=O)=O)CC4)ncn3)c2c1] | 4.50 | 447.1 | 0.97 | A |
| H7 | 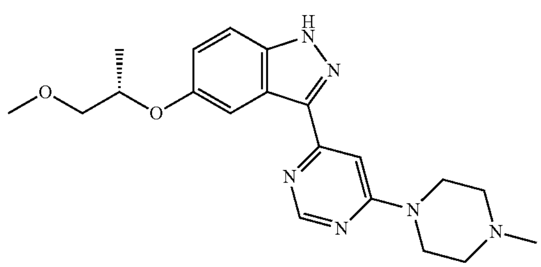 | 2.08 | 383.2 | 0.79 | A |
| H8 | 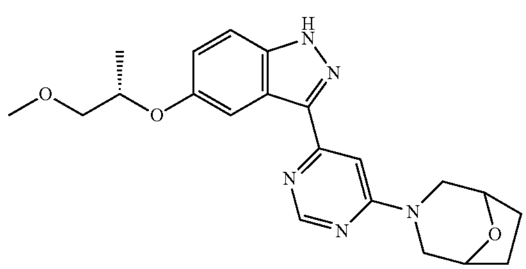 [SMILES: COC[C@H](C)Oc1ccc2[nH]nc(-c3cc(N4CC5CCC(C4)O5)ncn3)c2c1] | 9.93 | 396.1 | 0.99 | A |
| H9 | 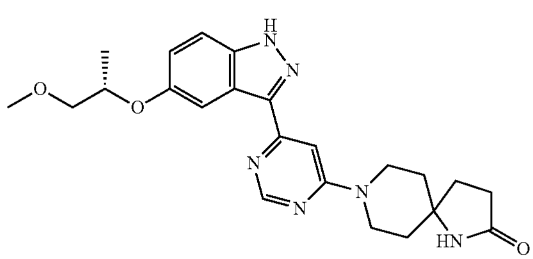 [SMILES: COC[C@H](C)Oc1ccc2[nH]nc(-c3cc(N4CCC5(CCC(=O)N5)CC4)ncn3)c2c1] | 4.36 | 437.3 | 0.98 | A |

TABLE H-continued

Examples H2-H17 were prepared from the chloropyrimidine from Step 3 Scheme H using the requisite amine following procedures similar to those described in steps 4 and 5.

| Example | Structure | LRRK2 IC$_{50}$ (nM) | m/z | RT (min) | Method |
|---|---|---|---|---|---|
| H10 | | 2.87 | 451.2 | 0.99 | A |
| H11 | | 2.85 | 437.3 | 0.97 | A |
| H12 | | 4.80 | 384.2 | 1.00 | A |
| H13 | | 5.27 | 384.2 | 0.99 | A |
| H14 | | 2.02 | 424.2 | 1.04 | A |

TABLE H-continued
Examples H2-H17 were prepared from the chloropyrimidine from Step 3 Scheme H using the requisite amine following procedures similar to those described in steps 4 and 5.
| Example | Structure | LRRK2 IC₅₀ (nM) | m/z | RT (min) | Method |
|---|---|---|---|---|---|
| H15 | 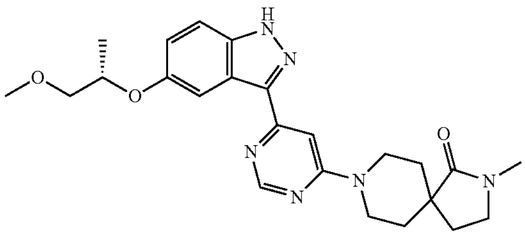 | 3.71 | 451.2 | 1.0 | A |
| H16 | 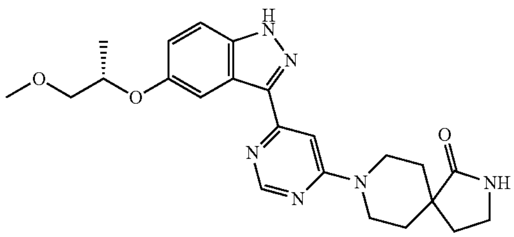 [SMILES: COC[C@H](C)Oc1ccc2[nH]nc(-c3cc(N4CCC5(CCNC5=O)CC4)ncn3)c2c1] | 2.83 | 437.2 | 0.98 | A |
| H17 | 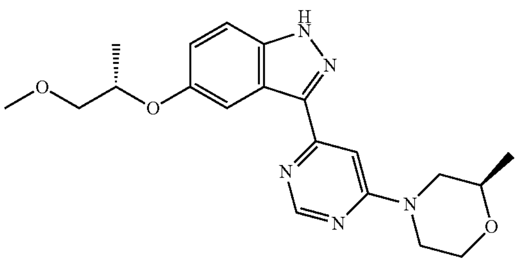 | 2.79 | 384.2 | 1.00 | A |
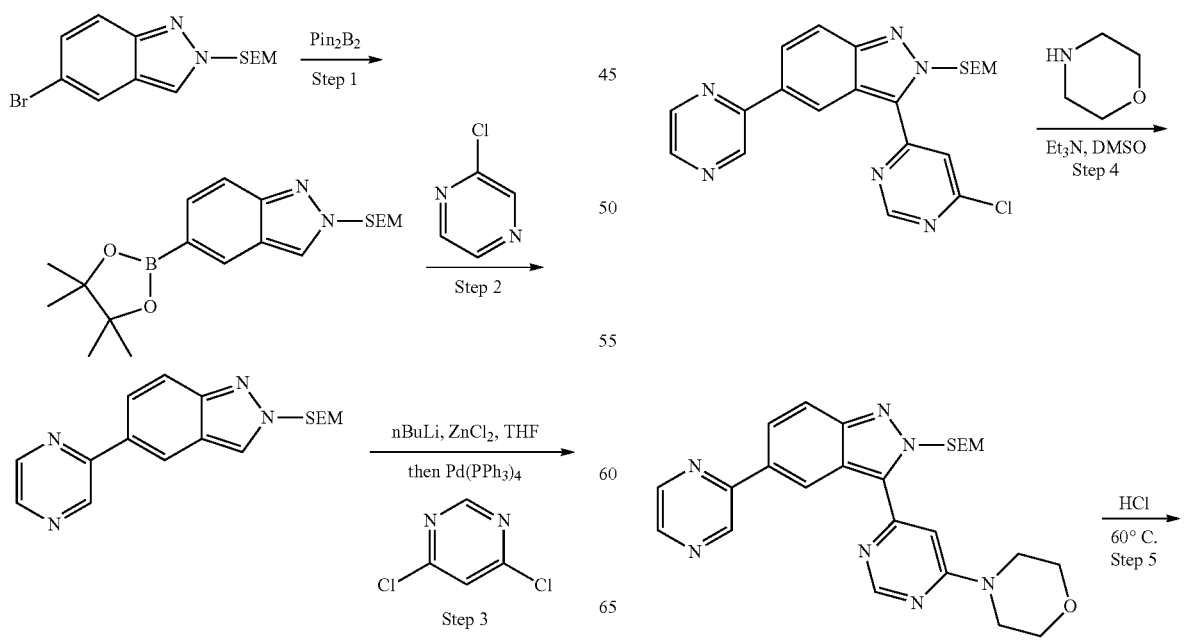
Scheme I:

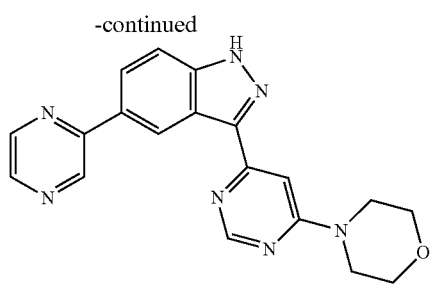

Example I1

Step 1: To a stirred solution of the bromoindazole (5.0 g, 15 mmol) in a mixed solvent of dioxane (100 mL) and water (10 mL) were added bis(pinacolato)diboron (4.26 g, 17 mmol), KOAc (3.0 g, 30 mmol), and [1,1'-Bis(diphenylphosphino)ferrocene]dichloropalladium(II) (1.12 g, 1.5 mmol). The flask was evacuated and recharged with argon gas, the reaction was then heated at reflux for 16 h. The reaction was cooled and filtered. The filtrate was evaporated to leave a residue which was purified by column chromatography on silica gel (elution with 30:1 petroleum ether:EtOAc) to yield the boronate ester. MS (ESI) m/z=375.2 [M+1]+.

Step 2: To a stirred solution of the boronate ester (2.5 g, 5.4 mmol) in a mixed solvent of dioxane (100 mL) and water (10 mL) were added 2-chloropyrazine (2.28 g, 20 mmol), $K_3PO_4$ (5.67 g, 27 mmol), and [1,1'-bis(diphenylphosphino)ferrocene]dichloropalladium(II) (1.0 g, 1.3 mmol). The flask was evacuated and recharged with argon, the reaction was then heated at reflux for 16 h. The reaction was cooled and filtered. The filtrate was evaporated to leave a residue which was purified by column chromatography on silica gel (elution with 40:1 petroleum ether:EtOAc) to yield the pyrazine adduct. MS (ES) m/z=327.2 [M+1]+.

Step 3: n-BuLi (1.6 M in hexane, 7.7 mL, 12.2 mmol) was added dropwise into a solution of SEM-protected indazole (950 mg, 2.9 mmol) in THF (20 mL) under $N_2$ at −78° C. The mixture was stirred for 2 h at −78° C. and then $ZnCl_2$ (6.4 mL of 1M solution in $Et_2O$, 6.4 mmol) was added dropwise. The reaction was stirred at −78° C. for 1 h and the cooling bath was removed for the mixture to warm to room temperature. A degassed solution of 4,6-dichloropyrimidine (1.1 g, 7.4 mmol) and $(Ph_3P)_4Pd$ (352 mg, 0.30 mmol) in THF (5 mL) was then added under $N_2$. The reaction was stirred at room temperature overnight and then concentrated in vacuo. The residue was washed thoroughly using EtOAc (200 mL) and filtered. The filtrate was concentrated under reduced pressure to leave a residue which was purified by column chromatography on silica gel (gradient elution with 30:1 to 5:1 petroleum ether:EtOAc) to yield the chloropyrimidine. MS (ESI) m/z=439.1 [M]+.

Step 4: A mixture of the chloropyrimidine (60 mg, 0.14 mmol), morpholine (30 mg, 0.33 mmol), and $Et_3N$ (70 mg, 0.66 mmol) in DMSO (2 mL) was heated at 110° C. in a sealed tube for 16 h. The reaction was cooled to room temperature and diluted with water (10 mL). The resulting layer was extracted with EtOAc (3×30 mL). The combined organic layers were washed with water (2×45 mL) and brine (45 mL), dried over $MgSO_4$, filtered and concentrated under vacuum to leave a residue which was purified by column chromatography on silica gel (elution with 30:1 petroleum ether:EtOAc) to yield the morpholine adduct. MS (ESI) m/z=490.1 [M+1]+.

Step 5: To a stirred solution of the above morpholine adduct (40 mg, 0.08 mmol) in methanol (4 mL) was added HCl (1 mL of 3M solution in MeOH, 3.0 mmol). The mixture was heated at 70° C. for 2 h. After cooling to room temperature the pH of the resulting mixture was adjusted to 7-8 using $NaHCO_3$. The mixture was filtered and the filtrate was concentrated under reduced pressure to leave a residue which was purified by column chromatography on silica gel (elution with 15:1 DCM:MeOH) to yield Example I1.

TABLE I

Examples I1-I2 were prepared using the procedures described in Scheme I.

| Example | Structure | LRRK2 $IC_{50}$ (nM) | LCMS data m/z | RT (min) | Method |
|---|---|---|---|---|---|
| I1 | 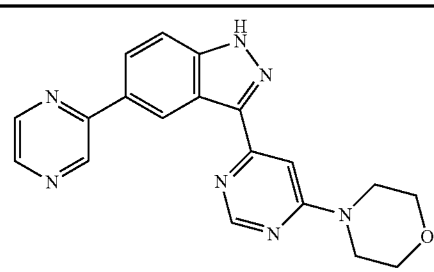 | 34.7 | 360.2 | 1.58 | C2 |
| I2 | 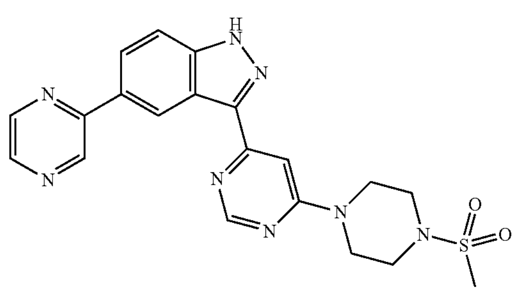 [SMILES: CS(=O)(=O)N1CCN(c2cc(-c3n[nH]c4ccc(-c5cnccn5)cc34)ncn2)CC1] | 19.2 | 437.1 | 1.58 | C2 |

Scheme J:

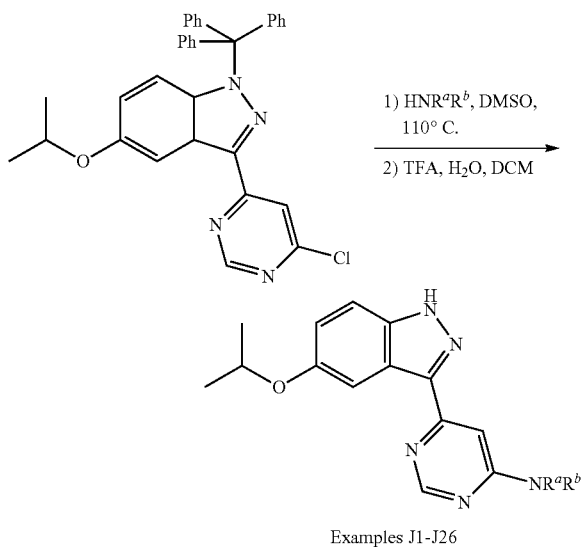

Examples J1-J26

Parallel preparation of examples J1-J26: To a set of 2-dram vials containing stir bars and the requisite amine (0.23 mmol) was added a slurry of the chloropyrimidine from Scheme C (30 mg, 0.056 mmol) in DMSO (0.3 mL) and diisopropylethylamine (0.049 mL, 0.28 mmol). The vials were capped and the mixtures were heated to 110° C. with stirring for 16 hours. The mixtures were cooled to RT. Water (2 mL) and DCM (2 mL) were added to each vial. The mixtures were transferred to a fritted barrel filter. The organic layers from the vials were drained into a new set of vials. Additional DCM (1 mL) was added to the aqueous layer and the layers were separated. The solvent from the combined organic layers was removed in vacuo (maximum temperature 40° C.). To each vial was then added DCM (1 mL) followed by TFA (0.50 mL) and water (0.050 mL). The vials were shaken at RT for 2 hours. The solvent was removed in vacuo. Each crude product was redissolved in 1 mL of DMSO and filtered. The crude products were purified by mass triggered HPLC. [Waters Sunfire C18 column, 5 μm, 19×100 mm, gradient range 5-10% initial to 25-50% final MeCN (0.1% formic acid) in water (0.1% formic acid) 50 mL/min, 8 min run time] to provide the examples J1-J26.

| Example | Structure | LCMS data m/z | RT (min) | Method | LRRK2 $IC_{50}$ (nM) |
|---|---|---|---|---|---|
| J1 | 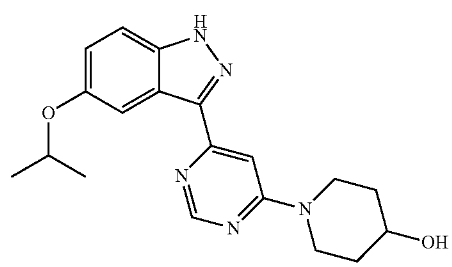 [SMILES: CC(C)Oc1ccc2[nH]nc(-c3cc(N4CCC(O)CC4)ncn3)c2c1] | 354.20 | 0.82 | D | 5.9 |
| J2 | 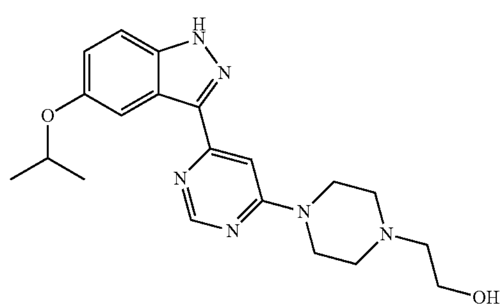 [SMILES: CC(C)Oc1ccc2[nH]nc(-c3cc(N4CCN(CCO)CC4)ncn3)c2c1] | 383.24 | 0.80 | D | 7.4 |
| J3 | 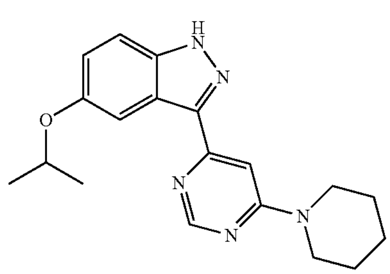 [SMILES: CC(C)Oc1ccc2[nH]nc(-c3cc(N4CCCCC4)ncn3)c2c1] | 338.21 | 1.10 | D | 10.6 |

-continued

| Example | Structure | LCMS data m/z | RT (min) | Method | LRRK2 IC$_{50}$ (nM) |
|---|---|---|---|---|---|
| J4 | 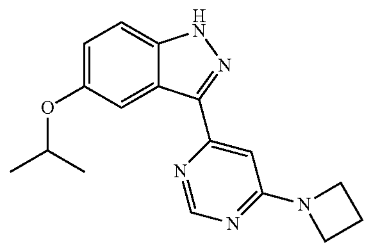 [SMILES: CC(C)Oc1ccc2[nH]nc(-c3cc(N4CCC4)ncn3)c2c1] | 310.21 | 0.88 | D | 7.9 |
| J5 | 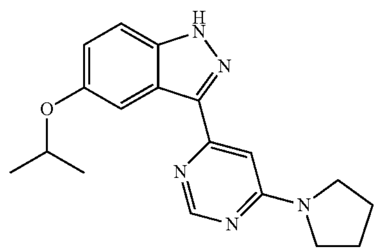 [SMILES: CC(C)Oc1ccc2[nH]nc(-c3cc(N4CCCC4)ncn3)c2c1] | 324.21 | 0.96 | D | 13.9 |
| J6 | 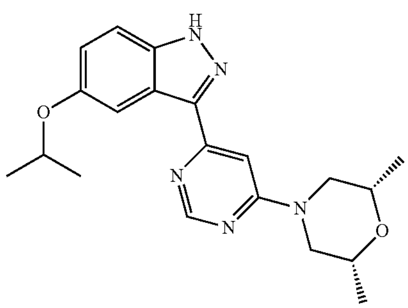 [SMILES: CC(C)Oc1ccc2[nH]nc(-c3cc(N4C[C@@H](C)O[C@@H](C)C4)ncn3)c2c1] | 368.23 | 1.07 | D | 7.8 |
| J7 | 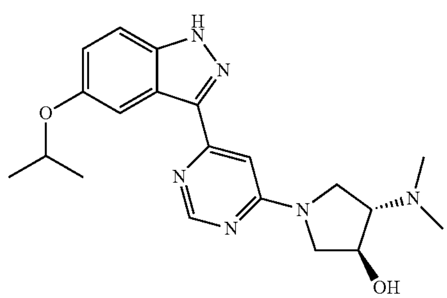 [SMILES: CC(C)Oc1ccc2[nH]nc(-c3cc(N4C[C@H](O)[C@@H](N(C)C)C4)ncn3)c2c1] | 383.23 | 0.76 | D | 15.3 |
| J8 | 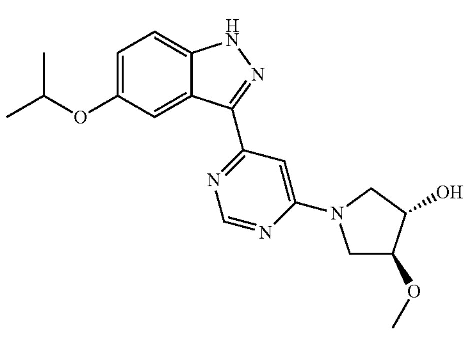 [SMILES: CO[C@H]1CN(c2cc(-c3n[nH]c4ccc(OC(C)C)cc34)ncn2)C[C@@H]1O] | 370.21 | 0.78 | D | 18.6 |

-continued

| Example | Structure | LCMS data m/z | RT (min) | Method | LRRK2 IC$_{50}$ (nM) |
|---|---|---|---|---|---|
| J9 | | 354.21 | 0.99 | D | 9.2 |
| J10 | | 360.19 | 0.96 | D | 11.1 |
| J11 | | 431.22 | 0.89 | D | 51.3 |
| J12 | | 376.20 | 0.87 | D | 22.6 |
| J13 | | 372.18 | 0.77 | D | 21.0 |

| Example | Structure | LCMS data m/z | RT (min) | Method | LRRK2 IC$_{50}$ (nM) |
|---|---|---|---|---|---|
| J14 | 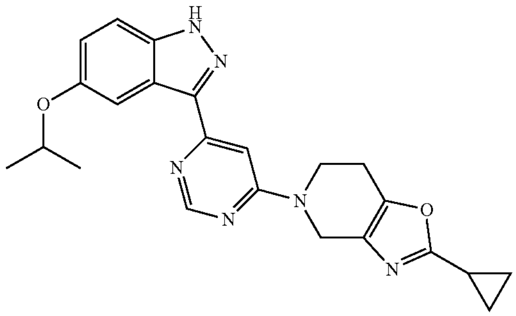 [SMILES: CC(C)Oc1ccc2[nH]nc(-c3cc(N4CCc5oc(C6CC6)nc5C4)ncn3)c2c1] | 417.23 | 1.09 | D | 30.1 |
| J15 | 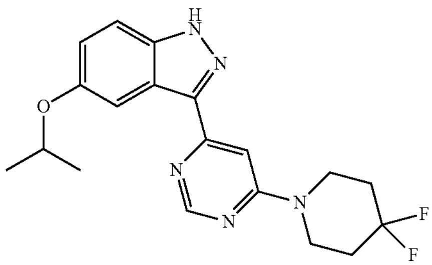 [SMILES: CC(C)Oc1ccc2[nH]nc(-c3cc(N4CCC(F)(F)CC4)ncn3)c2c1] | 374.20 | 1.09 | D | 20.2 |
| J16 | 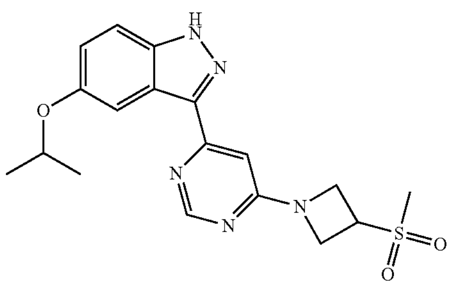 [SMILES: CC(C)Oc1ccc2[nH]nc(-c3cc(N4CC(S(C)(=O)=O)C4)ncn3)c2c1] | 388.18 | 0.78 | D | 13.3 |
| J17 | 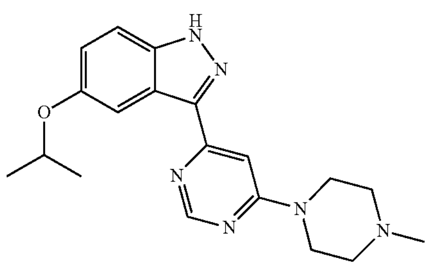 [SMILES: CC(C)Oc1ccc2[nH]nc(-c3cc(N4CCN(C)CC4)ncn3)c2c1] | 353.23 | 0.89 | D | 5.4 |
| J18 | 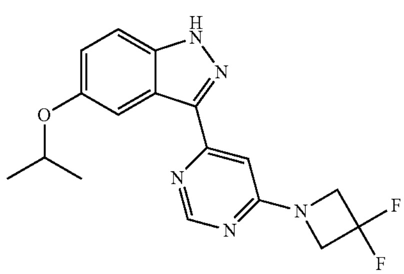 [SMILES: CC(C)Oc1ccc2[nH]nc(-c3cc(N4CC(F)(F)C4)ncn3)c2c1] | 346.17 | 0.98 | D | 24.3 |

| Example | Structure | LCMS data m/z | RT (min) | Method | LRRK2 IC$_{50}$ (nM) |
|---|---|---|---|---|---|
| J19 | 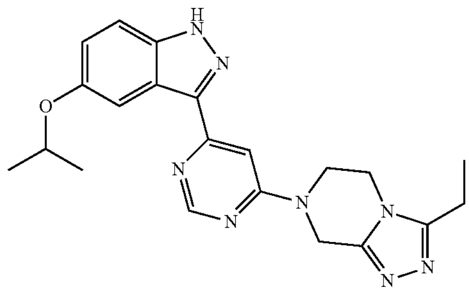 [SMILES: CCc1nnc2n1CCN(c1cc(-c3n[nH]c4ccc(OC(C)C)cc34)ncn1)C2] | 405.20 | 0.80 | D | 8.6 |
| J20 | 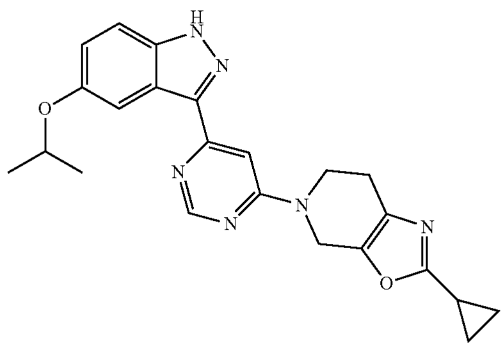 [SMILES: CC(C)Oc1ccc2[nH]nc(-c3cc(N4CCc5nc(C6CC6)oc5C4)ncn3)c2c1] | 417.23 | 1.08 | D | 43 |
| J21 | 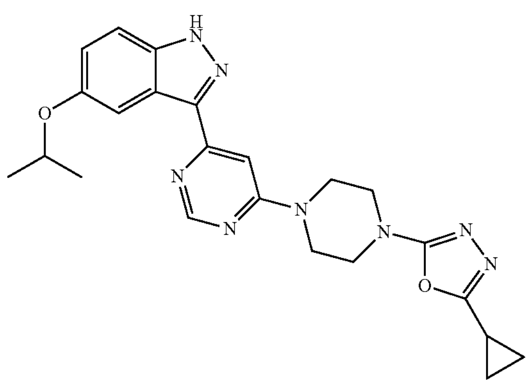 [SMILES: CC(C)Oc1ccc2[nH]nc(-c3cc(N4CCN(c5nnc(C6CC6)o5)CC4)ncn3)c2c1] | 447.29 | 0.96 | D | 14 |
| J22 | 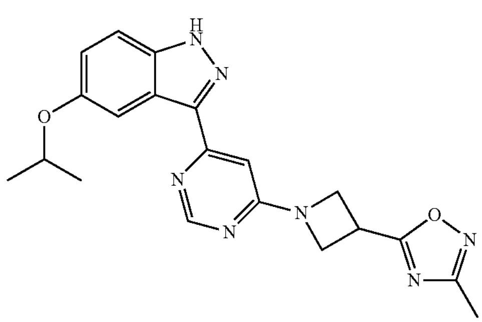 [SMILES: Cc1noc(C2CN(c3cc(-c4n[nH]c5ccc(OC(C)C)cc45)ncn3)C2)n1] | 392.21 | 0.89 | D | 9.3 |

-continued
| Example | Structure | LCMS data m/z | RT (min) | Method | LRRK2 IC$_{50}$ (nM) |
|---|---|---|---|---|---|
| J23 | 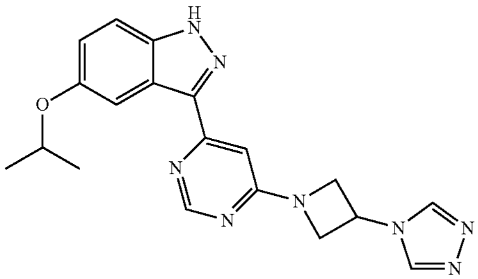 [SMILES: CC(C)Oc1ccc2[nH]nc(-c3cc(N4CC(n5cnnc5)C4)ncn3)c2c1] | 377.20 | 0.77 | D | 20.1 |
| J24 | 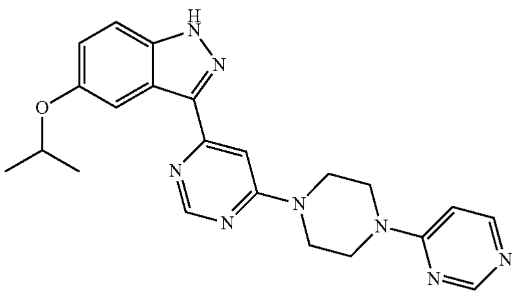 [SMILES: CC(C)Oc1ccc2[nH]nc(-c3cc(N4CCN(c5ccncn5)CC4)ncn3)c2c1] | 417.27 | 0.90 | D | 15.8 |
| J25 | 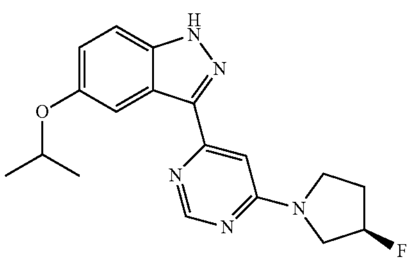 [SMILES: CC(C)Oc1ccc2[nH]nc(-c3cc(N4CC[C@@H](F)C4)ncn3)c2c1] | 342.19 | 0.92 | D | 8.7 |
| J26 | 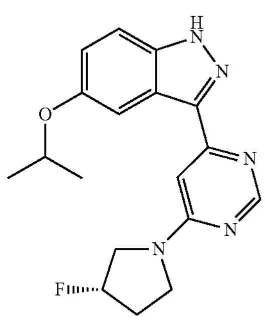 [SMILES: CC(C)Oc1ccc2[nH]nc(-c3cc(N4CC[C@H](F)C4)ncn3)c2c1] | 342.19 | 0.92 | D | 9.5 |
Scheme K:
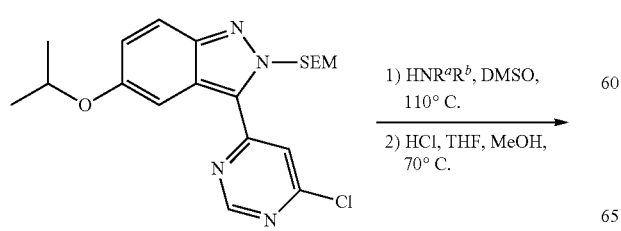
1) HNR$^a$R$^b$, DMSO, 110° C.
2) HCl, THF, MeOH, 70° C.
-continued
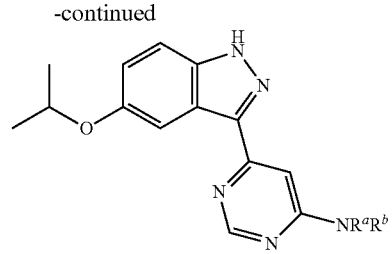
Examples K1-K21

Parallel preparation of examples K1-K21: To a set of vials containing the chloropyrimidine from Scheme D (30 mg, 0.072 mmol) in DMSO (0.3 mL) was added the requisite amine (0.086 mmol) and diisopropylethylamine (0.050 mL, 0.29 mmol). The vials were capped and the mixtures were heated to 110° C. with stirring for 3 hours. The mixtures were cooled to RT. Water (2 mL) was added to each vial. The aqueous phases were extracted with DCM (2×1 mL). The combined organic layers from each vial were transferred to a new set of vials and the solvent was removed in vacuo. To each vial was then added THF:MeOH (1:3, 1 mL) followed by HCl (4 N in dioxane, 0.20 mL, 0.80 mmol). The vials were capped and the solutions were heated to 70° C. for 0.5 h. The solutions were allowed to cool to RT and the solvent was then removed from the vials in vacuo. Each crude product was redissolved in 1 mL of DMSO and filtered. The crude products were purified by mass triggered HPLC using the following conditions: [Waters XBridge C18 column, 5 μm, 19×100 mm, gradient ranges from 10-35% initial to 49-75% MeCN (0.1% $NH_4OH$) in water (0.1% $NH_4OH$) 50 mL/min, 8 min run time] to provide examples K1-K21.

| Example | Structure | LCMS method m/z | RT (min) | method | LRRK2 $IC_{50}$ (nM) |
|---|---|---|---|---|---|
| K1 | | 438.25 | 0.98 | D | 5.1 |
| K2 | | 433.18 | 0.98 | D | 8.7 |
| K3 | | 367.22 | 1.00 | D | 6 |
| K4 | | 368.20 | 1.02 | D | 12.7 |

-continued

| Example | Structure | LCMS method m/z | RT (min) | method | LRRK2 IC$_{50}$ (nM) |
|---|---|---|---|---|---|
| K5 | 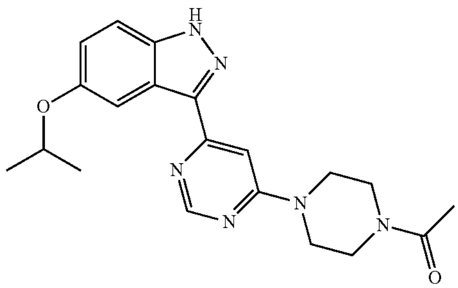 [SMILES: CC(=O)N1CCN(c2cc(-c3n[nH]c4ccc(OC(C)C)cc34)ncn2)CC1] | 381.18 | 0.84 | D | 11.2 |
| K6 | 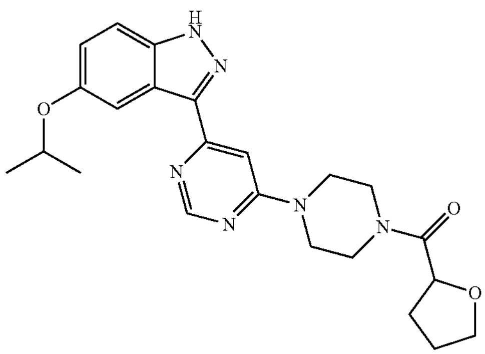 [SMILES: CC(C)Oc1ccc2[nH]nc(-c3cc(N4CCN(C(=O)C5CCCO5)CC4)ncn3)c2c1] | 437.23 | 0.90 | D | 58.1 |
| K7 | 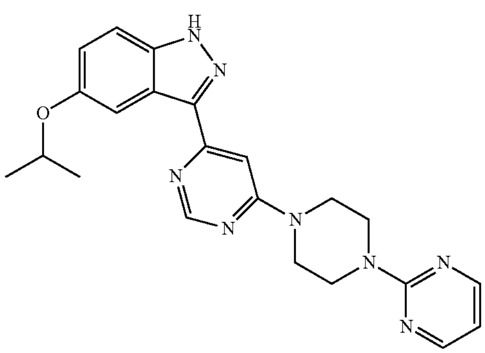 [SMILES: CC(C)Oc1ccc2[nH]nc(-c3cc(N4CCN(c5ncccn5)CC4)ncn3)c2c1] | 417.20 | 1.06 | D | 11.8 |
| K8 | 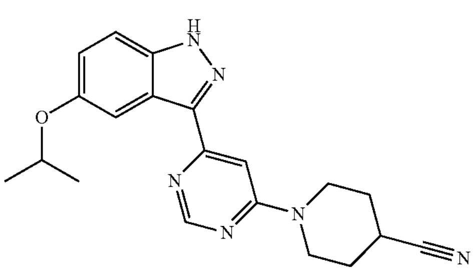 [SMILES: CC(C)Oc1ccc2[nH]nc(-c3cc(N4CCC(C#N)CC4)ncn3)c2c1] | 363.18 | 0.98 | D | 7.2 |

-continued

| Example | Structure | LCMS method m/z | RT (min) | method | LRRK2 IC$_{50}$ (nM) |
|---|---|---|---|---|---|
| K9 | 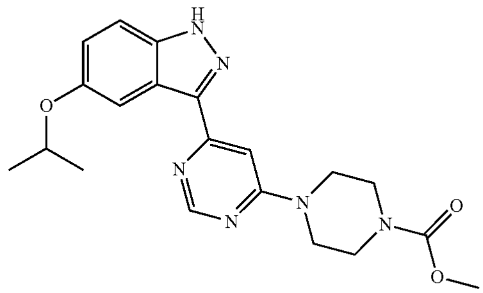 [SMILES: COC(=O)N1CCN(c2cc(-c3n[nH]c4ccc(OC(C)C)cc34)ncn2)CC1] | 397.18 | 0.97 | D | 10.2 |
| K10 | 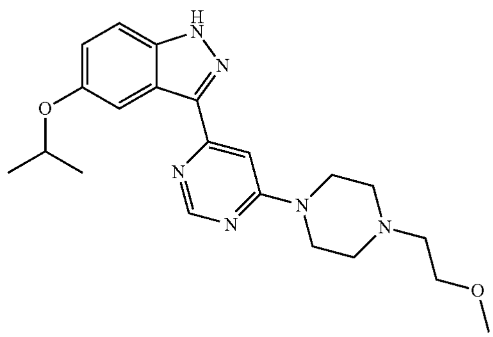 [SMILES: COCCN1CCN(c2cc(-c3n[nH]c4ccc(OC(C)C)cc34)ncn2)CC1] | 397.22 | 0.95 | D | 4.9 |
| K11 | 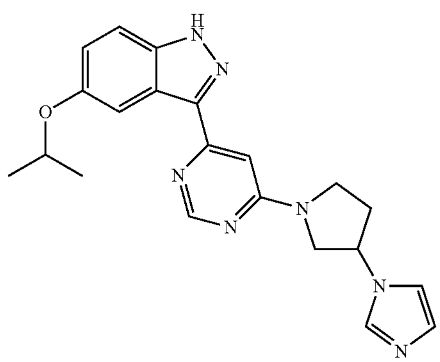 [SMILES: CC(C)Oc1ccc2[nH]nc(-c3cc(N4CCC(n5ccnc5)C4)ncn3)c2c1] | 390.19 | 0.82 | D | 11.3 |
| K12 | 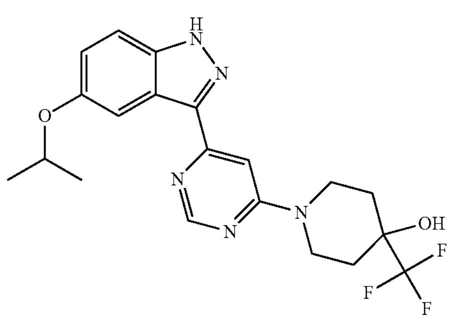 [SMILES: CC(C)Oc1ccc2[nH]nc(-c3cc(N4CCC(O)(C(F)(F)F)CC4)ncn3)c2c1] | 422.16 | 1.02 | D | 10.5 |
| K13 | 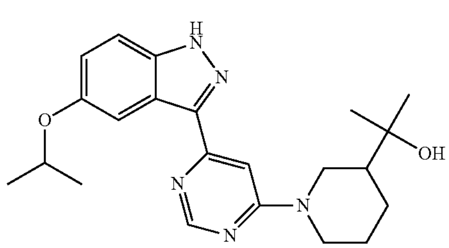 [SMILES: CC(C)Oc1ccc2[nH]nc(-c3cc(N4CCCC(C(C)(C)O)C4)ncn3)c2c1] | 396.21 | 1.02 | D | 6.9 |

-continued

| Example | Structure | LCMS method m/z | RT (min) | method | LRRK2 IC₅₀ (nM) |
|---|---|---|---|---|---|
| K14 | 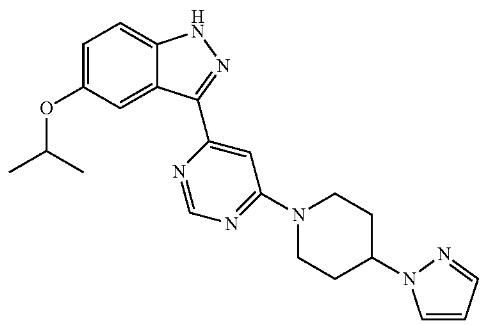 [SMILES: CC(C)Oc1ccc2[nH]nc(-c3cc(N4CCC(n5cccn5)CC4)ncn3)c2c1] | 404.21 | 1.00 | D | 15.3 |
| K15 | 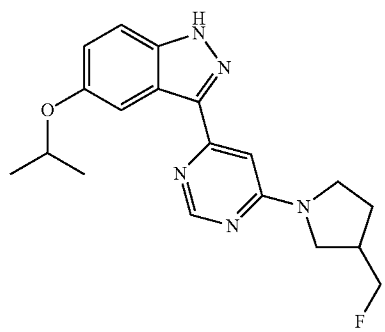 [SMILES: CC(C)Oc1ccc2[nH]nc(-c3cc(N4CCC(CF)C4)ncn3)c2c1] | 356.18 | 0.98 | D | 6.9 |
| K16 | 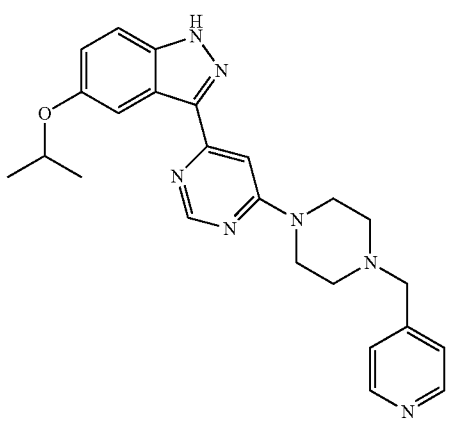 [SMILES: CC(C)Oc1ccc2[nH]nc(-c3cc(N4CCN(Cc5ccncc5)CC4)ncn3)c2c1] | 430.22 | 0.98 | D | 8.2 |
| K17 | 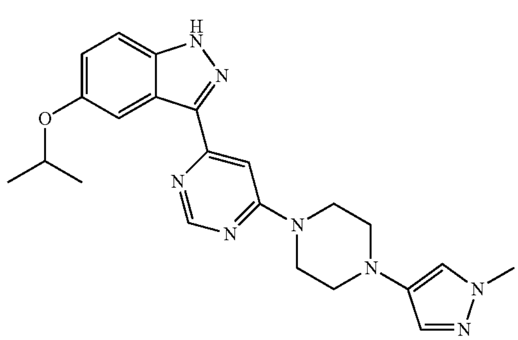 [SMILES: CC(C)Oc1ccc2[nH]nc(-c3cc(N4CCN(c5cnn(C)c5)CC4)ncn3)c2c1] | 419.22 | 0.93 | D | 5.4 |

| Example | Structure | LCMS method m/z | RT (min) | method | LRRK2 IC₅₀ (nM) |
|---|---|---|---|---|---|
| K18 | 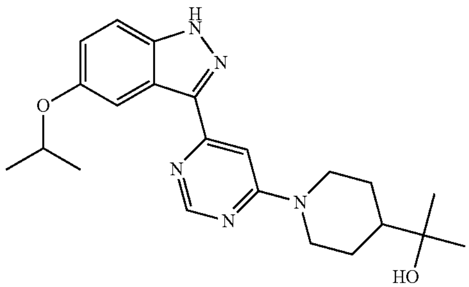 [SMILES: CC(C)Oc1ccc2[nH]nc(-c3cc(N4CCC(C(C)(C)O)CC4)ncn3)c2c1] | 396.21 | 0.99 | D | 5.4 |
| K19 | 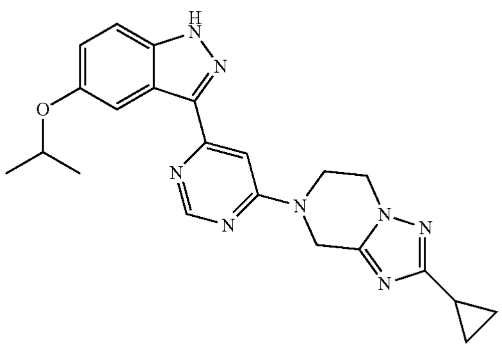 [SMILES: CC(C)Oc1ccc2[nH]nc(-c3cc(N4CCn5nc(C6CC6)nc5C4)ncn3)c2c1] | 417.20 | 0.95 | D | 18.2 |
| K20 | 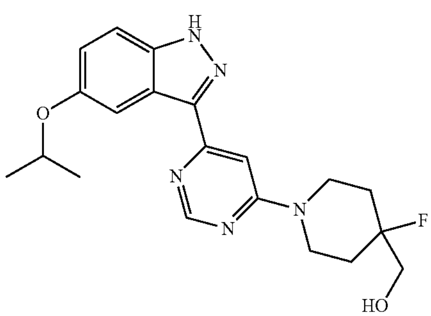 [SMILES: CC(C)Oc1ccc2[nH]nc(-c3cc(N4CCC(F)(CO)CC4)ncn3)c2c1] | 386.18 | 0.90 | D | 6.3 |
| K21 | 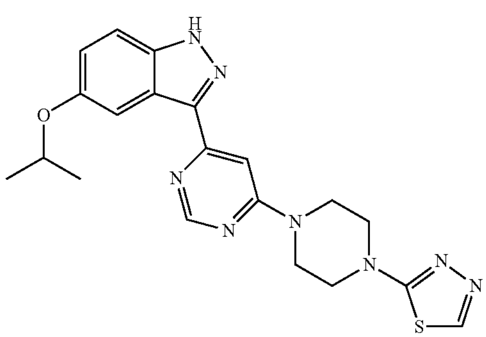 [SMILES: CC(C)Oc1ccc2[nH]nc(-c3cc(N4CCN(c5nncs5)CC4)ncn3)c2c1] | 423.16 | 0.92 | D | 17 |

Scheme L:

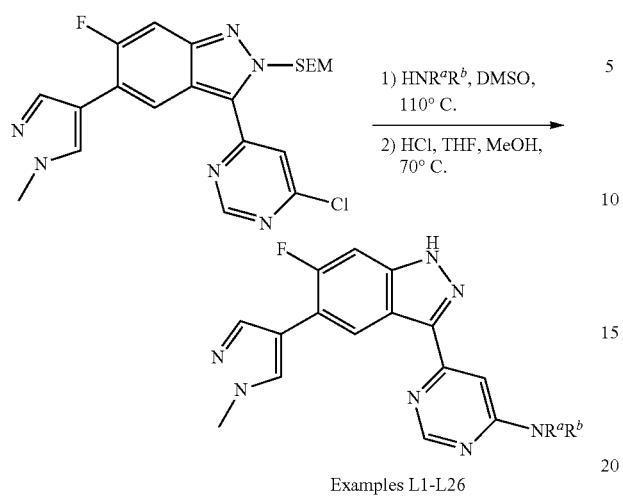

Examples L1-L26

Examples L1-L26 were prepared from the chloropyrimidine (synthesized in Scheme B) using the procedure described in Scheme K. The crude products were purified using the following mass triggered HPLC purification method: [Waters XBridge C18 column, 5 μm, 19×100 mm, gradient ranges from 10-20% initial to 35-55% MeCN (0.1% $NH_4OH$) in water (0.1% $NH_4OH$) 50 mL/min, 8 min run time]. Example L26 was repurified by mass triggered HPLC [Waters Sunfire C18 column, 5 μm, 19×100 mm, gradient from 5% initial to 35% MeCN (0.1% formic acid) in water (0.1% formic acid) 50 mL/min, 8 min run time].

| Example | Structure | LCMS data m/z | RT (min) | Method | LRRK2 IC$_{50}$ (nM) |
|---|---|---|---|---|---|
| L1 | | 417.16 | 0.68 | D | 63.9 |
| L2 | | 396.17 | 0.81 | D | 13.6 |
| L3 | | 414.16 | 0.90 | D | 23.4 |

| Example | Structure | LCMS data m/z | RT (min) | Method | LRRK2 IC$_{50}$ (nM) |
|---|---|---|---|---|---|
| L4 | 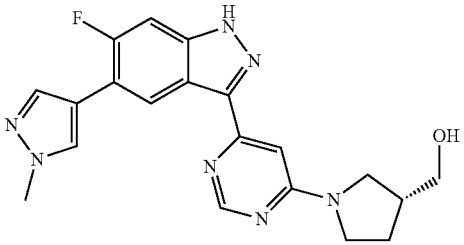 [SMILES: Cn1cc(-c2cc3c(-c4cc(N5CC[C@@H](CO)C5)ncn4)n[nH]c3cc2F)cn1] | 394.17 | 0.67 | D | 36.8 |
| L5 | 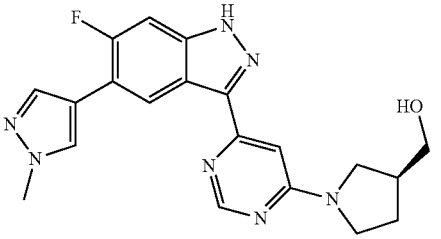 [SMILES: Cn1cc(-c2cc3c(-c4cc(N5CC[C@H](CO)C5)ncn4)n[nH]c3cc2F)cn1] | 394.17 | 0.67 | D | 37 |
| L6 | 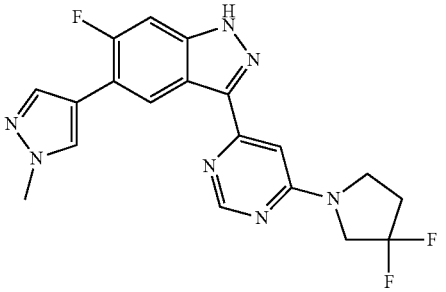 [SMILES: Cn1cc(-c2cc3c(-c4cc(N5CCC(F)(F)C5)ncn4)n[nH]c3cc2F)cn1] | 400.14 | 0.85 | D | 70.9 |
| L7 | 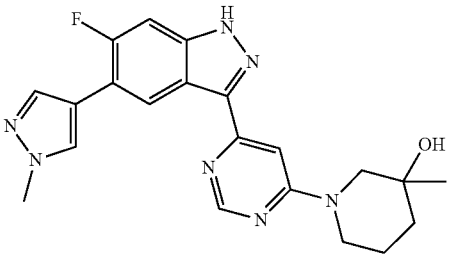 [SMILES: Cn1cc(-c2cc3c(-c4cc(N5CCCC(C)(O)C5)ncn4)n[nH]c3cc2F)cn1] | 408.19 | 0.76 | D | 67.5 |
| L8 | 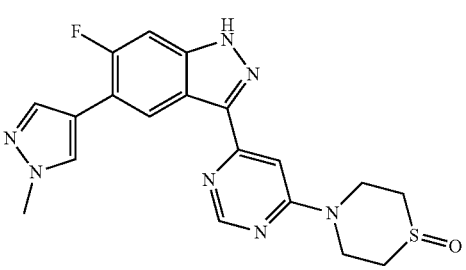 [SMILES: Cn1cc(-c2cc3c(-c4cc(N5CCS(=O)CC5)ncn4)n[nH]c3cc2F)cn1] | 412.13 | 0.63 | D | 130.7 |

| Example | Structure | LCMS data m/z | RT (min) | Method | LRRK2 IC$_{50}$ (nM) |
|---|---|---|---|---|---|
| L9 | 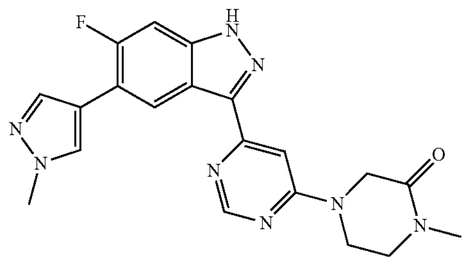 [SMILES: CN1CCN(c2cc(-c3n[nH]c4cc(F)c(-c5cnn(C)c5)cc34)ncn2)CC1=O] | 407.17 | 0.67 | D | 37.7 |
| L10 | 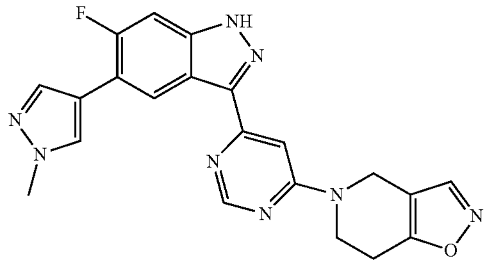 [SMILES: Cn1cc(-c2cc3c(-c4cc(N5CCc6oncc6C5)ncn4)n[nH]c3cc2F)cn1] | 417.15 | 0.81 | D | 453.3 |
| L11 | 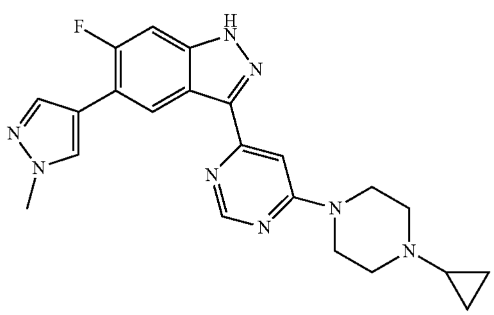 [SMILES: Cn1cc(-c2cc3c(-c4cc(N5CCN(C6CC6)CC5)ncn4)n[nH]c3cc2F)cn1] | 419.2 | 0.86 | D | 17.7 |
| L12 | 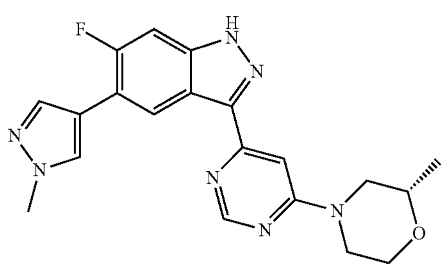 [SMILES: C[C@H]1CN(c2cc(-c3n[nH]c4cc(F)c(-c5cnn(C)c5)cc34)ncn2)CCO1] | 394.17 | 0.82 | D | 26.5 |
| L13 | 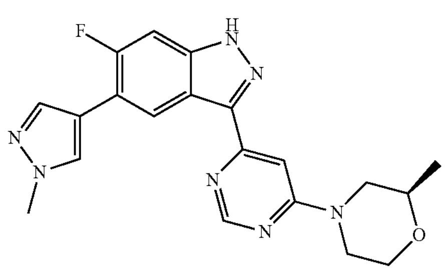 [SMILES: C[C@@H]1CN(c2cc(-c3n[nH]c4cc(F)c(-c5cnn(C)c5)cc34)ncn2)CCO1] | 394.17 | 0.82 | D | 20.5 |

-continued
| Example | Structure | LCMS data m/z | RT (min) | Method | LRRK2 IC$_{50}$ (nM) |
|---|---|---|---|---|---|
| L14 | 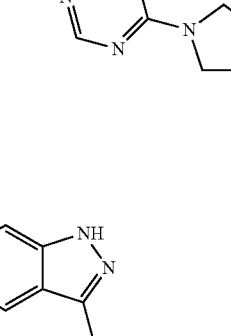 | 400.14 | 0.80 | D | 29.9 |
| L15 | 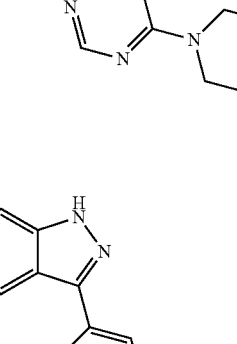 | 420.19 | 0.80 | D | 398.1 |
| L16 | 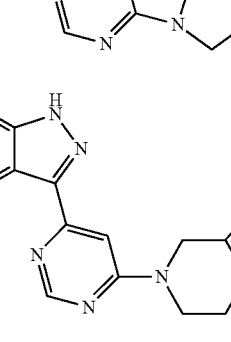 | 430.18 | 0.76 | D | 73.5 |
| L17 | 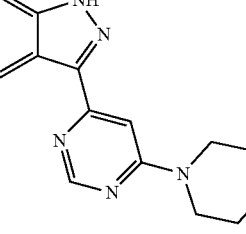 | 431.17 | 0.83 | D | 53.4 |
| L18 | 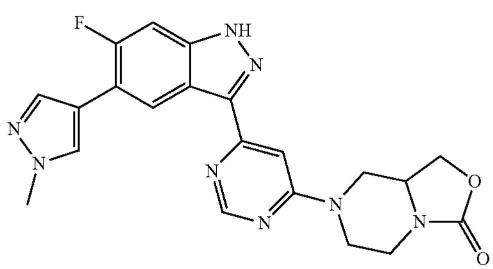 [SMILES: Cn1cc(-c2cc3c(-c4cc(N5CCN6C(=O)OCC6C5)ncn4)n[nH]c3cc2F)cn1] | 435.16 | 0.71 | D | 64.2 |

-continued
| Example | Structure | LCMS data m/z | RT (min) | Method | LRRK2 IC$_{50}$ (nM) |
|---|---|---|---|---|---|
| L19 | 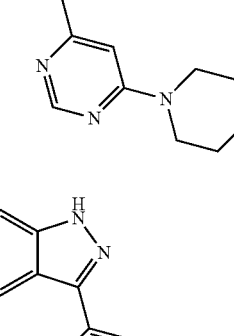 | 421.16 | 0.89 | D | 39.4 |
| L20 | 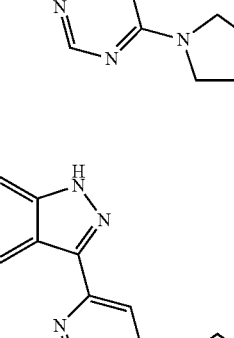 | 410.17 | 0.66 | D | 36.2 |
| L21 | 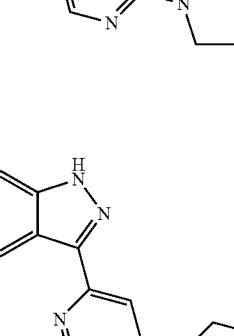 | 423.2 | 0.64 | D | 67.1 |
| L22 | 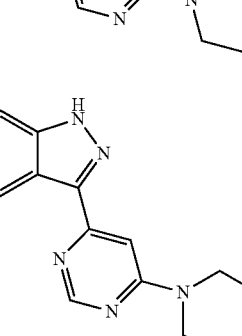 | 428.12 | 0.70 | D | 145.9 |
| L23 | 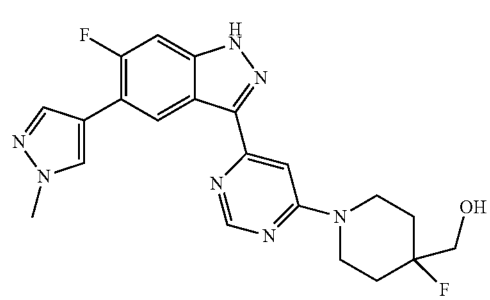 [SMILES: Cn1cc(-c2cc3c(-c4cc(N5CCC(F)(CO)CC5)ncn4)n[nH]c3cc2F)cn1] | 426.18 | 0.73 | D | 15.3 |

| Example | Structure | LCMS data m/z | RT (min) | Method | LRRK2 IC$_{50}$ (nM) |
|---|---|---|---|---|---|
| L24 | | 407.2 | 0.75 | D | 58 |
| L25 | | 437.21 | 0.69 | D | 12.6 |
| L26 | | 428.17 | 0.75 | D | 11.1 |

Scheme M:

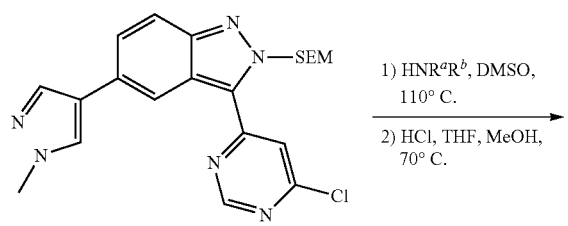

1) HNR$^a$R$^b$, DMSO, 110° C.
2) HCl, THF, MeOH, 70° C.

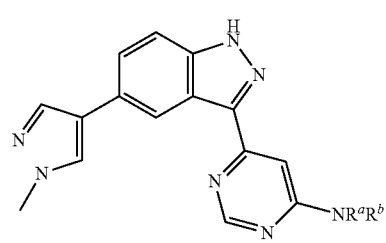

Examples M1-M29

Examples M1-M28 were prepared using the chloropyrimidine, (synthesized following the protocol described in Scheme B), employing the procedure described in Scheme K. The crude products were purified by mass-triggered HPLC purification using the following method: [Waters XBridge C18 column, 5 μm, 19×100 mm, gradient ranges from 5-20% initial to 35-55% MeCN (0.1% NH$_4$OH) in water (0.1% NH$_4$OH) 25 mL/min, 8 min run time], Examples M26-M28 were repurified by mass triggered HPLC [Waters Sunfire C18 column], 5 μm, 19×100 mm, gradient from 5% initial to 35% MeCN (0.1% formic acid) in water (0.1% formic acid) 50 mL/min, 8 min run time.

| Example | Structure | LCMS data | | | LRRK2 |
| | | m/z | RT (min) | Method | IC$_{50}$ (nM) |
| --- | --- | --- | --- | --- | --- |
| M1 | 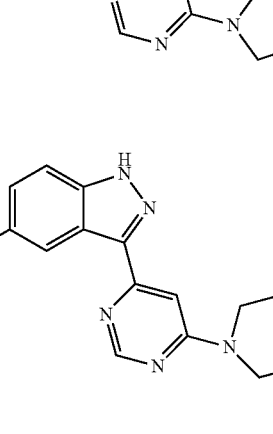 | 376.18 | 0.72 | D | 4 |
| M2 | | 396.17 | 0.86 | D | 2.2 |
| M3 | 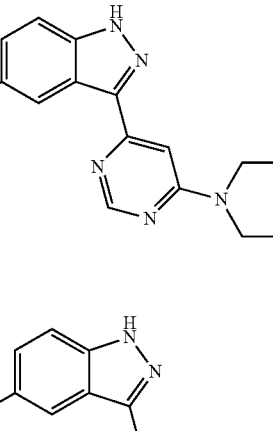 | 399.17 | 0.64 | D | 8.5 |
| M4 | 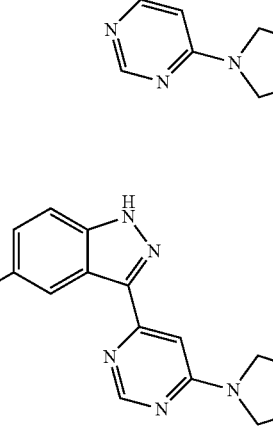 | 378.18 | 0.77 | D | 2.3 |
| M5 |  | 376.18 | 0.64 | D | 2.5 |

-continued
| Example | Structure | LCMS data m/z | RT (min) | Method | LRRK2 IC$_{50}$ (nM) |
|---|---|---|---|---|---|
| M6 | 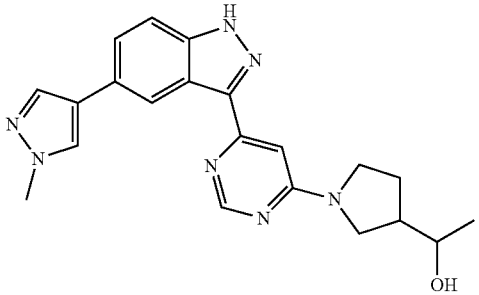 [SMILES: CC(O)C1CCN(c2cc(-c3n[nH]c4ccc(-c5cnn(C)c5)cc34)ncn2)C1] | 390.2 | 0.69 | D | 2.3 |
| M7 | 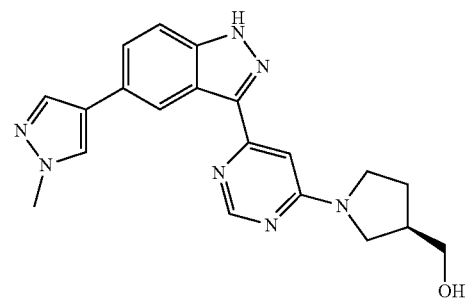 [SMILES: Cn1cc(-c2ccc3[nH]nc(-c4cc(N5CC[C@@H](CO)C5)ncn4)c3c2)cn1] | 376.18 | 0.63 | D | 2.9 |
| M8 | 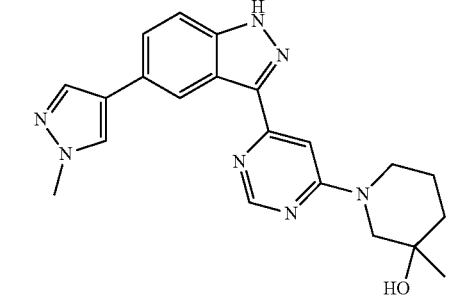 [SMILES: Cn1cc(-c2ccc3[nH]nc(-c4cc(N5CCCC(C)(O)C5)ncn4)c3c2)cn1] | 390.2 | 0.73 | D | 7.9 |
| M9 | 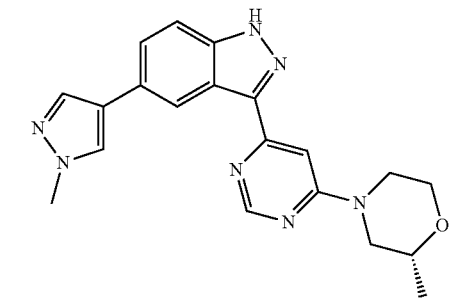 [SMILES: C[C@@H]1CN(c2cc(-c3n[nH]c4ccc(-c5cnn(C)c5)cc34)ncn2)CCO1] | 376.18 | 0.78 | D | 1.9 |
| M10 | 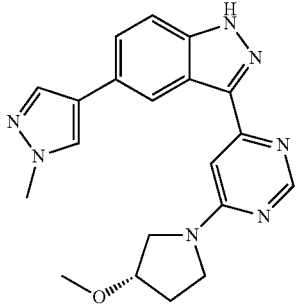 [SMILES: CO[C@H]1CCN(c2cc(-c3n[nH]c4ccc(-c5cnn(C)c5)cc34)ncn2)C1] | 376.18 | 0.72 | D | 2.6 |

-continued

| Example | Structure | LCMS data m/z | RT (min) | Method | LRRK2 IC$_{50}$ (nM) |
|---|---|---|---|---|---|
| M11 | | 394.14 | 0.60 | D | 26.8 |
| M12 | | 376.18 | 0.78 | D | 2.2 |
| M13 | | 382.15 | 0.78 | D | 3.8 |
| M14 | | 413.18 | 0.79 | D | 2.8 |
| M15 | | 417.17 | 0.67 | D | 6.3 |

|         |           | LCMS data |          |        | LRRK2          |
|---------|-----------|-----------|----------|--------|----------------|
| Example | Structure | m/z       | RT (min) | Method | IC$_{50}$ (nM) |
| M16     |           | 402.2     | 0.67     | D      | 10.9           |
| M17     |           | 405.21    | 0.61     | D      | 13.5           |
| M18     |           | 410.13    | 0.66     | D      | 22.4           |
| M19     |           | 389.21    | 0.70     | D      | 4.6            |
| M20     |           | 390.20    | 0.70     | D      | 8.9            |

-continued

| Example | Structure | LCMS data m/z | RT (min) | Method | LRRK2 IC$_{50}$ (nM) |
|---|---|---|---|---|---|
| M21 | 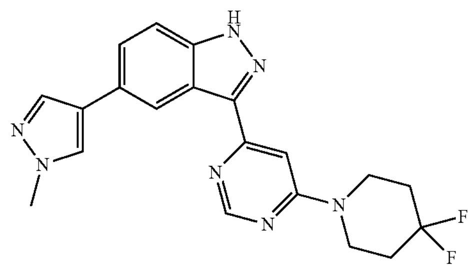 [SMILES: Cn1cc(-c2ccc3[nH]nc(-c4cc(N5CCC(F)(F)CC5)ncn4)c3c2)cn1] | 396.17 | 0.88 | D | 4.6 |
| M22 | 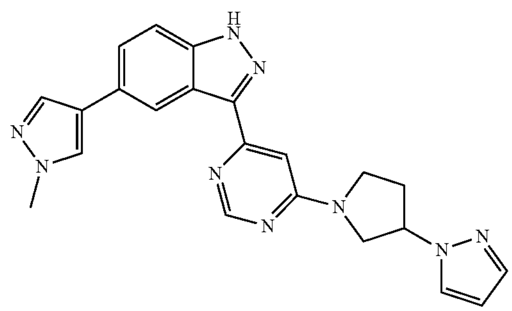 [SMILES: Cn1cc(-c2ccc3[nH]nc(-c4cc(N5CCC(n6cccn6)C5)ncn4)c3c2)cn1] | 412.19 | 0.73 | D | 3.6 |
| M23 | 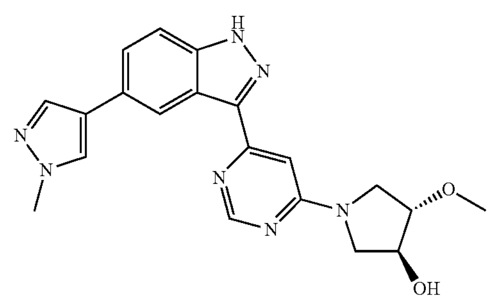 [SMILES: CO[C@H]1CN(c2cc(-c3n[nH]c4ccc(-c5cnn(C)c5)cc34)ncn2)C[C@@H]1O] | 392.18 | 0.62 | D | 6 |
| M24 | 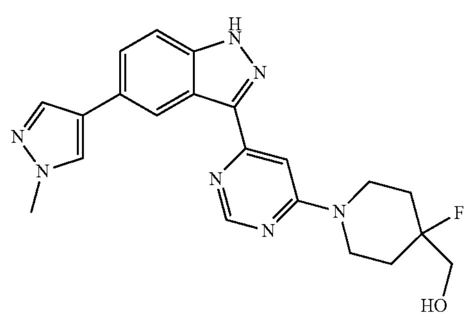 [SMILES: Cn1cc(-c2ccc3[nH]nc(-c4cc(N5CCC(F)(CO)CC5)ncn4)c3c2)cn1] | 408.19 | 0.69 | D | 2.9 |
| M25 | 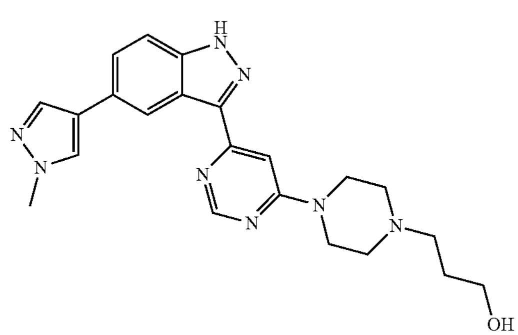 [SMILES: Cn1cc(-c2ccc3[nH]nc(-c4cc(N5CCN(CCCO)CC5)ncn4)c3c2)cn1] | 419.22 | 0.65 | D | 3 |

| Example | Structure | LCMS data m/z | RT (min) | Method | LRRK2 IC$_{50}$ (nM) |
|---|---|---|---|---|---|
| M26 | 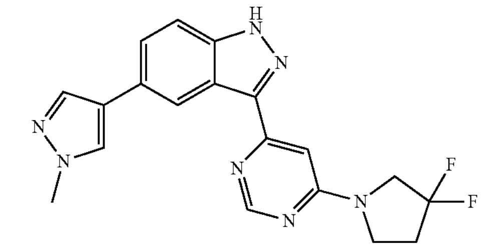 [SMILES: Cn1cc(-c2ccc3[nH]nc(-c4cc(N5CCC(F)(F)C5)ncn4)c3c2)cn1] | 382.15 | 0.81 | D | 3.7 |
| M27 | 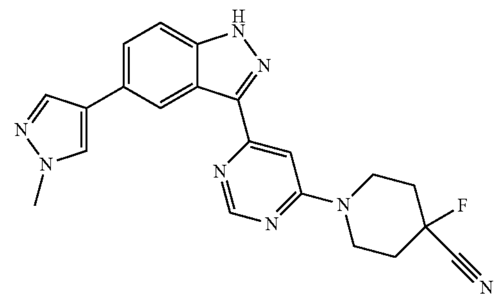 [SMILES: Cn1cc(-c2ccc3[nH]nc(-c4cc(N5CCC(F)(C#N)CC5)ncn4)c3c2)cn1] | 403.17 | 0.85 | D | 3 |
| M28 | 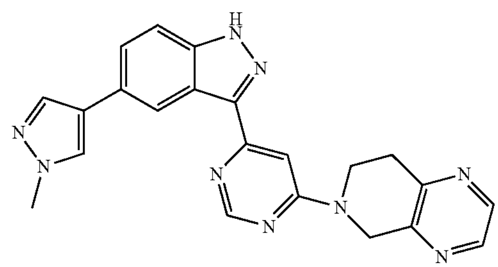 [SMILES: Cn1cc(-c2ccc3[nH]nc(-c4cc(N5CCc6nccnc6C5)ncn4)c3c2)cn1] | 410.18 | 0.72 | D | 2.7 |

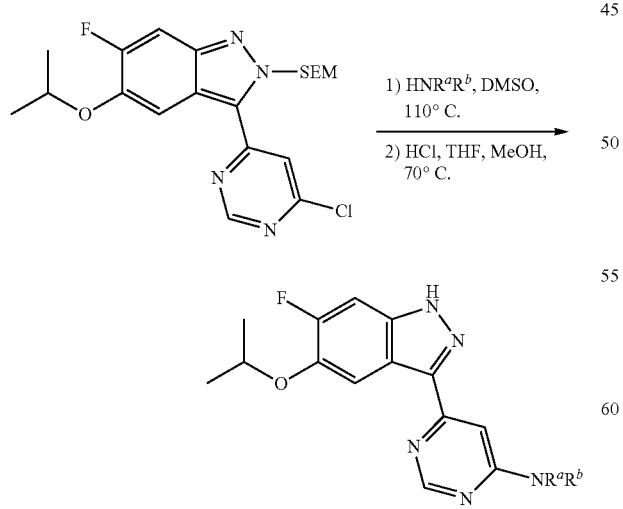

Scheme N:

Examples N1-N25

Examples N1 were prepared from chloropyrimidine (Scheme D2) using the procedure described in Scheme K. The crude products were purified using the following mass triggered HPLC purification method: [Waters Sunfire C18 column, 5 μm, 19×100 mm, gradient from 5% initial to 35% MeCN (0.1% formic acid) in water (0.1% formic acid) 50 mL/min, 8 min run time. Examples N24-N25 were repurified by mass triggered HPLC [Waters XBridge C18 column, 5 μm, 19×100 mm, gradient range from 10% initial to 95% final MeCN (0.1% NH$_4$OH) in water (0.1% NH$_4$OH) 50 mL/min, 8 min run time].

|         |           | LCMS data |        |        | LRRK2 |
|---------|-----------|-----------|--------|--------|-------|
| Example | Structure | m/z | RT (min) | Method | IC$_{50}$ (nM) |
| N1 | | 395.17 | 0.86 | D | 7.1 |
| N2 | | 429.2 | 0.88 | D | 5.6 |
| N3 | | 426.15 | 1.14 | D | 26.6 |
| N4 | | 475.18 | 0.89 | D | 2.5 |

-continued
| Example | Structure | LCMS data m/z | RT (min) | Method | LRRK2 IC$_{50}$ (nM) |
|---|---|---|---|---|---|
| N5 | 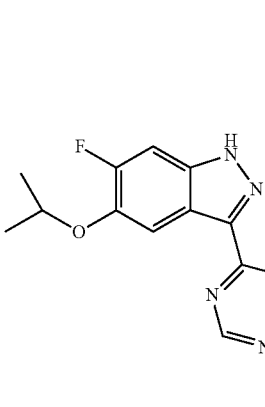 | 477.17 | 1.13 | D | 176 |
| N6 | 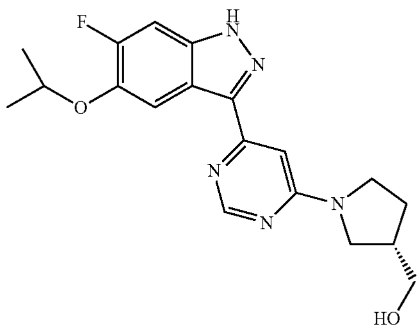 [SMILES: CC(C)Oc1cc2c(-c3cc(N4CC[C@H](CO)C4)ncn3)n[nH]c2cc1F] | 372.18 | 0.84 | D | 10.2 |
| N7 | 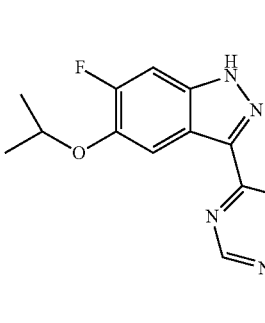 | 372.18 | 0.84 | D | 2.9 |
| N8 | 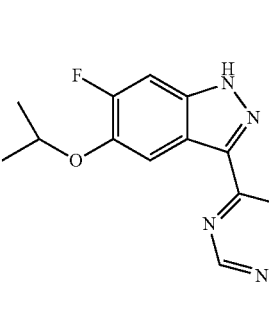 | 378.15 | 1.04 | D | 6.1 |
| N9 | 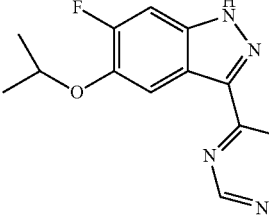 | 390.13 | 0.81 | D | 6.1 |

-continued

| Example | Structure | m/z | RT (min) | Method | LRRK2 IC$_{50}$ (nM) |
|---|---|---|---|---|---|
| N10 | 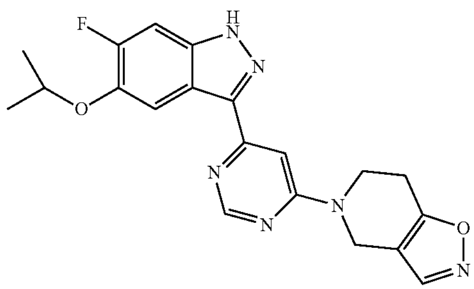 [SMILES: CC(C)Oc1cc2c(-c3cc(N4CCc5oncc5C4)ncn3)n[nH]c2cc1F] | 395.15 | 1.01 | D | 9.8 |
| N11 | 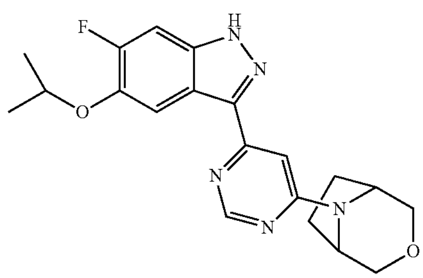 [SMILES: CC(C)Oc1cc2c(-c3cc(N4C5CCC4COC5)ncn3)n[nH]c2cc1F] | 384.18 | 1.00 | D | 18.2 |
| N12 | 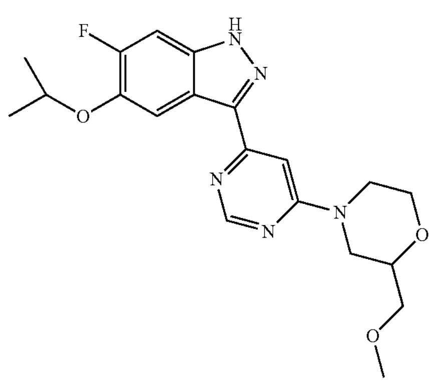 [SMILES: COCC1CN(c2cc(-c3n[nH]c4cc(F)c(OC(C)C)cc34)ncn2)CCO1] | 402.19 | 0.99 | D | 2.9 |
| N13 | 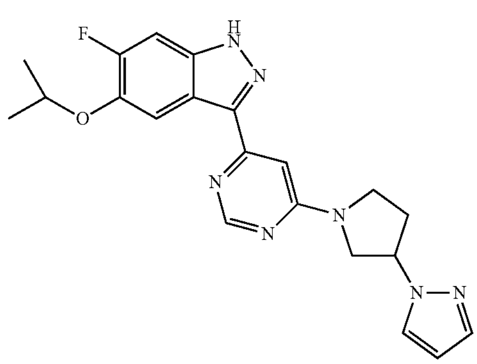 [SMILES: CC(C)Oc1cc2c(-c3cc(N4CCC(n5cccn5)C4)ncn3)n[nH]c2cc1F] | 408.19 | 0.94 | D | 6.1 |

-continued

| Example | Structure | m/z | RT (min) | Method | LRRK2 IC$_{50}$ (nM) |
|---|---|---|---|---|---|
| N14 | 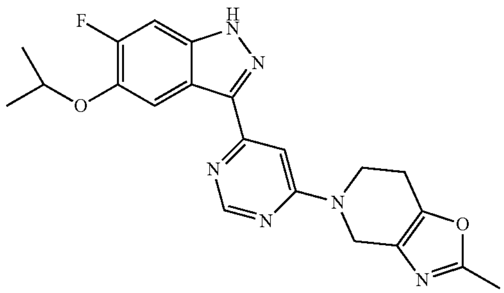 [SMILES: Cc1nc2c(o1)CCN(c1cc(-c3n[nH]c4cc(F)c(OC(C)C)cc34)ncn1)C2] | 409.17 | 1.03 | D | 6.4 |
| N15 | 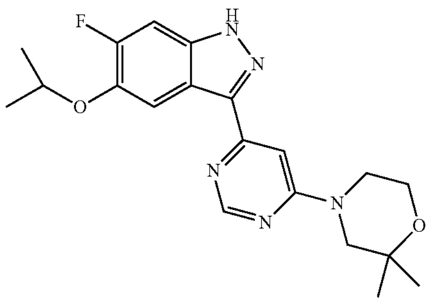 [SMILES: CC(C)Oc1cc2c(-c3cc(N4CCOC(C)(C)C4)ncn3)n[nH]c2cc1F] | 386.19 | 1.06 | D | 6.2 |
| N16 | 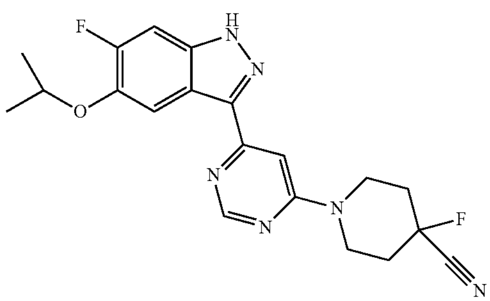 [SMILES: CC(C)Oc1cc2c(-c3cc(N4CCC(F)(C#N)CC4)ncn3)n[nH]c2cc1F] | 399.17 | 1.09 | D | 17.7 |
| N17 | 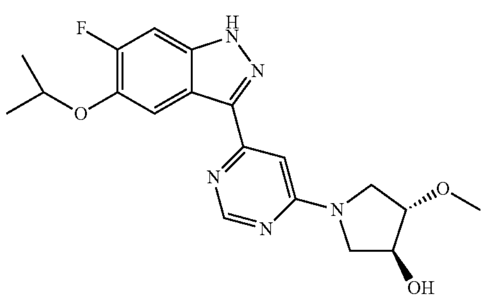 [SMILES: CO[C@H]1CN(c2cc(-c3n[nH]c4cc(F)c(OC(C)C)cc34)ncn2)C[C@@H]1O] | 388.17 | 0.82 | D | 7.7 |
| N18 | 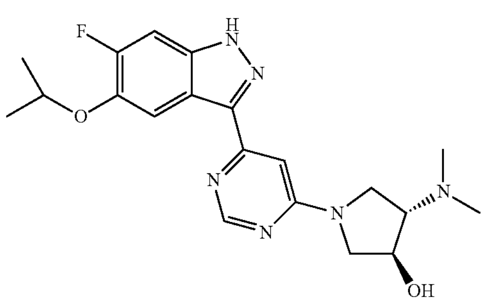 [SMILES: CC(C)Oc1cc2c(-c3cc(N4C[C@H](O)[C@@H](N(C)C)C4)ncn3)n[nH]c2cc1F] | 401.2 | 0.80 | D | 7.9 |

-continued

| Example | Structure | m/z | RT (min) | Method | LRRK2 IC$_{50}$ (nM) |
|---|---|---|---|---|---|
| N19 | 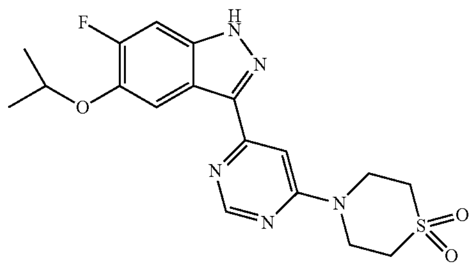 [SMILES: CC(C)Oc1cc2c(-c3cc(N4CCS(=O)(=O)CC4)ncn3)n[nH]c2cc1F] | 406.13 | 0.90 | D | 24 |
| N20 | 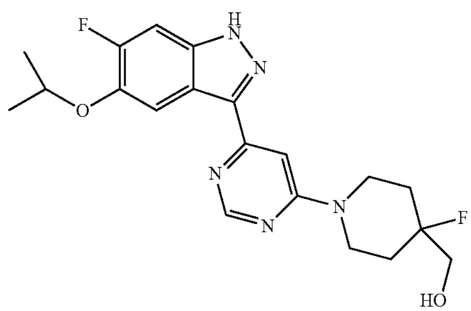 [SMILES: CC(C)Oc1cc2c(-c3cc(N4CCC(F)(CO)CC4)ncn3)n[nH]c2cc1F] | 404.18 | 0.92 | D | 2.3 |
| N21 | 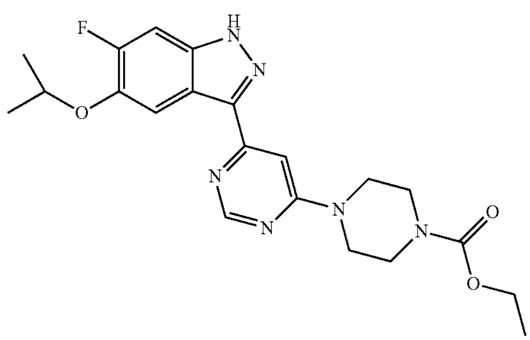 [SMILES: CCOC(=O)N1CCN(c2cc(-c3n[nH]c4cc(F)c(OC(C)C)cc34)ncn2)CC1] | 429.2 | 1.06 | D | 6.1 |
| N22 | 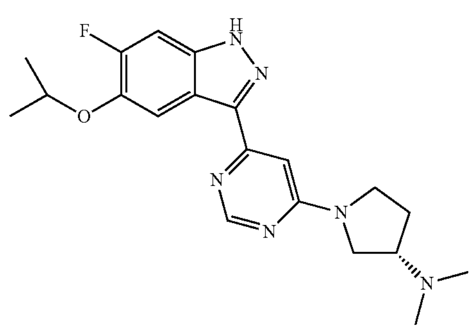 [SMILES: CC(C)Oc1cc2c(-c3cc(N4CC[C@H](N(C)C)C4)ncn3)n[nH]c2cc1F] | 385.21 | 0.92 | D | 7 |

| Example | Structure | LCMS data m/z | RT (min) | Method | LRRK2 IC$_{50}$ (nM) |
|---|---|---|---|---|---|
| N23 | 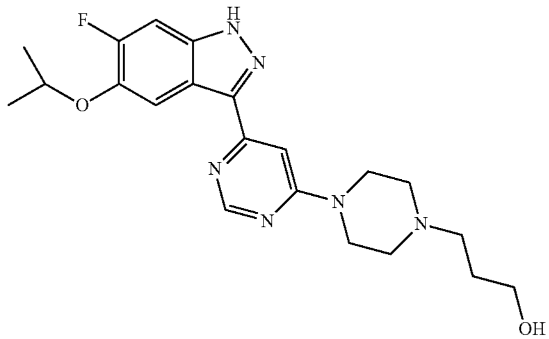 [SMILES: CC(C)Oc1cc2c(-c3cc(N4CCN(CCCO)CC4)ncn3)n[nH]c2cc1F] | 415.22 | 0.87 | D | 3.1 |
| N24 | 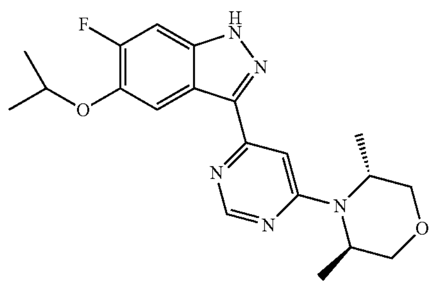 [SMILES: CC(C)Oc1cc2c(-c3cc(N4[C@H](C)COC[C@H]4C)ncn3)n[nH]c2cc1F] | 386.19 | 1.05 | D | 62.1 |
| N25 | 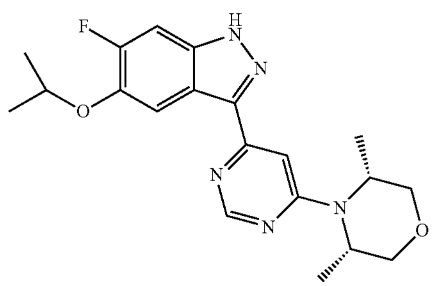 [SMILES: CC(C)Oc1cc2c(-c3cc(N4[C@H](C)COC[C@@H]4C)ncn3)n[nH]c2cc1F] | 386.19 | 1.08 | D | 5.4 |

Scheme O:

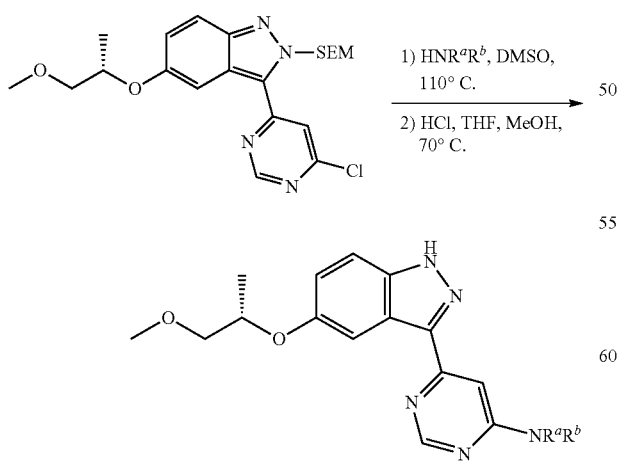

Examples O1-O23 were prepared from chloropyrimidine (synthesized following the procedure similar to Scheme H employing (R)-(−)-1-methoxy-2-propanol in step 1) using the procedure described in Scheme K. The crude products were purified using the following mass triggered HPLC purification method: [Waters XBridge C18 column, 5 μm, 19×100 mm, gradient ranges from 15-20% initial to 35-65% MeCN (0.1% NH$_4$OH) in water (0.1% NH$_4$OH) 50 mL/min, 8 min run time].

| Example | Structure | m/z | RT (min) | Method | LRRK2 IC$_{50}$ (nM) |
|---------|-----------|-----|----------|--------|----------------------|
| O1 | 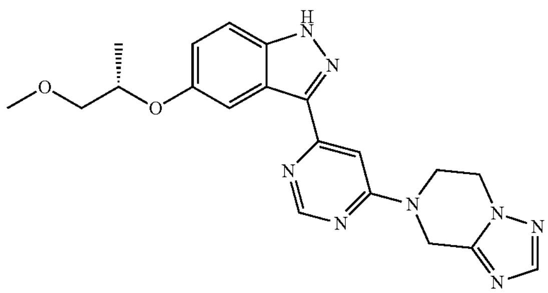 [SMILES: COC[C@H](C)Oc1ccc2[nH]nc(-c3cc(N4CCn5ncnc5C4)ncn3)c2c1] | 407.19 | 0.74 | D | 20.2 |
| O2 | 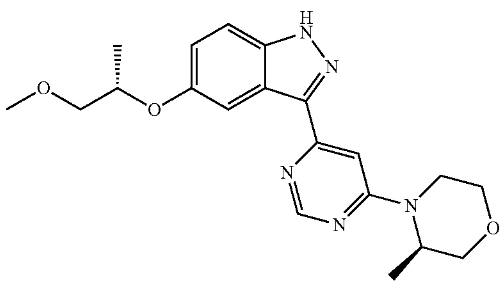 [SMILES: COC[C@H](C)Oc1ccc2[nH]nc(-c3cc(N4CCOC[C@H]4C)ncn3)c2c1] | 384.2 | 0.87 | D | 20.2 |
| O3 | 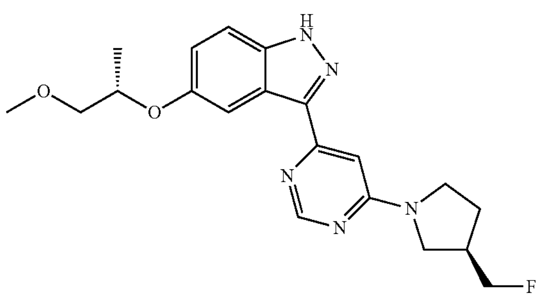 [SMILES: COC[C@H](C)Oc1ccc2[nH]nc(-c3cc(N4CC[C@@H](CF)C4)ncn3)c2c1] | 386.19 | 0.87 | D | 2.7 |
| O4 | 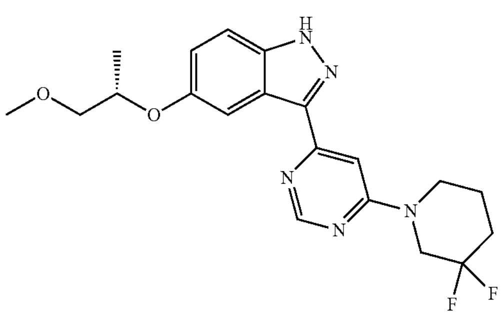 [SMILES: COC[C@H](C)Oc1ccc2[nH]nc(-c3cc(N4CCCC(F)(F)C4)ncn3)c2c1] | 404.18 | 0.97 | D | 2.8 |
| O5 | 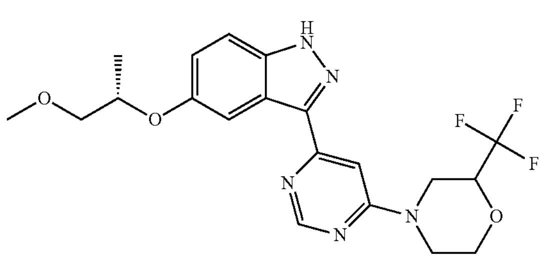 [SMILES: COC[C@H](C)Oc1ccc2[nH]nc(-c3cc(N4CCOC(C(F)(F)F)C4)ncn3)c2c1] | 438.17 | 1.01 | D | 8.6 |

-continued

| Example | Structure | m/z | RT (min) | Method | IC$_{50}$ (nM) |
|---|---|---|---|---|---|
| O6 | 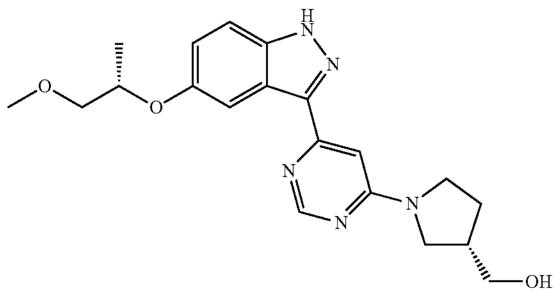 [SMILES: COC[C@H](C)Oc1ccc2[nH]nc(-c3cc(N4CC[C@H](CO)C4)ncn3)c2c1] | 384.2 | 0.72 | D | 6 |
| O7 | 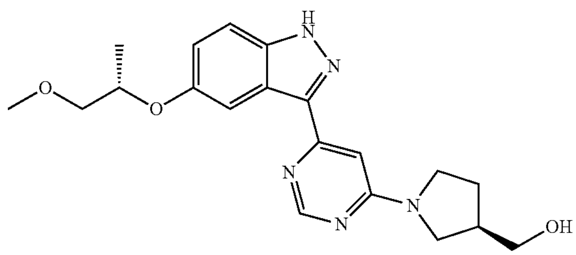 [SMILES: COC[C@H](C)Oc1ccc2[nH]nc(-c3cc(N4CC[C@@H](CO)C4)ncn3)c2c1] | 384.2 | 0.72 | D | 3.6 |
| O8 | 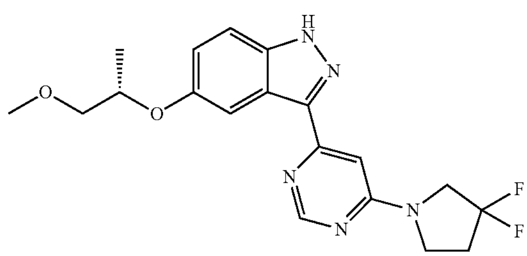 [SMILES: COC[C@H](C)Oc1ccc2[nH]nc(-c3cc(N4CCC(F)(F)C4)ncn3)c2c1] | 390.17 | 0.91 | D | 12.6 |
| O9 | 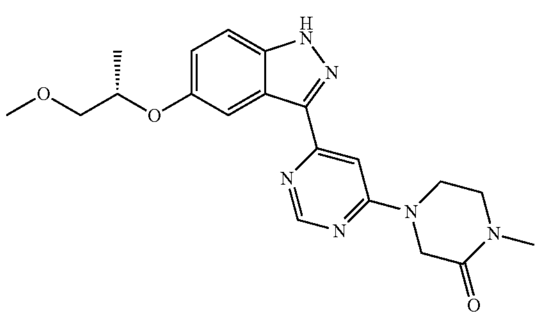 | 397.19 | 0.73 | D | 10.9 |
| O10 | 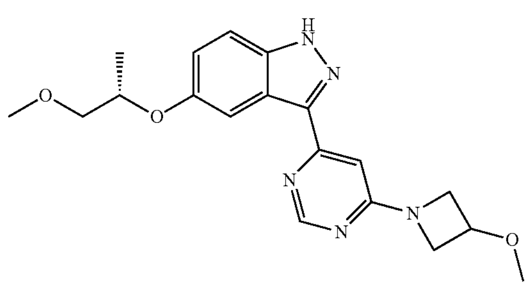 | 370.18 | 0.79 | D | 5.6 |

-continued
| Example | Structure | LCMS data m/z | RT (min) | Method | LRRK2 IC$_{50}$ (nM) |
|---|---|---|---|---|---|
| O11 | 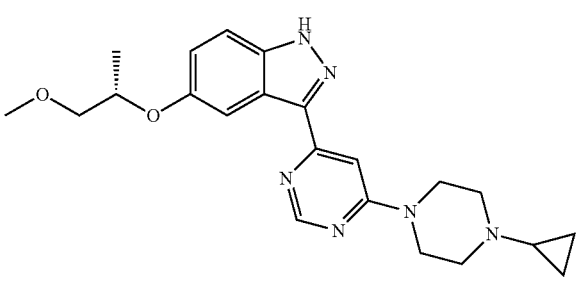 [SMILES: COC[C@H](C)Oc1ccc2[nH]nc(-c3cc(N4CCN(C5CC5)CC4)ncn3)c2c1] | 409.2 | 0.93 | D | 4.1 |
| O12 | 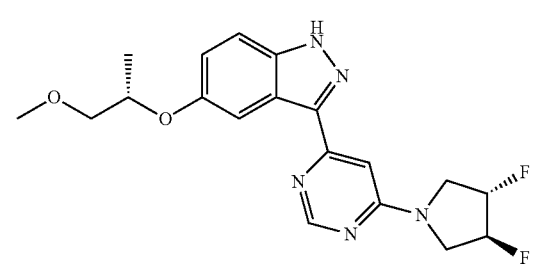 [SMILES: COC[C@H](C)Oc1ccc2[nH]nc(-c3cc(N4C[C@H](F)[C@@H](F)C4)ncn3)c2c1] | 390.17 | 0.86 | D | 7.9 |
| O13 | 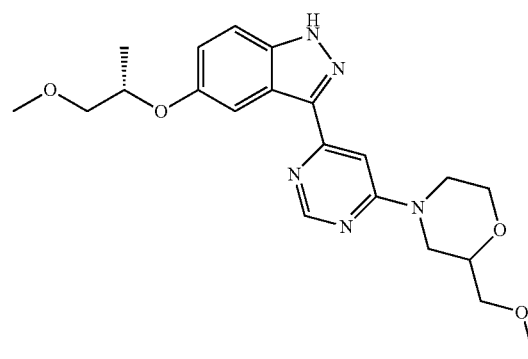 | 414.21 | 0.85 | D | 3.6 |
| O14 | 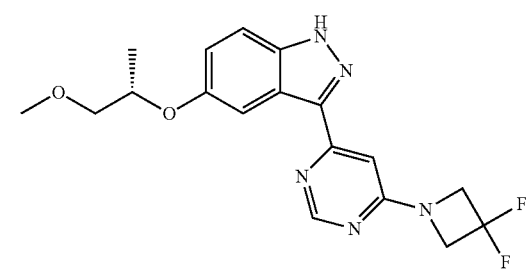 [SMILES: COC[C@H](C)Oc1ccc2[nH]nc(-c3cc(N4CC(F)(F)C4)ncn3)c2c1] | 376.15 | 0.88 | D | 7.6 |
| O15 | 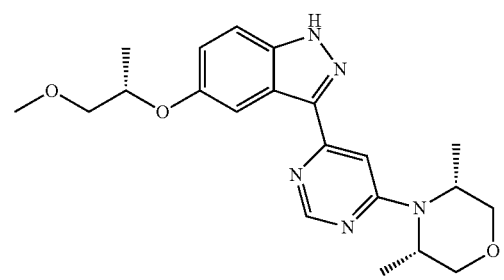 [SMILES: COC[C@H](C)Oc1ccc2[nH]nc(-c3cc(N4[C@H](C)COC[C@@H]4C)ncn3)c2c1] | 398.21 | 0.94 | D | 7.4 |

-continued

| Example | Structure | LCMS data m/z | RT (min) | Method | LRRK2 IC$_{50}$ (nM) |
|---|---|---|---|---|---|
| O16 | 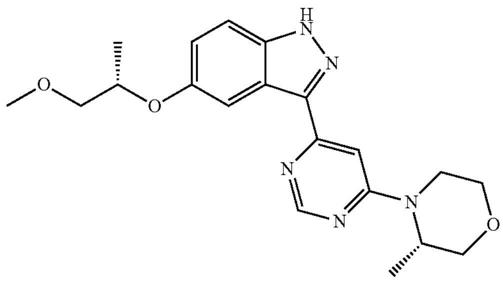 [SMILES: COC[C@H](C)Oc1ccc2[nH]nc(-c3cc(N4CCOC[C@@H]4C)ncn3)c2c1] | 384.2 | 0.87 | D | 6 |
| O17 | 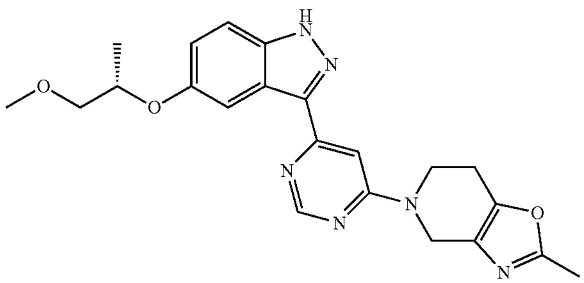 | 421.19 | 0.89 | D | 8.4 |
| O18 | 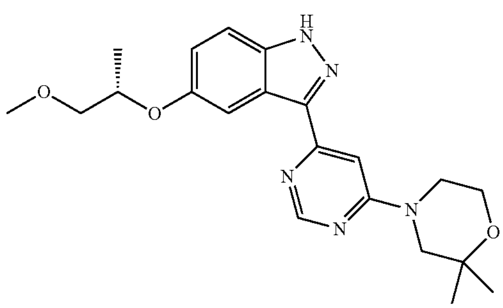 | 398.21 | 0.92 | D | 5.3 |
| O19 | 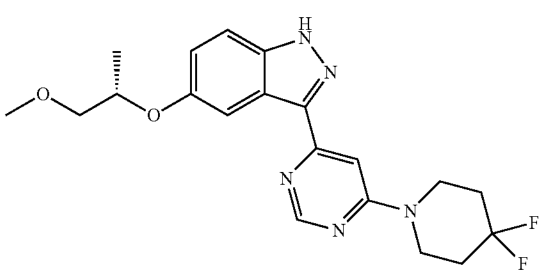 [SMILES: COC[C@H](C)Oc1ccc2[nH]nc(-c3cc(N4CCC(F)(F)CC4)ncn3)c2c1] | 404.18 | 0.99 | D | 8 |
| O20 | 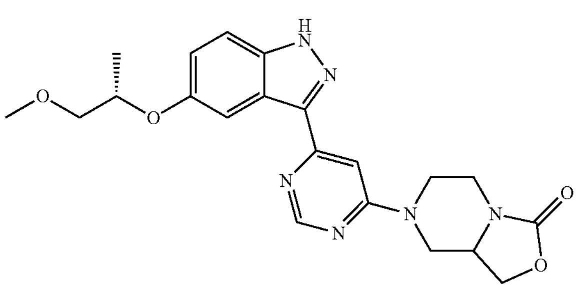 [SMILES: COC[C@H](C)Oc1ccc2[nH]nc(-c3cc(N4CCN5C(=O)OCC5C4)ncn3)c2c1] | 425.19 | 0.77 | D | 8.8 |

-continued
| Example | Structure | LCMS data m/z | RT (min) | Method | LRRK2 IC$_{50}$ (nM) |
|---|---|---|---|---|---|
| O21 | 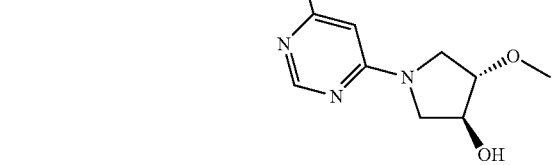 | 400.19 | 0.71 | D | 19.8 |
| O22 | 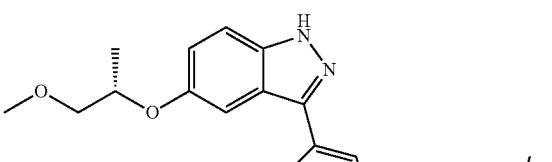 | 413.22 | 0.69 | D | 6.6 |
| O23 | 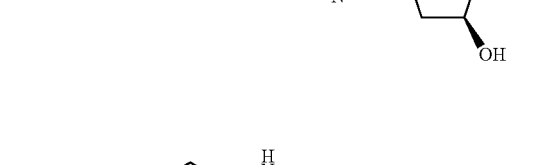 | 453.22 | 0.74 | D | 3.5 |
Scheme P:
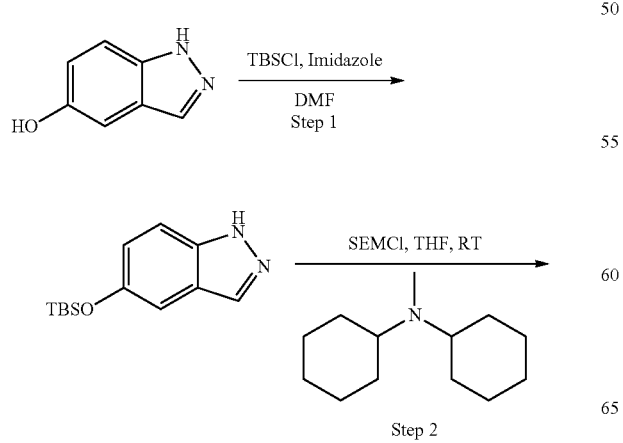
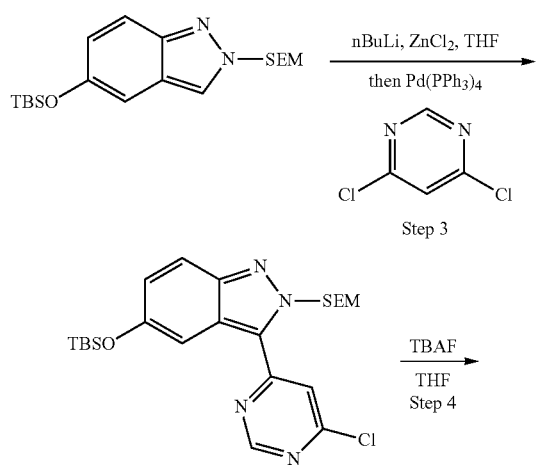

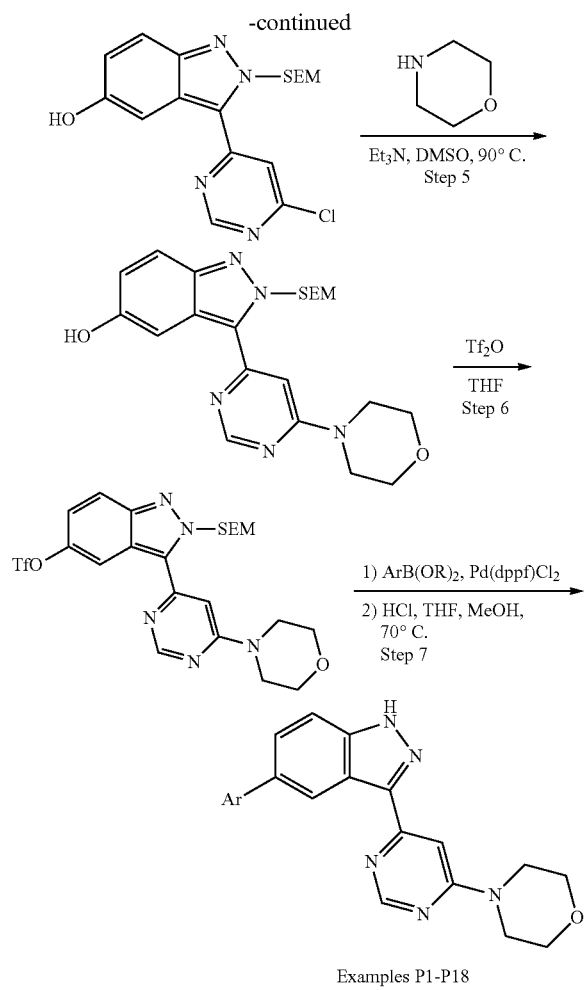

Examples P1-P18

Step 1: To an ice-cooled mixture of 5-hydroxyindazole (53.6 g, 400 mmol) and imidazole (40.8 g, 600 mmol) in DMF (1 L) was added TBSCl (72 g, 480 mmol) over a period of 30 min. The ice-bath was removed and the reaction was stirred at RT overnight. Water (1 L) was added to the reaction slowly and the resulting mixture was extracted with EtOAc (2×500 mL). The combined organic layers were washed with water (2×500 mL) and brine (500 mL), dried over Na$_2$SO$_4$, filtered, and evaporated under reduced pressure to afford a residue which was purified by flash chromatography on silica gel (elution with 6:1 to 2:1 petroleum ether:EtOAc) to afford the silyl ether: MS (ESI): m/z=249.1 [M+H]$^+$.

Step 2: To a solution of above compound (92 g, 371 mmol) and N,N-dicyclohexyl methylamine (86.8 g, 445 mmol) in THF (600 mL) was slowly added SEMCl (68.2 g, 408 mmol). The resulting mixture was stirred at room temperature overnight and then filtered. The filtrate was concentrated in vacuo to give a residue which was purified by flash chromatography on silica gel (gradient elution with 60:1 to 10:1 petroleum ether:EtOAc) to afford the product: MS (ESI) m/z=379 [M+H]$^+$.

Step 3: To a cold (−78° C.), stirred solution of SEM-protected indazole (60 g, 159 mmol) in THF (480 mL) was added n-BuLi (218 mL of 1.6M in hexane, 349 mmol) dropwise under N$_2$. The mixture was stirred for 2 h at −78° C. and then ZnCl$_2$ (280 mL of 1M solution in diethyl ether, 280 mmol) was added dropwise. After being stirred at −78° C. for an additional 1 h, the cooling bath was removed and the mixture was allowed to warm to room temperature. After that time, a degassed solution of 4,6-dichloropyrimidine (21 g, 173 mmol) and (Ph$_3$P)$_4$Pd (9.1 g, 7.9 mmol) in THF (120 mL) was then added under N$_2$. The reaction was stirred at room temperature overnight and then concentrated in vacuo to leave a residue which was purified by flash chromatography on silica gel (gradient elution with 100:1 to 60:1 petroleum ether: EtOAc) to yield the chloropyrimidine. MS (ESI) m/z=491.1 [M]$^+$.

Step 4: The chloropyrimidine (28 g, 57 mmol) and TBAF (22.4 g, 86 mmol) were mixed in THF (300 mL) and stirred at room temperature for 2 h. The THF was removed under reduced pressure and the residue was purified by flash chromatography on silica gel (elution with petroleum ether:EtOAc 3:1 to 1:1) to yield the hydroxyindazole. MS (ESI) m/z=377.1 [M+H]$^+$.

Step 5: The chloropyrimidine from step 4 (5 g, 13.27 mmol), morpholine (3.48 ml, 39.8 mmol) and Et$_3$N (11.09 ml, 80 mmol) were dissolved in DMSO (40 ml). The mixture was heated at 90° C. in a sealed flask for 1 h. The mixture was diluted with EtOAc, washed with water and brine, dried over MgSO$_4$, filtered, and concentrated under reduced pressure to leave a residue which was purified by flash column chromatography on silica gel (gradient elution with 15-70% EtOAc in hexane) to afford the desired morpholine adduct. LCMS 428.2 [M+H]$^+$.

Step 6: To a cold (0° C.), stirred mixture of phenol (1.28 g, 3.0 mmol) and pyridine (1.19 g, 15 mmol) in THF (12 mL) was added Tf$_2$O (2.54 g, 9 mmol) dropwise. After the addition was complete, the mixture was stirred at 0° C. for 15 min followed by at room temperature for 45 min. The reaction mixture was washed with water (5 mL). Organic layer was separated, dried over Na$_2$SO$_4$, filtered and concentrated under reduced pressure to leave a residue which was purified using flash chromatography on silica (gradient elution with 10:1 to 4:1 petroleum ether:EtOAc) to yield the desired triflate as a white solid. MS (ESI) m/z=560.1 [M+1]$^+$.

Step 7: Parallel preparation of examples P1-P18: A set of vials each containing the triflate (25 mg, 0.0745 mmol), 2M K$_2$CO$_3$ $_{(aq.)}$ (0.134 mmol) and the requisite boronic acid/ester (0.045 mmol) in dioxane (1 mL) were transferred into a glove box under an atmosphere of nitrogen. To each vial was added Pd(dppf)Cl$_2$, (3.7 mg, 0.0045 mmol). Each vial was capped and the mixture was heated to 100° C. with stirring for 3 hours. After that time, the mixtures were allowed to cool to RT and removed from the glove box. DCM (1 mL) was added to each vial followed by SiliaMetS® DMT resin (0.0135 mmol). The mixtures were allowed to stir at RT overnight. The mixtures were then filtered. To each vial was added water. The mixtures were then extracted with DCM (1×). The organic layer from each vial was transferred to a clean vial and the solvent was removed in vacuo. To each vial was then added THF:MeOH (1:3, 1 mL) followed by HCl (4 N in dioxane, 0.20 mL, 0.80 mmol). The vials were capped and the solutions were heated to 70° C. for 0.5 h. The solutions were allowed to cool to RT and the solvent was then removed from the vials in vacuo. Each crude product was redissolved in 1 mL of DMSO and filtered. The crude products were purified by mass triggered HPLC using the following conditions: [Waters Sunfire C18 column, 5 μm, 19×100 mm, gradient from 5% initial to a final range of 25-45% MeCN (0.1% formic acid) in water (0.1% formic acid) 50 mL/min, 8 min run time.]

| Example | Structure | LCMS data m/z | Ret time (min) | method | LRRK2 IC₅₀ (nM) |
|---|---|---|---|---|---|
| P1 | 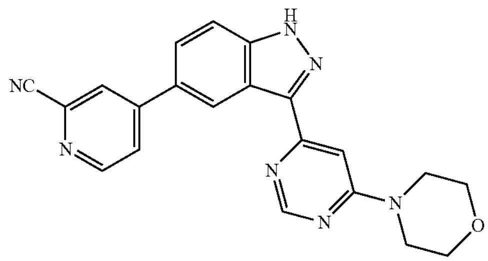 [SMILES: N#Cc1cc(-c2ccc3[nH]nc(-c4cc(N5CCOCC5)ncn4)c3c2)ccn1] | 384.15 | 0.83 | D | 340.1 |
| P2 | 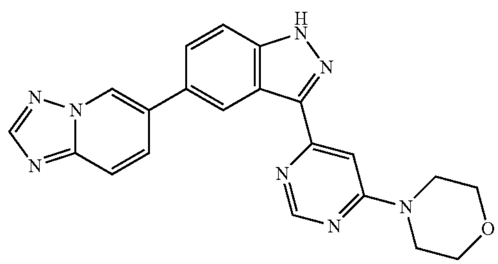 [SMILES: c1nc(-c2n[nH]c3ccc(-c4ccc5ncnn5c4)cc23)cc(N2CCOCC2)n1] | 399.16 | 0.71 | D | 192.7 |
| P3 | 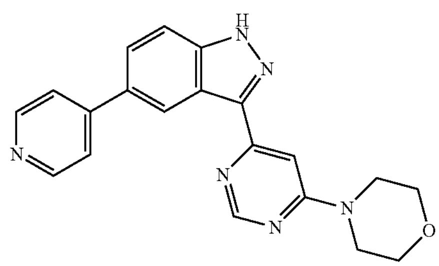 [SMILES: c1cc(-c2ccc3[nH]nc(-c4cc(N5CCOCC5)ncn4)c3c2)ccn1] | 359.15 | 0.75 | D | 96.7 |
| P4 | 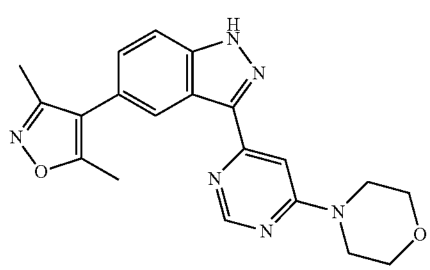 [SMILES: Cc1noc(C)c1-c1ccc2[nH]nc(-c3cc(N4CCOCC4)ncn3)c2c1] | 377.17 | 0.85 | D | 48.7 |
| P5 | 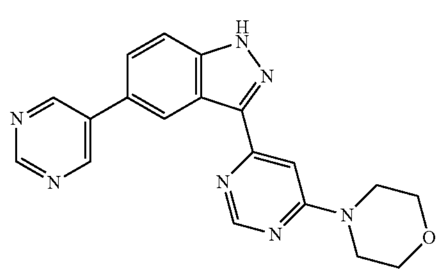 [SMILES: c1ncc(-c2ccc3[nH]nc(-c4cc(N5CCOCC5)ncn4)c3c2)cn1] | 360.15 | 0.68 | D | 40.7 |

-continued
| Example | Structure | LCMS data m/z | Ret time (min) | method | LRRK2 IC$_{50}$ (nM) |
|---|---|---|---|---|---|
| P6 | 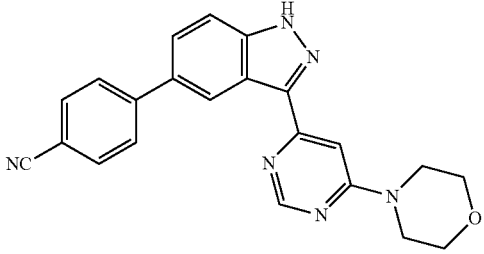 [SMILES: N#Cc1ccc(-c2ccc3[nH]nc(-c4cc(N5CCOCC5)ncn4)c3c2)cc1] | 383.15 | 0.94 | D | 149.8 |
| P7 | 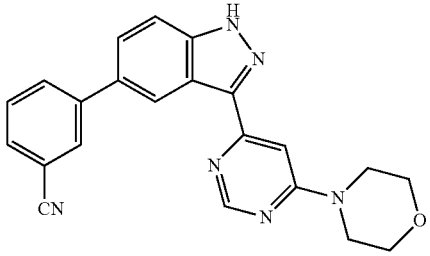 [SMILES: N#Cc1cccc(-c2ccc3[nH]nc(-c4cc(N5CCOCC5)ncn4)c3c2)c1] | 383.15 | 0.95 | D | 81.3 |
| P8 | 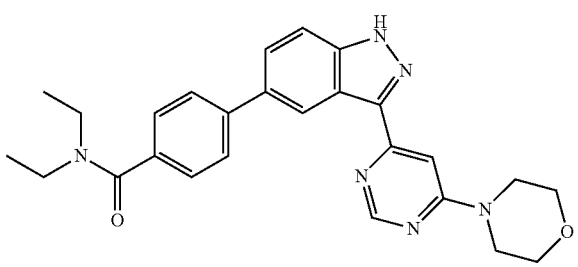 [SMILES: CCN(CC)C(=O)c1ccc(-c2ccc3[nH]nc(-c4cc(N5CCOCC5)ncn4)c3c2)cc1] | 457.23 | 0.92 | D | 607.5 |
| P9 | 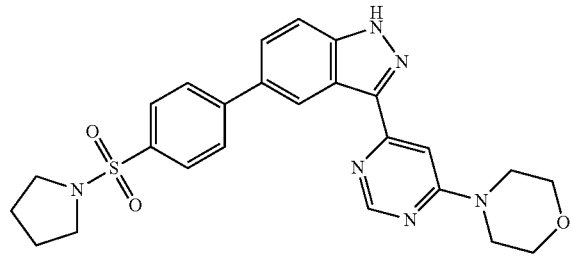 [SMILES: O=S(=O)(c1ccc(-c2ccc3[nH]nc(-c4cc(N5CCOCC5)ncn4)c3c2)cc1)N1CCCC1] | 491.18 | 0.96 | D | 914.4 |
| P10 | 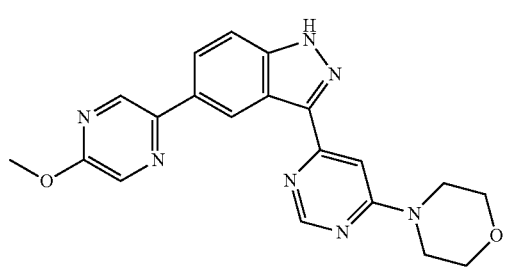 [SMILES: COc1cnc(-c2ccc3[nH]nc(-c4cc(N5CCOCC5)ncn4)c3c2)cn1] | 390.16 | 0.89 | D | 271.5 |

| Example | Structure | LCMS data m/z | Ret time (min) | method | LRRK2 IC$_{50}$ (nM) |
|---|---|---|---|---|---|
| P11 | 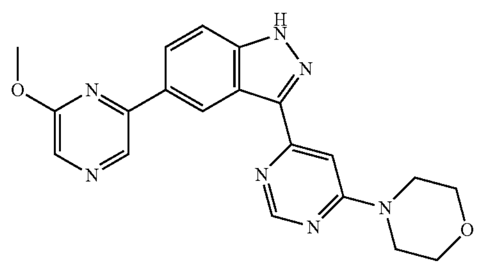 [SMILES: COc1cncc(-c2ccc3[nH]nc(-c4cc(N5CCOCC5)ncn4)c3c2)n1] | 390.16 | 0.87 | D | 18.3 |
| P12 | 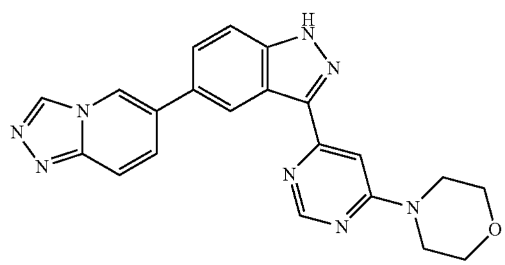 [SMILES: c1nc(-c2n[nH]c3ccc(-c4ccc5nncn5c4)cc23)cc(N2CCOCC2)n1] | 399.16 | 0.63 | D | 56.1 |
| P13 | 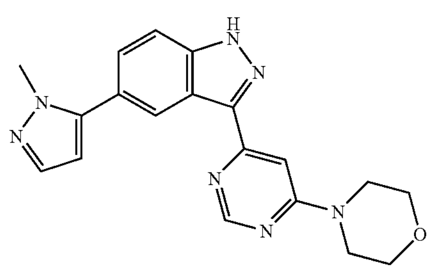 [SMILES: Cn1nccc1-c1ccc2[nH]nc(-c3cc(N4CCOCC4)ncn3)c2c1] | 362.17 | 0.74 | D | 45.7 |
| P14 | 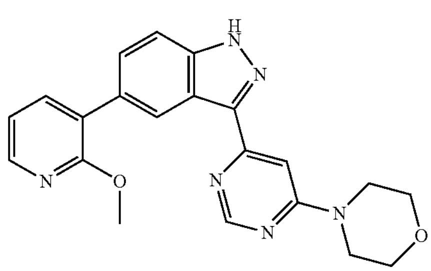 [SMILES: COc1ncccc1-c1ccc2[nH]nc(-c3cc(N4CCOCC4)ncn3)c2c1] | 389.17 | 0.90 | D | 37.7 |
| P15 | 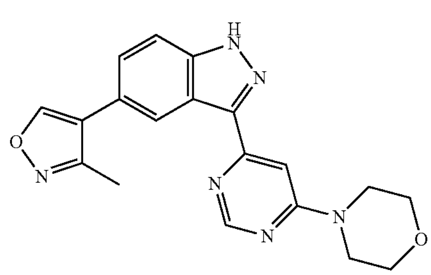 [SMILES: Cc1nocc1-c1ccc2[nH]nc(-c3cc(N4CCOCC4)ncn3)c2c1] | 363.15 | 0.81 | D | 59 |

| Example | Structure | LCMS data m/z | Ret time (min) | method | LRRK2 IC$_{50}$ (nM) |
|---|---|---|---|---|---|
| P16 | 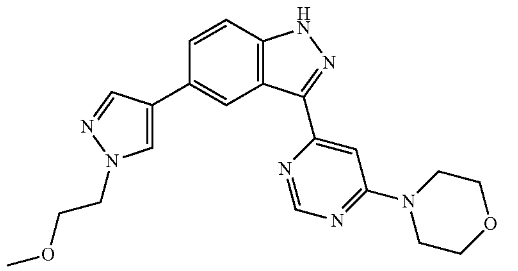 [SMILES: COCCn1cc(-c2ccc3[nH]nc(-c4cc(N5CCOCC5)ncn4)c3c2)cn1] | 406.19 | 0.73 | D | 1.5 |
| P17 | 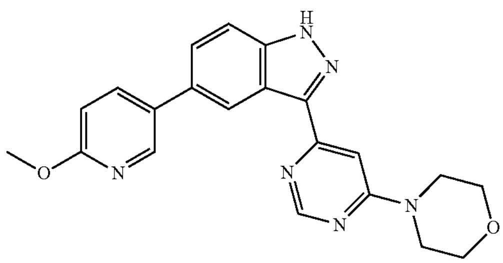 [SMILES: COc1ccc(-c2ccc3[nH]nc(-c4cc(N5CCOCC5)ncn4)c3c2)cn1] | 389.17 | 0.91 | D | 31.2 |
| P18 | 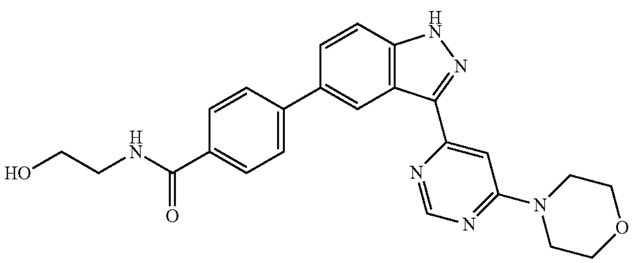 [SMILES: O=C(NCCO)c1ccc(-c2ccc3[nH]nc(-c4cc(N5CCOCC5)ncn4)c3c2)cc1] | 445.19 | 0.66 | D | 153.6 |

Scheme Q:

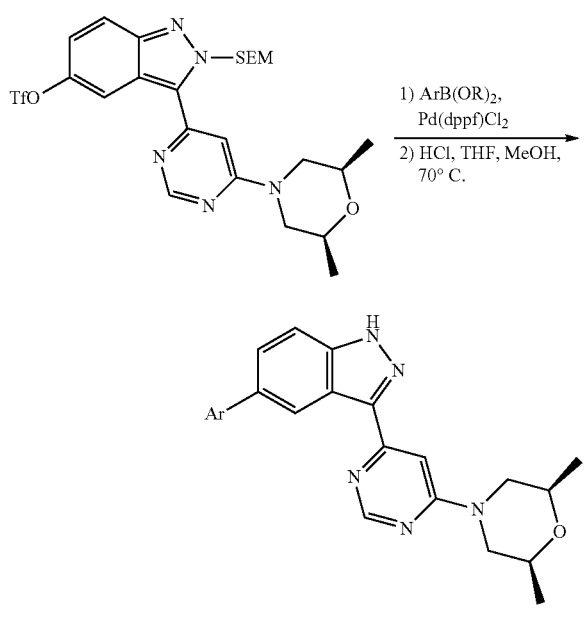

Examples Q1-Q20

Parallel preparation of examples Q1-Q20: A set of vials each containing the triflate (synthesized following the procedure similar to Scheme P employing cis-2,6-dimethylmorpholine in step 5) (25 mg, 0.0745 mmol), 2M K$_2$CO$_3$ $_{(aq.)}$ (0.134 mmol), and the requisite boronic acid/ester (0.045 mmol) in dioxane (1 mL) were transferred into a glove box under an atmosphere of nitrogen. To each vial was added Pd(dppf)Cl$_2$ (3.7 mg, 0.0045 mmol). Each vial was capped and the mixture was heated to 100° C. with stirring for 3 hours. After that time, the mixtures were allowed to cool to RT and removed from the glove box. DCM (1 mL) was added to each vial followed by SiliaMetS® DMT resin (0.0135 mmol). The mixtures were allowed to stir at RT overnight. The mixtures were then filtered. To each vial was added water. The mixtures were then extracted with DCM (1×). The organic layer from each vial was transferred to a clean vial and the solvent was removed in vacuo. To each vial was then added THF:MeOH (1:3, 1 mL) followed by HCl (4 N in dioxane, 0.20 mL, 0.80 mmol). The vials were capped and the solutions were heated to 70° C. for 0.5 h. The solutions were allowed to cool to RT and the solvent was then removed from the vials in vacuo. Each crude product was redissolved in 1 mL of DMSO and filtered. Examples Q1-Q10 were purified by mass triggered HPLC using the following conditions: [Waters Sunfire C18 column, 5 μm, 19×100 mm, gradient from 10% initial to 25-40% final MeCN (0.1% TFA) in water (0.1% TFA) 50 mL/min, 8 min run time.] Examples Q11-Q12 were purified using the following conditions: [Waters Sunfire C18 column, 5 μm, 19×100 mm, gradient from a range of 10% initial to 40-45% final MeCN (0.1% formic acid) in water (0.1% formic acid) 25 mL/min, 8 min run time]. Examples Q13-Q20 were originally purified using the TFA conditions above and were repurified using the following conditions: [Waters XBridge C18 column, 5 μm, 19×100 mm, gradient ranges from a range 10-30% initial to 40-70% MeCN (0.1% NH$_4$OH) in water (0.1% NH$_4$OH) 50 mL/min, 8 min run time].

| Example | Structure | LCMS data m/z | Ret time (min) | method | LRRK2 IC$_{50}$ (nM) |
|---|---|---|---|---|---|
| Q1 | | 427.19 | 0.84 | D | 240.1 |
| Q2 | | 417.2 | 1.04 | D | 158.5 |
| Q3 | | 390.2 | 0.88 | D | 32.1 |
| Q4 | | 401.2 | 0.95 | D | 2.2 |

-continued

| Example | Structure | LCMS data | | | LRRK2 |
|---|---|---|---|---|---|
| | | m/z | Ret time (min) | method | IC$_{50}$ (nM) |
| Q5 | 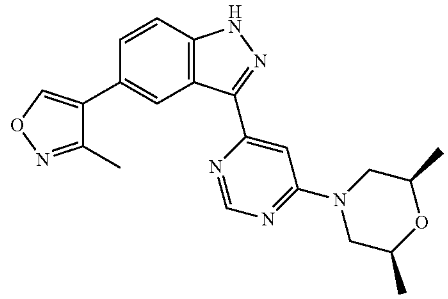 [SMILES: Cc1nocc1-c1ccc2[nH]nc(-c3cc(N4C[C@@H](C)O[C@@H](C)C4)ncn3)c2c1] | 391.18 | 0.95 | D | 40 |
| Q6 | 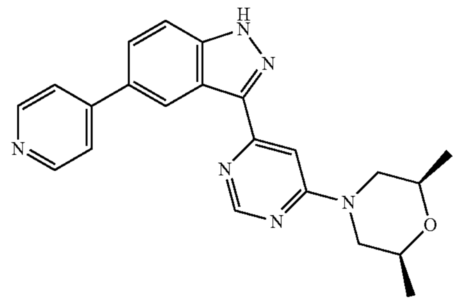 [SMILES: C[C@@H]1CN(c2cc(-c3n[nH]c4ccc(-c5ccncc5)cc34)ncn2)C[C@H](C)O1] | 387.19 | 0.88 | D | 49.5 |
| Q7 | 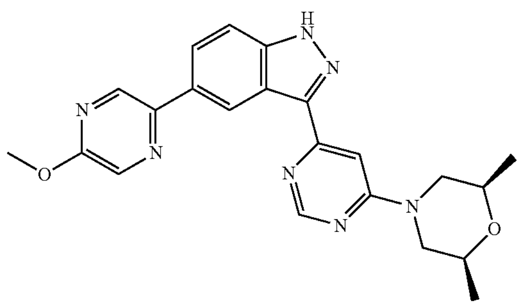 | 418.19 | 1.04 | D | 63.4 |
| Q8 | 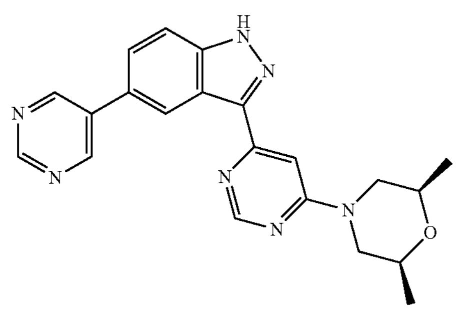 [SMILES: C[C@@H]1CN(c2cc(-c3n[nH]c4ccc(-c5cncnc5)cc34)ncn2)C[C@H](C)O1] | 388.18 | 0.81 | D | 30.3 |
| Q9 | 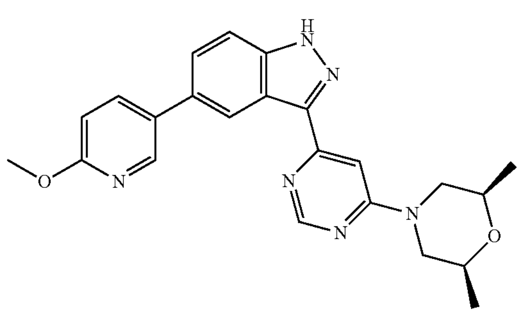 | 417.2 | 1.05 | D | 41.1 |

-continued

| Example | Structure | LCMS data m/z | Ret time (min) | method | LRRK2 IC$_{50}$ (nM) |
|---|---|---|---|---|---|
| Q10 | 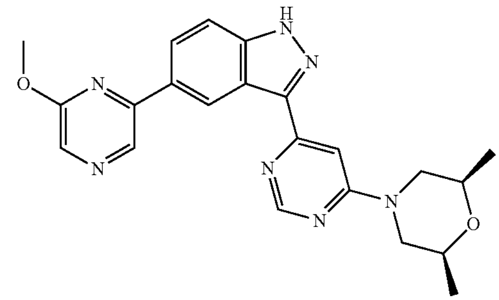 [SMILES: COc1cncc(-c2ccc3[nH]nc(-c4cc(N5C[C@@H](C)O[C@@H](C)C5)ncn4)c3c2)n1] | 418.19 | 1.01 | D | 2.4 |
| Q11 | 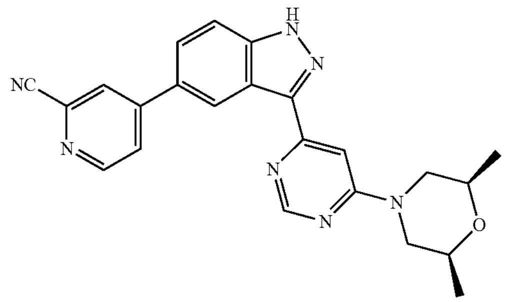 [SMILES: C[C@@H]1CN(c2cc(-c3n[nH]c4ccc(-c5ccnc(C#N)c5)cc34)ncn2)C[C@H](C)O1] | 412.18 | 0.98 | D | 171.7 |
| Q12 | 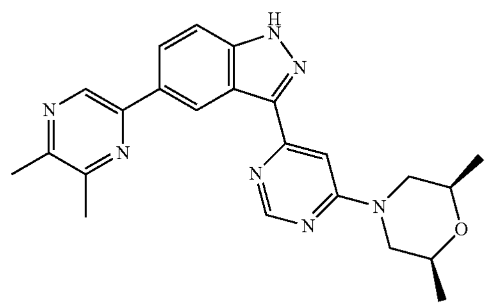 | 416.21 | 0.98 | D | 17.4 |
| Q13 | 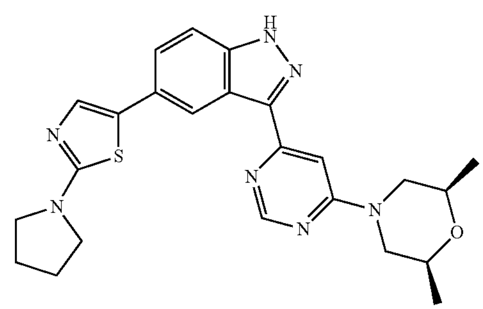 [SMILES: C[C@@H]1CN(c2cc(-c3n[nH]c4ccc(-c5cnc(N6CCCC6)s5)cc34)ncn2)C[C@H](C)O1] | 462.2 | 1.07 | D | 7.6 |
| Q14 | 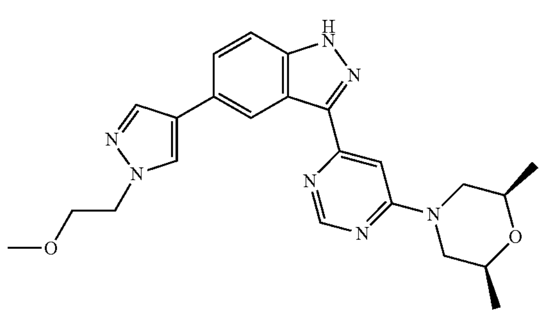 | 434.22 | 0.86 | D | 1.8 |

-continued

| Example | Structure | LCMS data m/z | Ret time (min) | method | LRRK2 IC$_{50}$ (nM) |
|---|---|---|---|---|---|
| Q15 | 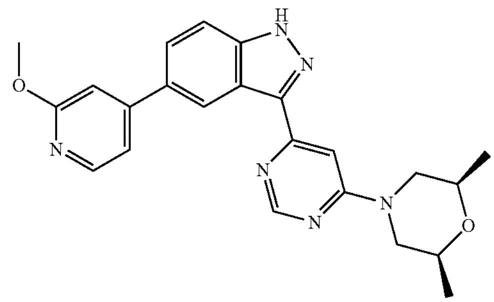 [SMILES: COc1cc(-c2ccc3[nH]nc(-c4cc(N5C[C@@H](C)O[C@@H](C)C5)ncn4)c3c2)ccn1] | 417.2 | 1.04 | D | 155.1 |
| Q16 | 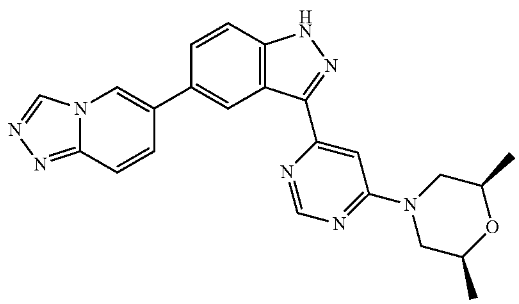 [SMILES: C[C@@H]1CN(c2cc(-c3n[nH]c4ccc(-c5ccc6nncn6c5)cc34)ncn2)C[C@H](C)O1] | 427.19 | 0.76 | D | 60.6 |
| Q17 | 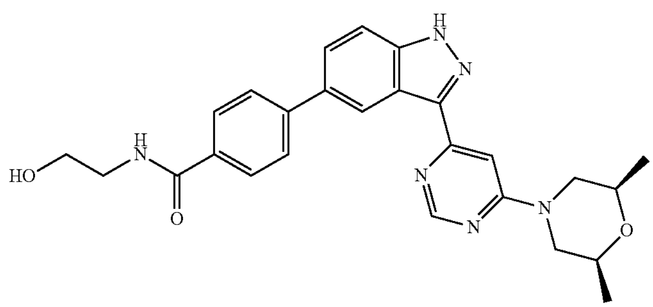 [SMILES: C[C@@H]1CN(c2cc(-c3n[nH]c4ccc(-c5ccc(C(=O)NCCO)cc5)cc34)ncn2)C[C@H](C)O1] | 473.22 | 0.78 | D | 77 |
| Q18 | 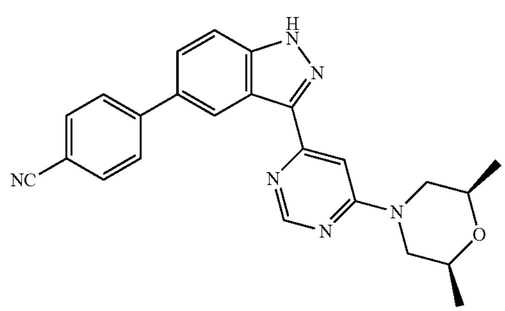 [SMILES: C[C@@H]1CN(c2cc(-c3n[nH]c4ccc(-c5ccc(C#N)cc5)cc34)ncn2)C[C@H](C)O1] | 411.19 | 1.07 | D | 177.4 |
| Q19 | 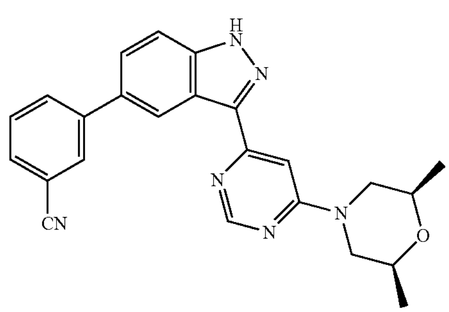 [SMILES: C[C@@H]1CN(c2cc(-c3n[nH]c4ccc(-c5cccc(C#N)c5)cc34)ncn2)C[C@H](C)O1] | 411.19 | 1.08 | D | 47.9 |

| Example | Structure | LCMS data m/z | Ret time (min) | method | LRRK2 IC$_{50}$ (nM) |
|---|---|---|---|---|---|
| Q20 | 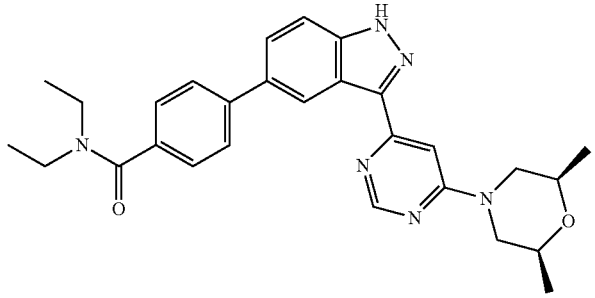 [SMILES: CCN(CC)C(=O)c1ccc(-c2ccc3[nH]nc(-c4cc(N5C[C@@H](C)O[C@@H](C)C5)ncn4)c3c2)cc1] | 485.26 | 1.04 | D | 847.1 |

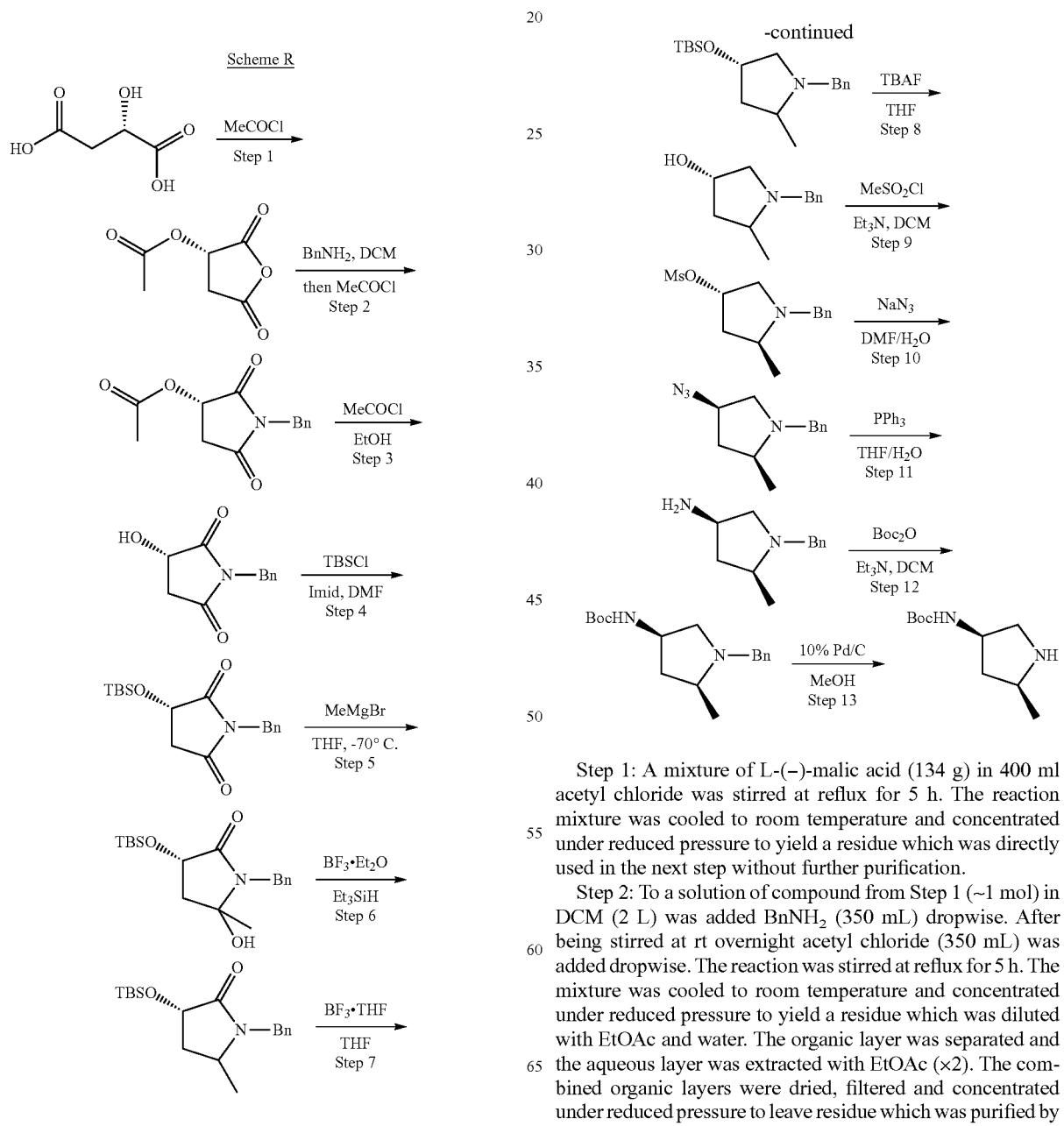

Step 1: A mixture of L-(−)-malic acid (134 g) in 400 ml acetyl chloride was stirred at reflux for 5 h. The reaction mixture was cooled to room temperature and concentrated under reduced pressure to yield a residue which was directly used in the next step without further purification.

Step 2: To a solution of compound from Step 1 (~1 mol) in DCM (2 L) was added BnNH$_2$ (350 mL) dropwise. After being stirred at rt overnight acetyl chloride (350 mL) was added dropwise. The reaction was stirred at reflux for 5 h. The mixture was cooled to room temperature and concentrated under reduced pressure to yield a residue which was diluted with EtOAc and water. The organic layer was separated and the aqueous layer was extracted with EtOAc (×2). The combined organic layers were dried, filtered and concentrated under reduced pressure to leave residue which was purified by column chromatography on silica gel (elution with 3:1 petroleum ether:EtOAc) to afford the desired product as a white solid.

Step 3: To a stirred solution of compound from Step 2 (116 g, 0.47 mol) in EtOH (1.2 L) was added acetyl chloride (62 ml) dropwise at rt. After the addition was complete the mixture was heated at 50° C. for 4 h. The reaction was cooled to rt and concentrated under reduced pressure to yield a residue. To this residue was added toluene and the resulting mixture was concentrated and dried to leave a residue which was recrystallized from toluene to afford the desired product as a white solid.

Step 4: To a stirred mixture of compound from Step 3 (86 g, 0.42 mol) and imidazole (43 g, 0.63 mol) in DMF (700 mL) was added TBSCl (75 g, 0.50 mol). The reaction was stirred at rt overnight. The reaction was diluted with EtOAc (2 L) and washed with water (2×500 ml) and brine (2×500 ml), dried, filtered and concentrated under reduced pressure to leave a residue which was purified by column chromatography on silica gel (elution with 30:1 petroleum ether:EtOAc) to afford the desired product as a white solid Step 5: To a cold (−70° C.), stirred solution of compound from Step 4 (160 g, 0.5 mol) in THF (1.5 L) was added MeMgBr (333 ml of 1.0 M solution in THF, 1.0 mol) dropwise. The reaction mixture was slowly warmed to −25° C. and then to −15° C. slowly before being quenched with a saturated aqueous solution of NH$_4$Cl. The organic layer was separated and the aqueous layer was extracted with EtOAc. The combined organic layers were dried, filtered and concentrated under reduced pressure to leave a residue which was purified by column chromatography on silica gel (elution with 30:1 petroleum ether:EtOAc) to afford the desired product as a white solid.

Step 6: To a cold (−70° C.), stirred solution of compound from Step 5 (67.5 g, 0.2 mol) in DCM (1 L) was added Et$_3$SiH (234 g, 2.0 mol) followed by BF$_3$.Et$_2$O (37 ml, 0.3 mol) dropwise. The cold bath was removed and the mixture was warmed to rt before being quenched by a saturated aqueous solution of NaHCO$_3$. The resulting layer was extracted with DCM, dried, filtered and concentrated under reduced pressure to leave a residue which was purified by column chromatography on silica gel (elution with 30:1 petroleum ether:EtOAc) to obtain the desired product as a yellow oil.

Step 7: A mixture of compound from Step 6 (62 g, 0.194 mol) and BH$_3$.THF (486 ml of 1.0 M solution in THF, 0.486 mol) in THF (100 mL) was stirred at reflux for 6 h. The reaction was cooled to rt and EtOH (100 ml) was added dropwise. The resulting mixture was stirred at reflux for additional 2 h. The reaction was cooled to rt and concentrated under reduced pressure to leave a residue which was redissolved in DCM and washed with a saturated aqueous solution of NaHCO$_3$. The organic layer was dried, filtered and concentrated under reduced pressure to yield a yellow oil which was used in the next step without further purification.

Step 8: A mixture of compound from Step 7 (~60 g, 0.194 mol) and TBAF (76 g, 0.291 mol) in THF (600 mL) was stirred at rt overnight. The reaction mixture was concentrated under reduced pressure to leave a residue which was purified by column chromatography on silica gel (elution with 1:1 to 0:100 petroleum ether:EtOAc) to afford the desired product as a yellow oil.

Step 9: To a cold (0° C.), stirred solution of compound from Step 8 (36 g, 0.188 mol) in DCM (350 mL) was added Et$_3$N (40 ml, 0.28 mol) followed by MeSO$_2$Cl (25.8 g, 0.226 mol) dropwise. After being stirred at 0° C. for 2 h the mixture was washed with water and brine, dried, filtered and concentrated under reduced pressure to leave a residue which was purified by column chromatography on silica gel (elution with 10:1 to 5:1 petroleum ether:EtOAc) to afford the desired product as a yellow oil.

Step 10: A mixture of compound from Step 9 (25 g, 0.093 mol) and NaN$_3$ (18 g, 0.279 mol) in DMF (300 mL) and water (30 mL) was stirred at 100° C. overnight. The reaction mixture was cooled to rt and diluted with EtOAc. The resulting layer was washed with water and brine, dried, filtered and concentrated under reduced pressure to leave a residue which was used in the next step without further purification.

Step 11: To a stirred mixture of compound from Step 10 (0.093 mol) and PPh$_3$ (73 g, 0.279 mol) in THF (300 mL) and water (30 mL) was stirred at 90° C. for 2 h. The reaction mixture was concentrated under reduced pressure to yield a residue which was diluted with water (200 mL) followed by 6N HCl until pH 1-2. The resulting layer extracted with EtOAc (×3). The aqueous layer was adjusted to pH 9-10 by using NaOH (10% aq.) which was then extracted with DCM (×5). The combined organic layers were washed with brine, dried, filtered and concentrated under reduced pressure to yield a residue which was used in the next step without further purification.

Step 12: To a solution of compound amine from Step 11 (~0.093 mol) in DCM (250 mL) was added Et$_3$N (20 ml, 0.14 mol) followed by Boc$_2$O (24 g, 0.112 mol). After being stirred at rt for 2 h the mixture was washed with water and brine, dried, filtered and concentrated under reduced pressure to leave a residue which was purified by column chromatography on silica gel (elution with 20:1 to 5:1 petroleum ether:EtOAc) to afford the desired product as a yellow oil.

Step 13: To a stirred solution of compound from Step 12 (36 g, 0.14 mol) in MeOH (500 mL) was added 10% wet Pd/C (5 g). The flask was evacuated and back-filled with H$_2$ (×2). The resulting mixture was then stirred at 45° C. for 20 h. The reaction was filtrated and the filtrate was concentrated to obtain the desired amine as a gray solid.

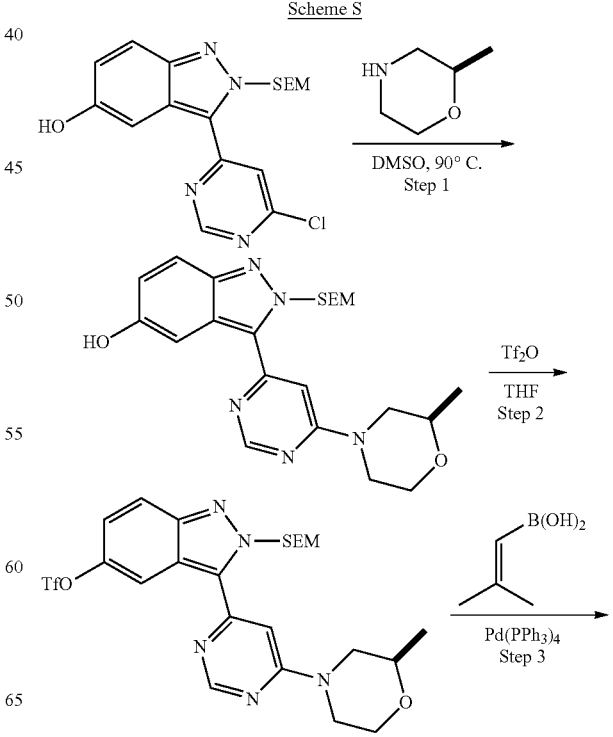

-continued

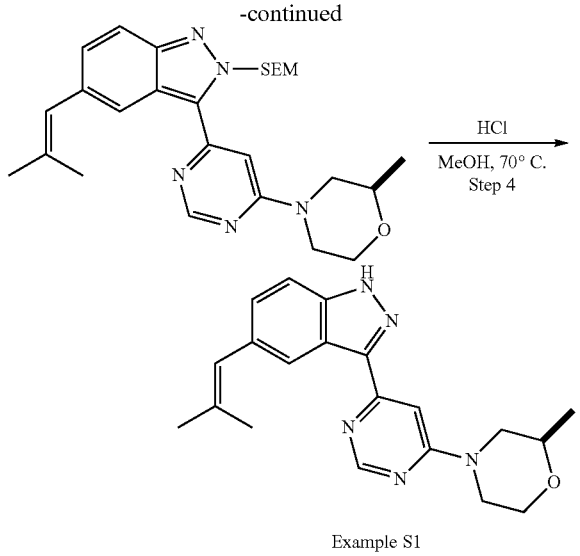

Example S1

Step 1: This step was carried out following the same procedure described by Step 5 in Scheme P using the methylmorpholine as the amine.

Step 2: This step was carried out following the same procedure described by Step 6 in Scheme P.

Step 3: A mixture of the triflate from step 2 (0.2 g, 0.35 mmol), 2-methylprop-1-enylboronic acid (0.07 g, 0.7 mmol), $Na_2CO_3$ (0.11 g, 1.04 mmol) and $Pd(PPh_3)_4$ (0.04 g, 0.035 mmol) in dioxane/$H_2O$ (10 mL/1 mL) was degassed and recharged with argon gas followed by heating at 100° C. overnight. The reaction was cooled to rt and filtered. The filtrate was concentrated under reduced pressure to leave a residue which was purified by prep-TLC plate (elution with petroleum ether:EtOAc=3:2) to provide the desired adduct as a yellow solid.

Step 4: Example S1 was prepared after the removal of SEM group described by Step 4 in Scheme D (Method B). LCMS: 350.2 $[M+1]^+$ (ret. time=1.73 min, condition C4); LRRK2 $IC_{50}$: 16.4 nM.

TABLE S

Examples S2-S6 were prepared following the procedure described in Scheme S utilizing the requisitie amines

| Example | Structure | LRRK2 $IC_{50}$ (nM) | LCMS data m/z | RT (min) | Method |
|---|---|---|---|---|---|
| S2 | 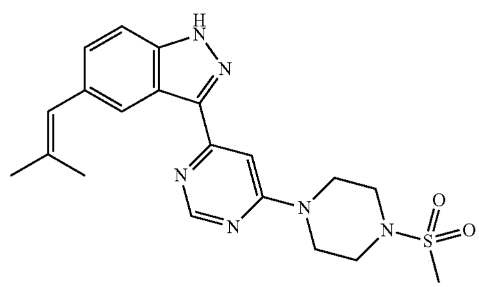 [SMILES: CC(C)=Cc1ccc2[nH]nc(-c3cc(N4CCN(S(C)(=O)=O)CC4)ncn3)c2c1] | 28.8 | 413.1 | 1.73 | C4 |
| S3 | 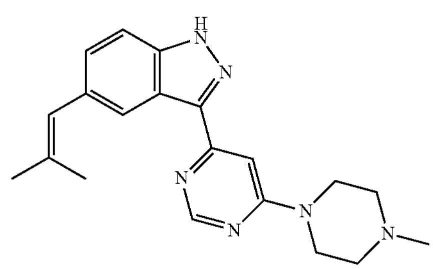 [SMILES: CC(C)=Cc1ccc2[nH]nc(-c3cc(N4CCN(C)CC4)ncn3)c2c1] | 32.9 | 349.1 | 1.19 | C6 |
| S4 | 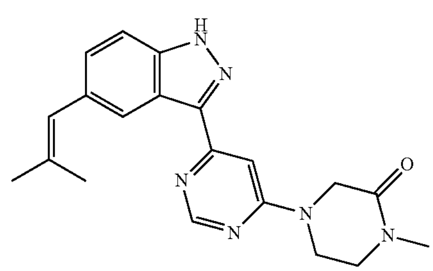 [SMILES: CC(C)=Cc1ccc2[nH]nc(-c3cc(N4CCN(C)C(=O)C4)ncn3)c2c1] | 36.2 | 363.1 | 1.71 | C4 |

TABLE S-continued

Examples S2-S6 were prepared following the procedure described in Scheme S utilizing the requisitie amines

| Example | Structure | LRRK2 IC$_{50}$ (nM) | LCMS data m/z | RT (min) | Method |
|---|---|---|---|---|---|
| S5 | | 20.3 | 364.1 | 1.41 | C6 |
| S6 | | 16.4 | 396.1 | 1.98 | C1 |

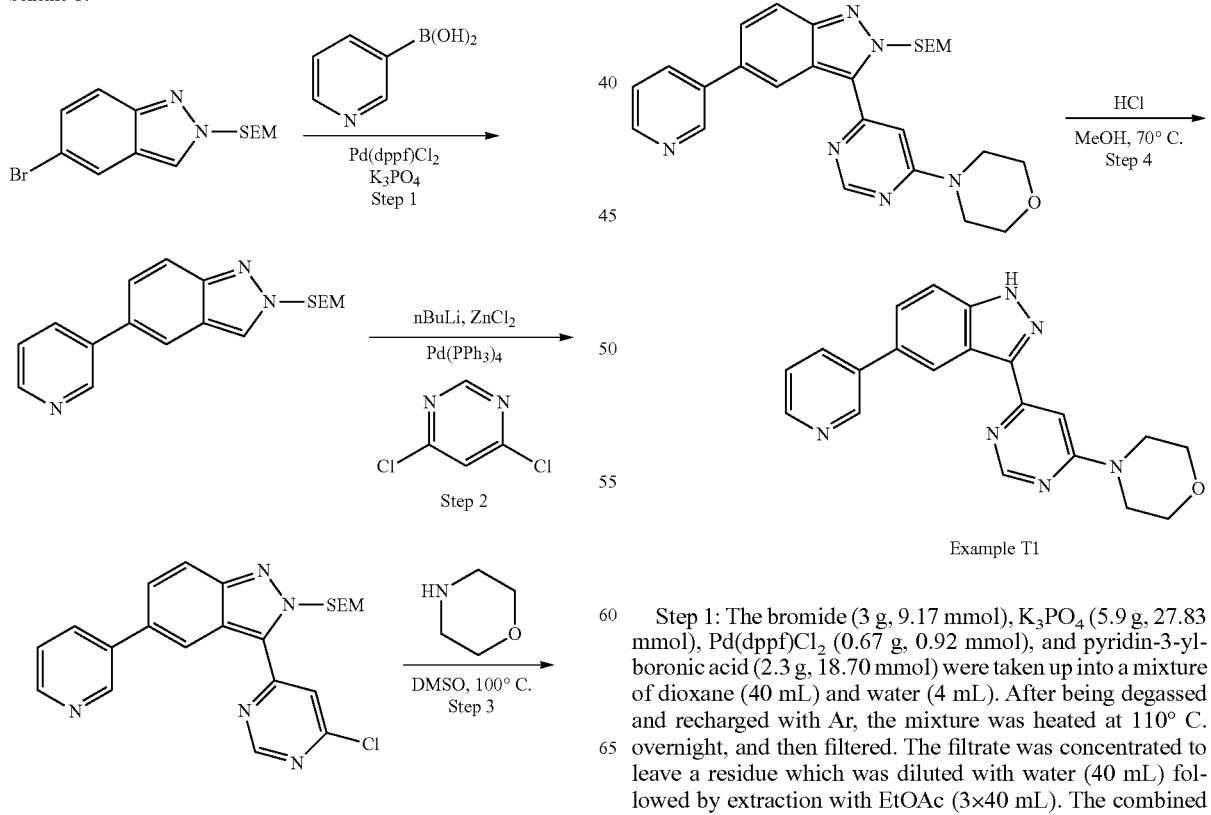

Example T1

Step 1: The bromide (3 g, 9.17 mmol), K$_3$PO$_4$ (5.9 g, 27.83 mmol), Pd(dppf)Cl$_2$ (0.67 g, 0.92 mmol), and pyridin-3-yl-boronic acid (2.3 g, 18.70 mmol) were taken up into a mixture of dioxane (40 mL) and water (4 mL). After being degassed and recharged with Ar, the mixture was heated at 110° C. overnight, and then filtered. The filtrate was concentrated to leave a residue which was diluted with water (40 mL) followed by extraction with EtOAc (3×40 mL). The combined organic layers were washed with brine (50 mL), dried over Na₂SO₄, filtered and concentrated to leave a residue which was purified by column chromatography on silica gel (gradient elution with 10:1 to 2:1 petroleum ether:EtOAc) to yield the pyridyl adduct as a yellow solid.

Step 2: n-BuLi (9 mL of 1.6 M in hexane, 14.4 mmol) was added dropwise into a cold (−78° C.) solution of compound from Step 1 (2.3 g, 7.08 mmol) in THF (20 mL) under N₂. The mixture was stirred for 2 h at −78° C. and then ZnCl₂ (14.4 mL of 1 M solution in diethyl ether, 14.4 mmol) was added dropwise. The reaction was stirred at −78° C. for 1 h followed by warming up to room temperature. A degassed solution containing 4,6-dichloropyrimidine (1.58 g, 10.60 mmol) and Pd(PPh₃)₄ (0.51 g, 0.44 mmol) in THF (8 mL) was then added at room temperature under N₂. The reaction was stirred at room temperature overnight and then concentrated in vacuo to leave a residue. Water was added and the aqueous layer was extracted thoroughly with EtOAc (3×50 mL). The combined organic layers were dried, filtered and concentrated under reduced to leave a residue which was purified by column chromatography on silica gel (gradient elution with 10:1 to 1:1 petroleum ether:EtOAc) to yield the desired chloropyrimidine as an off-yellow solid.

Step 3: A solution of the chloropyrimidine (150 mg, 0.34 mmol), morpholine (50 mg, 0.57 mmol) and Et₃N (100 mg, 1 mmol) in DMSO (2 ml) was stirred at 100° C. overnight. Water (50 mL) was added and the resulted mixture was extracted with EtOAc (3×20 mL). The combined organic layers were dried over Na₂SO₄, filtered and concentrated under reduced pressure to yield the desired morpholine adduct which was directly used in the next step without further purification.

Step 4: To a solution of the above morpholine adduct in MeOH (5 mL) was added a solution of HCl in dioxane (2 mL of 3.5 M solution in dioxane). The solution was stirred at 70° C. for 3 h. After being cooled to room temperature the pH of the resulting mixture was adjusted to 7-8 using NaHCO₃. The mixture was filtered and the filtrate was concentrated to leave a residue which was purified by Prep-HPLC to yield Example T1. LCMS 359.2 [M+1]⁺ (ret time=1.61 min, condition C2); LRRK2 IC₅₀: 5.5 nM.

Example T2 was synthesized using similar procedure described in Scheme T. LCMS 436.1 [M+1]⁺ (ret time=1.60 min, condition C2); LRRK2 IC₅₀: 7.3 nM.

Example T2

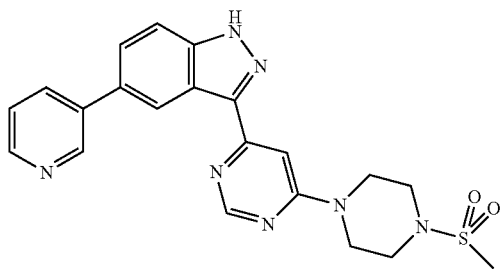

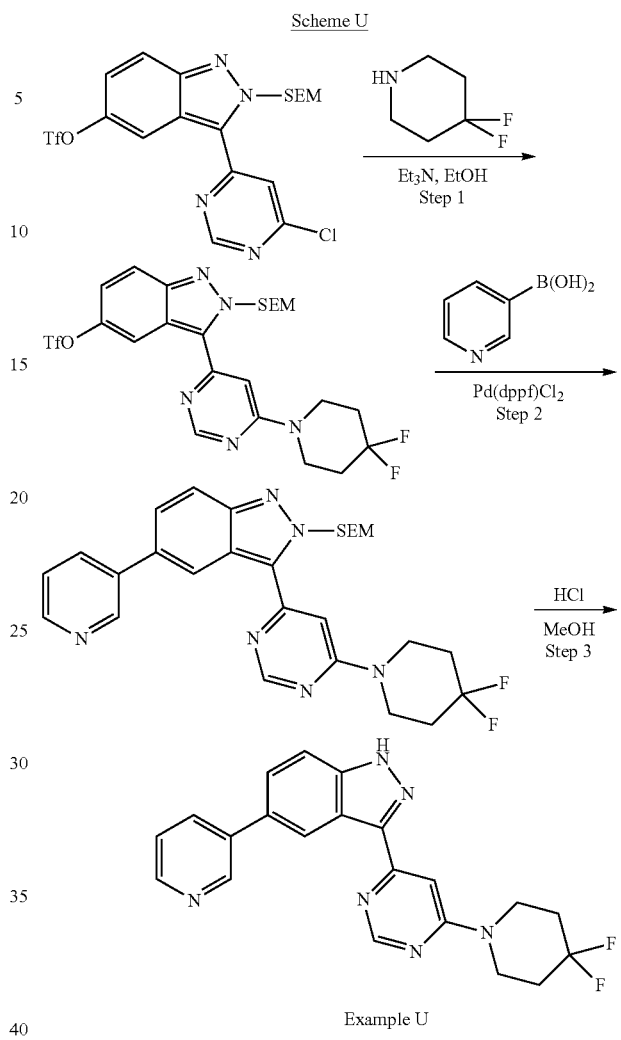

Scheme U

Example U

Step 1: A sealed tube containing a mixture of the chloropyrimidine (1.60 g, 3.14 mmol), triethylamine (1.90 g, 18.81 mmol) and 4,4-difluoropiperidine (0.57 g, 4.71 mmol) in EtOH (20 mL) was heated at 100° C. for 6 h. After being cooled to room temperature, the reaction was concentrated under reduced pressure to leave a residue which was purified by flash chromatography on silica (gradient elution with 10:1 to 4:1 petroleum ether:EtOAc) to provide the desired adduct as an off-yellow solid.

Step 2: A mixture of the triflate (0.10 g, 0.17 mmol), pyridin-3-ylboronic acid (0.031 g, 0.25 mmol), Na₂CO₃ (0.054 g, 0.51 mmol) and Pd(dppf)Cl₂ (0.013 g, 0.018 mmol) in a mixture of toluene (1 mL), EtOH (0.5 mL) and water (0.5 mL) was degassed and recharged with argon gas. After being heated at 70° C. overnight the mixture was filtered. The filtrate was concentrated under reduced pressure to leave a residue which was purified by Prep-TLC plate (elution with 3:2 petroleum ether:EtOAc) to afford the desired coupled product as a yellow solid.

Step 3: To a stirred solution of above adduct (0.080 g, 0.15 mmol) in MeOH (2 mL) was added HCl (1.3 mL of 3.5 M solution in 1,4-dioxane). After being stirred at 70° C. for 2 h the mixture was cooled to room temperature. The pH was adjusted to 11-12 using 10% aq. K₂CO₃. The volatiles were then removed under reduced pressure and the mixture was partitioned between ethyl acetate and water (5 mL/5 mL). The organic layer was separated and the aqueous layer was extracted with ethyl acetate (2×5 mL). The combined organic layers were dried over $Na_2SO_4$, filtered and concentrated in vacuo to leave a residue which was purified by Prep-TLC plate (elution with 3:2 petroleum ether:EtOAc) to provide Example U. MS (ESI) m/z=393.2 [M+1]$^+$ (ret time=1.82 min, condition C2); LRRK2 IC$_{50}$: 11.1 nM.

TABLE U

Example U1-U29 were prepared following the procedures described in Scheme U utilizing the requisite amine (step 1) and requisite boronic acid (step 2).

| Example | Structure | LRRK2 IC$_{50}$ (nM) | m/z | RT (min) | Method |
|---|---|---|---|---|---|
| U1 | 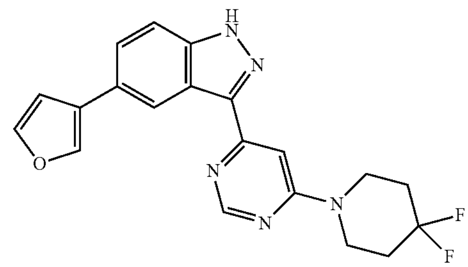 | 86.2 | 382.2 | 1.96 | C2 |
| U2 | 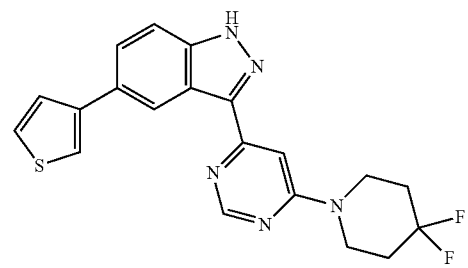 | 347.8 | 398.1 | 2.06 | C2 |
| U3 | 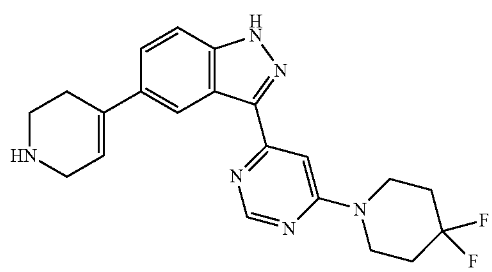 | 119.7 | 397.3 | 1.69 | C2 |
| U4 | 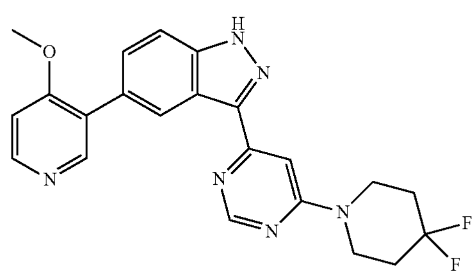 | 6.66 | 423.3 | 1.74 | C2 |
| U5 | 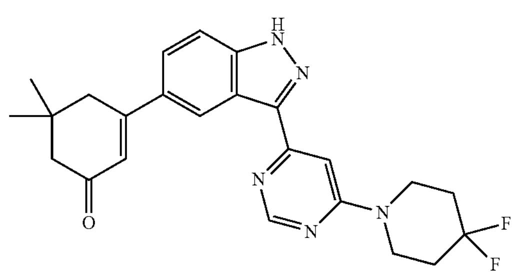 | 7.08 | 438.3 | 1.93 | C2 |

TABLE U-continued

Example U1-U29 were prepared following the procedures described in Scheme U utilizing the requisite amine (step 1) and requisite boronic acid (step 2).

| Example | Structure | LRRK2 IC$_{50}$ (nM) | m/z | RT (min) | Method |
|---|---|---|---|---|---|
| U6 | | 2.16 | 382.2 | 1.69 | C2 |
| U7 | | 5.69 | 382.1 | 1.64 | C2 |
| U8 | | 19.01 | 348.1 | 1.30 | C6 |
| U9 | | 36.4 | 364.1 | 1.09 | C3 |
| U10 | | 2.2 | 379.0 | 1.62 | C4 |

TABLE U-continued

Example U1-U29 were prepared following the procedures described in Scheme U utilizing the requisite amine (step 1) and requisite boronic acid (step 2).

| Example | Structure | LRRK2 IC$_{50}$ (nM) | m/z | RT (min) | Method |
|---|---|---|---|---|---|
| U11 | 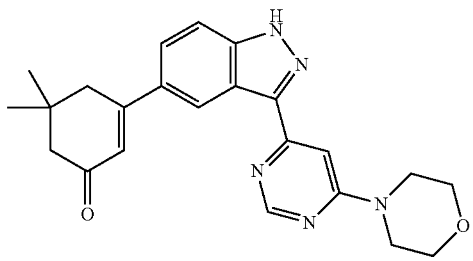 | 1.63 | 404.2 | 1.79 | C2 |
| U12 | 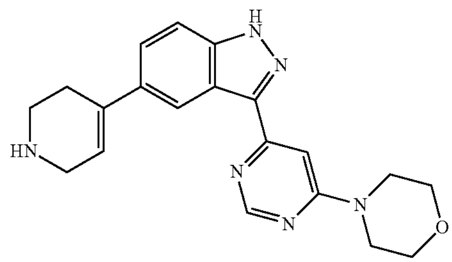 | 71.6 | 363.1 | 1.05 | C6 |
| U13 | 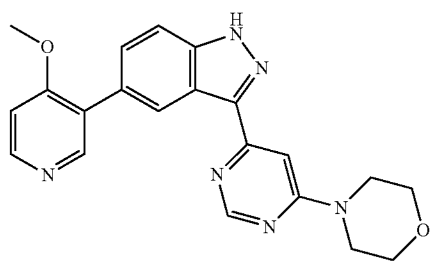 | 1.72 | 389.2 | 1.56 | C2 |
| U14 | 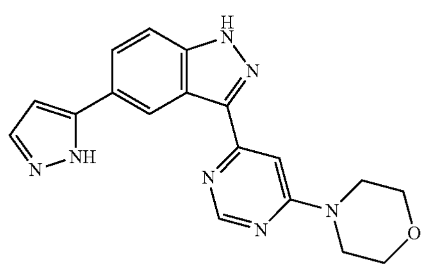 | 2.63 | 348.3 | 1.50 | C2 |
| U15 | 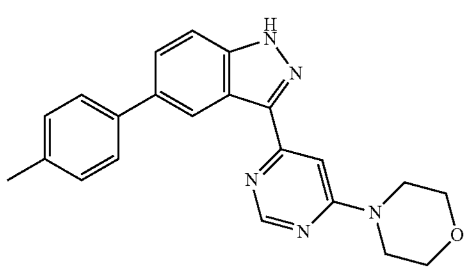 | 251.1 | 372.3 | 2.0 | C2 |

TABLE U-continued

Example U1-U29 were prepared following the procedures described in Scheme U utilizing the requisite amine (step 1) and requisite boronic acid (step 2).

| Example | Structure | LRRK2 IC$_{50}$ (nM) | m/z | RT (min) | Method |
|---|---|---|---|---|---|
| U16 | | 2.3 | 348.3 | 1.44 | C2 |
| U17 | | 1.63 | 376.3 | 1.65 | C2 |
| U18 | | 266.5 | 393.1 | 1.78 | C2 |
| U19 | | 2.58 | 376.1 | 1.51 | C1 |
| U10 | | 1.58 | 466.1 | 1.56 | C2 |

TABLE U-continued
Example U1-U29 were prepared following the procedures described in Scheme U utilizing the requisite amine (step 1) and requisite boronic acid (step 2).
| Example | Structure | LRRK2 IC$_{50}$ (nM) | LCMS data m/z | RT (min) | Method |
|---|---|---|---|---|---|
| U21 | 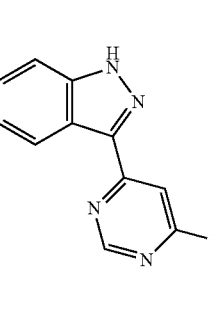 | 61.5 | 405.1 | 2.04 | C1 |
| U22 | 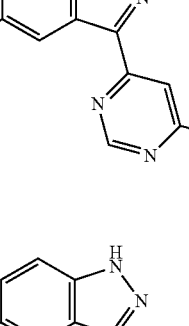 | 9.03 | 389.2 | 1.91 | C1 |
| U23 | 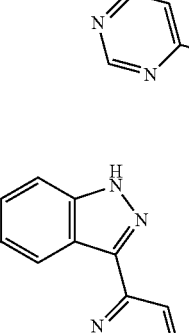 | 1.26 | 430.2 | 1.54 | C1 |
| U24 | 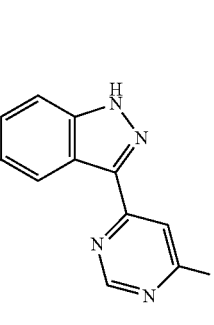 | 0.96 | 389.2 | 1.56 | C1 |
| U25 | 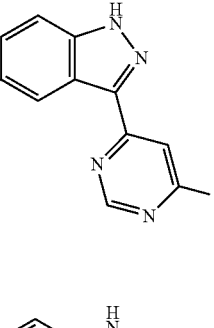 | 2.34 | 389.2 | 1.61 | C1 |

TABLE U-continued

Example U1-U29 were prepared following the procedures described in Scheme U utilizing the requisite amine (step 1) and requisite boronic acid (step 2).

| Example | Structure | LRRK2 IC$_{50}$ (nM) | m/z | RT (min) | Method |
|---|---|---|---|---|---|
| U26 | 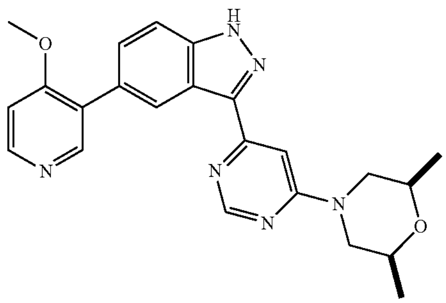 | 0.75 | 417.1 | 1.74 | C1 |
| U27 | 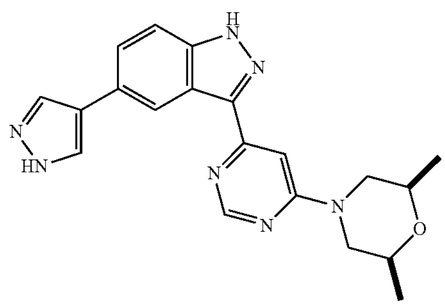 | 1.35 | 376.3 | 1.61 | C2 |
| U28 | 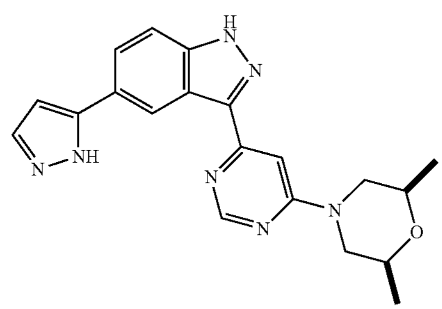 | 1.44 | 376.3 | 1.66 | C2 |
| U29 | 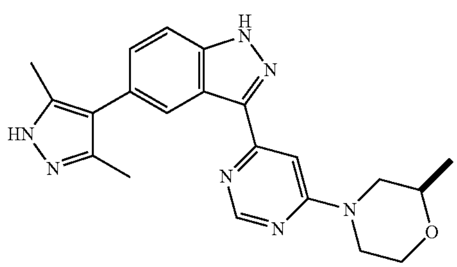 | 3.20 | 390.1 | 1.59 | C1 |

Scheme V:

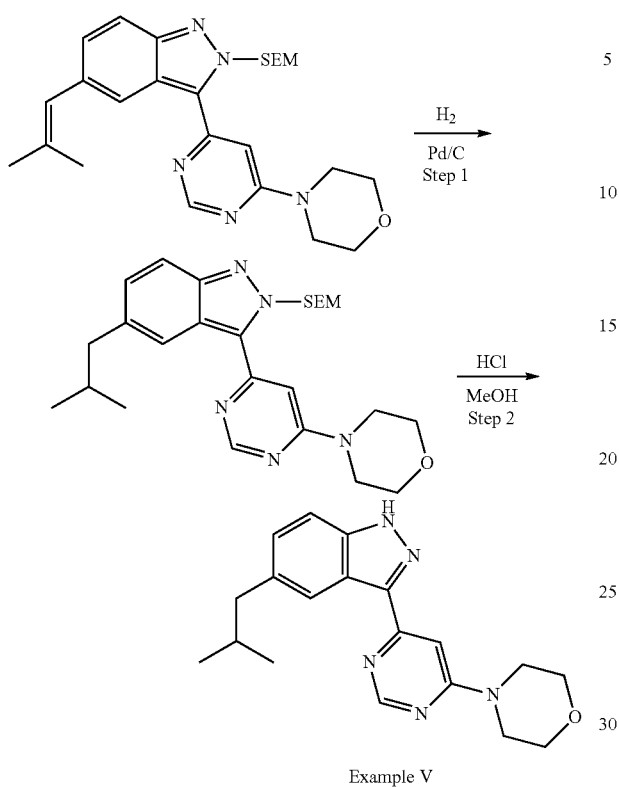

Example V

Step 1: A stirred solution of the alkene prepared following the same method described in Scheme S (step 1-3) (0.12 g, 0.26 mmol) in MeOH (20 mL) was added 10% Pd/C (0.03 g). The reaction mixture was stirred at 50° C. under $H_2$ (10 atm) for 4 h. The reaction mixture was filtered and the filtrate was concentrated to afford the desired hydrogenated product which was used in the next step without further purification.

Step 2: To a stirred solution of above compound (0.1 g, 0.21 mmol) in MeOH (3 mL) was added HCl (2 mL of 3.5 M solution in 1,4-dioxane). The mixture was stirred at 70° C. for 2 h. After being cooled to room temperature the pH of the resulting mixture was adjusted to 11-12 using 10% aq. $K_2CO_3$. The volitiles were then removed under reduced pressure and the residue was partitioned between ethyl acetate and water (5 mL/5 mL). The organic layer was separated and the aqueous layer was extracted with ethyl acetate (2×5 mL). The combined organic layers were dried over $Na_2SO_4$, filtered and concentrated in vacuo to leave a residue which was purified by Prep-TLC plate (elution with 3:2 petroleum ether:EtOAc) to afford Example V as a yellow solid. MS (ESI) m/z=338.1 [M+1]$^+$ (ret. time 1.72 min, condition C4); LRRK2 IC$_{50}$: 56 nM.

Scheme W

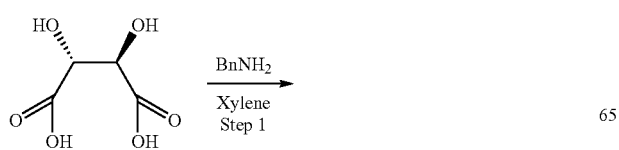

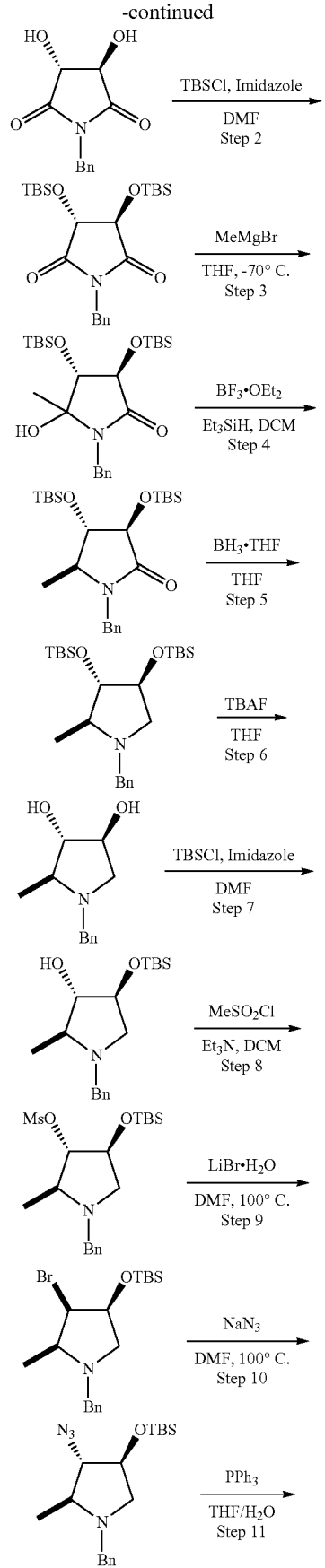

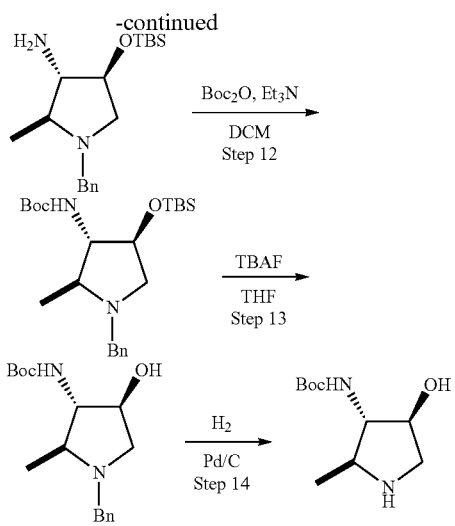

Step 1: A mixture of L-tartaric acid (250 g, 1.67 mol) and BnNH$_2$ (178 g, 1.67 mol) in xylene (1.5 L) was stirred under reflux for 4 h using a Dean-Stark water separator. The reaction was cooled to room temperature with stirring and filtrated. The solid was washed with EtOH to afford the desired product as a yellow solid.

Step 2: To a stirred solution of diol from Step 1 (275 g, 1.24 mol) in DMF (1.8 L) was added imidazole (254 g, 3.73 mol) followed by TBSCl (467 g, 3.11 mol). The reaction mixture was stirred at rt overnight before being diluted with EtOAc. The resulting layer was washed with water and brine, dried, filtered and concentrated to leave a residue which was purified by column chromatography on silica gel (elution with petroleum ether:EtOAc 100:1) to afford the desired product as a colorless oil.

Step 3: To a cold (−70° C.), stirred solution of compound from Step 2 (270 g, 0.6 mol) in THF (3 L) was added MeMgBr (400 ml of 1.0 M solution in THF, 1.2 mol) dropwise. The reaction mixture was slowly warmed to −10° C. and then to rt before being quenched with a saturated aqueous solution of NH$_4$Cl. The organic layer was separated and the aqueous layer was extracted with EtOAc. The combined organic layers were dried, filtered and concentrated under reduced pressure to leave a residue which and purified by column chromatography on silica gel (gradient elution with 50:1 to 10:1 petroleum ether:EtOAc) to afford the desired product as a white solid.

Step 4: To a cold (−70° C.), stirred solution of compound from Step 3 (350 g, 0.75 mol) in DCM (2 L) was added Et$_3$SiH (870 g, 7.5 mol) followed by a solution of BF$_3$.Et$_2$O (139 ml, 1.125 mol) dropwise. The reaction mixture was warmed up to rt before being quenched with a saturated aqueous solution of NaHCO$_3$. The organic layer was separated and the aqueous layer was extracted with DCM. The combined organic layers were dried, filtered and concentrated under reduced pressure to leave a residue which and purified by column chromatography on silica gel (elution with petroleum ether:EtOAc 10:1) to afford the desired product as a colorless oil.

Step 5: A mixture of compound from Step 4 (325 g, 0.72 mol) and BH$_3$.THF (1800 mL of 1.0 M solution in THF, 1.8 mol) in THF (500 mL) was stirred at reflux for 6 h. The reaction was cooled and EtOH (300 ml) was added dropwise. The mixture was stirred at reflux for additional 2 h followed by cooling to rt. The reaction mixture was concentrated to leave a residue which was dissolved in DCM. The organic layer was washed with a saturated aqueous solution of NaHCO$_3$, dried, filtered and concentrated to afford the desired product as a yellow oil.

Step 6: To a stirred solution of compound from Step 5 (438 g, 1.0 mol) in THF (2.5 L) was added TBAF (657 g, 2.5 mol) and the resulting mixture was stirred at rt overnight. The reaction mixture concentrated under reduced pressure to leave a residue which was directly purified by column chromatography on silica gel (gradient elution with 1:1 to 0:100 petroleum ether:EtOAc) to afford the dial as a white solid.

Step 7: To a solution of diol from Step 6 (95 g, 0.46 mol) in DMF (1 L) was added imidazole (47 g, 0.69 mol) followed by TBSCl (76 g, 0.5 mol). The reaction was stirred at rt overnight. The reaction was diluted with EtOAc and the resulting layer was washed with water and brine, dried, filtered and concentrated under reduced pressure to leave a residue which was purified by column chromatography on silica gel (elution with 4:1 petroleum ether:EtOAc) to afford the desired product as a yellow oil.

Step 8: To a cold (0° C.), stirred solution of alcohol from Step 7 (75 g, 0.234 mol) in DCM (750 mL) was added Et$_3$N (49 ml, 0.35 mol) followed by MeSO$_2$Cl (32 g, 0.28 mol) dropwise. The resulting mixture was stirred at 0° C. for 2 h. The mixture was washed with water and brine, dried, filtered and concentrated to afford the desired mesylate as a brown oil which was directly used in the next step without further purification.

Step 9: A mixture of mesylate from Step 8 (93 g, 0.233 mol) and LiBr.H$_2$O (245 g, 2.33 mol) in DMF (1 L) was stirred at 100° C. overnight, After being cooled to room temperature the reaction was diluted with EtOAc. The resulting layer was washed with water and brine, dried, filtered and concentrated under reduced pressure to leave a residue which was purified by column chromatography on silica gel (elution with 50:1 petroleum ether:EtOAc) to afford the desired product as a colorless oil.

Step 10: A mixture of bromide from Step 9 (64 g, 0.167 mol) and NaN$_3$ (33 g, 0.5 mol) in DMF (600 mL) and water (50 mL) was stirred at 100° C. for 2 days. After being cooled to room temperature the reaction was diluted with EtOAc, washed with water and brine, dried, filtered and concentrated to leave a brown oil which was directly used in the next step without further purification.

Step 11: A mixture of azide from Step 10 (0.344 mol) and PPh$_3$ (262 g, 1.0 mol) in THF (1.5 L) and water (150 mL) was stirred at 90° C. for 2 h. The reaction was concentrated under reduced pressure to leave a residue which was diluted with water (500 ml) followed by the addition of 6N HCl until pH 1-2. The aqueous layer was extracted with EtOAc. The aqueous phase was adjusted to pH 9-10 by adding an aqueous solution of NaOH (10%). The resulting layer was extracted with DCM. The organic layer was washed with brine, dried, filtered and concentrated under reduced pressure to afford the desired amine as a brown oil.

Step 12: To a stirred solution of amine from Step 11 (156 g, 0.49 mol) in DCM (2 L) was added Et$_3$N (103 ml, 0.73 mol) followed by Boc$_2$O (128 g, 0.59 mol). After being stirred at rt for 2 h the reaction was washed with water and brine, dried, filtered and concentrated under reduced pressure to leave a residue which was purified by column chromatography on silica gel (elution with 20:1 petroleum ether:EtOAc) to afford the desired product as a white solid.

Step 13: To a stirred solution of compound from Step 12 (60 g, 0.143 mol) in THF (1 L) was added TBAF (56 g, 0.214 mol) and the resulting mixture was stirred at room temperature overnight. The mixture was concentrated and the residue was purified by column chromatography on silica gel (gradient elution with 1:1 to 1:5 Petroleum ether:EtOAc) to afford the desired product as a white solid.

Step 14: To a stirred solution of compound from Step 13 (39 g, 0.127 mol) in MeOH (800 mL) was added 10% wet Pd/C (4 g). The flask was evacuated and back-filled with $H_2$ (×2). The resulting mixture was then stirred at 30° C. for 24 h. The reaction was filtrated and the filtrate was concentrated to obtain the desired amine as a gray solid.

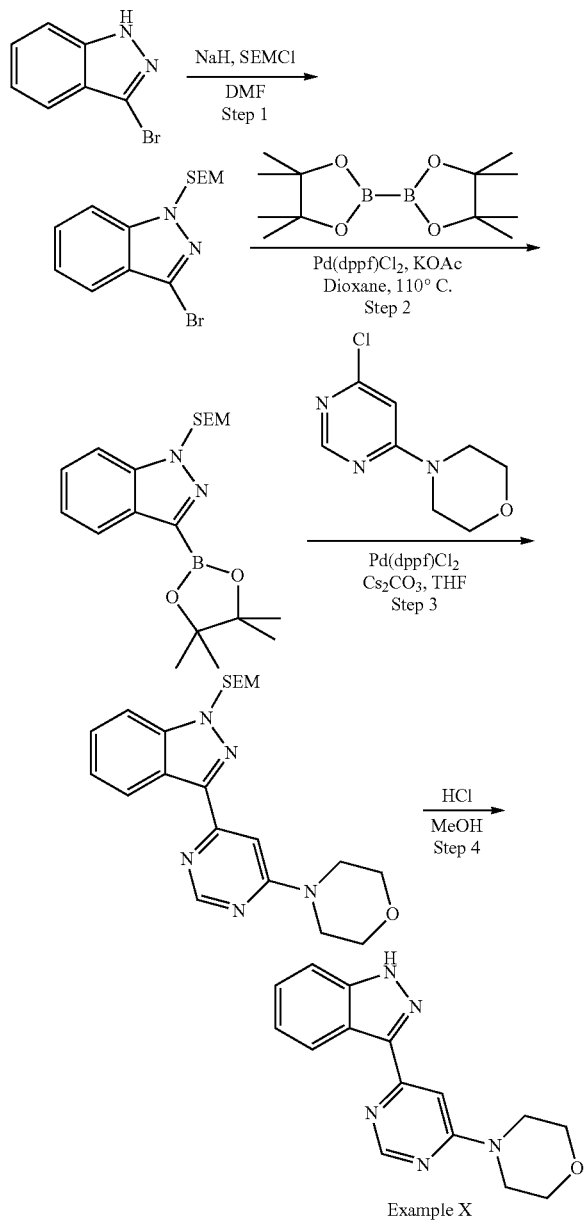

Scheme X

Step 1:To a cold (0° C.), stirred solution of 3-bromoindazole (1.0 g, 5.08 mmol) in DMF (25 mL) was added NaH (0.24 g of 60% in oil, 6.09 mmol) in portions. After 15 min, SEMCl (1.08 mL, 6.09 mmol) was added and the mixture was stirred at room temperature overnight. The reaction was quenched with a saturated aqueous solution of $NH_4Cl$ and the resulting layer was extracted with EtOAc (×2). The combined organic layers were dried, filtered and concentrated under reduced pressure to leave a residue which was purified by flash chromatography on silica (elution with 100:1 to 10:1 hexane:EtOAc) to yield the desired product as an oil.

Step 2:A mixture of bromoindazole from Step 1 (0.35 g, 1.05 mmol), KOAc (0.42 g, 4.22 mmol), $Pd(dppf)Cl_2$ (0.15 g, 0.21 mmol) and bis(pinacolato)diboron (0.32 g, 1.27 mmol) in 1,4-dioxane (5.3 mL) was heated at 80° C. for 12 h. After being cooled to room temperature the mixture was concentrated under reduced pressure to leave a residue which was purified by Prep-TLC on silica (elution with 10:1 hexane:EtOAc) to yield the desired boronate ester.

Step 3: A mixture of boronate ester from Step 2 (101 mg, 0.27 mmol), 4-(6-chloropyrimidin-4-yl)morpholine (65 mg, 0.324 mmol), $Cs_2CO_3$ (264 mmol, 0.81 mmol) and Pd(dppf)$Cl_2$ (40 mg, 0.054 mmol) in THF (1.35 mL) was heated at 80° C. for 1.5 h. The reaction was cooled to room temperature and filtered through a pad of celite. The solid was washed with DCM. The filtrate was concentrated under reduced pressure to leave a residue which was purified by Prep-TLC on silica (elution with 10:1 hexane:EtOAc) to yield the pyrimidine adduct as a white solid.

Step 4:This step was carried out following the procedure described by step 4 in Scheme D. LCMS: 282.0 (ret. time=1.81 min, condition B); LRRK2 $IC_{50}$: 134.3 nM.

LCMS Conditions:

Condition A: Column: SUPELCO Ascentis Express C18, 3×50 mm, 2.7 urn, Mobile phase: A: Water (0.05% TFA) B: Acetonitrile (0.05% TFA), UV: 200-400 nm

| [Gradient Table] | | | |
|---|---|---|---|
| Time (min) | Flow Rate | % A | % B |
| Initial | 1.25 | 90 | 10 |
| 0.8 | 1.25 | 1 | 99 |
| 1.99 | 1.25 | 1 | 99 |
| 2.00 | 1.25 | 90 | 10 |

Condition B: Agilent 6140 Quadruple Easy Access LC/MS; Column: Agilent Zorbax SB-C18, 3.0×50 mm, 1.8 μm; Solvent A: Water with 0.1% TFA; Solvent B: acetonitrile with 0.1% TFA; Flow Rate: 1 mL/min; Dual wavelength UV Detection at 220 nm and 254 nm; Gradient: 10% Solvent B to 95% Solvent B over 1.5 min., isocratic at 95% Solvent B for 1.2 min., gradient to 10% Solvent B over 0.1 min., isocratic at 10% Solvent B for 0.8 min.

Condition C1: Mobile Phase: A: Water (10 mM $NH_4HCO_3$) B: Acetonitrile, Gradient: 5%-95% B in 1.5 min, Flow Rate: 1.8 mL/min, Column: XBridge C18, 4.6*50 mm, 3.5 um.

Condition C2: Mobile Phase: A: Water (10 mM $NH_4HCO_3$) B: Acetonitrile, Gradient: 5% B for 0.2 min, increase to 95% B within 1.5 min, 95% B for 1.5 min, back to 5% B within 0.01 min., Flow Rate: 1.8 mL/min, Column: XBridge C18, 4.6*50 mm, 3.5 um.

Condition C3: Mobile Phase: A: Water (0.01% TFA) B: MeCN (0.01% TFA), Gradient: 5%-95% B in 1.2 min, Flow Rate: 2.0 ml/min, Column: Merck C18, 50 mm, 3 mm.

Condition C4: Mobile Phase: A: Water (0.01% TFA) B: MeCN (0.01% TFA), Gradient: 5%-95% B in 1.5 min, Flow Rate: 1.8 ml/min, Column: Sunfire C18, 4.6*50 mm, 3.5 um, Condition C5: Mobile Phase: A: Water (0.01% TFA) B: MeCN (0.01% TFA), Gradient: 5%-95% B in 1.5 min, Flow Rate: 2.0 ml/min, Column: XBridge C18, 4.6*50 mm, 3.5 urn.

Condition C6: Column: SunFire C18, 4.6×50 mm, 3.5 urn, Mobile phase: H₂O (0.05% TFA) (A)/MeCN (0.05% TFA) (B), Elution program: Gradient from 5 to 95% of B in 1.2 min at 2 ml/min.

Condition D: Waters Acquity UPLC/MS, Electrospray positive ion mode; Column: Waters Acquity UPLC BEH C18, 2.1×50 mm, 1.7 micron; Gradient elution 5:95 to 100:0 MeCN (0.1% NH₄OH): water (0.1% NH₄OH) over 1.4 min 0.8 mL/min; UV: 220 nm.

Biological Assays

The data presented for the 5 mM and Km ATP LanthaScreen™ Assay represents mean IC₅₀ values based on several test results and may have reasonable. deviations depending on the specific conditions and reagents used. Reagents for the LRRK2 5 mM and Km ATP LanthaScreen™ Assay were purchased from Life Technologies Corporation.

LRRK2 5 mM ATP LanthaScreen™ Assay a) 400 nl of a 1:2.15 serial dilution of test compound(98 µM top assay concentration) is spotted via Labcyte Echo to certain wells in a 384 well black, untreated plate. Control wells contain 400 nl of either DMSO or 400 nl of a known inhibitor in DMSO.

b) 10 µl of a 2.5 nM LRRK2(G2019S mutation, GST-LRRK2(amino acids 970-2527)) enzyme solution in 1× assay buffer(50 mM Tris pH 8.5, 10 mM MgCl₂, 0.01% Brij-35, 1.0 mM EGTA, 2 mM DTT, 0.05 mM NaVO₄) is added to all wells.

c) A 30 minute room temperature incubation is followed by addition of 10 µl of 800 nM fluorescein labeled LRRKtide peptide substrate and 10 mM ATP solution in 1× assay buffer to all wells.

d) After a 35 minute room temperature incubation, 20 µl of TR-FRET Dilution Buffer(Invitrogen PV3756B) containing 4 nM Tb-labeled anti-phospho LRRKtide antibody and 20 mM EDTA is added to all wells.

e) Plates are incubated at room temperature for 1 hour and read on an Envision™ multi-mode plate reader with LanthaScreen™ settings. Results are analysed using Assay Data Analyzer.

LRRK2 Km ATP LanthaScreen™ Assay a) 400 nl of a 1:2.15 serial dilution of test compound(98 µM top assay concentration) is spotted via Labcyte Echo to certain wells in a 384 well black, untreated plate. Control wells contain 400 nl of either DMSO or 400 nl of a known inhibitor in DMSO.

b) 10 µl of a 2.5 nM LRRK2(G2019S mutation, GST-LRRK2(amino acids 970-2527)) enzyme solution in 1× assay buffer(50 mM Tris pH 8.5, 10 mM MgCl₂, 0.01% Brij-35, 1 mM EGTA, 2 mM DTT, 0.05 mM NaVO₄) is added to all wells.

c) A 30 minute room temperature incubation is followed by addition of 10 µl of 800 nM fluorescein labeled LRRKtide peptide substrate and 184 µM ATP solution in 1× assay buffer to all wells.

d) After a 60 minute room temperature incubation, 20 µl of TR-FRET Dilution Buffer(Invitrogen PV3756B) containing 4 nM Tb-labeled anti-phospho LRRKtide antibody and 20 mM EDTA is added to all wells.

e) Plates are incubated at room temperature for 1 hour and read on an Envision™ multi-mode plate reader with LanthaScreen™ settings. Results are analysed using Assay Data Analyzer.

TABLE A 5 mM ATP LanthaScreen ™ Assay Data of representative compounds
In the table below, representative examples are provided with their respective IC₅₀ in the 5 mM ATP LanthaScreen ™ Assay. Preferred compounds have an IC₅₀ less than 1 µM in the 5 mM ATP LanthaScreen Assay.

| Example | IC₅₀ (nM) |
| --- | --- |
| A1 | 41 |
| A3 | 36 |
| A8 | 14 |
| D6 | 96 |
| K10 | 24 |
| D15 | 34 |
| D2 | 67 |
| D24 | 28 |
| H4 | 33 |
| D41 | 22 |
| D32 | 30 |

TABLE B

Kinase selectivity of representative compounds
Kinase selectivity was performed using Z'-LYTE ™ or Adapta ® assay platforms available from Life Technologies Corporation. Values in Table B are percent inhibition in the presence of 1 µM of the representative Example.

| Kinase | Assay Platform | D15 | D6 | D25 | D2 |
| --- | --- | --- | --- | --- | --- |
| AURKB (Aurora B) | A | 18 | 16 | 14 | 9 |
| BRAF V599E | A | 28 | 2 | 7 | −11 |
| CDK1/cyclin B | A | 10 | 7 | 17 | 7 |
| CHEK2 (CHK2) | A | 13 | 7 | 8 | 1 |
| CLK2 | A | 70 | 66 | 89 | 79 |
| DYRK1A | A | 30 | 12 | 39 | 13 |
| IRAK1 | B | −3 | −1 | 15 | −7 |
| JAK3 | A | 9 | 5 | 8 | 8 |
| MAPK1 (ERK2) | A | 16 | 7 | 0 | 5 |
| MAPK8 (JNK1) | A | 56 | 28 | 56 | 28 |

A—Z-LYTE ™;
B—Adapta ®

The invention claimed is:

1. A compound of the formula:

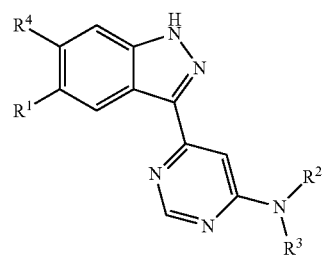

wherein R¹ is selected from the group consisting of:
  a) hydrogen,
  b) halo,
  c) cyano,
  d) hydroxyl,
  e) C$_{2-6}$ alkenyl, which is optionally substituted with one to three substitutents independently selected from the group consisting of halo, cyano and R⁵;
  f) OC$_{2-6}$ alkenyl, which is optionally substituted with one to three substitutents independently selected from the group consisting of halo, cyano and R⁵;

g) $R^5$,
h) $OR^5$,
i) $R^7$,
j) $S(O)_m R^5$,
k) $S(O)_m R^7$,
l) $(C=O)R^7$,
m) $(C=O)R^5$,
n) $(C=O)OR^5$, and
o) $NR^c R^d$;

$R^2$ is selected from the group consisting of hydrogen and $C_{1-6}$ alkyl, which is optionally substituted with one to three substitutents independently selected from the group consisting of:
a) halo,
b) cyano,
c) $R^5$,
d) $R^7$,
e) $OR^5$, and
f) $NR^c R^d$;

$R^3$ is selected from the group consisting of:
a) hydrogen,
b) $C_{1-6}$ alkyl, which is optionally substituted with one to three substitutents independently selected from the group consisting of halo, cyano, $OR^5$ and $NR^c R^d$,
c) $C_{3-8}$ cycloalkyl, which is optionally substituted with one to three substitutents independently selected from the group consisting of halo, cyano, $OR^5$ and $NR^c R^d$,
d) heterocyclyl, which is optionally substituted with one to three substitutents independently selected from the group consisting of halo, cyano, oxo, $R^5$, $OR^5$ and $NR^c R^d$,
e) heteroaryl, which is optionally substituted with one to three substitutents independently selected from the group consisting of halo, cyano, oxo, $R^5$, $OR^5$ and $NR^c R^d$;
f) $C_{4-8}$ cycloalkenyl, which is optionally substituted with one to three substitutents independently selected from the group consisting of halo, cyano, $OR^5$ and $NR^c R^d$,
g) $(C=O)R^7$,
h) $(C=O)R^5$,
i) $S(O)_m R^5$, and
j) $S(O)_m R^7$;

or $R^2$ and $R^3$ can be taken together with the atoms to which they are attached to form a 3 to 8 membered heterocyclic ring, wherein said ring may contain from one to three heteroatoms selected from N, O and S, wherein the sulfur is optionally oxidized to the sulfone or sulfoxide, and which ring is optionally substituted with one to four substituents each independently selected from the group consisting of:
a) halo,
b) oxo,
c) cyano,
d) $OR^5$,
e) $NR^c R^d$,
f) $SO_3H$,
g) $S(O)_m R^5$,
h) $S(O)_m R^7$
i) $R^5$,
j) $R^6$,
k) $R^7$,
l) $(C=O)R^5$,
m) $(C=O)OR^5$,
n) $(C=O)R^7$, and
o) $(C=O)NR^c R^d$;

$R^4$ is selected from the group consisting of hydrogen, halo, cyano, $OR^5$, aryl, heteroaryl, $C_{3-8}$ cycloalkyl, $C_{4-8}$ cycloalkenyl, $C_{4-8}$ heterocycloalkyl and $C_{1-6}$ alkyl, which is optionally substituted with one to three substitutents independently selected from the group consisting of halo, cyano, $OC_{1-3}$ alkyl, $NR^c R^d$ and hydroxyl;

or $R^1$ and $R^4$ can be taken together with the atoms to which they are attached to form a 3 to 8 membered heterocyclic ring, wherein said ring may contain from one to three heteroatoms selected from N, O and S, wherein the sulfur is optionally oxidized to the sulfone or sulfoxide, and which ring is optionally substituted with one to four substituents each independently selected from the group consisting of:
a) halo,
b) oxo,
c) cyano,
d) $R^5$, and
e) $R^7$ $R^5$ is selected from the group consisting of hydrogen and $C_{1-6}$ alkyl, which is optionally substituted with one to three substituents independently selected from the group consisting of:
a) halo,
b) hydroxyl,
c) $OC_{1-6}$ alkyl,
d) $NR^c R^d$,
e) $(C=O)NR^c R^d$,
f) $S(O)_m R^8$,
g) $S(O)_m R^7$,
h) $R^7$, and
i) $OR^7$;

$R^6$ is $C_{1-6}$ alkyl, which is optionally substituted with one to three substituents independently selected from the group consisting of halo and hydroxyl;

or $R^5$ and $R^6$ can be taken together with the atoms to which they are attached to form a 4 to 8 membered heterocyclic, 3 to 8 membered carbocyclic, aryl or heteroaryl ring, wherein said heterocyclic and heteroaryl rings may contain from one to three heteroatoms selected from N, O and S, wherein said heterocyclic, carbocyclic, aryl and heteroaryl rings are optionally substituted with one to three substituents independently selected from the group consisting of:
a) halo,
b) oxo,
c) cyano,
d) hydroxyl,
e) $C_{1-3}$ alkyl, which is optionally substituted with one to three halo,
f) $C_{3-8}$ cycloalkyl,
g) $OC_{1-3}$ alkyl, which is optionally substituted with one to three halo, and
h) $OC_{3-8}$ cycloalkyl;

$R^7$ is selected from the group consisting of $C_{4-8}$ heterocyclyl, $C_{3-8}$ cycloalkyl, $C_{4-8}$ cycloalkenyl, aryl or heteroaryl, wherein said heterocyclyl, cycloalkyl, cycloalkenyl, aryl and heteroaryl groups are optionally substituted with one to three substituents independently selected from the group consisting of
a) halo,
b) cyano,
c) hydroxyl,
d) oxo,
e) $C_{1-3}$ alkyl, which is optionally substituted with one to four substituents independently selected from the group consisting of hydroxyl, halo, cyano, heterocyclyl, $OC_{1-3}$ alkyl and $NR^c R^d$, f) $OC_{1-3}$ alkyl, which is optionally substituted with one to four substituents independently selected from the group consisting of hydroxyl, halo, cyano, heterocyclyl, $OC_{1-3}$ alkyl $NR^cR^d$, aryl and heteroaryl,
g) $C_{3-8}$ cycloalkyl, which is optionally substituted with one to four substituents independently selected from the group consisting of hydroxyl, halo, cyano, heterocyclyl, $OC_{1-3}$ alkyl and $NR^cR^d$,
h) aryl, which is optionally substituted with one to four substituents independently selected from the group consisting of hydroxyl, halo, cyano, heterocyclyl, $OC_{1-3}$ alkyl, $S(O)_mNR^cR^d$, $C(O)NR^cR^d$ and $NR^cR^d$,
i) heteroaryl, which is optionally substituted with one to four substituents independently selected from the group consisting of hydroxyl, halo, cyano, heterocyclyl, $OC_{1-3}$ alkyl, $S(O)_mNR^cR^d$, $C(O)NR^cR^d$ and $NR^cR^d$,
j) heterocyclyl, which is optionally substituted with one to four substituents independently selected from the group consisting of hydroxyl, halo, cyano, $OC_{1-3}$ alkyl and $NR^cR^d$,
k) $C_{4-8}$ cycloalkenyl, which is optionally substituted with one to four substituents independently selected from the group consisting of hydroxyl, halo, cyano, heterocyclyl, $OC_{1-3}$ alkyl and $NR^cR^d$;
$R^8$ is hydrogen or $C_{1-6}$ alkyl, which is optionally substituted with one to three substituents independently selected from the group consisting of:
a) halo,
b) cyano,
c) hydroxyl,
d) $OC_{1-3}$ alkyl, which is optionally substituted with one to four substituents independently selected from the group consisting of hydroxyl, halo and $NR^cR^d$, and
e) $C_{3-8}$ cycloalkyl;
$R^c$ is selected from the group consisting of:
a) hydrogen,
b) $C_{1-3}$ alkyl, which is optionally substituted with one to three substituents independently selected from the group consisting of halo, hydroxyl, cyano, heteroaryl, aryl, $NH(C_{1-3}$ alkyl), $N(C_{1-3}$ alkyl$)_2$, $OC_{1-6}$ alkyl, and $C_{3-8}$ cycloalkyl;
$R^d$ is selected from the group consisting of:
a) hydrogen,
b) $C_{3-8}$ cycloalkyl,
c) $C_{3-6}$ heterocyclyl,
d) $C_{1-3}$ alkyl,
e) (C=O)$C_{1-3}$ alkyl,
f) aryl, and
g) heteroaryl;
wherein said cycloalkyl, heterocyclyl, alkyl, aryl and heteroaryl groups are each optionally substituted with one to three substituents independently selected from the group consisting of halo, hydroxyl, cyano, $R^8$, $SO_2R^8$, $OC_{1-6}$ alkyl and $C_{3-8}$ cycloalkyl;
or $R^c$ and $R^d$ can be taken together with the atoms to which they are attached to form a 3 to 8 membered heterocyclic ring, wherein said ring may contain from one to three heteroatoms selected from N, O and S, wherein the sulfur is optionally oxidized to the sulfone or sulfoxide, and which ring is optionally substituted with one to four substituents each independently selected from the group consisting of halo, cyano, hydroxyl, $C_{1-3}$ alkyl and $OC_{1-3}$ alkyl;
m is an integer from zero to two,
or a pharmaceutically acceptable salt thereof.
2. The compound of claim 1 wherein $R^1$ is selected from the group consisting of:
$R^5$, $OR^5$ and $R^7$, or a pharmaceutically acceptable salt thereof.
3. The compound of claim 2 wherein $R^1$ is selected from the group consisting of:
$OR^5$ and $R^7$, or a pharmaceutically acceptable salt thereof.
4. The compound of claim 3 wherein $R^1$ is selected from the group consisting of:
$OC_{1-3}$ alkyl, aryl and heteroaryl, wherein said aryl and heteroaryl groups are optionally substituted with one to three substituents independently selected from the group consisting of halo, hydroxyl, $C_{1-3}$ alkyl and $OC_{1-3}$ alkyl, or a pharmaceutically acceptable salt thereof.
5. The compound of claim 4 wherein $R^4$ is selected from the group consisting of:
hydrogen and halo, or a pharmaceutically acceptable salt thereof.
6. The compound of claim 5 wherein $R^2$ and $R^3$ can be taken together with the atoms to which they are attached to form a 3 to 8 membered heterocyclic ring, wherein said ring may contain from one to three heteroatoms selected from N, O and S, wherein the sulfur is optionally oxidized to the sulfone or sulfoxide, and which ring is optionally substituted with one to four substituents each independently selected from the group consisting of:
a) halo,
b) oxo,
c) cyano,
d) $OR^5$,
e) $NR^cR^d$,
f) $SO_3H$,
g) $S(O)_mR^5$,
h) $S(O)_mR^7$
i) $R^5$,
j) $R^6$,
k) $R^7$,
l) (C=O)$R^5$,
m) (C=O)$OR^5$,
n) (C=O)$R^7$, and
o) (C=O)$NR^cR^d$;
or a pharmaceutically acceptable salt thereof.
7. The compound of claim 6 wherein $R^2$ and $R^3$ can be taken together with the atoms to which they are attached to form a 6 membered heterocyclic ring, wherein said ring may contain from one to three heteroatoms selected from N, O and S, wherein the sulfur is optionally oxidized to the sulfone or sulfoxide, and which ring is optionally substituted with one to four substituents each independently selected from the group consisting of:
a) halo,
b) oxo,
c) $OR^5$,
d) $NR^cR^d$,
e) $S(O)_mR^5$,
f) $S(O)_mR^7$,
g) $R^5$,
h) $R^6$,
i) $R^7$,
j) (C=O)$R^5$,
k) (C=O)$OR^5$, and
l) (C=O)$R^7$,
or a pharmaceutically acceptable salt thereof.

8. A compound selected from
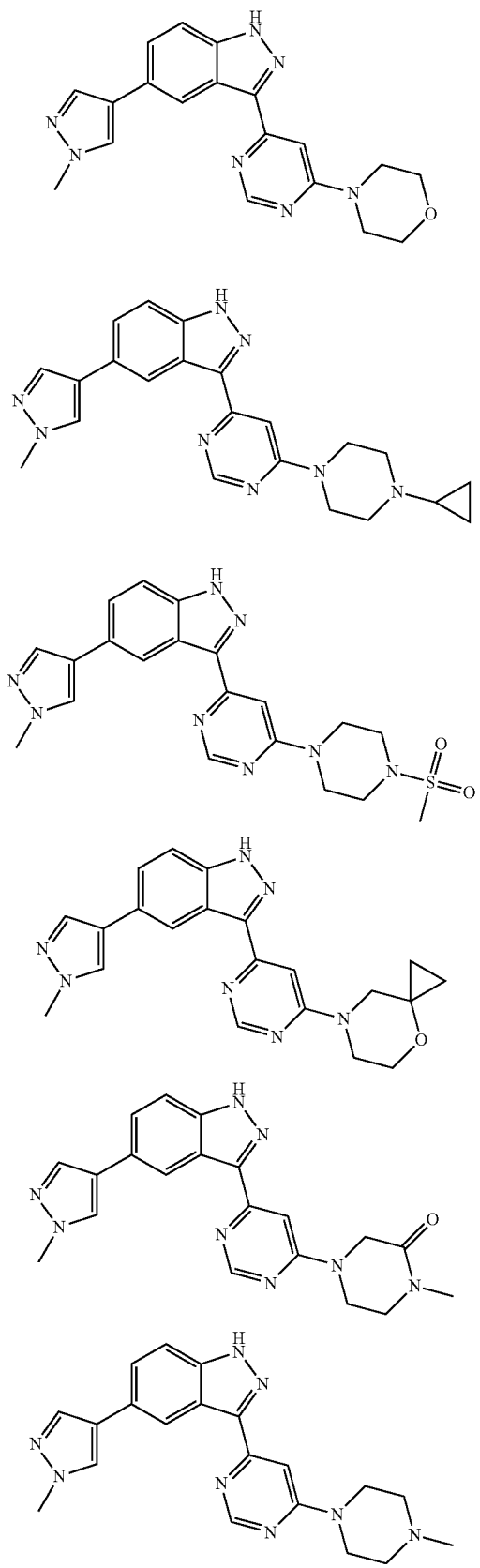
-continued
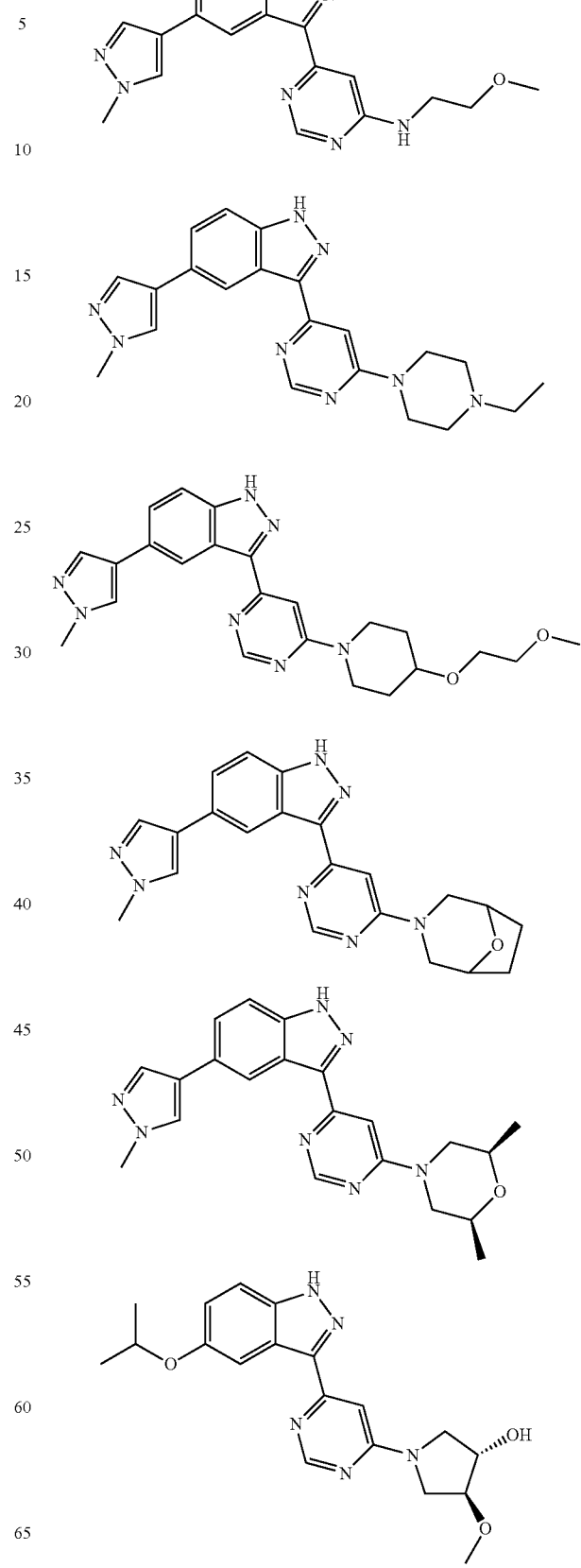

233
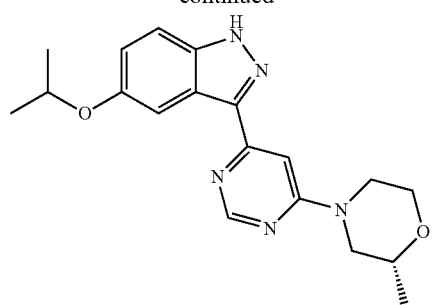
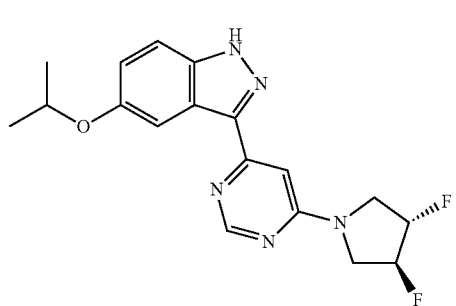
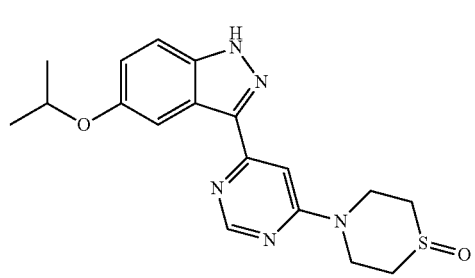
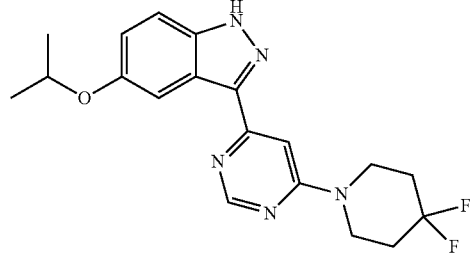
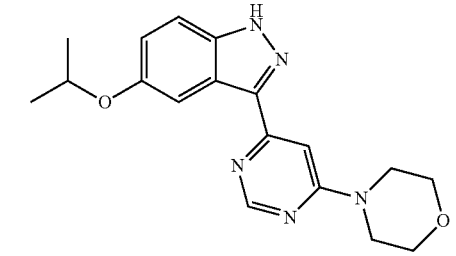
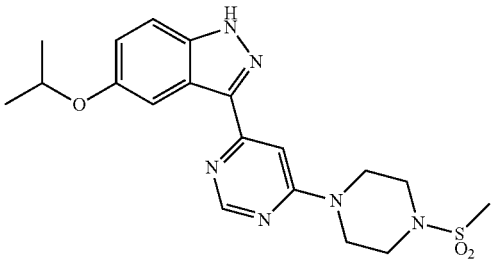
234
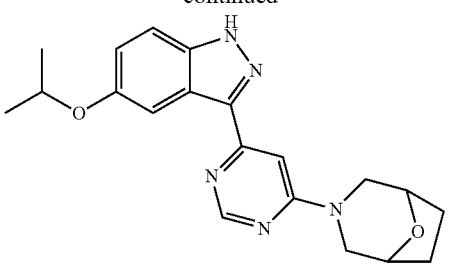
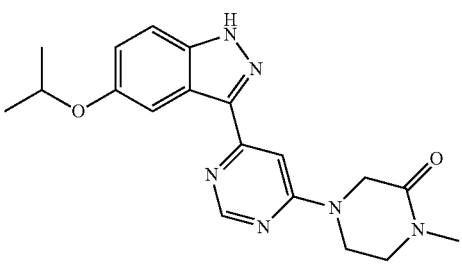
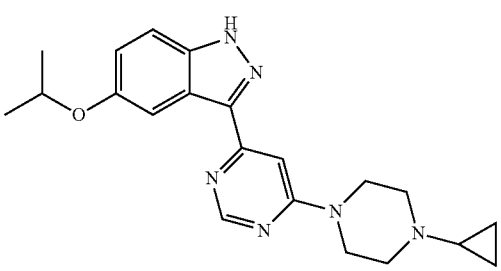
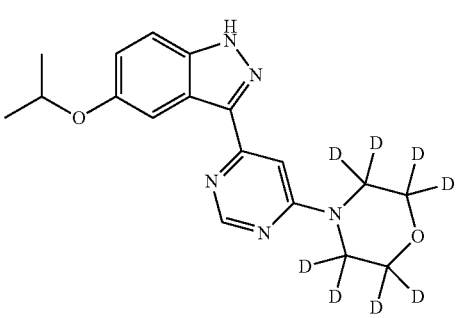
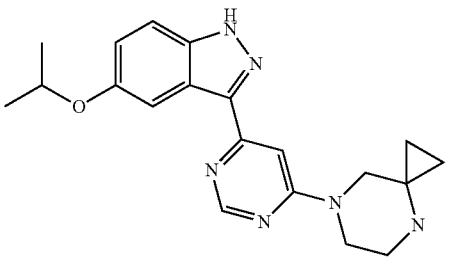
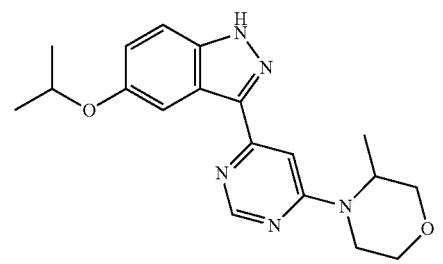

-continued
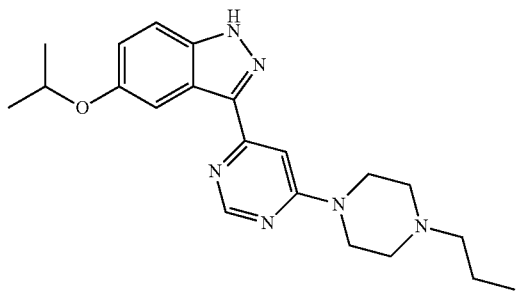
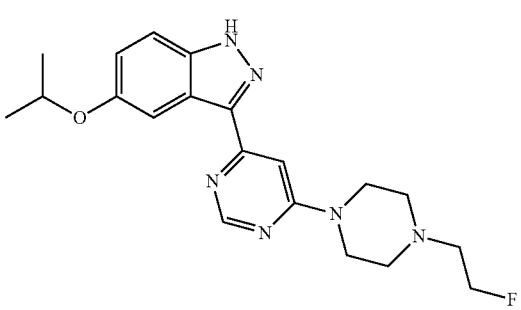
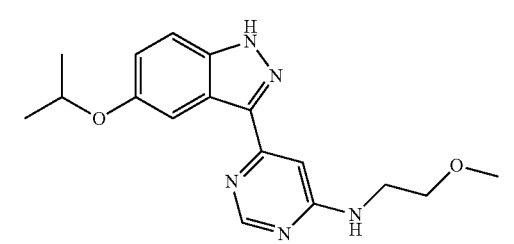
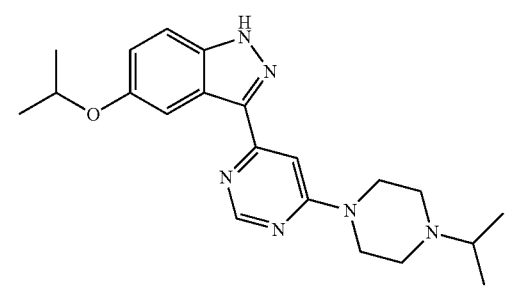
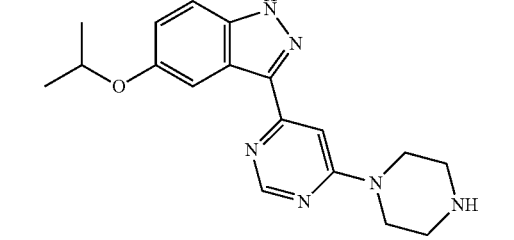
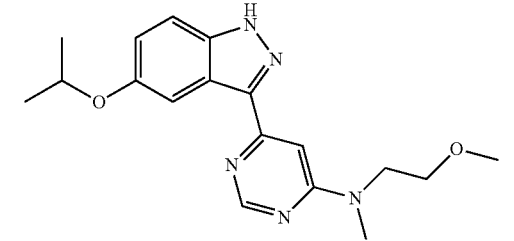
-continued
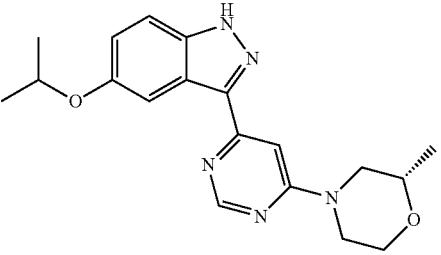
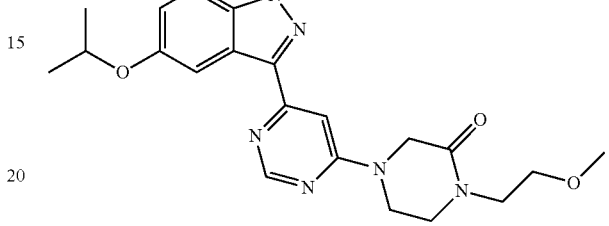
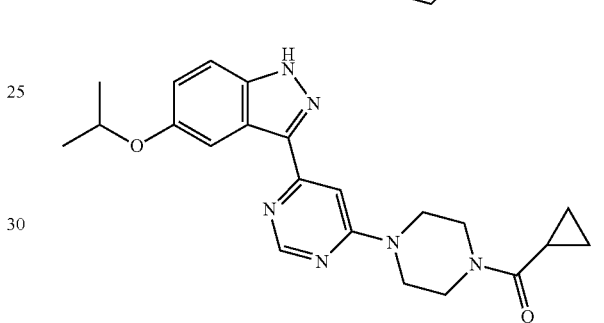
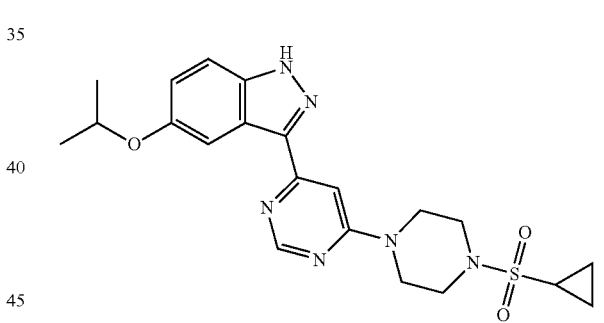
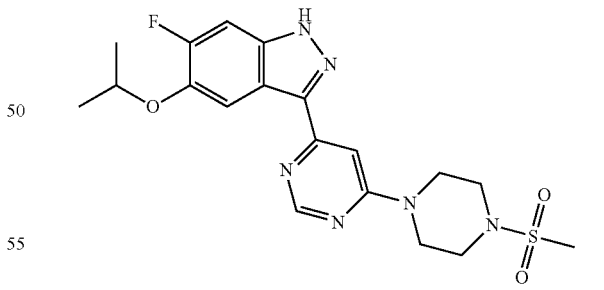
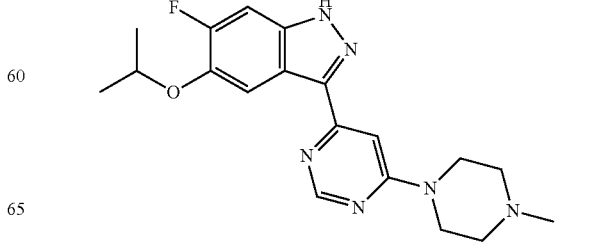

237
-continued
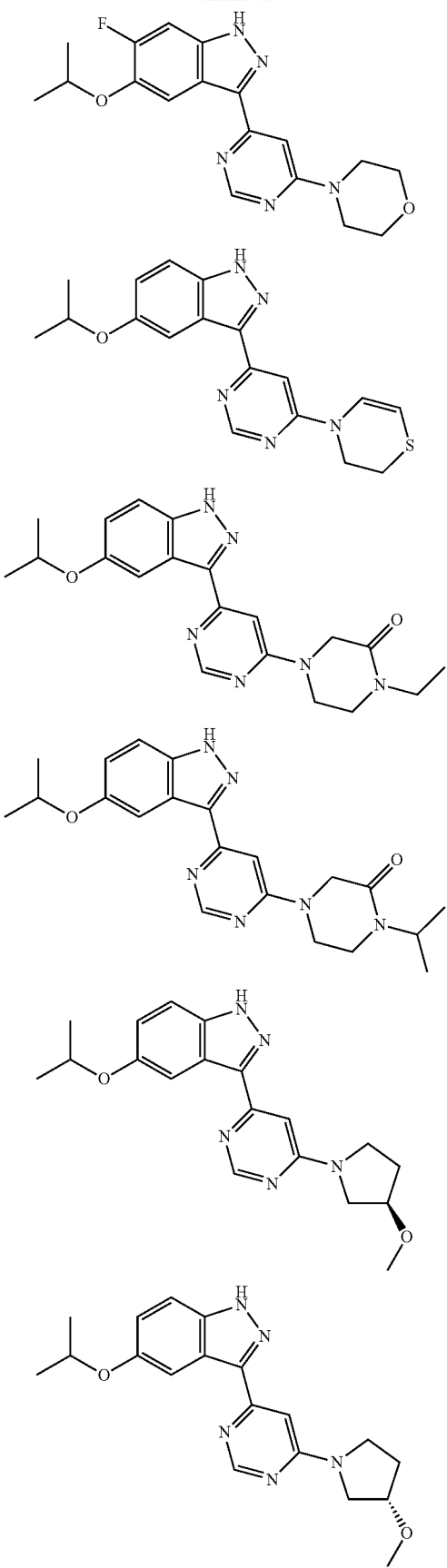
238
-continued
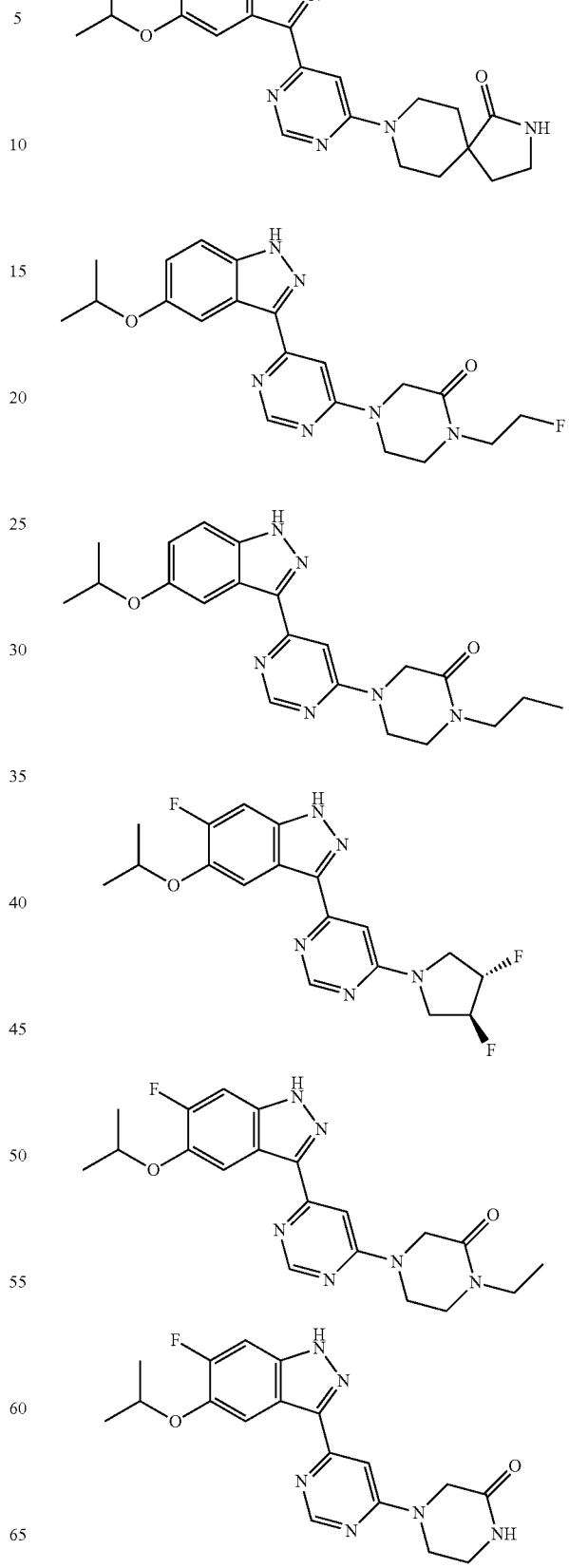

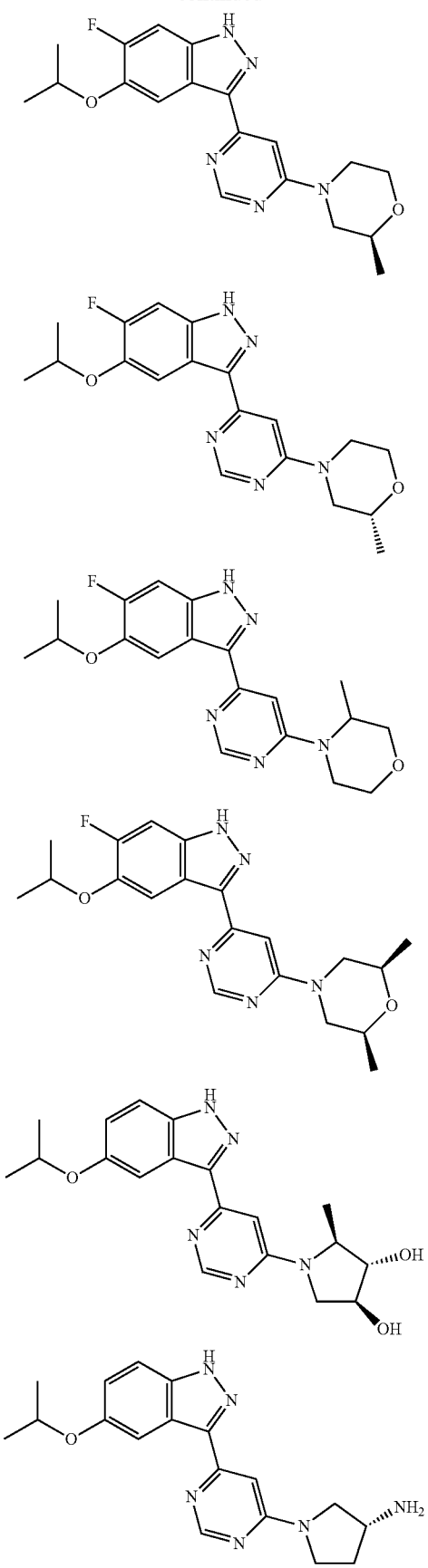
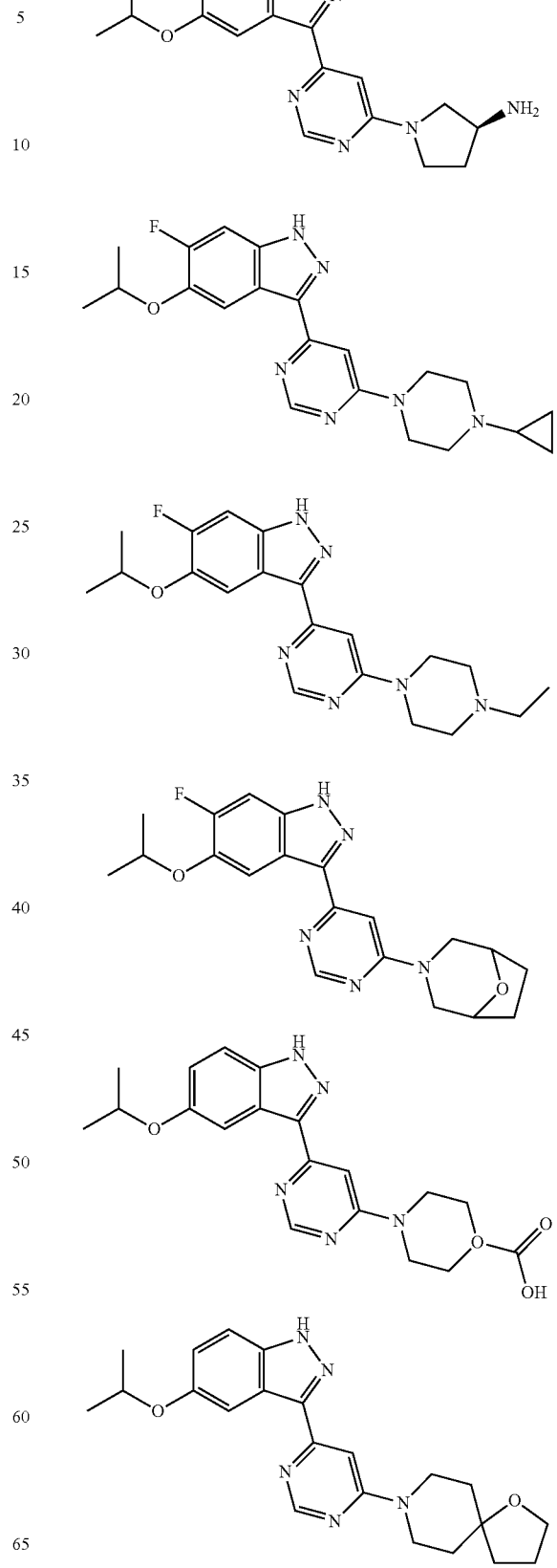

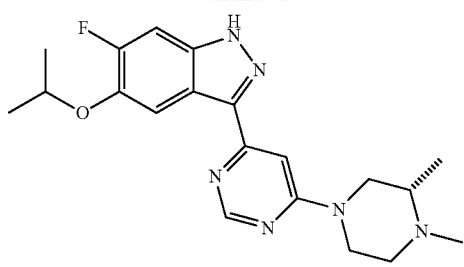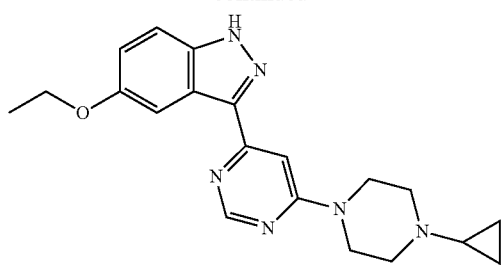

243
-continued
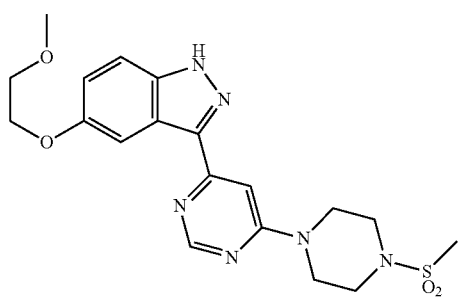
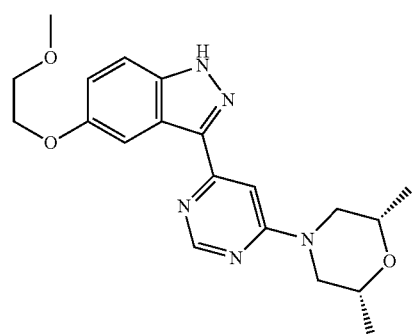
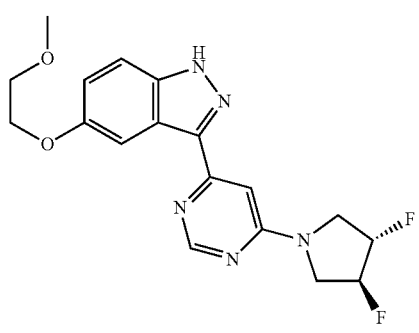
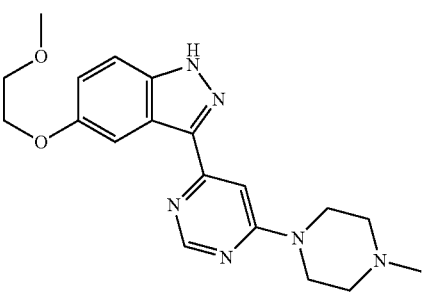
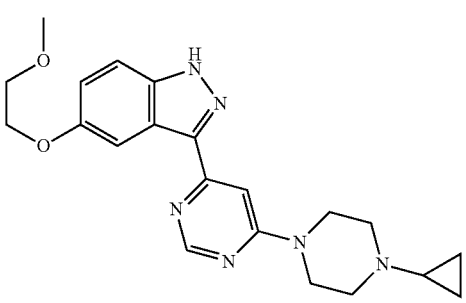
244
-continued
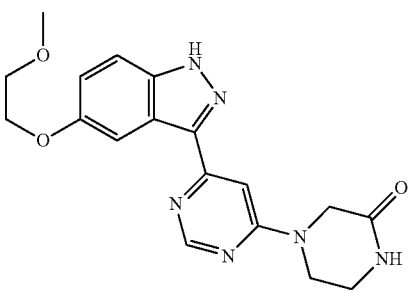
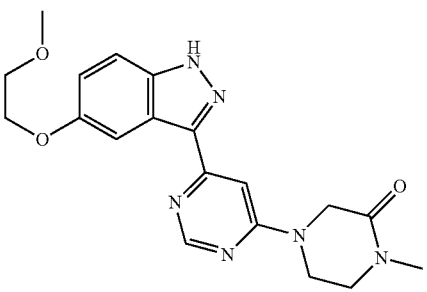
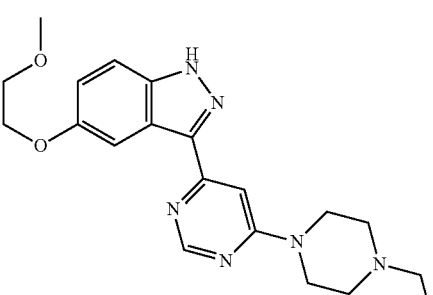
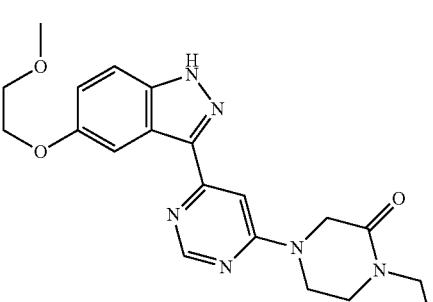
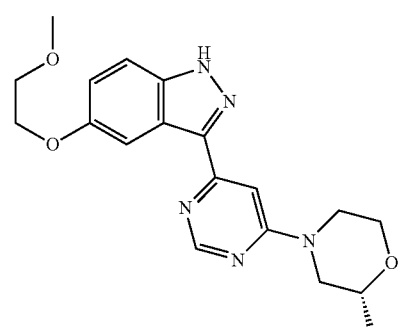

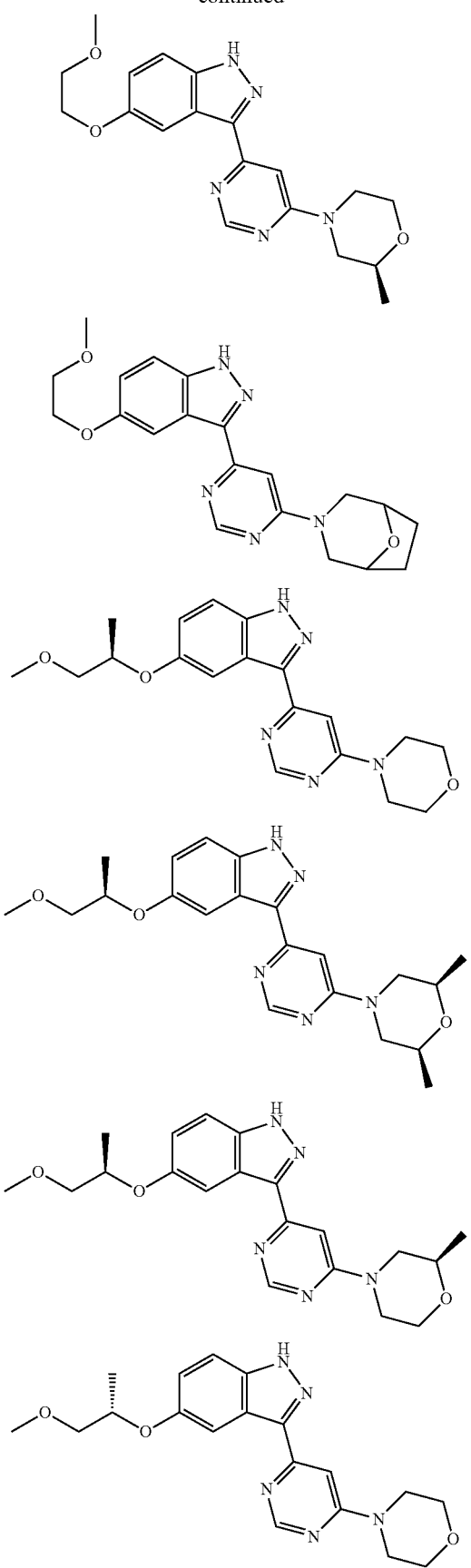
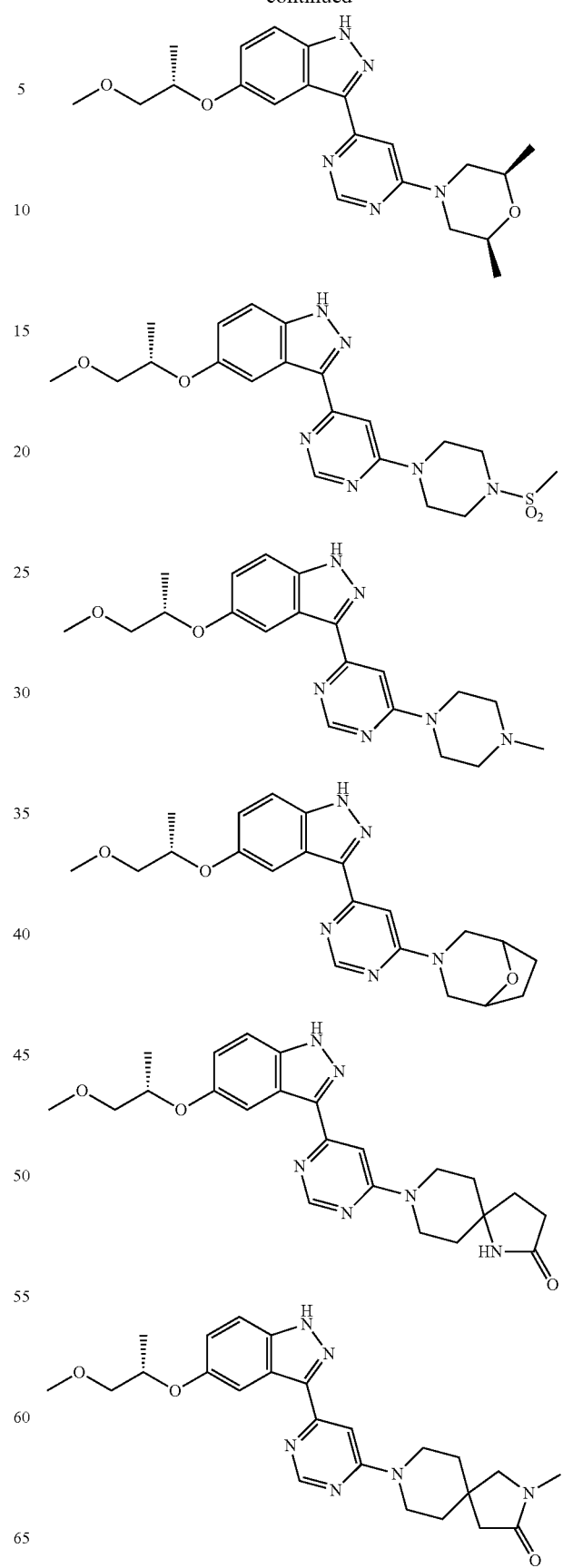

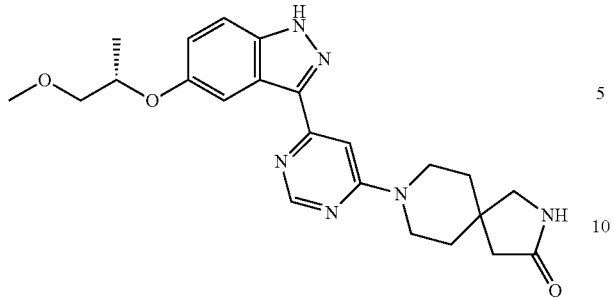
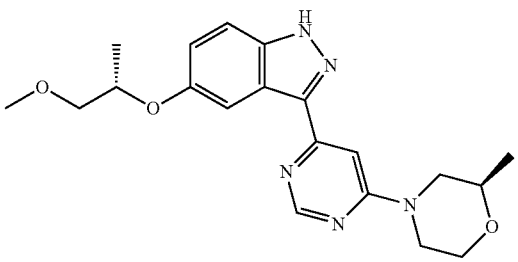

249
-continued
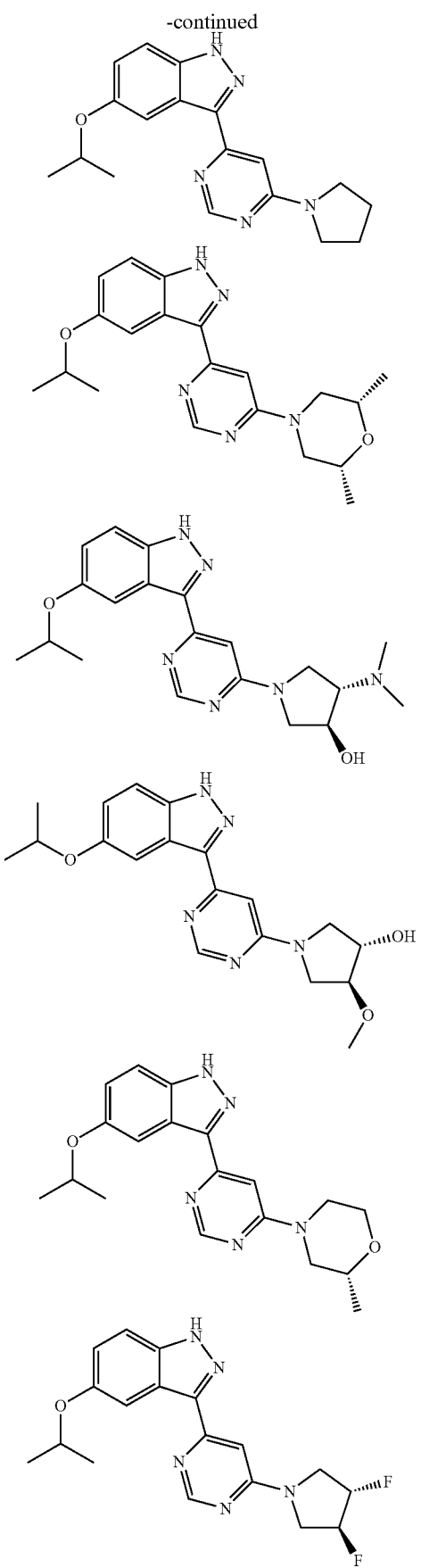
250
-continued
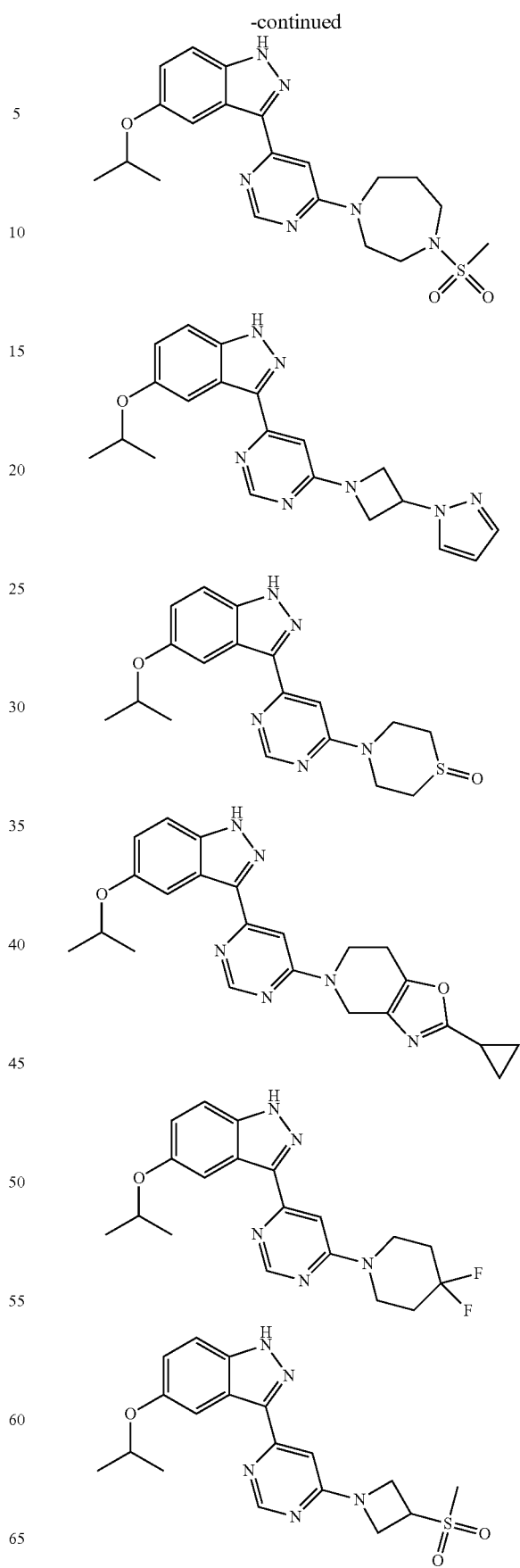

251
-continued
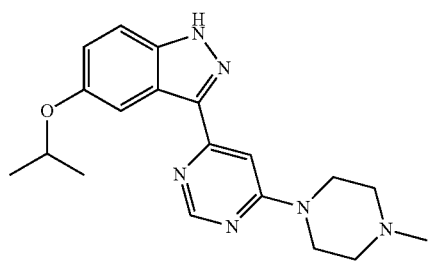
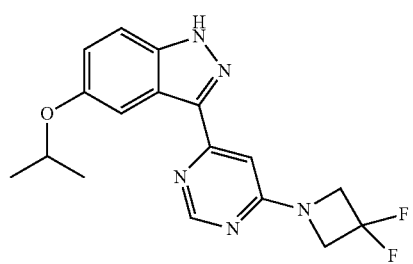
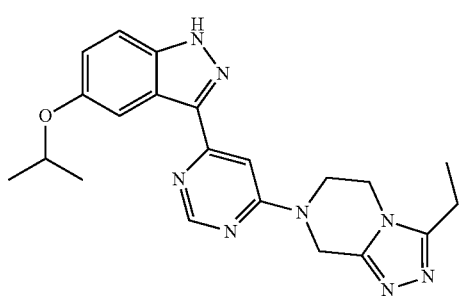
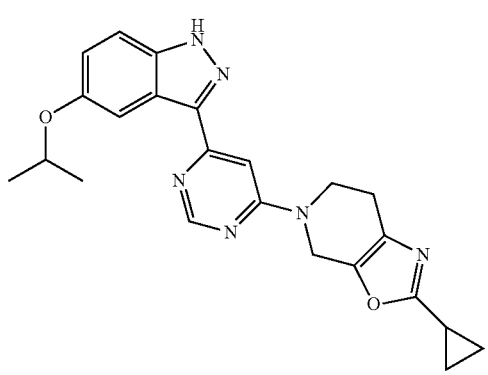
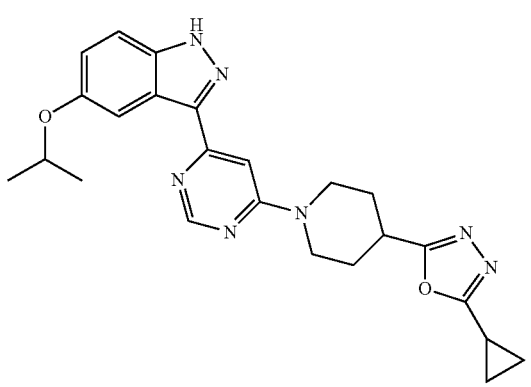
252
-continued
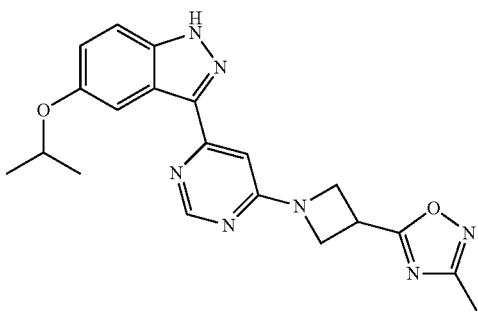
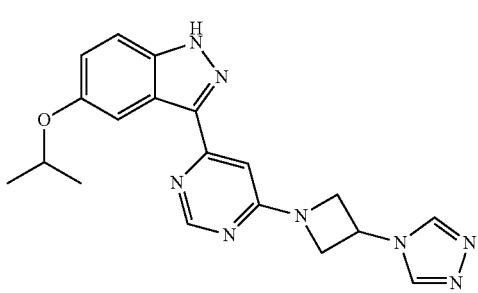
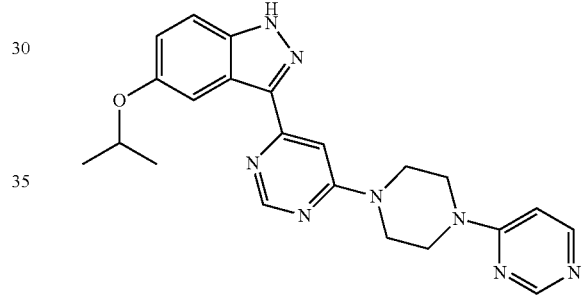
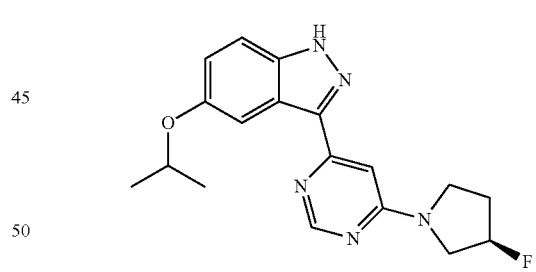
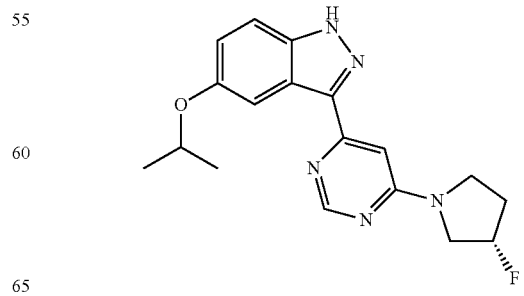

253
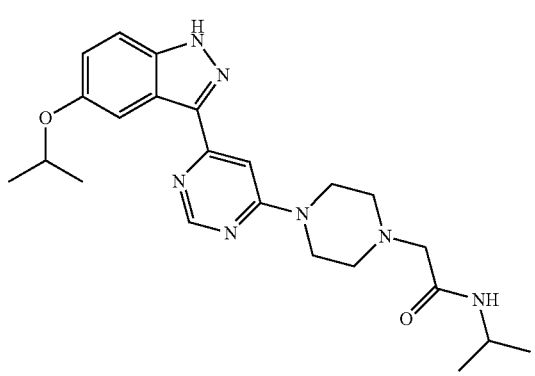
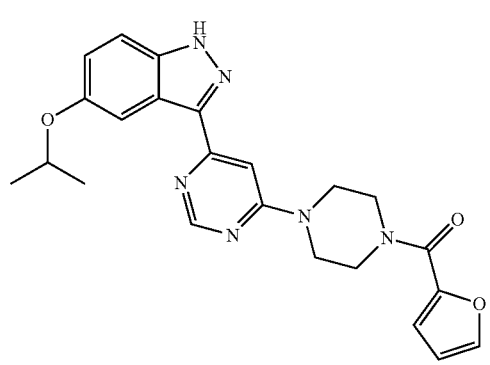
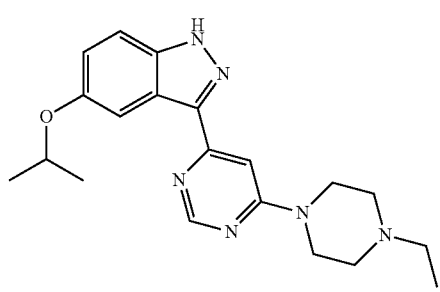
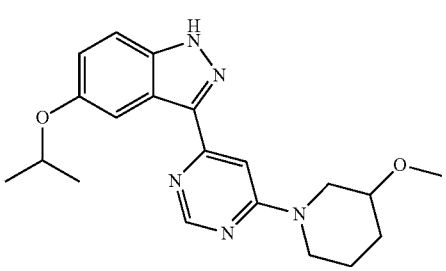
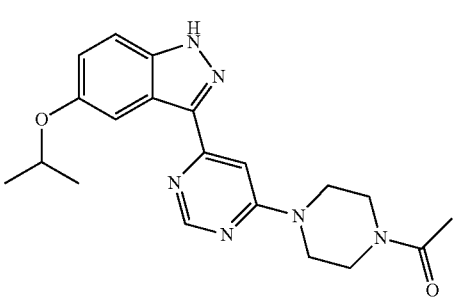
254
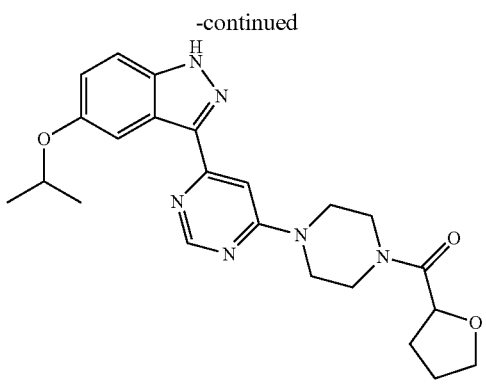
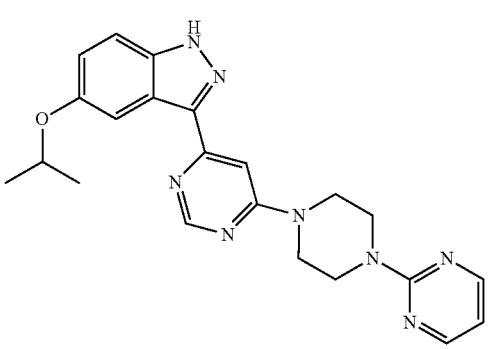
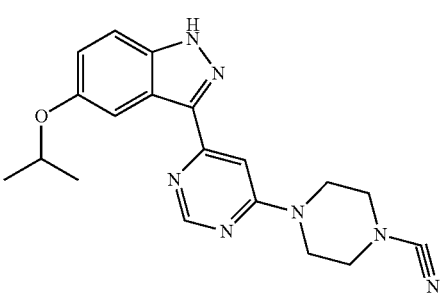
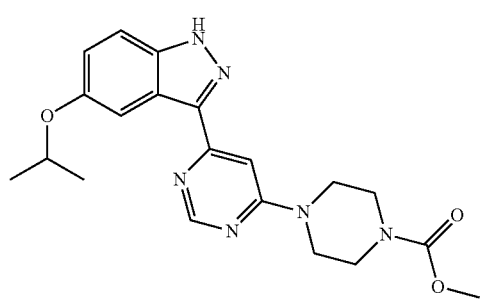
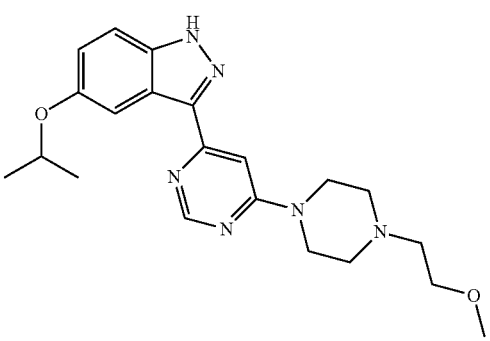

255
-continued
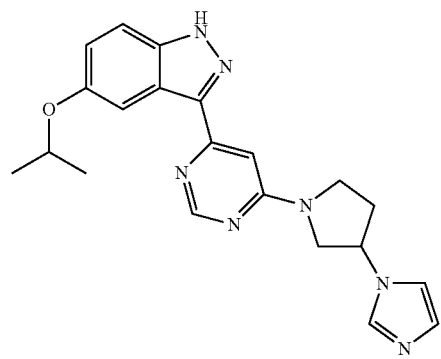
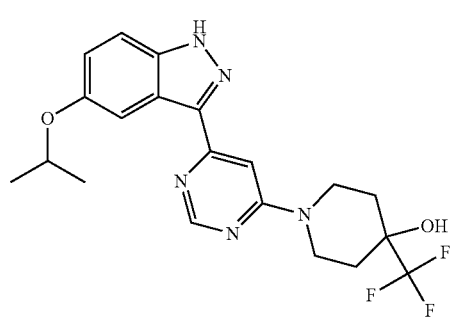
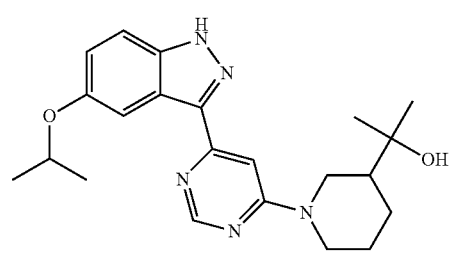
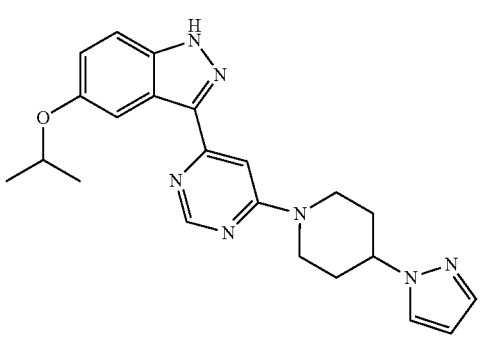
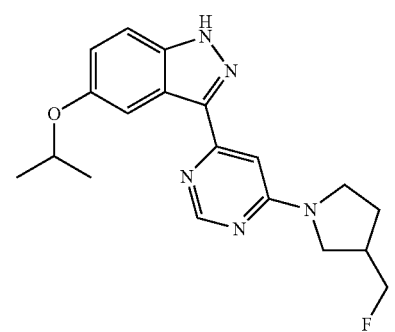
256
-continued
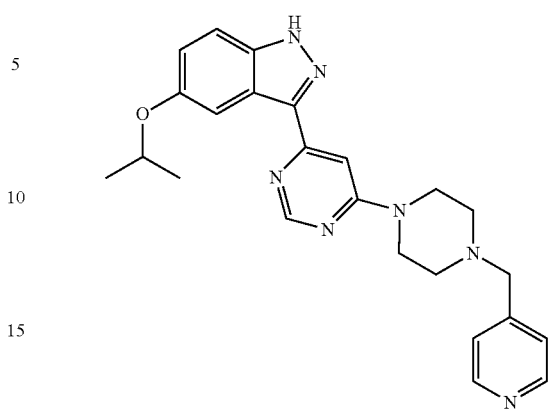
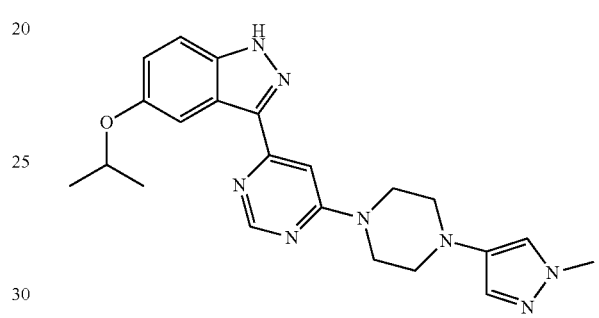
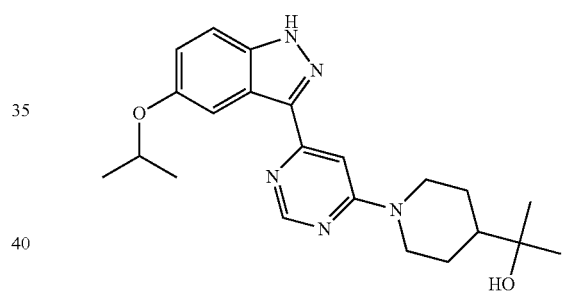
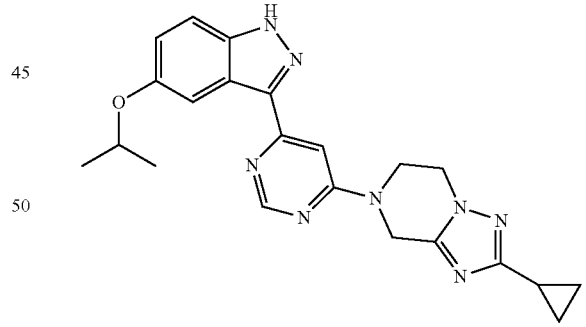
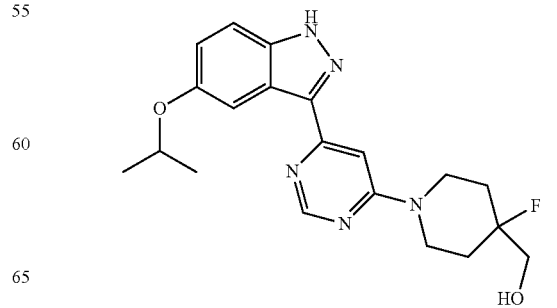

257
-continued
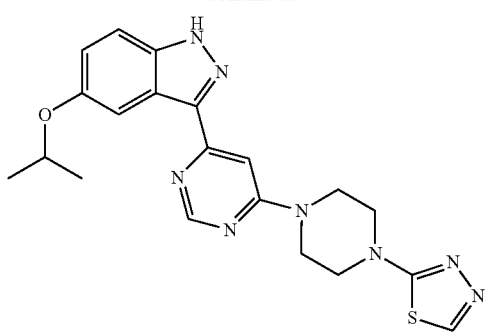
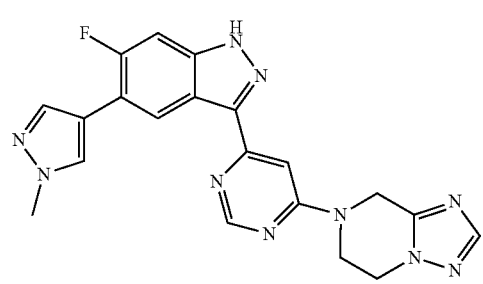
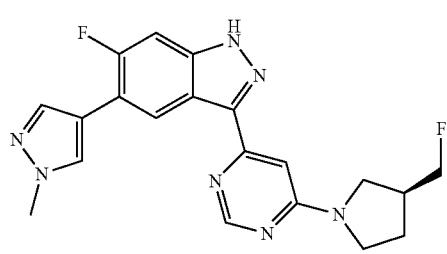
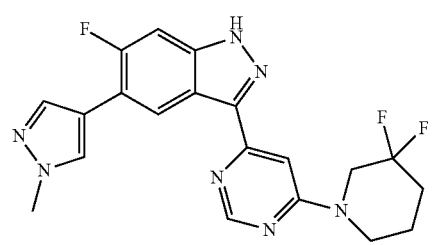
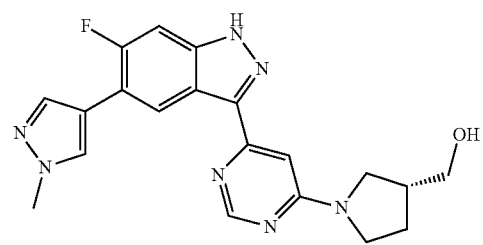
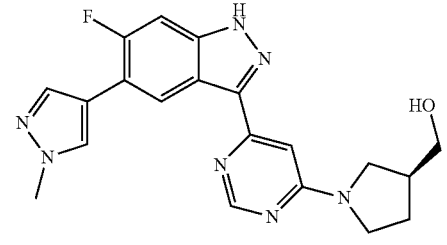
258
-continued
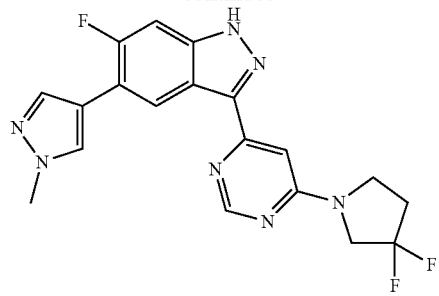
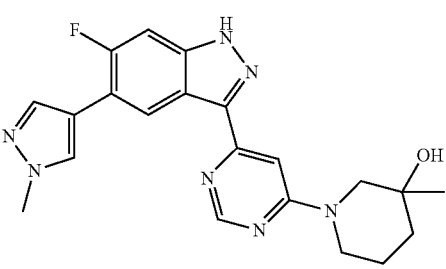
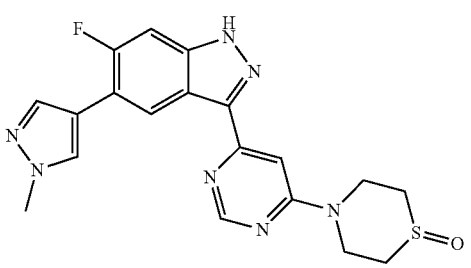
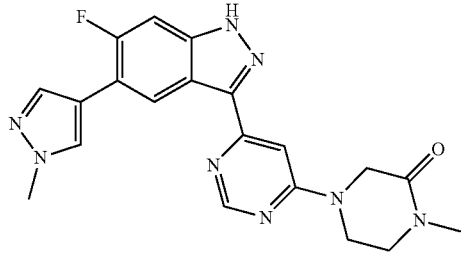
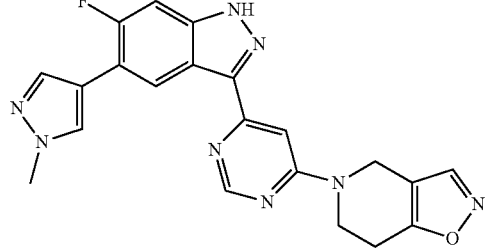
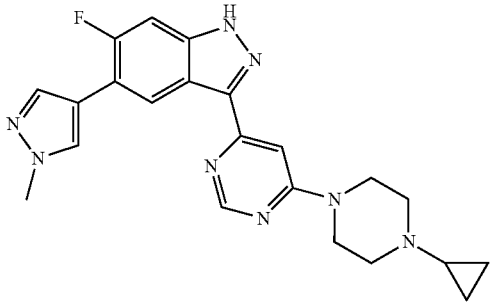

259
-continued
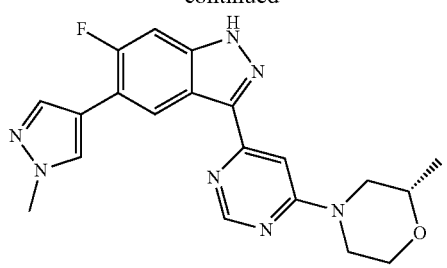
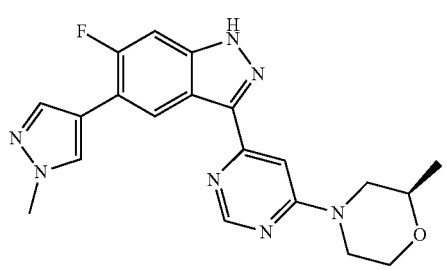
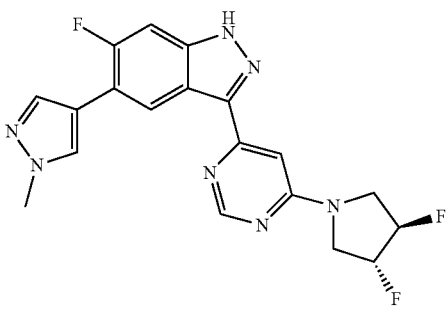
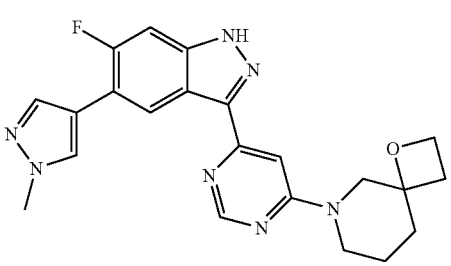
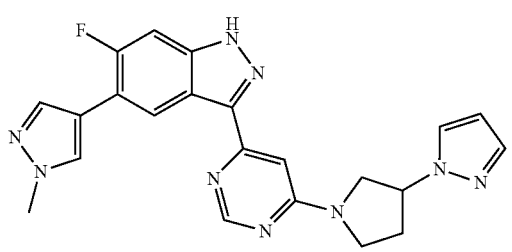
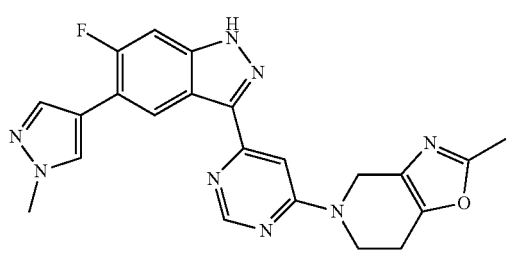
260
-continued
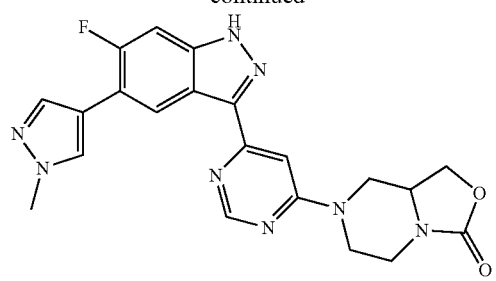
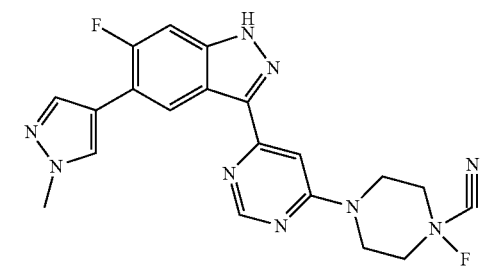
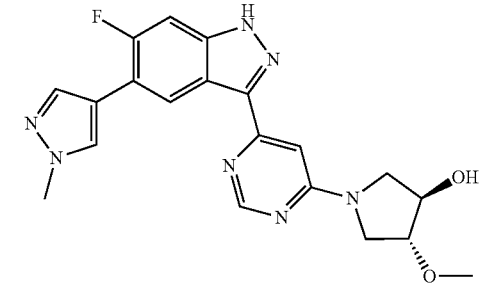
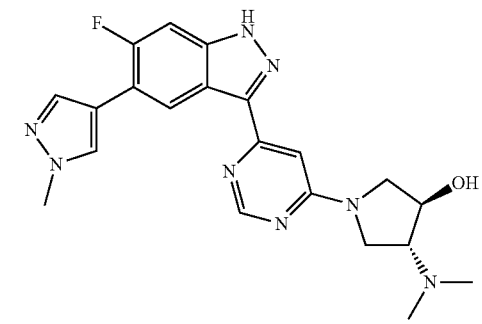
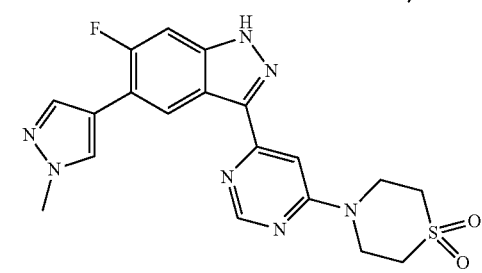
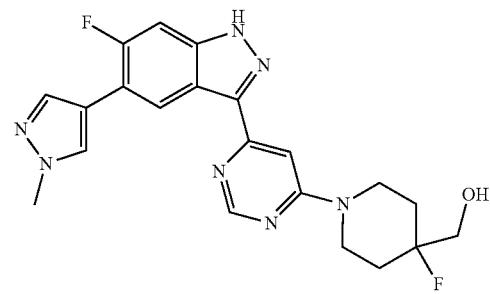

261
-continued
262
-continued
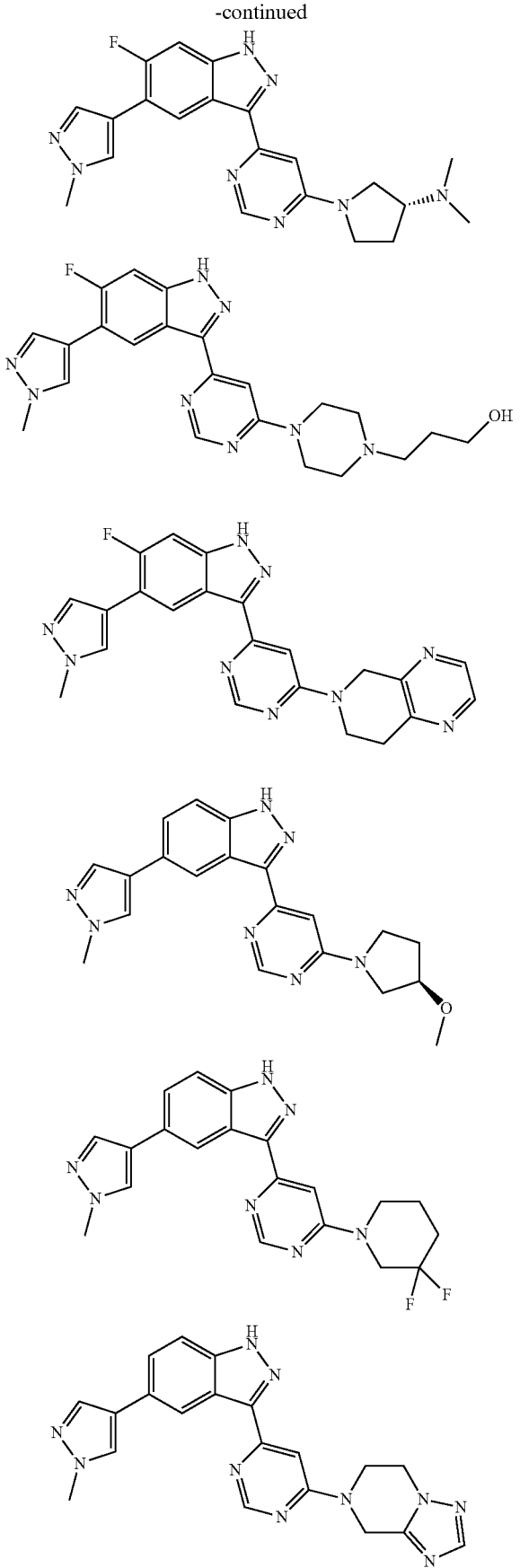
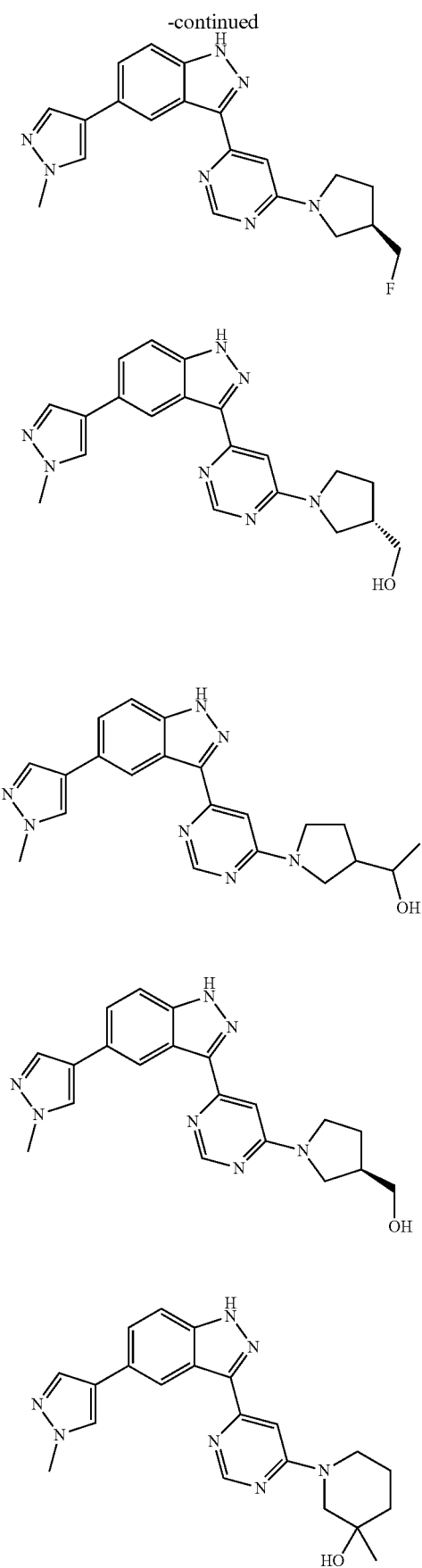

263
-continued
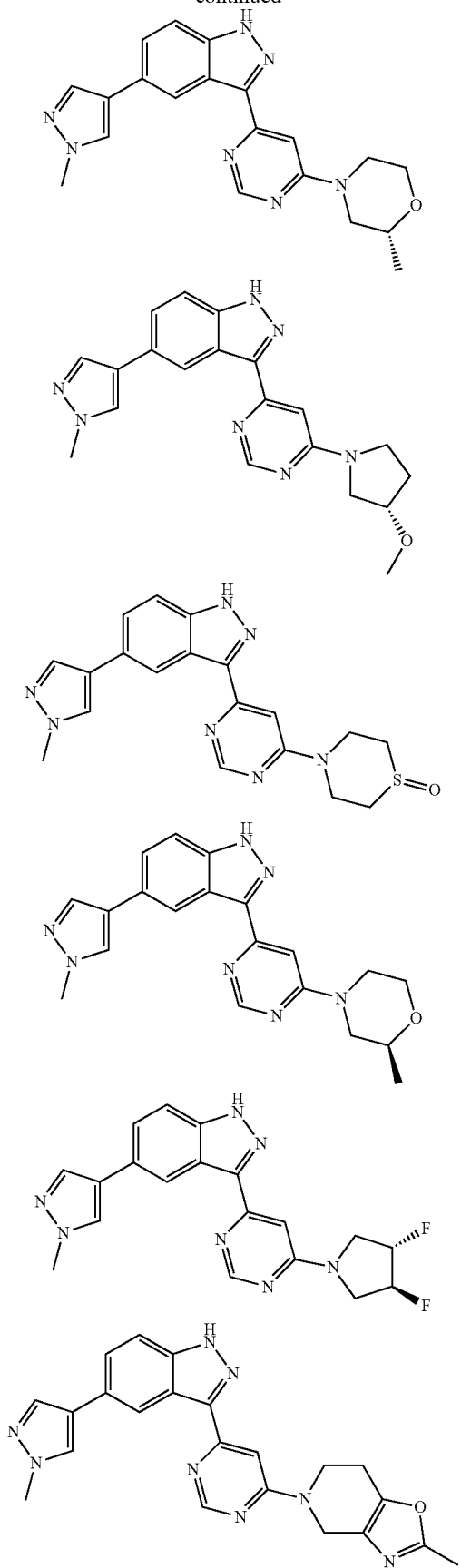
264
-continued
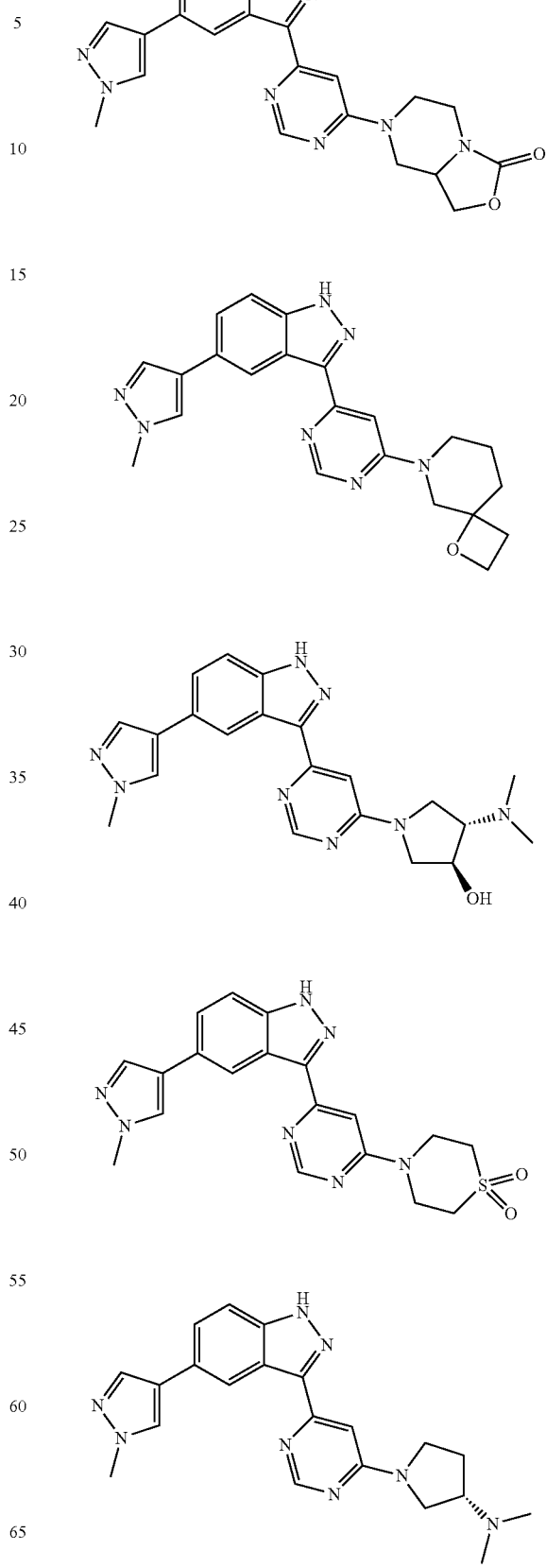

265
-continued
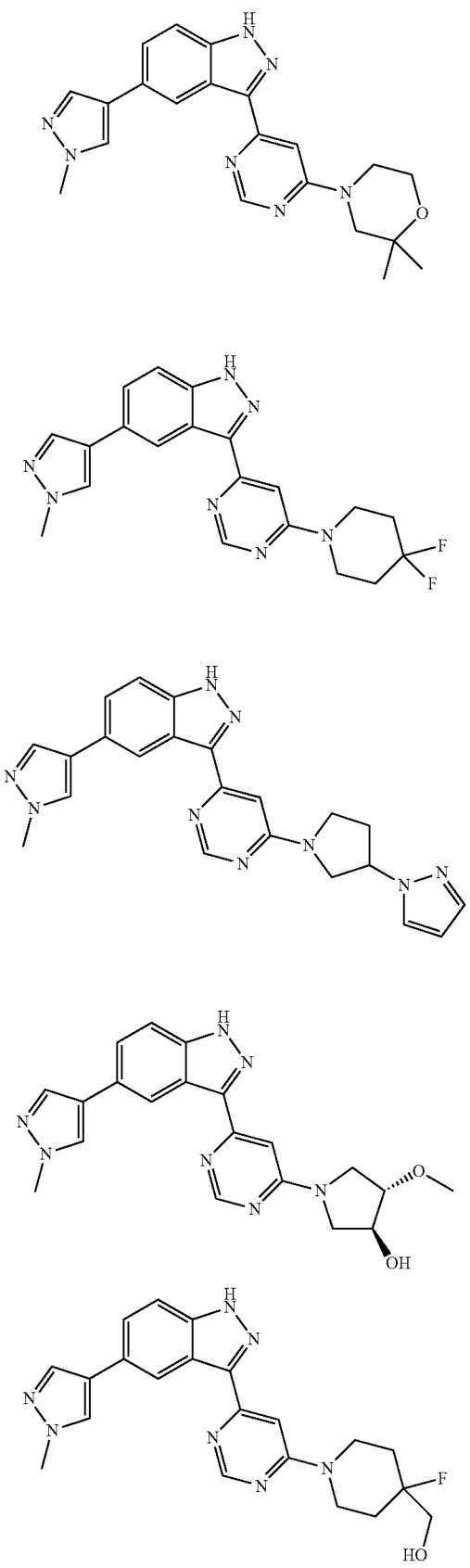
266
-continued
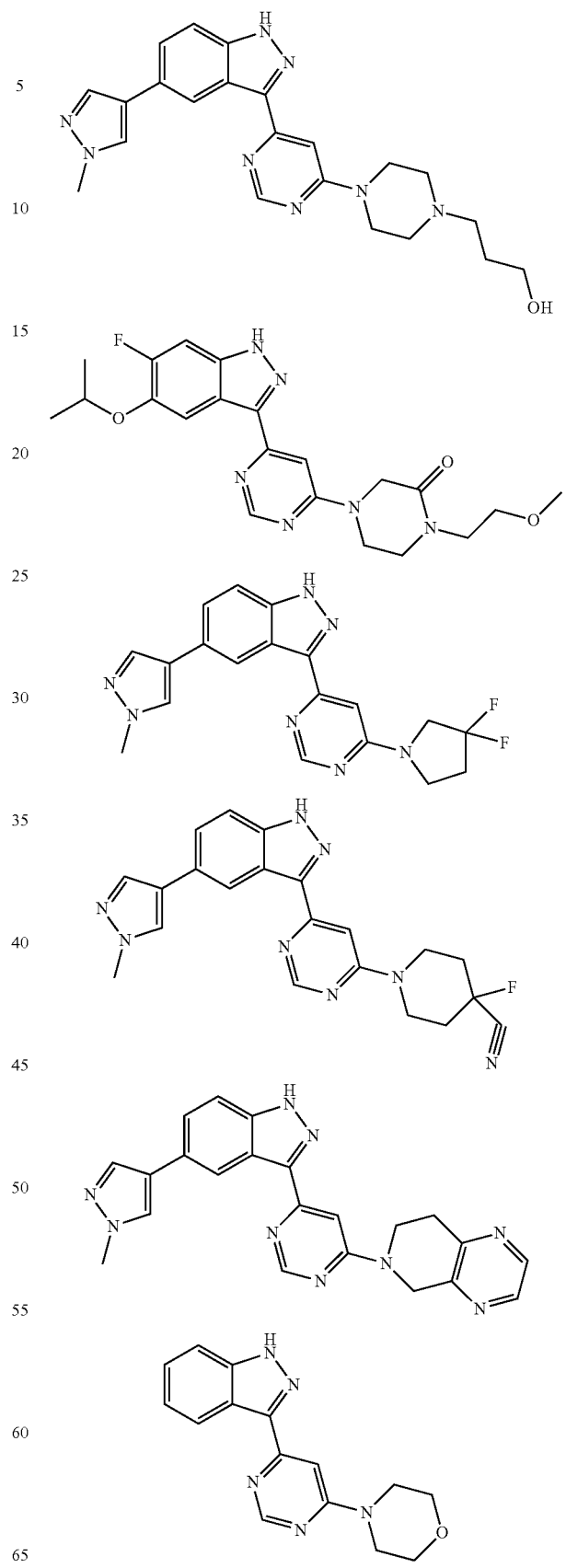

267
-continued
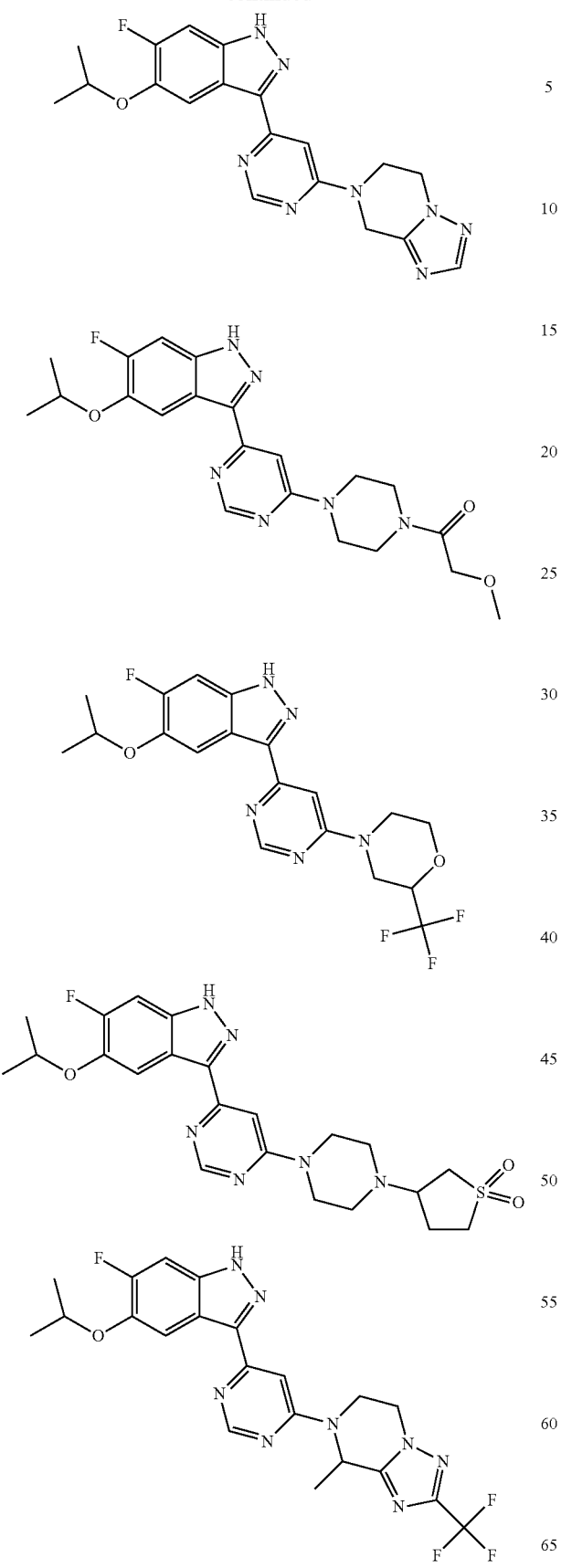
268
-continued
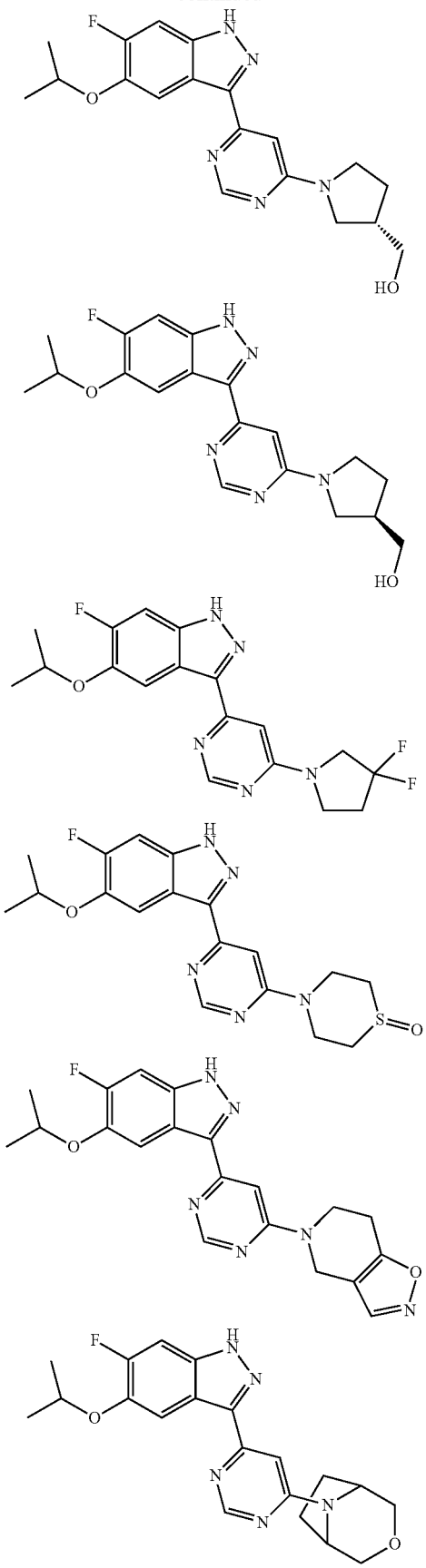

269
-continued
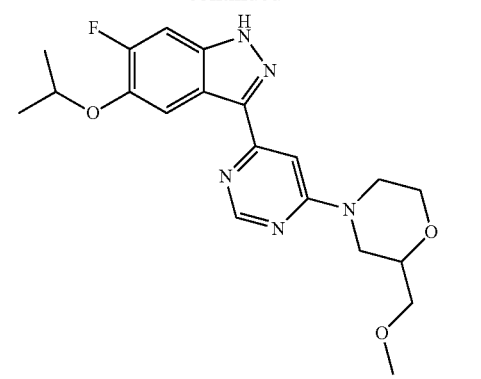
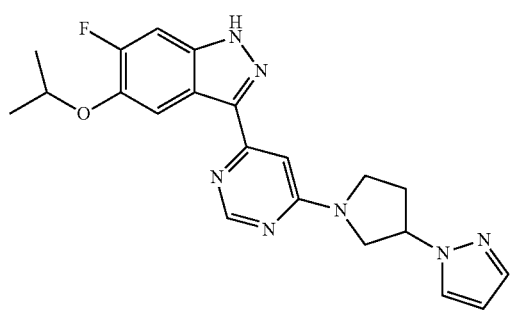
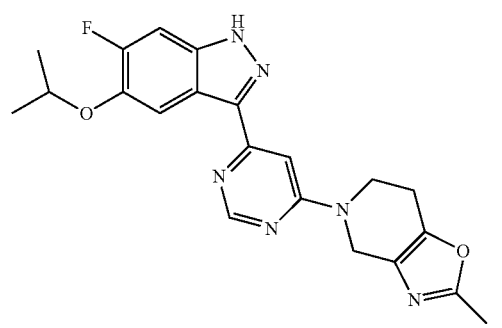
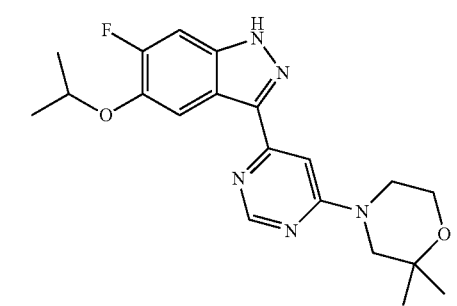
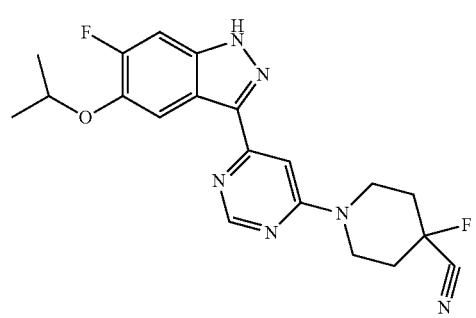
270
-continued
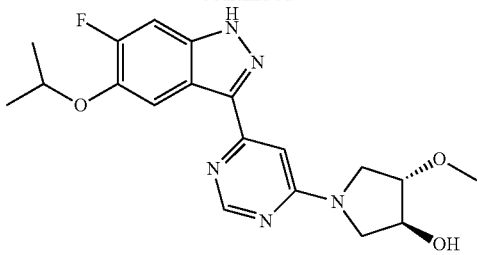
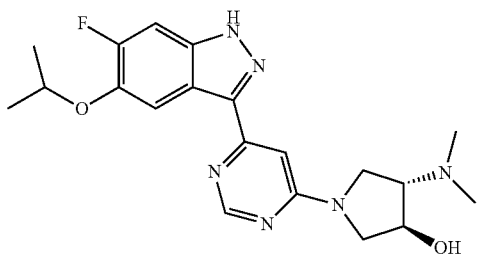
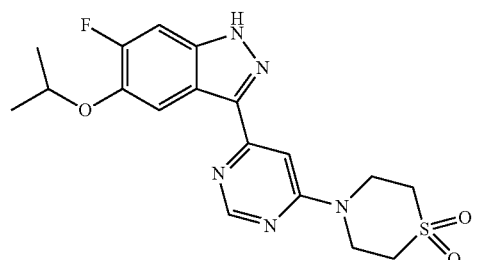
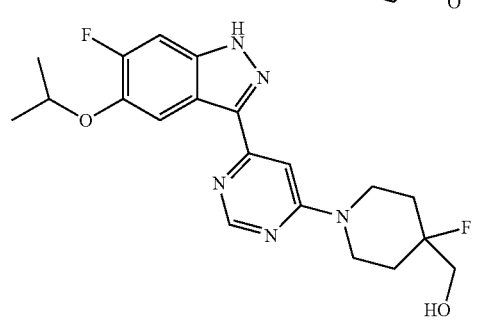
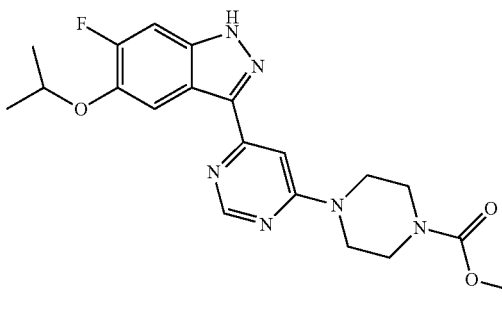
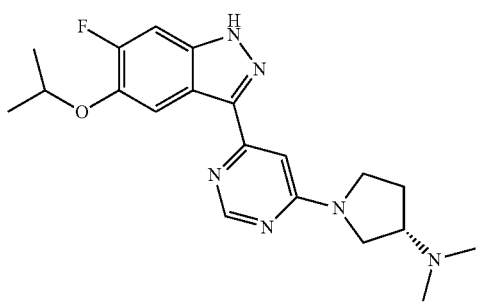

271
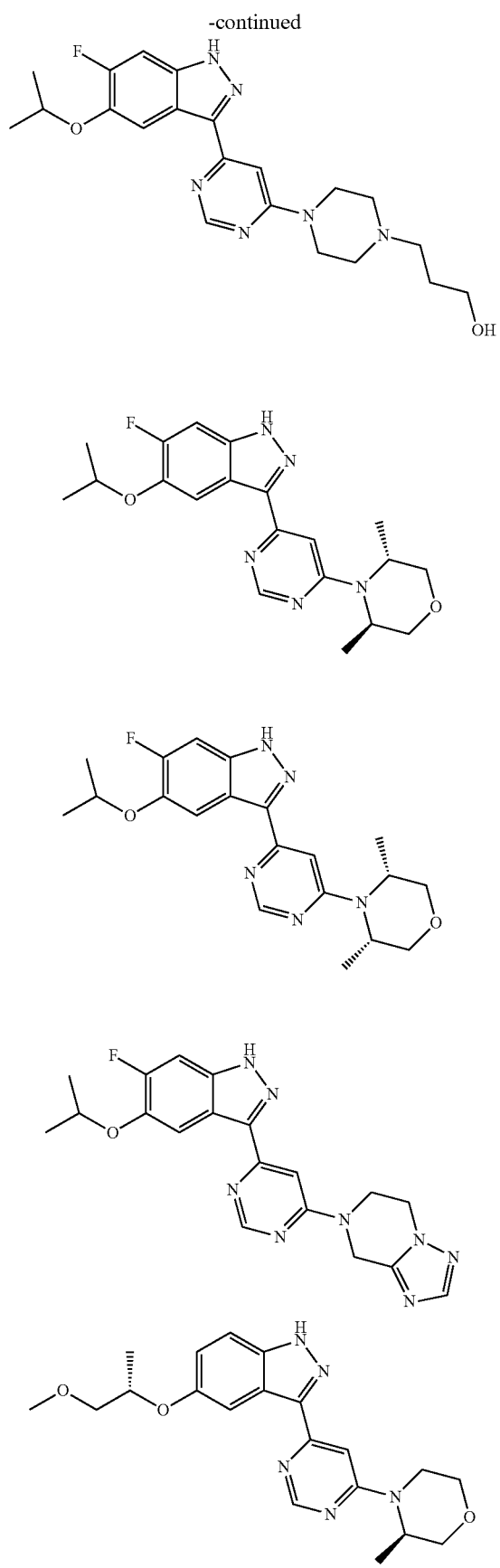
272
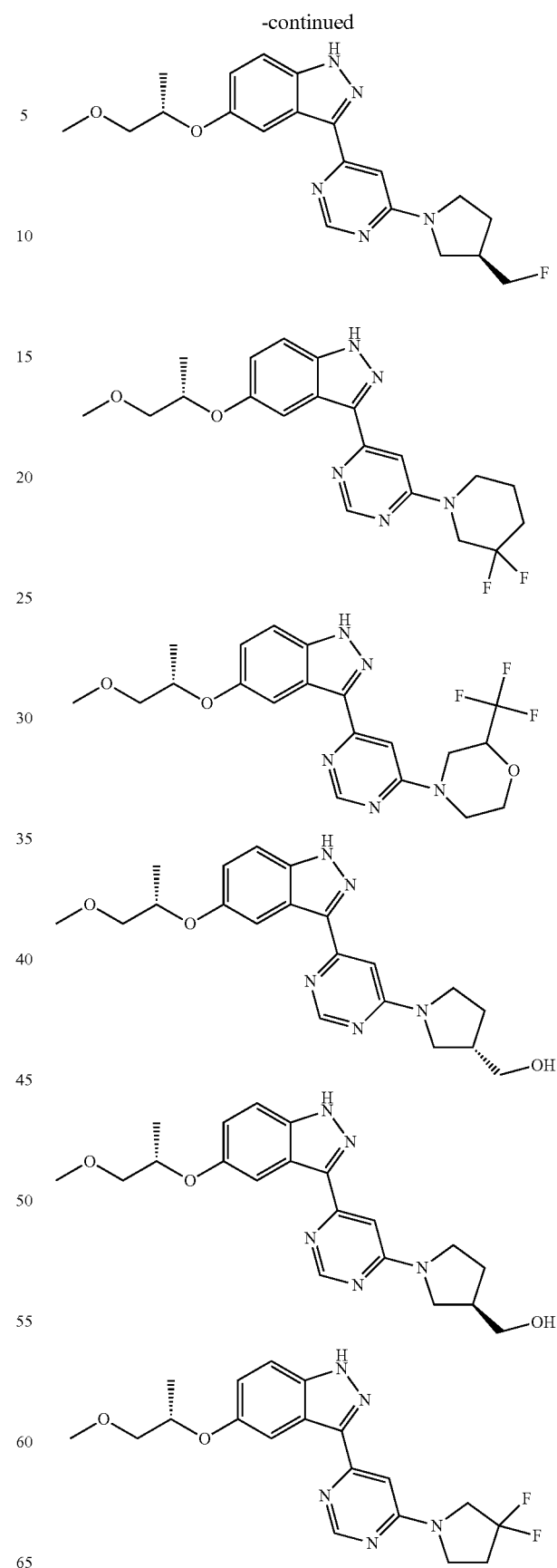

273
-continued
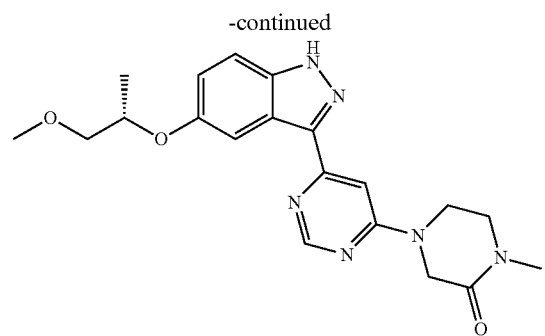
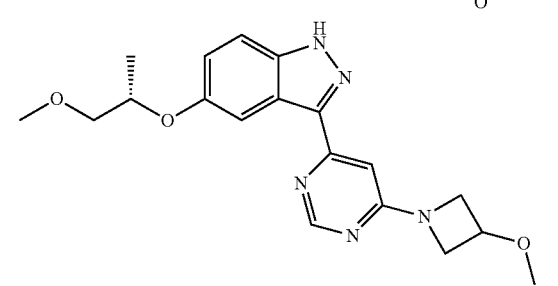
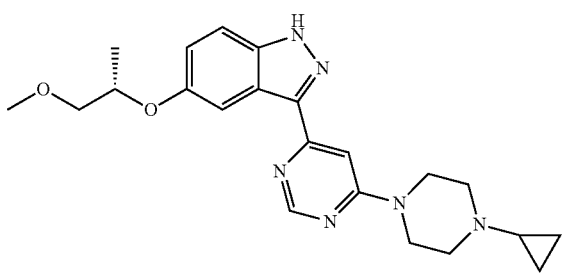
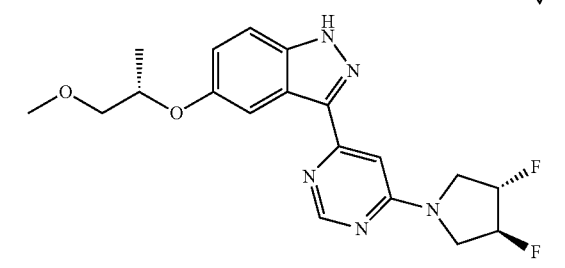
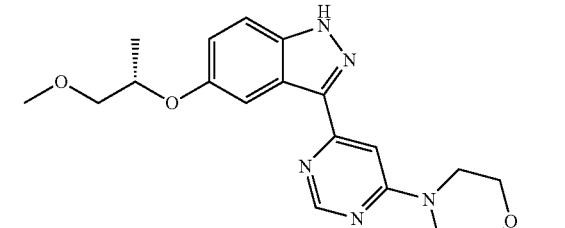
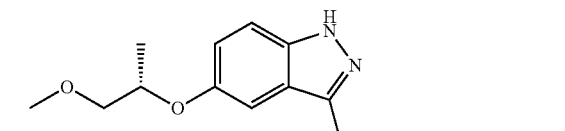
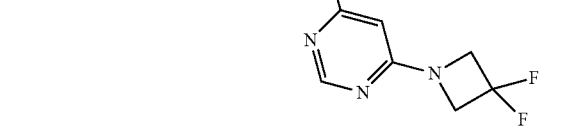
274
-continued
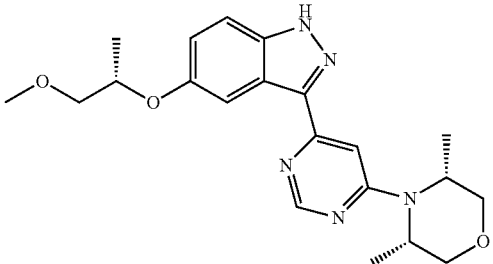
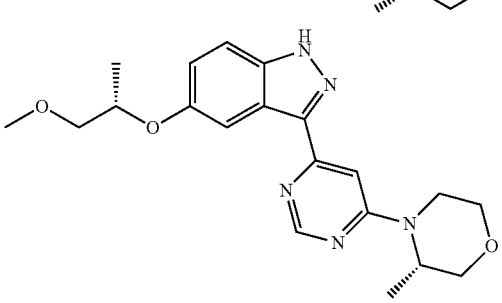
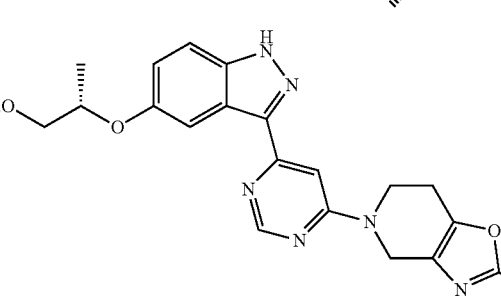
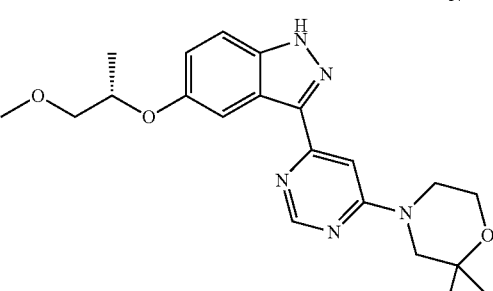
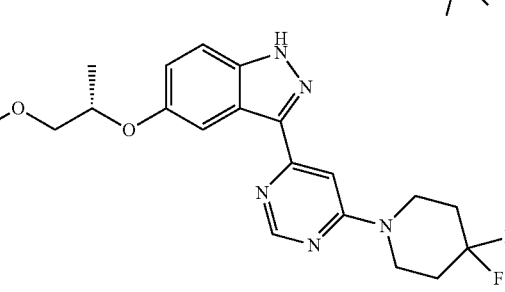
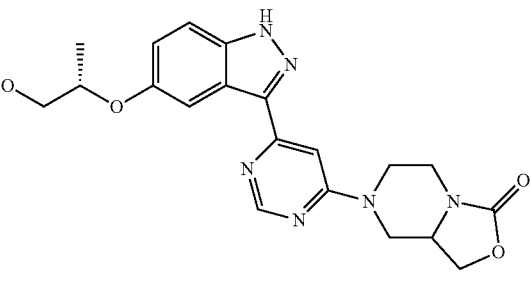

275
-continued
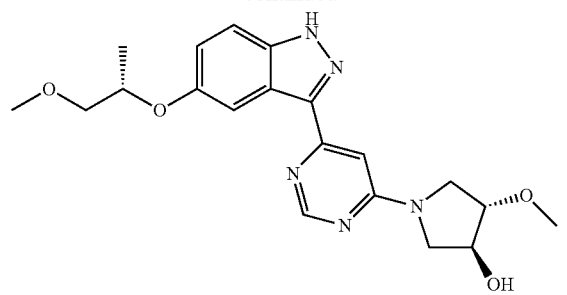
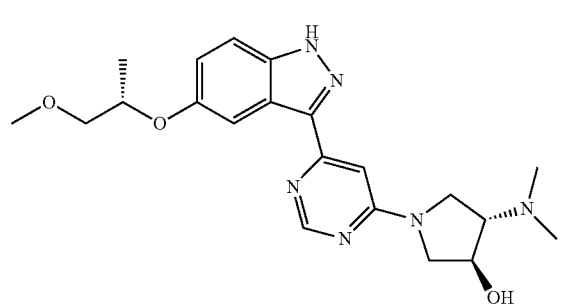
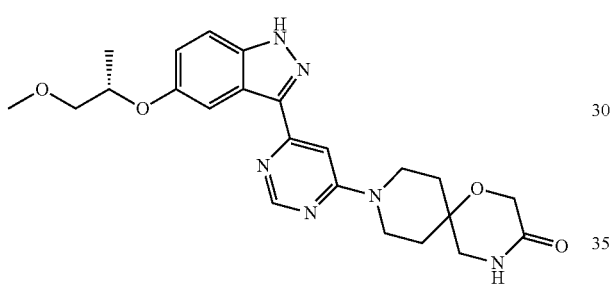
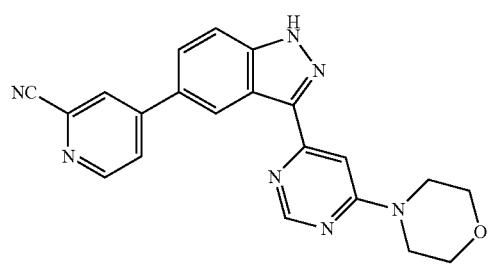
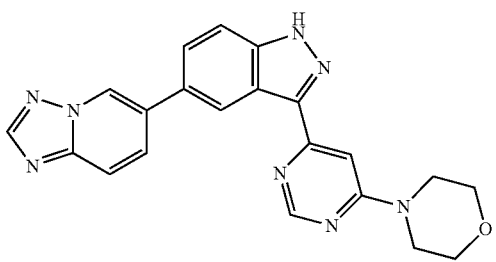
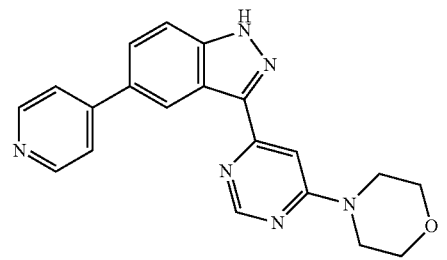
276
-continued
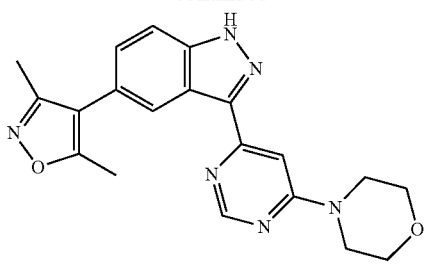
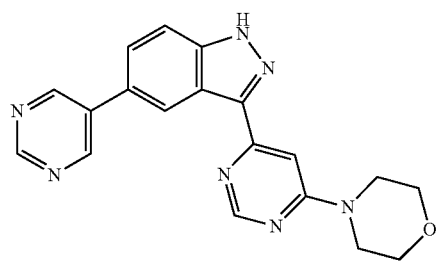
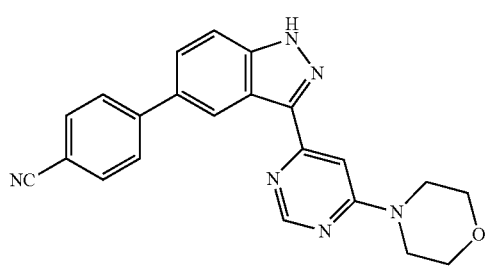
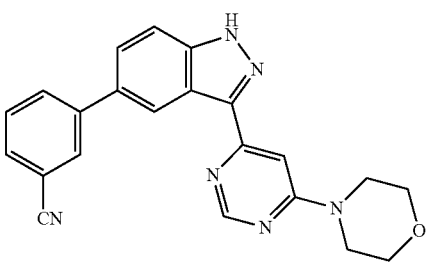
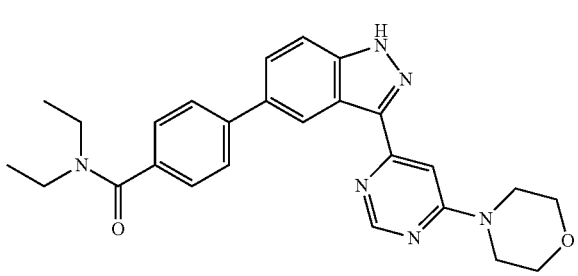
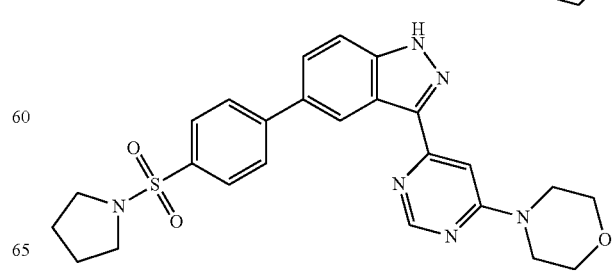

277
-continued
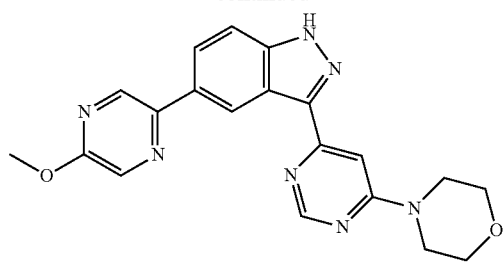
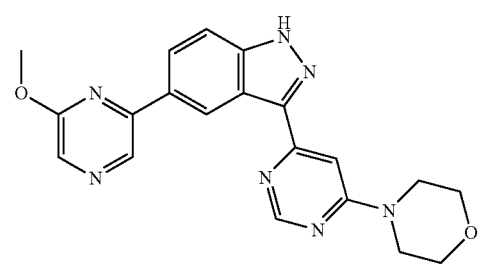
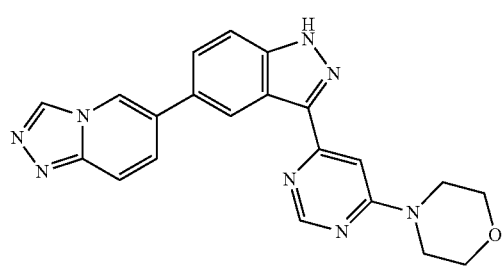
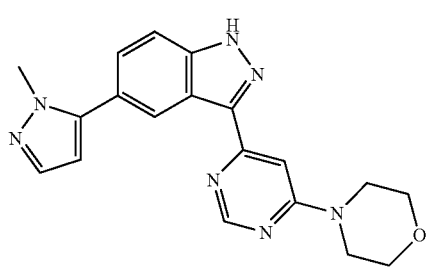
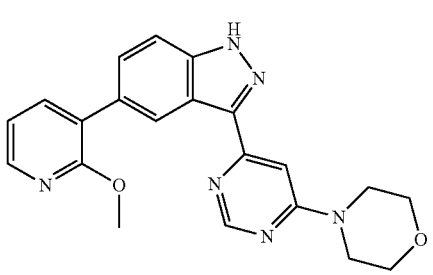
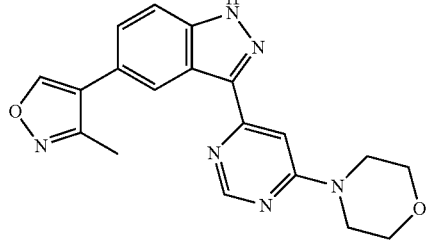
278
-continued
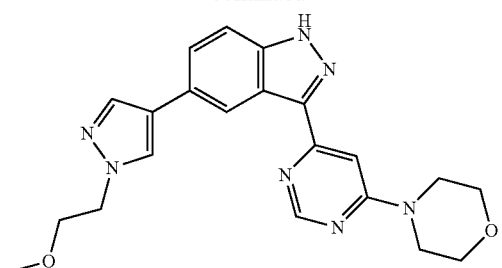
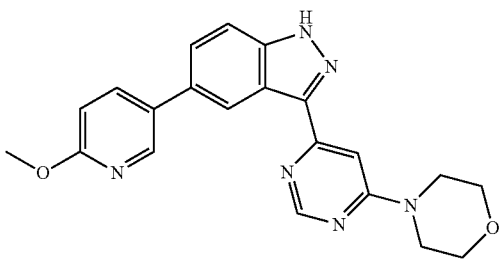
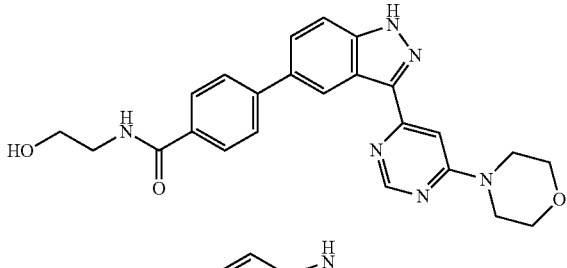
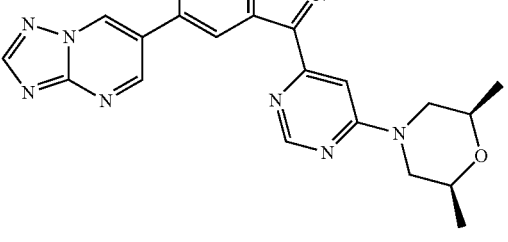
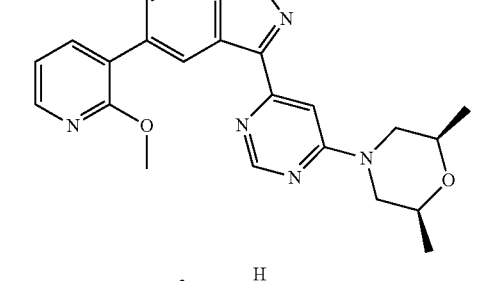
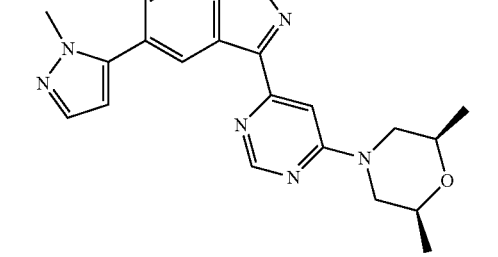

279
-continued
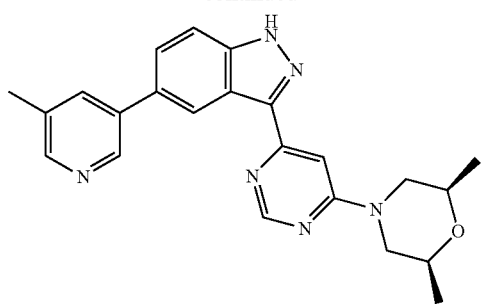
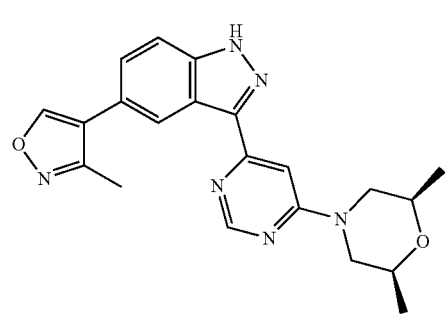
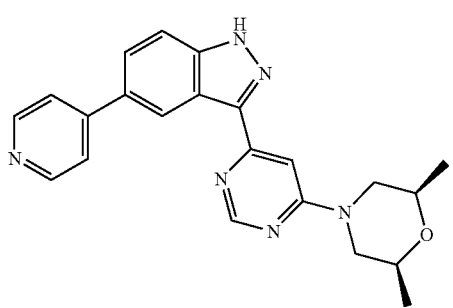
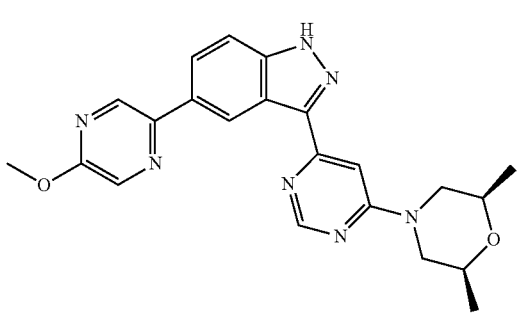
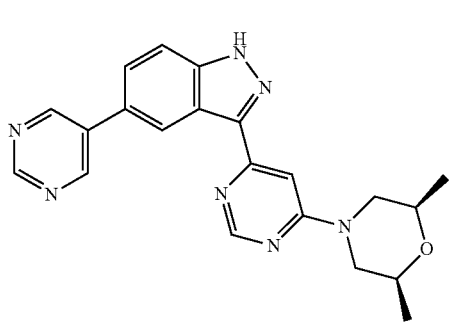
280
-continued
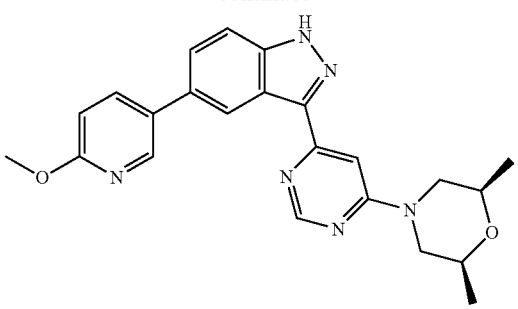
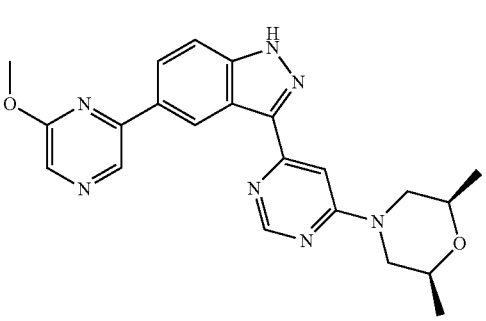
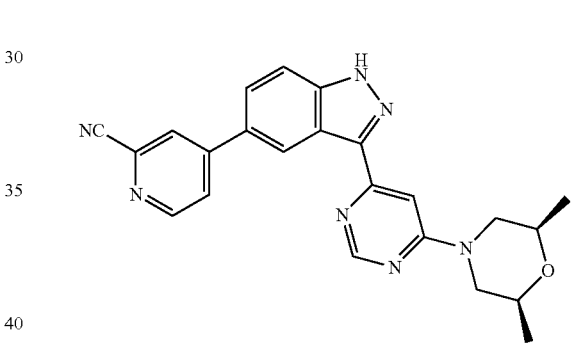
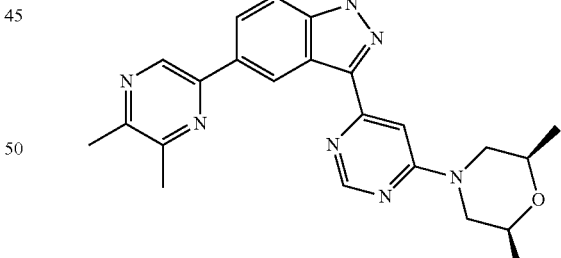
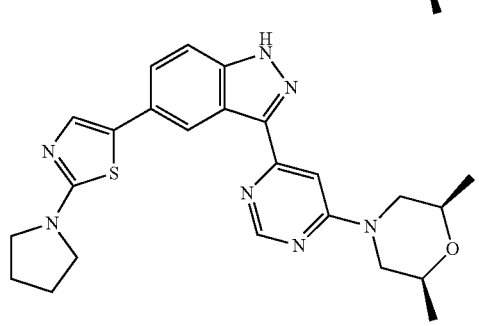

281
-continued
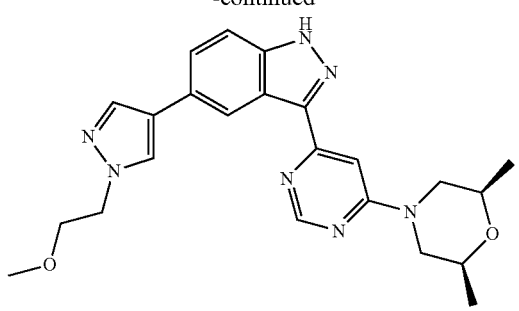
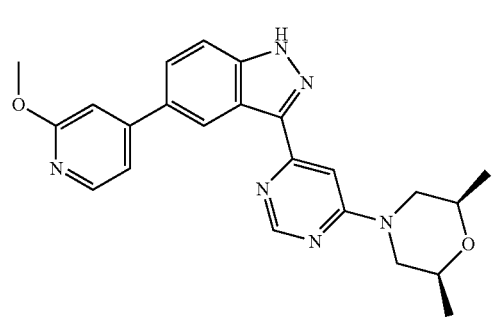
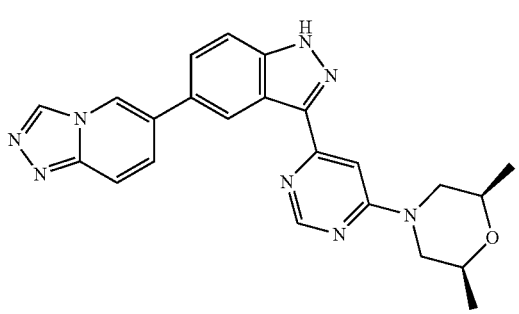
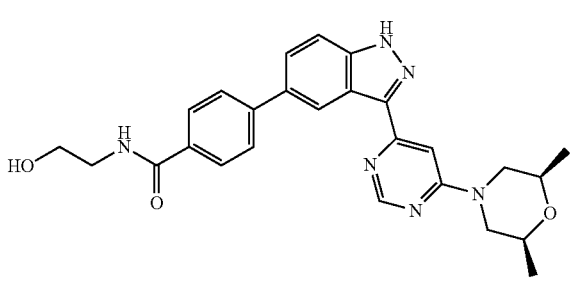
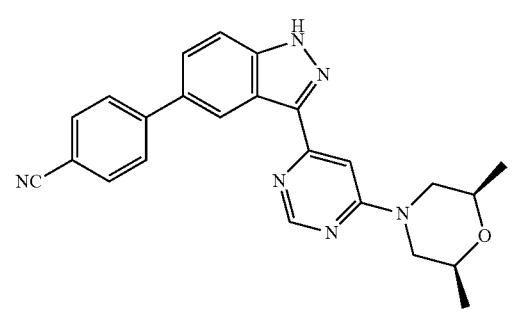
282
-continued
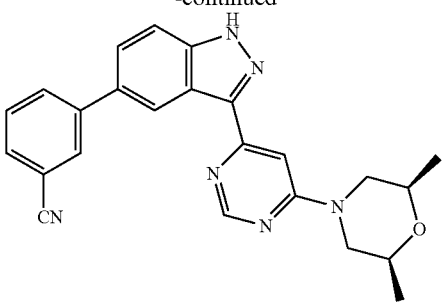
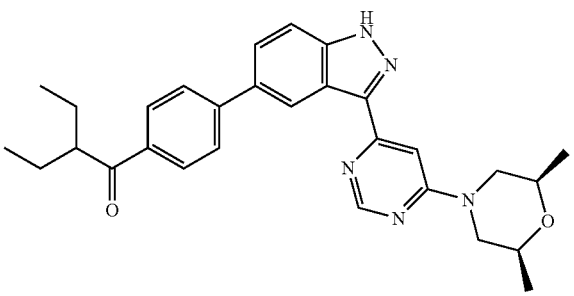
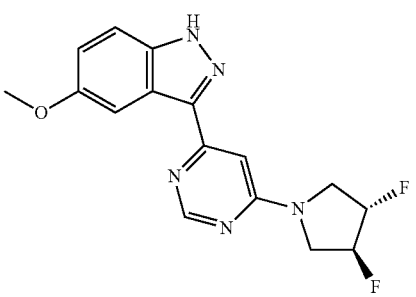
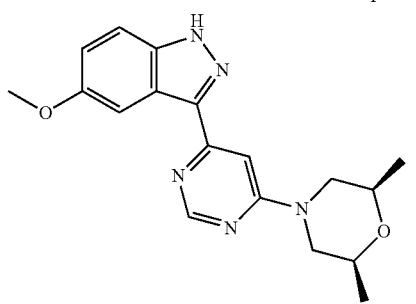
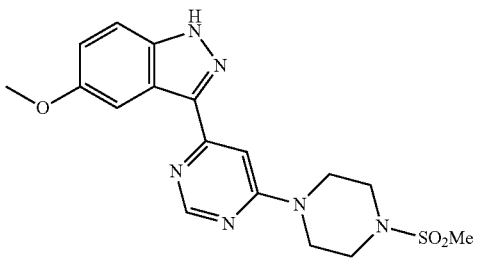
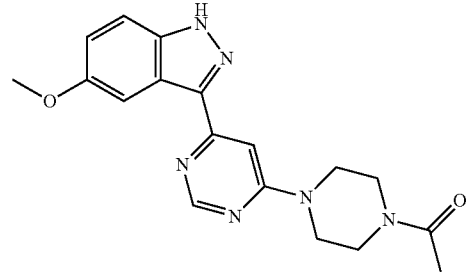

283
-continued
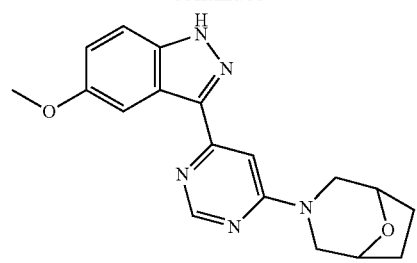
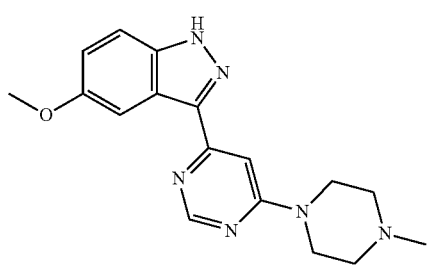
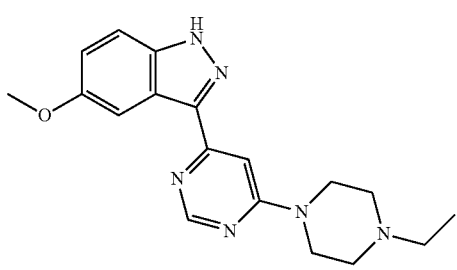
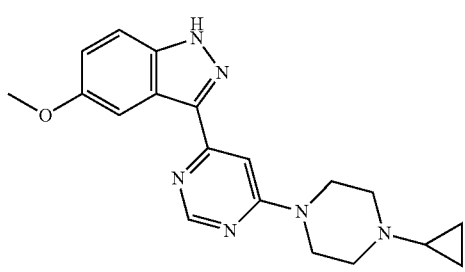
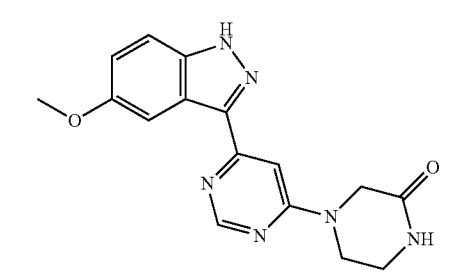
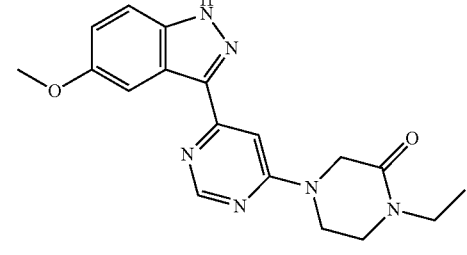
284
-continued
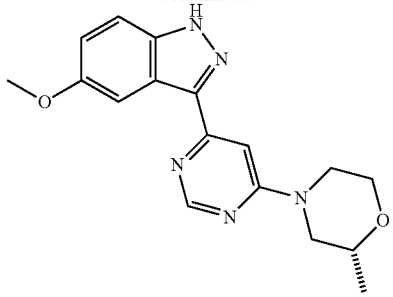
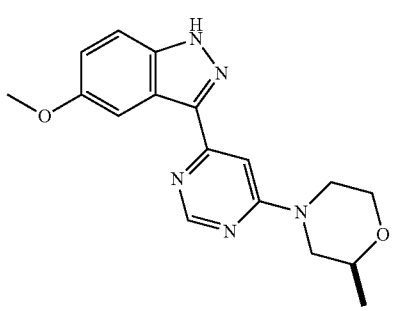
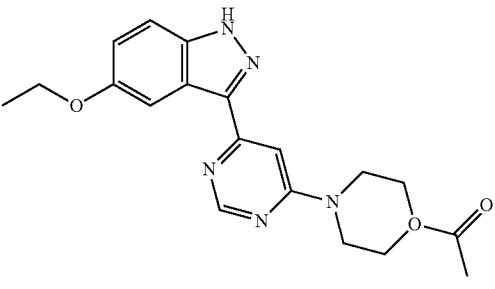
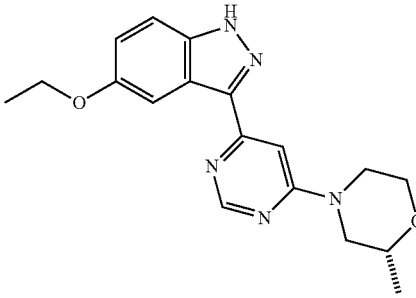
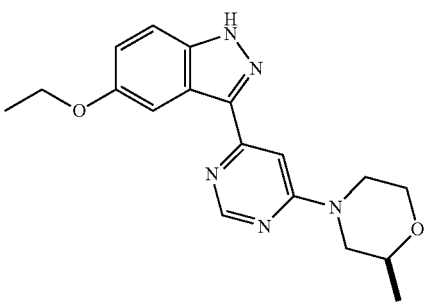

285
-continued
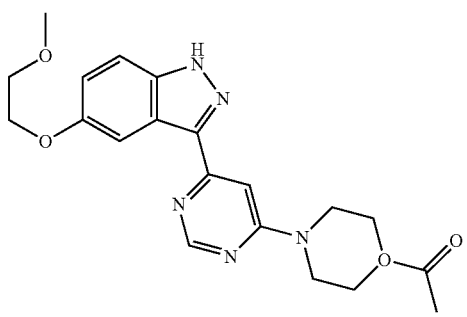
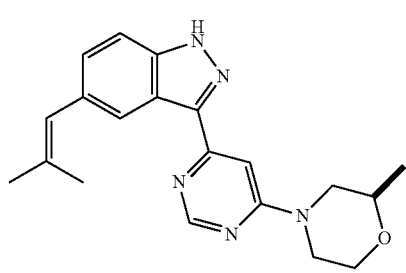
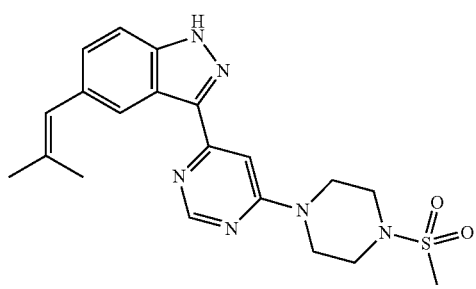
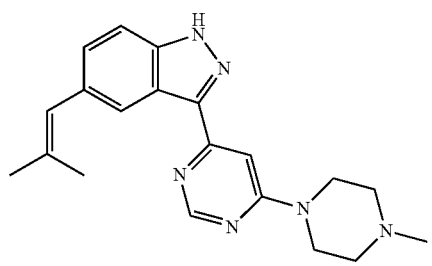
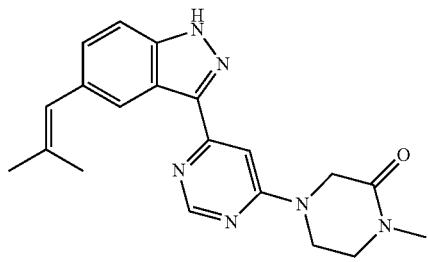
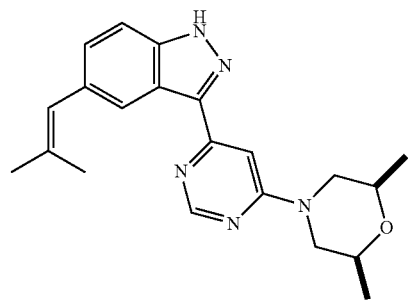 [SMILES: CC(C)=Cc1ccc2[nH]nc(-c3cc(N4C[C@@H](C)O[C@@H](C)C4)ncn3)c2c1]
286
-continued
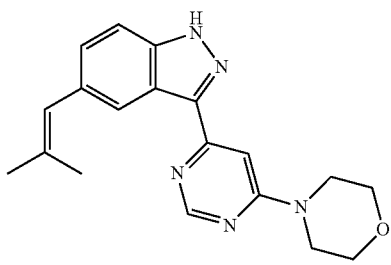 [SMILES: CC(C)=Cc1ccc2[nH]nc(-c3cc(N4CCOCC4)ncn3)c2c1]
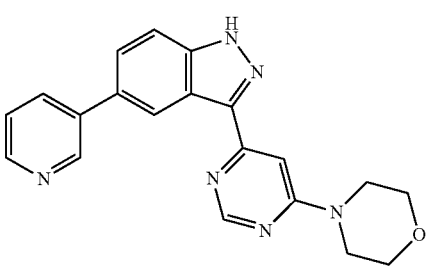
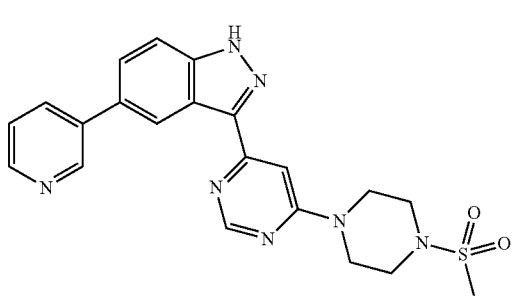
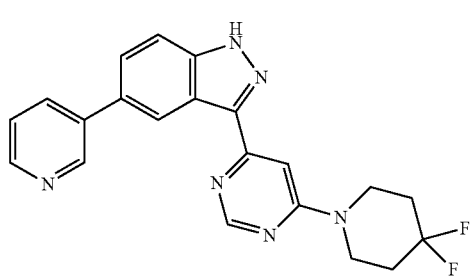
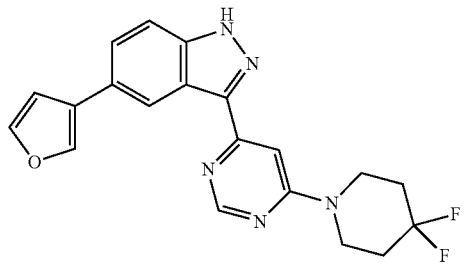 [SMILES: FC1(F)CCN(c2cc(-c3n[nH]c4ccc(-c5ccoc5)cc34)ncn2)CC1]
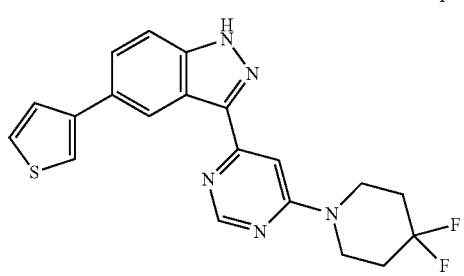

287
-continued
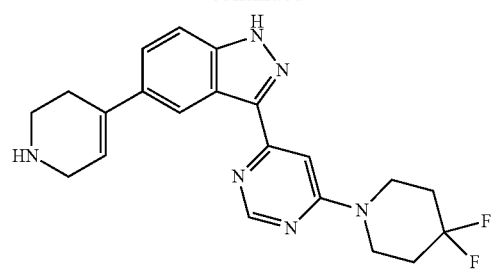
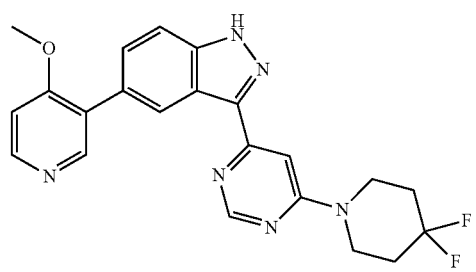 [SMILES: COc1ccncc1-c1ccc2[nH]nc(-c3cc(N4CCC(F)(F)CC4)ncn3)c2c1]
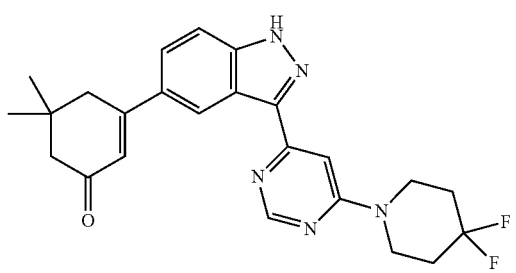 [SMILES: CC1(C)CC(=O)C=C(c2ccc3[nH]nc(-c4cc(N5CCC(F)(F)CC5)ncn4)c3c2)C1]
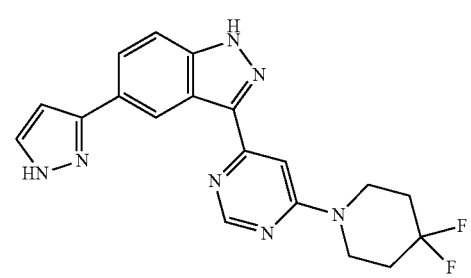 [SMILES: FC1(F)CCN(c2cc(-c3n[nH]c4ccc(-c5cc[nH]n5)cc34)ncn2)CC1]
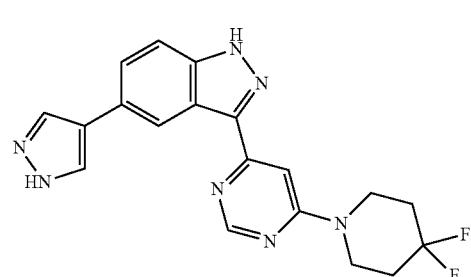
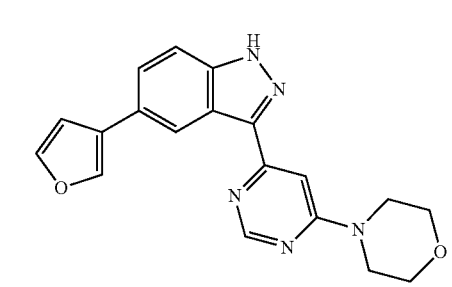
288
-continued
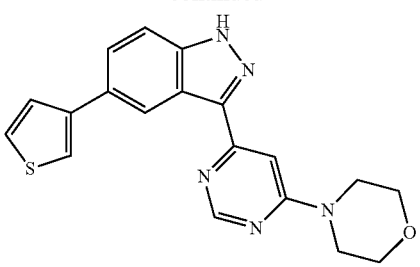 [SMILES: c1nc(-c2n[nH]c3ccc(-c4ccoc4)cc23)cc(N2CCOCC2)n1]
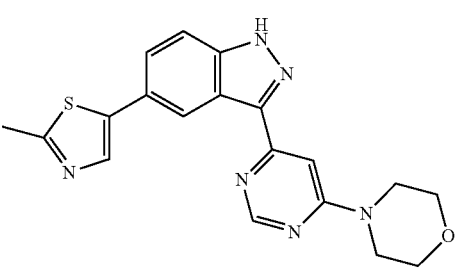 [SMILES: Cc1ncc(-c2ccc3[nH]nc(-c4cc(N5CCOCC5)ncn4)c3c2)s1]
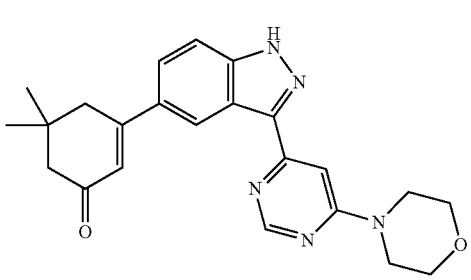 [SMILES: CC1(C)CC(=O)C=C(c2ccc3[nH]nc(-c4cc(N5CCOCC5)ncn4)c3c2)C1]
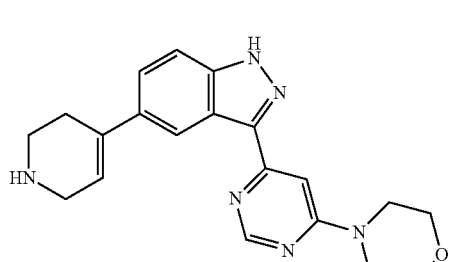
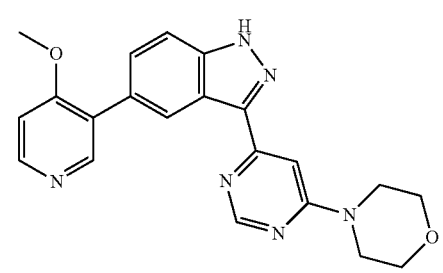 [SMILES: COc1ccncc1-c1ccc2[nH]nc(-c3cc(N4CCOCC4)ncn3)c2c1]
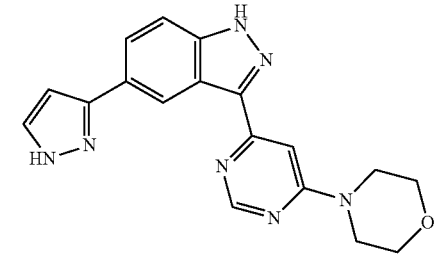

289
-continued
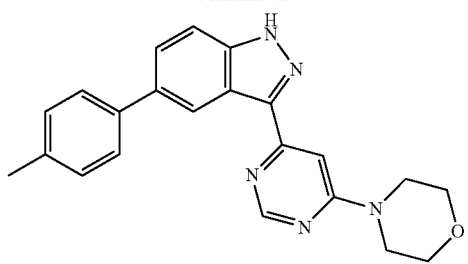 [SMILES: Cc1ccc(-c2ccc3[nH]nc(-c4cc(N5CCOCC5)ncn4)c3c2)cc1]
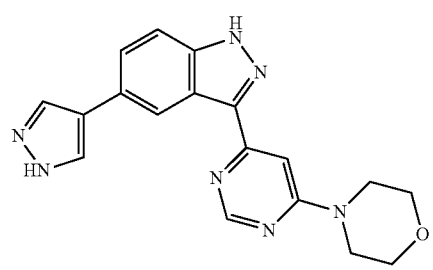 [SMILES: c1nc(-c2n[nH]c3ccc(-c4cn[nH]c4)cc23)cc(N2CCOCC2)n1]
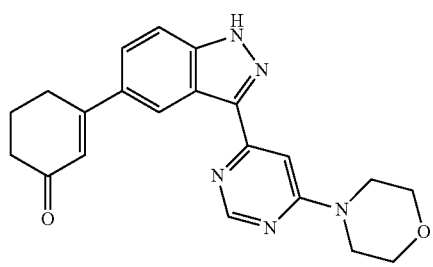 [SMILES: O=C1C=C(c2ccc3[nH]nc(-c4cc(N5CCOCC5)ncn4)c3c2)CCC1]
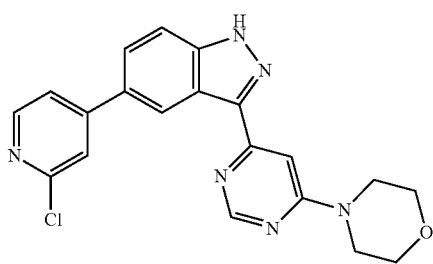 [SMILES: Clc1cc(-c2ccc3[nH]nc(-c4cc(N5CCOCC5)ncn4)c3c2)ccn1]
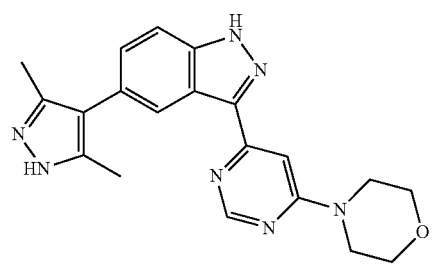 [SMILES: Cc1n[nH]c(C)c1-c1ccc2[nH]nc(-c3cc(N4CCOCC4)ncn3)c2c1]
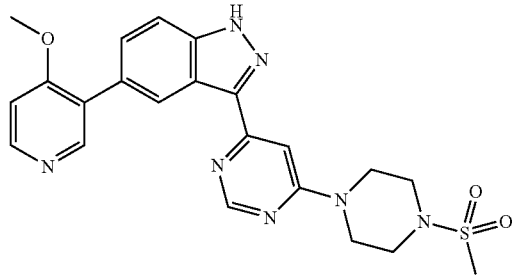 [SMILES: COc1ccncc1-c1ccc2[nH]nc(-c3cc(N4CCN(S(C)(=O)=O)CC4)ncn3)c2c1]
290
-continued
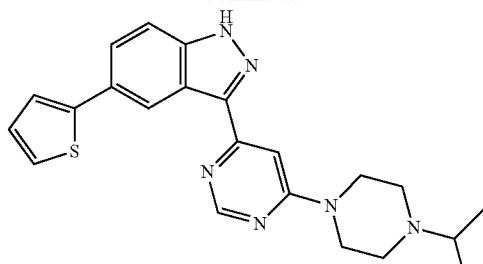
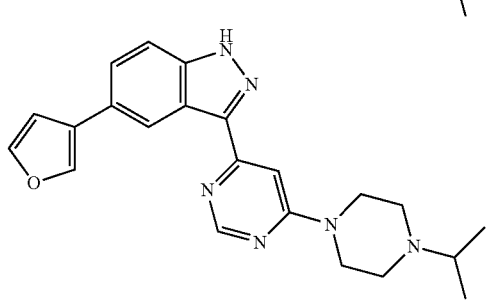
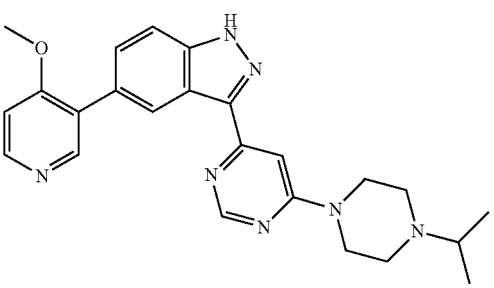 [SMILES: COc1ccncc1-c1ccc2[nH]nc(-c3cc(N4CCN(C(C)C)CC4)ncn3)c2c1]
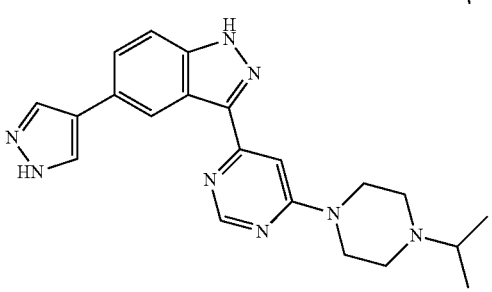
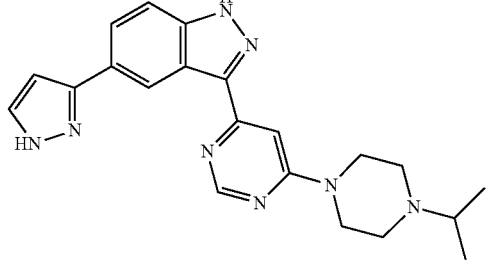
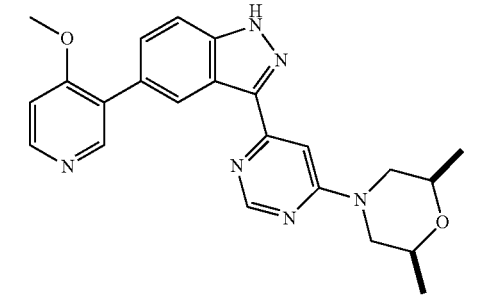 [SMILES: COc1ccncc1-c1ccc2[nH]nc(-c3cc(N4C[C@@H](C)O[C@@H](C)C4)ncn3)c2c1]

291
-continued
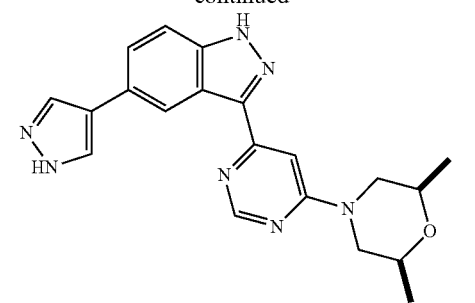
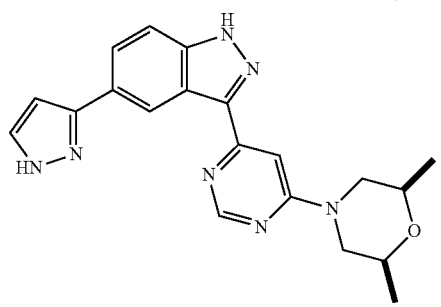
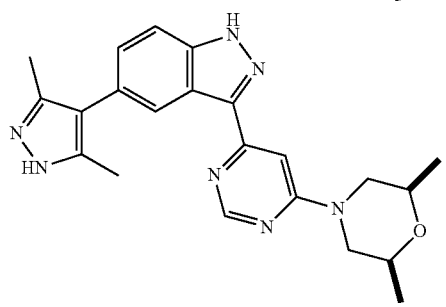
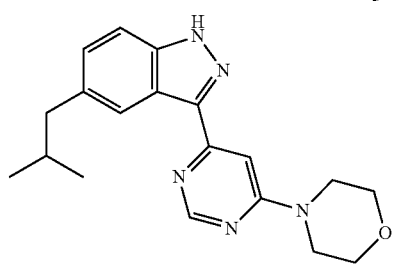
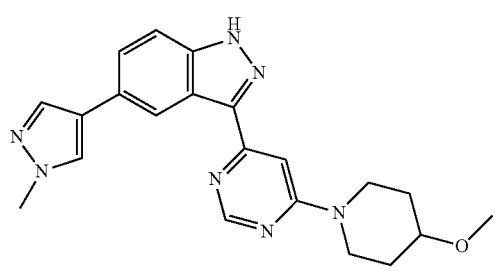
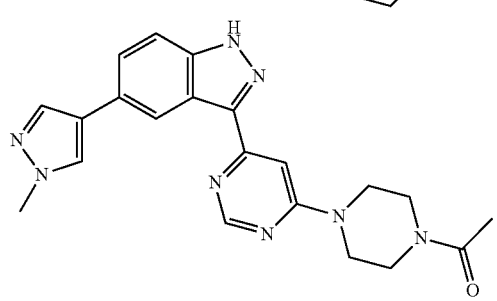
292
-continued
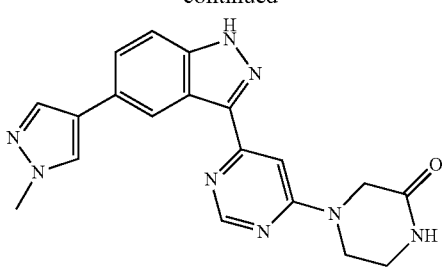
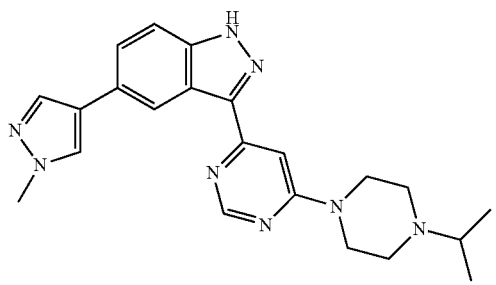
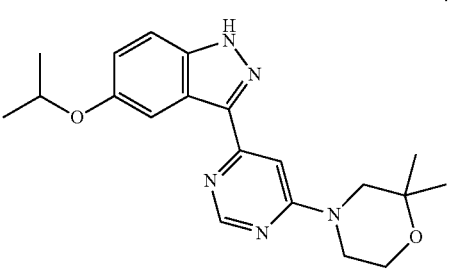
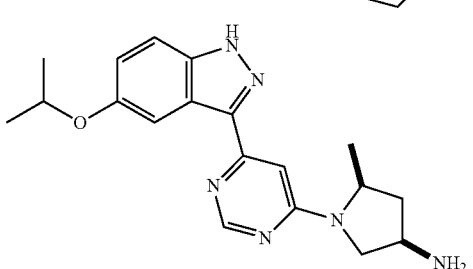
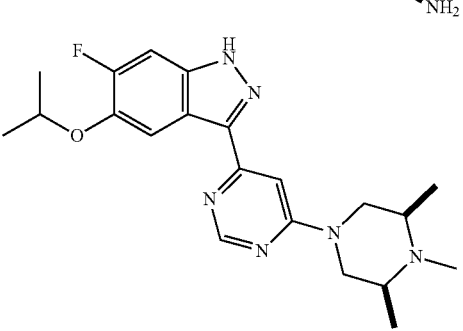
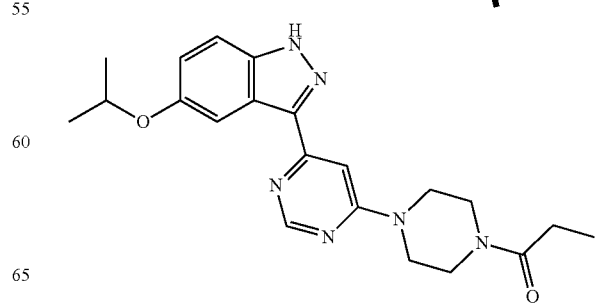

293
-continued
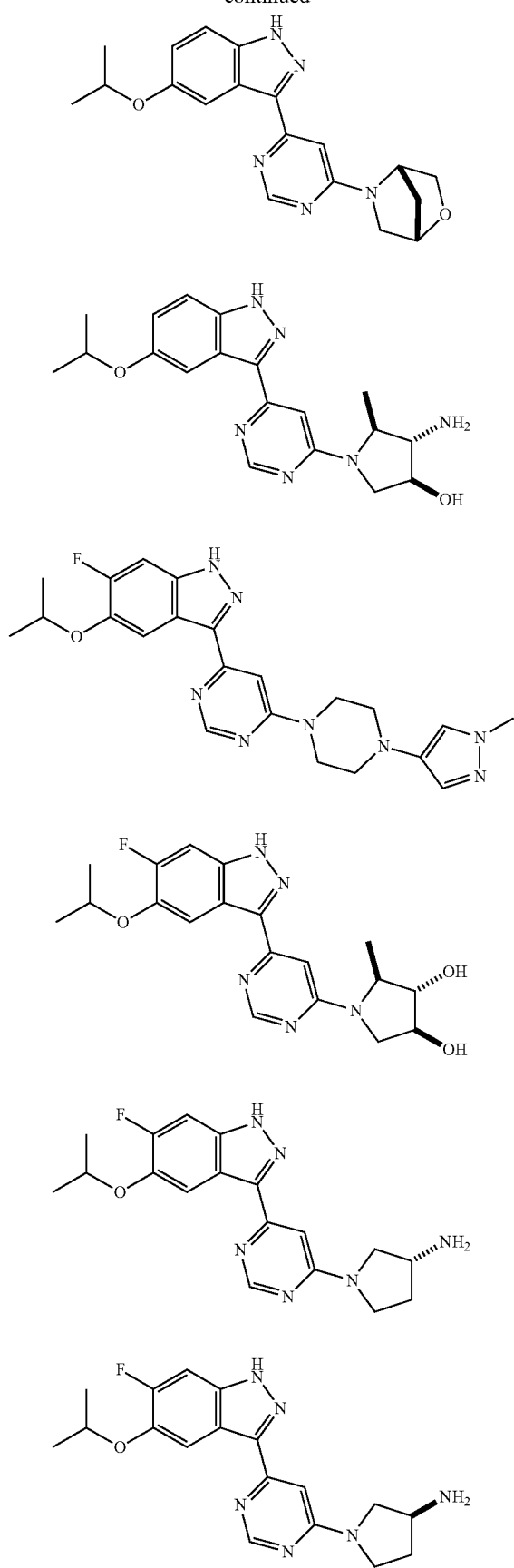
294
-continued
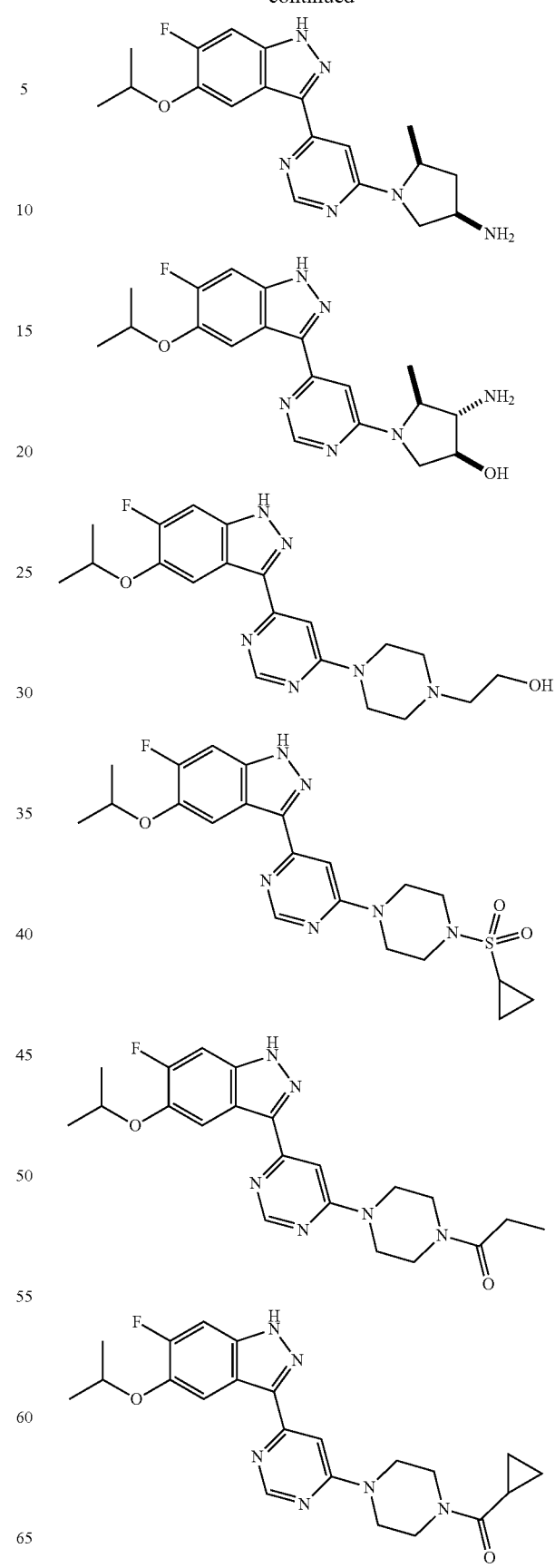

295
-continued
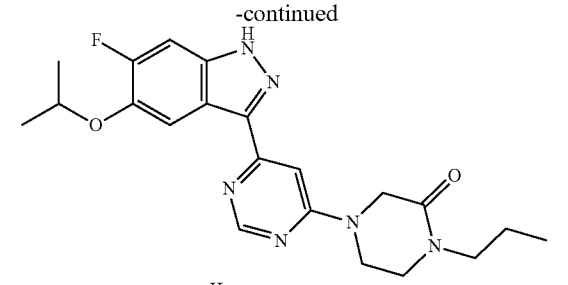
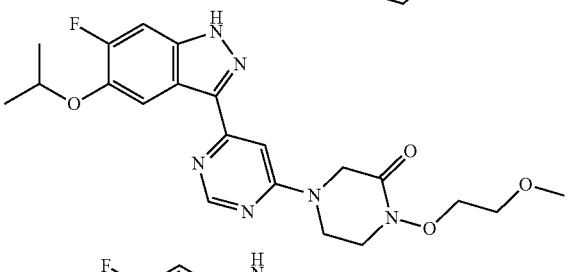
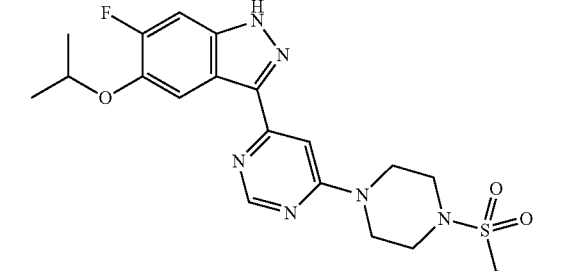
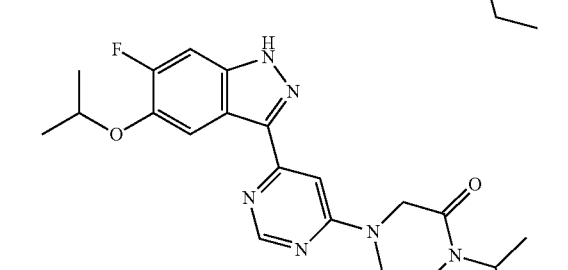
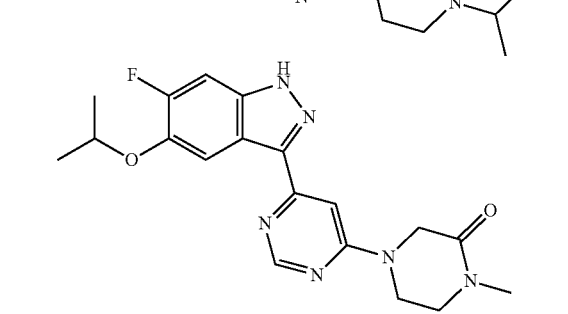
or a pharmaceutically acceptable salt thereof.
9. The compound of claim 8 selected from
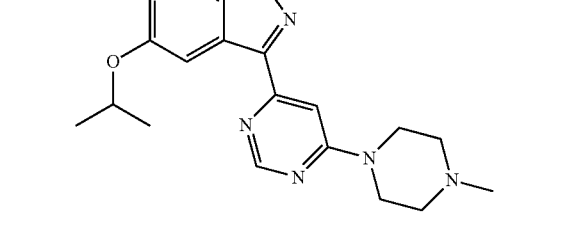
296
-continued
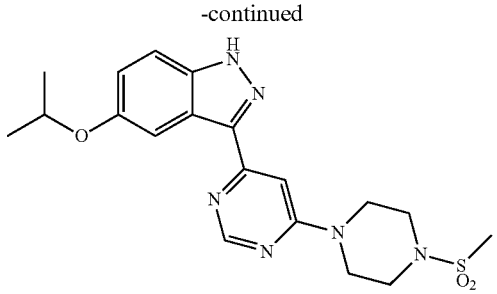
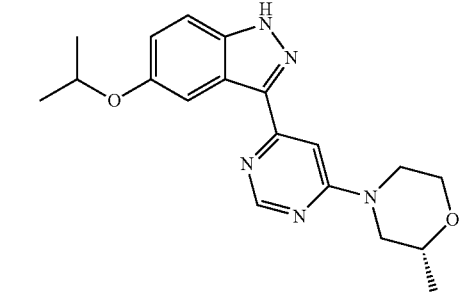
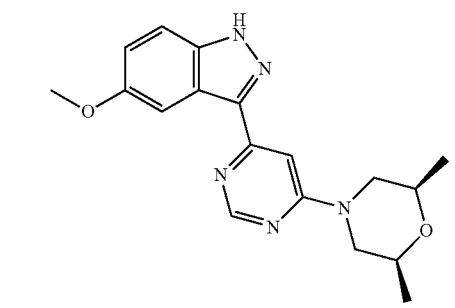
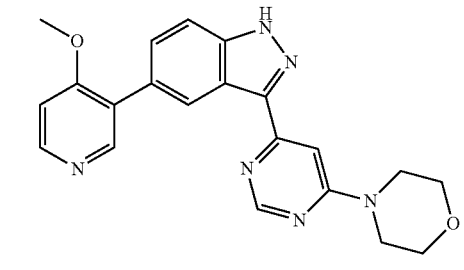
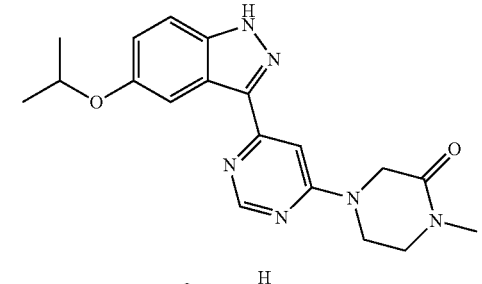
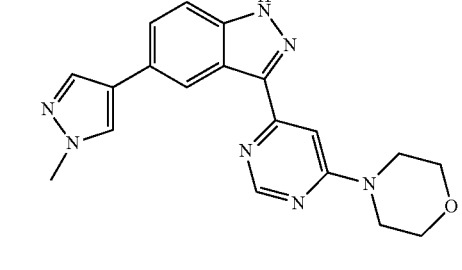

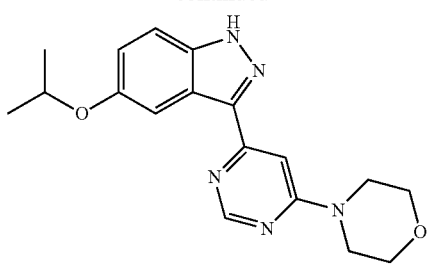

or a pharmaceutically acceptable salt thereof.

10. The compound of claim 9 selected from

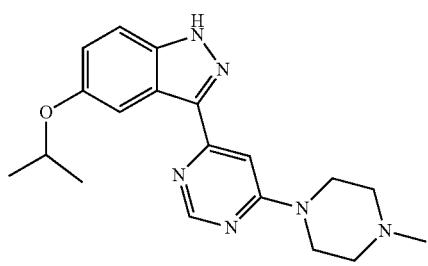 [SMILES: CC(C)Oc1ccc2[nH]nc(-c3cc(N4CCN(C)CC4)ncn3)c2c1]

or a pharmaceutically acceptable salt thereof.

11. The compound of claim 9 selected from

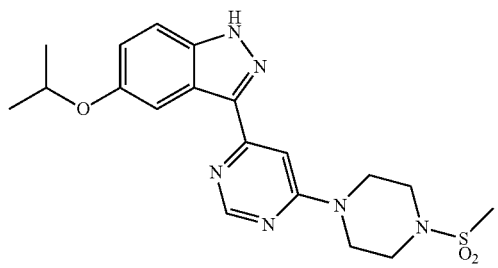 [SMILES: CC(C)Oc1ccc2[nH]nc(-c3cc(N4CCN(S(C)(=O)=O)CC4)ncn3)c2c1]

or a pharmaceutically acceptable salt thereof.

12. The compound of claim 9 selected from

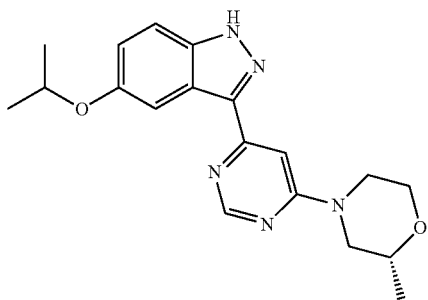 [SMILES: CC(C)Oc1ccc2[nH]nc(-c3cc(N4CCO[C@H](C)C4)ncn3)c2c1]

or a pharmaceutically acceptable salt thereof.

13. The compound of claim 9 selected from

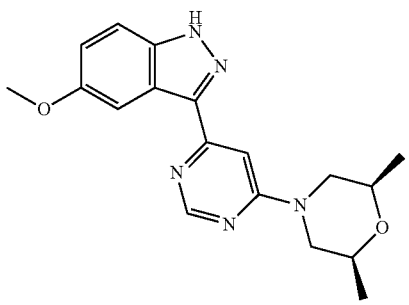

or a pharmaceutically acceptable salt thereof.

14. The compound of claim 9 selected from

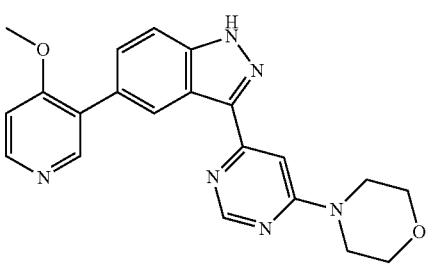 [SMILES: COc1ccncc1-c1ccc2[nH]nc(-c3cc(N4CCOCC4)ncn3)c2c1]

or a pharmaceutically acceptable salt thereof.

15. The compound of claim 9 selected from

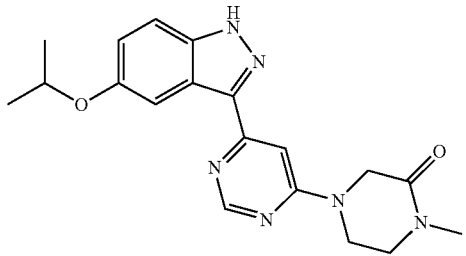 [SMILES: CC(C)Oc1ccc2[nH]nc(-c3cc(N4CCN(C)C(=O)C4)ncn3)c2c1]

or a pharmaceutically acceptable salt thereof.

16. The compound of claim 9 selected from

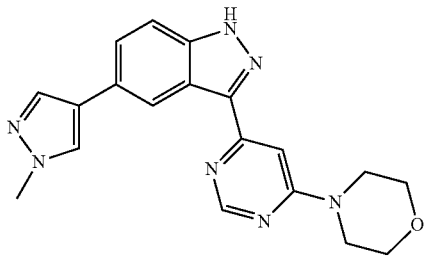 [SMILES: Cn1cc(-c2ccc3[nH]nc(-c4cc(N5CCOCC5)ncn4)c3c2)cn1]

or a pharmaceutically acceptable salt thereof.

17. The compound of claim 9 selected from
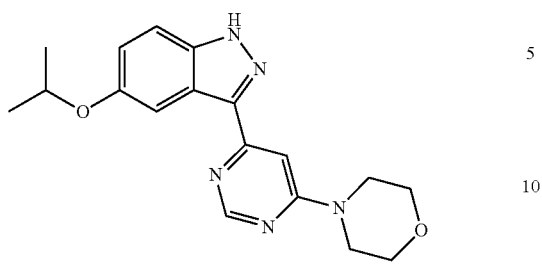
or a pharmaceutically acceptable salt thereof.
18. A pharmaceutical composition comprising a compound of claim 1, and a pharmaceutically acceptable carrier.
* * * * *